(12) United States Patent
Meyer et al.

(10) Patent No.: US 7,312,248 B2
(45) Date of Patent: Dec. 25, 2007

(54) CONTROL OF PARASITES IN ANIMALS BY THE USE OF NOVEL TRIFLUOROMETHANESULFONANILIDE OXIME ETHER DERIVATIVES

(75) Inventors: Adam Gerhard Meyer, Richmond (AU); Kevin Norman Winzenberg, Camberwell (AU); David G. Sawutz, Maplewood, NJ (US); Andris Juris Liepa, Wheelers Hill (AU)

(73) Assignee: Schering-Plough Animal Health Corporation, Summit, NJ (US)

( * ) Notice: Subject to any disclaimer, the term of this patent is extended or adjusted under 35 U.S.C. 154(b) by 0 days.

(21) Appl. No.: 11/231,423

(22) Filed: Sep. 21, 2005

(65) Prior Publication Data

US 2006/0063841 A1    Mar. 23, 2006

Related U.S. Application Data

(60) Provisional application No. 60/612,539, filed on Sep. 23, 2004.

(51) Int. Cl.
  *A01N 41/06*    (2006.01)
  *A61K 31/18*    (2006.01)
(52) U.S. Cl. ......................... 514/602; 564/97
(58) Field of Classification Search ................ 514/602; 564/97
See application file for complete search history.

(56) References Cited

U.S. PATENT DOCUMENTS

| | | |
|---|---|---|
| 3,852,416 A | 12/1974 | Grubb et al. |
| 3,950,360 A | 4/1976 | Aoki et al. |
| 3,984,564 A | 10/1976 | Aoki et al. |
| 4,199,569 A | 4/1980 | Chabala et al. |
| 4,224,901 A | 9/1980 | Carey, Jr. |
| 4,310,519 A | 1/1982 | Albers-Schonberg et al. |
| 4,311,857 A | 1/1982 | Nagabhushan |
| 4,341,782 A | 7/1982 | Konishi et al. |
| 4,582,918 A | 4/1986 | Nagabhushan et al. |
| 4,743,700 A | 5/1988 | Jommi et al. |
| 4,820,695 A | 4/1989 | Debono et al. |
| 4,876,352 A | 10/1989 | Schumacher et al. |
| 4,916,154 A | 4/1990 | Asato et al. |
| 4,973,750 A | 11/1990 | Nagabhushan et al. |

(Continued)

FOREIGN PATENT DOCUMENTS

EP    0019450 B1    2/1983

(Continued)

OTHER PUBLICATIONS

Hirano Masachika, "Insecticide and Acaricide Containing Trifluoromethanesulfon Anilide Derivative as an Active Ingredient", Patent Abstracts of Japan vol. 006, No. 266, Dec. 25, 1982.

(Continued)

*Primary Examiner*—Yvonne (Bonnie) Eyler
*Assistant Examiner*—Chukwuma Nwaonicha
(74) *Attorney, Agent, or Firm*—Kiera A. Mathey; Michael D. Davis

(57) ABSTRACT

Novel trifluoromethanesulfonanilide oxime ether compounds useful for controlling endo and/or ectoparasites in the environment are provided, together with methods of making the same, and methods of using the inventive compounds to treat parasite infestations in vivo or ex vivo.

17 Claims, 12 Drawing Sheets

U.S. PATENT DOCUMENTS

| | | | |
|---|---|---|---|
| 5,089,480 | A | 2/1992 | Gibson et al. |
| 5,105,009 | A | 4/1992 | Jommi et al. |
| 5,177,465 | A | 1/1993 | Bunce |
| 5,184,573 | A | 2/1993 | Stevens, Jr. |
| 5,227,494 | A | 7/1993 | Schumacher et al. |
| 5,288,710 | A | 2/1994 | Cvetovich |
| 5,352,832 | A | 10/1994 | Wu et al. |
| 5,382,673 | A | 1/1995 | Clark et al. |
| 5,399,717 | A | 3/1995 | Cvetovich et al. |
| 5,555,848 | A | 9/1996 | Trujillo et al. |
| 5,567,844 | A | 10/1996 | Jommi et al. |
| 5,663,361 | A | 9/1997 | Towson et al. |
| 5,958,888 | A | 9/1999 | Macy et al. |
| 6,054,434 | A | 4/2000 | Kropp et al. |
| 6,177,465 | B1 | 1/2001 | Tanaka |
| 6,239,112 | B1 | 5/2001 | Macy et al. |
| 6,270,768 | B1 | 8/2001 | O'Connell et al. |
| 6,271,255 | B1 | 8/2001 | Leadlay et al. |
| 6,333,022 | B1 | 12/2001 | Tanaka |
| 6,339,063 | B1 | 1/2002 | Kropp et al. |
| 6,437,151 | B2 | 8/2002 | Leadlay et al. |
| 6,455,535 | B1 | 9/2002 | Uehara et al. |
| 6,472,371 | B1 | 10/2002 | Dirlam et al. |
| 6,492,419 | B1 | 12/2002 | Shepherd |
| 6,514,945 | B1 | 2/2003 | Boettner |
| 2003/0064939 | A1 | 4/2003 | Sklavounos et al. |
| 2004/0082553 | A1 | 4/2004 | Boojamra et al. |
| 2005/0182031 | A1 | 8/2005 | Hecker et al. |
| 2005/0182059 | A1 | 8/2005 | Winzenberg et al. |
| 2005/0182139 | A1 | 8/2005 | Shuster et al. |
| 2006/0128779 | A1 | 6/2006 | Winzenberg et al. |
| 2006/0281695 | A1 | 12/2006 | Meyer et al. |

FOREIGN PATENT DOCUMENTS

| | | | |
|---|---|---|---|
| EP | 0236618 | B1 | 2/1991 |
| EP | 1097932 | A1 | 5/2001 |
| JP | 08291146 | * | 11/1996 |
| JP | 10007657 | * | 11/1996 |
| JP | 10007657 | * | 1/1998 |
| JP | 10017419 | * | 1/1998 |
| JP | 10025213 | * | 1/1998 |
| JP | 11060562 | * | 3/1999 |
| WO | WO 2004011429 | * | 2/2004 |

OTHER PUBLICATIONS

International Search Report for International Application No. PCT/US2005/033791 mailed May 4, 2006—5pgs.

Grochowski, et al., Synthesis, "A New Synthesis of O-Alkylhydroxylamines", 1976, pp. 682-684.

Harrington, et al., J. Med. Chem.,"Antiinflammatory Agents. I. 3-Benzoylfluoroalkanesulfonanilides", Jan. 1970, vol. 13, p. 137.

Horner, et al., J. Med. Chem., "Analogs of 3-Amino-7-chlor-1,2,4-benzotriazine 1-Oxide as Antimalarial Agents1", 1968, vol. 11, pp. 946-949.

Ishikawa, et al., Journal of Antibiotics, "Studies on anti-MRSA parenteral cephalosporins. II. Synthesis and antibacterial activity of 7:beta-12-(5-amino-1,2,4-thiadiazol-3-yl) -2(Z)-a[koxyiminoacetamido]-3-(substituted imidazo[1,2-b]pyridazinium-1-yl)methyl-3-cephem-4-carboxylates and related compounds", 2000, vol. 53, No. 10, pp. 1071-1085, Abstract Only.

Kornblum, et al., J. Org. Chem., "Conversion of Nitro Paraffins into Aldeydes and Ketones1", 1982, vol. 47, pp. 4534-4538.

Leonard, et al., J. Org. Chem., "Cinnolines. I. Synthesis of Aminoacetophenones and Aminopropiophenones1", 1946, vol. 11, pp. 405-418.

McKay, et al., Can. J. Chem., "Bacteriostats III. Oxyamines and their Derivatives1", 1960, vol. 38, pp. 343-358.

Petrassi, et al., Organic Letters, "The Copper-Mediated Cross-Coupling of Phenylboronic Acids and N-Hydroxyphthalimide at Room Temperature: Synthesis of Aryloxyamines", 2001, vol. 3, No. 1, pp. 139-142.

Pfeiffer, et al., Berichte d. D. Chem, Geselischaft., "Constitution of dimethylglyoxime-nickel", 1930, vol. 63B, pp. 1811-1816+ABSTRACT.

Reid, et al., Tetrahedron Letters, "Addition of Nitroalkanes to Ortho-Halo-Nitrobenzenes. A New Synthesis of 4-Chloro-7-(Trifluoromethyl)Quinoline.", 1990, vol. 31, No. 8, pp. 1093-1096.

Simpson, et al., O. J. Chem. Soc., "o-Amino-ketones of the Acetophenone and Benzophenone Types.", 1945, pp. 646-657.

Sugasawa, et al., Journal of the American Chemical Society, "Aminohaloborane in Organic Synthesis. I. Specific Ortho Substitution Reaction of Anilines1", Jul. 19, 1978, vol. 100, pp. 4842-4852.

Tsuji, et al., Chem. Pharm. Bull., "Studies on Antiiinflammatory Agents. I. Synthesis and Pharmacological Properties of 2'-Phenoxy-methanesulfonanilide Derivatives", 1992, vol. 40, 9, pp. 2399-2409.

U.S. Appl. No. 60/688,898 for "Control of Parasites in Animals by N-[(Phenyloxy)Phenyl]-1,1,1-Trifluoromethanesulfonamide and N-[(Phenvlsulfanvl)Phenyl]-1.1.1-Trifluoromethanesulfonamide Derivatives". filed Jun. 9, 2005.

"Ferimzone", DISEASEProjects, Takeda Chemical, PJB Publications Ltd., D0007L, May 2003, 2 pgs.

"Nihon.Nohyaku", PESTProjects, PJB Publications Ltd., May 2001, Aug. 2002 & Aug. 2003, 5 pgs.

"Tebufenozide", PESTProjects, Rohm, et al., PJB Publications Ltd., P0027L, Sep. 1999 & May 2003, 8 pgs.

U.S. Appl. No. 60/612,539 for "Control of Parasites in Animals by the use of Novel Trifluoromethanesulfonanilide Oxime Ether Derivatives", filed Sep. 23, 2004.

U.S. Appl. No. 60/629,699 for "Control of Parasites in Animals by the use of Parasiticidal-2-Phenyl-3-(1H-Pyrrol-2-Yl)Acrylonitrile Derivatives", filed Nov. 19, 2004.

U.S. Appl. No. 60/688,898 for "Control of Parasites in Animals by N-[(Phenyloxy)Phenyl]-1,1,1-Trifluoromethanesulfonamide and N-[(Phenvlsulfanvl)Phenvi]-1.1.1-Trifluoromethanesulfonamide Derivatives". filed Jun. 9, 2005.

* cited by examiner (Scheme 1)

(Scheme 2)

(Scheme 3)

(Scheme 4)

(Scheme 5)

(Scheme 6)

(Scheme 7)

(Scheme 8)

CONTROL OF PARASITES IN ANIMALS BY THE USE OF NOVEL TRIFLUOROMETHANESULFONANILIDE OXIME ETHER DERIVATIVES

CROSS-REFERENCE TO RELATED APPLICATIONS

This application is a non-provisional application that claims priority under 35 U.S.C. § 119(e) of provisional application U.S. Ser. No. 60/612,539 filed Sep. 23, 2004, the contents of which are hereby incorporated by reference in their entireties.

BACKGROUND OF THE INVENTION

1. Field of the Invention

The present invention relates to new trifluoromethanesulfonanilide oxime ether derivatives useful as parasiticides, compositions containing the compounds, and methods of treatment using the compounds, especially to control animal parasites, e.g., ecto- and endoparasites such as fleas, acaridae, helminths, and nematodes. The invention also relates to the use of a combination of a parasiticide of this invention and one or more additional parasiticides or other agents useful in killing parasites.

2. BACKGROUND

The control of animal parasites is essential, especially in the areas of production and companion animals. Existing methods of treatment are being compromised due to growing resistance to current commercial parasiticides, such as the benzimidazoles and ivermectins. The discovery of more effective ways to control animal parasites is therefore imperative.

Trifluoromethanesulfonanilide oxime ether derivatives have been reported in the patent literature.

In JP 08291146 trifluoromethanesulfonanilide oxime ether derivatives of Formula A have been disclosed:

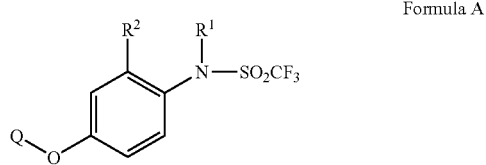

Formula A wherein:

$R^1$ is either hydrogen, $C_2$-$C_{10}$ alkanoyl or benzoyl optionally substituted by 1 or 2 substituents selected from halo or $C_1$-$C_4$ alkyl;

$R^2$ is either methoxycarbonyl, acetyl, —C(=NOCH$_3$)CH$_3$ or C(=NOCH$_2$CH$_3$)CH$_3$; and Q is either 2-pyrimidinyl, 5-halo-2-pyrimidinyl or 6-halo-3-pyridazinyl.

These compounds have been said to show potent herbicidal activity without damaging rice seedlings.

In JP 10007657 trifluoromethanesulfonanilide oxime ether derivatives of Formula B have been disclosed:

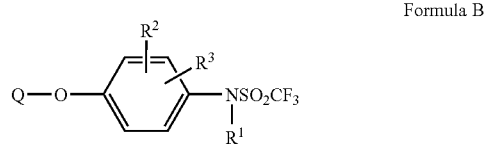

Formula B wherein:

$R^1$ is either hydrogen, $C_2$-$C_6$ alkanoyl or benzoyl;

$R^2$ and $R^3$ are independently selected from hydrogen, halo, nitro, cyano, (substituted)lower alkyl, (substituted) lower alkoxy, lower alkoxycarbonyl, acetyl, —C(=NO CH$_3$)CH$_3$ or $R^2$ and $R^3$ is Ph to form a naphthalene ring; and Q is either (substituted)pyrazinyl, (substituted)4-pyrimidinyl, (substituted)oxazolyl, (substituted)thiazolyl, (substituted)quinoxalyl, (substituted)quinazolyl, (substituted)thiadiazolyl, (substituted)tetrazolyl, (substituted)benzoxazolyl, (substituted)benzothiazolyl, (substituted)triazolyl, (substituted)triazinyl, (substituted)pyrazolyl or (substituted)isoxazolyl.

These compounds have been said to show herbicidal activity without damaging rice plants.

In JP 10017419 and JP 10025213 trifluoromethanesulfonanilide oxime ether derivatives of Formula C have been disclosed:

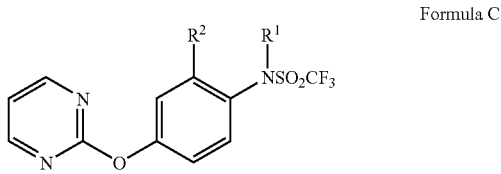

Formula C wherein:

$R^1$ is either hydrogen or $C_2$-$C_5$ alkanoyl; and $R^2$ is either hydrogen, chlorine, methoxycarbonyl or C(=NOCH$_3$)CH$_3$;

These compounds have been said to show herbicidal activity without damaging rice seedlings.

In JP 11060562 trifluoromethanesulfonanilide oxime ether derivatives of Formula D have been disclosed:

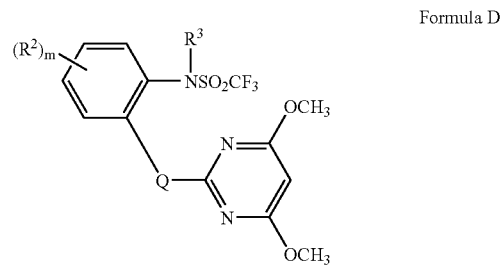

Formula D wherein:

$R^1$ is (optionally)substituted alkyl or (optionally)substituted alkenyl;

$R^2$ is either hydrogen, halo, (optionally)substituted alkoxy or (optionally)substituted alkyl;

$R^3$ is either, hydrogen, (optionally)substituted alkyl, benzyl, acyl, alkoxycarbonyl, (optionally)substituted carbamoyl, (optionally)substituted thiocarbamoyl or —SO$_2$R$^1$;

Q is either —CH(NR$^4$R$^5$) or C(=NR$^6$) [R$^4$, R$^5$ and R$^6$ is either hydrogen, (optionally)substituted alkyl, alkenyl, alkynyl, cycloalkyl, (optionally)substituted phenyl, acyl, alkoxycarbonyl, (optionally)substituted carbamoyl, (optionally) substituted thiocarbamoyl, —SO$_2$R$^1$, NR$^7$R$^8$, or —OR$^9$. R$^4$ and R$^5$, connected through a nitrogen atom, may form a nitrogen-containing heterocyclic group which possesses one or more heteroatoms]; and m is 1 to 4;

These compounds have been said to show herbicidal activity. In PCT Int. Appl. WO 2004 11, 429 trifluoromethanesulfonanilide oxime ether derivatives of Formula E have been disclosed:

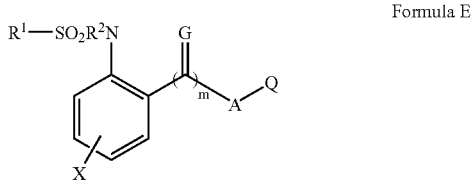

wherein:

R¹ is halo($C_1$-$C_6$)alkyl;

R² is either hydrogen $C_1$-$C_6$ alkyl or the like,

A is $C_1$-$C_6$ alkylene or the like;

G is O, S, $NR^3$, $NOR^4$ or $NNR^5R^6$;

m is 0 or 1;

X is substituted phenyl, phenoxy, or the like; and

Q is an optionally substituted heterocycle having at least one ring-constituent nitrogen atom at which the heterocycle is bonded to A.

These compounds have been said to show herbicidal activity. In the general area of insecticidal and acaricidal control, Japanese Laid-open Patent 57-156407A discloses trifluoromethanesulfonanilide compounds of Formula F:

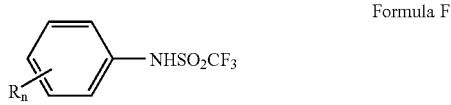

wherein:

R is selected from alkyl, alkoxyalkyl, haloalkyl, haloalkoxy, alkylcarbonyl, alkoxycarbonyl or halo; and n is 1 to 5.

A pesticidal composition which comprises the ester 2-methoxycarbonyl-4-chlorotrifluoromethanesulfonanilide (Formula G) as an active ingredient is disclosed in U.S. Pat. Nos. 6,177,465 and 6,333,022. Examples of the pests controlled by the composition include insects and acarina such as indoor mites, fleas, cockroaches and so on. The composition is said to be very effective for controlling house dust mites.

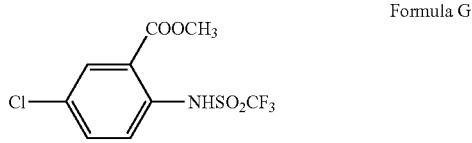

In spite of the forgoing, work in this area has continued to provide improved methods of controlling insects and acarina as well as compounds useful for the same and related purposes.

The citation of any reference herein should not be construed as an admission that such reference is available as "prior art" to the instant application.

SUMMARY OF THE INVENTION

Accordingly, the present invention provides oxime ether derivatives that are effective anti-parasite agents.

In one embodiment, the invention provides a trifluoromethanesulfonanilide oxime ether compound of Formula (I)

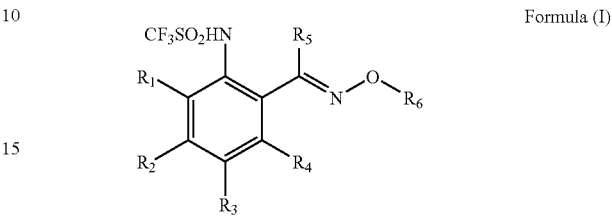

or a pharmaceutically acceptable salt thereof or a solvate thereof.

$R_1$, $R_2$, $R_3$ and $R_4$ are independently selected from the following: hydrogen, formyl, carboxyl, cyano, hydroxy, amino, nitro, thiol, halo and the following optionally substituted moieties: alkyl, alkenyl, alkynyl, cycloalkyl, cycloalkenyl, aryl, heterocyclyl, heteroaryl, alkanoyl, aroyl, heterocycloyl, heteroaroyl, alkoxycarbonyl, aryloxycarbonyl, heterocyclyloxycarbonyl, heteroaryloxycarbonyl, alkylaminocarbonyl, arylaminocarbonyl, heterocyclylaminocarbonyl, heteroarylaminocarbonyl, alkoxy, alkenyloxy, cycloalkoxy, cycloalkenyloxy, alkoxy, aryloxy, heterocyclyloxy, alkanoate, aryloate, heterocyclyloate, heteroaryloate, alkylsulfonate, arylsulfonate, heterocyclylsulfonate, heteroarylsulfonate, alkylamino, alkenylamino, arylamino, heterocyclylamino, heteroarylamino, alkylcarbonylamino, arylcarbonylamino, heterocyclylcarbonylamino, heteroarylcarbonylamino, alkylthio, alkenylthio, cycloalkylthio, cycloalkenylthio, arylthio, heterocyclylthio, heteroarylthio, alkylsulfinyl, alkenylsulfinyl, cycloalkylsulfinyl, cycloalkenylsulfinyl, arylsulfinyl, heterocyclylsulfinyl, heteroarylsulfinyl, alkylsulfonyl, alkenylsulfonyl, cycloalkylsulfonyl, cycloalkenylsulfonyl, arylsulfonyl, heterocyclylsulfonyl, heteroarylsulfonyl, haloalkyl, haloalkenyl, haloalkynyl, haloalkoxy, haloalkenyloxy, haloalkylsulfonate, haloalkylcarbonylamino, haloalkylthio, haloalkylsulfinyl and haloalkylsulfonyl.

Preferably, the above described optionally substituted moieties for $R_1$, $R_2$, $R_3$ and $R_4$ have the following size ranges: ($C_1$-$C_{20}$)alkyl, ($C_2$-$C_6$)alkenyl, ($C_2$-$C_6$)alkynyl, ($C_3$-$C_{10}$)cycloalkyl, ($C_3$-$C_{10}$)cycloalkenyl, aryl, heterocyclyl, heteroaryl, ($C_1$-$C_6$)alkanoyl, aroyl, heterocycloyl, heteroaroyl, ($C_1$-$C_6$)alkoxycarbonyl, aryloxycarbonyl, heterocyclyloxycarbonyl, heteroaryloxycarbonyl, ($C_1$-$C_6$)alkylaminocarbonyl, arylaminocarbonyl, heterocyclylaminocarbonyl, heteroarylaminocarbonyl, ($C_1$-$C_6$)alkoxy, ($C_2$-$C_6$)alkenyloxy, ($C_3$-$C_{10}$)cycloalkoxy, ($C_3$-$C_{10}$)cycloalkenyloxy, ($C_1$-$C_6$)alkoxy($C_1$-$C_6$)alkoxy, aryloxy, heterocyclyloxy, ($C_1$-$C_6$)alkanoate, aryloate, heterocyclyloate, heteroaryloate, ($C_1$-$C_6$)alkylsulfonate, arylsulfonate, heterocyclylsulfonate, heteroarylsulfonate, ($C_1$-$C_6$)alkylamino, ($C_2$-$C_6$)alkenylamino, arylamino, heterocyclylamino, heteroarylamino, ($C_1$-$C_6$)alkylcarbonylamino, arylcarbonylamino, heterocyclylcarbonylamino, heteroarylcarbonylamino, ($C_1$-$C_6$)alkylthio, ($C_2$-$C_6$)alkenylthio, ($C_3$-$C_{10}$)cycloalkylthio, ($C_3$-$C_{10}$)cycloalkenylthio, arylthio, heterocyclylthio, heteroarylthio, ($C_1$-$C_6$)alkylsulfinyl, ($C_2$-$C_6$)alkenylsulfinyl, ($C_3$-$C_{10}$)cycloalkylsulfinyl, ($C_3$-$C_{10}$)cycloalkenylsulfinyl, arylsulfinyl, heterocyclylsulfinyl, heteroarylsulfinyl, ($C_1$-$C_6$)alkylsulfonyl, ($C_2$-$C_6$)alkenylsulfonyl, ($C_3$-$C_{10}$)cycloalkylsulfonyl, ($C_3$-$C_{10}$)cycloalkenylsulfonyl, arylsulfonyl, heterocyclylsulfonyl, heteroarylsulfonyl, ($C_1$-$C_6$)haloalkyl, ($C_2$-$C_6$)haloalkenyl, ($C_2$-$C_6$)haloalkynyl, ($C_1$-$C_6$)haloalkoxy, ($C_2$-$C_6$)haloalkenyloxy, ($C_1$-$C_6$)haloalkylsulfonate, ($C_1$-$C_6$)haloalkylcarbonylamino, ($C_1$-$C_6$)haloalkylthio, ($C_1$-$C_6$)haloalkylsulfinyl and ($C_1$-$C_6$)haloalkylsulfonyl.

$R_5$ is selected from hydrogen, halogen, cyano and the following optionally substituted moieties: alkyl, alkenyl, alkynyl, cycloalkyl, cycloalkenyl, cycloalkylalkyl, cycloalkenylalkyl, aryl, arylalkyl, heterocyclyl, haloalkyl, haloalkenyl and haloalkynyl. Preferably, the above described optionally substituted moieties for $R_5$ have the following size ranges: ($C_1$-$C_{20}$)alkyl, ($C_2$-$C_6$)alkenyl, ($C_2$-$C_6$)alkynyl, ($C_3$-$C_{10}$)cycloalkyl, ($C_3$-$C_{10}$)cycloalkenyl, ($C_3$-$C_{10}$)cycloalkyl($C_1$-$C_6$)alkyl, ($C_3$-$C_{10}$)cycloalkenyl($C_1$-$C_6$)alkyl, aryl, aryl($C_1$-$C_6$)alkyl, ($C_1$-$C_6$)haloalkyl, ($C_2$-$C_6$)haloalkenyl and halo($C_2$-$C_6$)alkynyl.

$R_6$ is selected from hydrogen and the following optionally substituted moieties: alkyl, alkenyl, alkynyl, cycloalkyl, cycloalkenyl, cycloalkylalkyl, cycloalkenylalkyl, aryl, arylalkyl, arylalkenyl, heterocyclyl, heterocyclylalkyl, heteroaryl, heteroarylalkyl, heteroarylalkenyl, alkanoyl, aroyl, heterocycloyl, heteroaroyl, cyanoalkyl, alkoxyalkyl, cycloalkoxyalkyl, aryloxyalkyl, alkylthioalkyl, cycloalkylthioalkyl, arylthioalkyl, alkylsulfinylalkyl, cycloalkylsulfinylalkyl, arylsulfinylalkyl, alkylsulfonylalkyl, cycloalkylsulfonylalkyl, arylsulfonylalkyl, haloalkyl, haloalkenyl and haloalkynyl.

Preferably, the above described optionally substituted moieties for $R_6$ have the following size ranges: ($C_1$-$C_{20}$)alkyl, ($C_2$-$C_6$)alkenyl, ($C_2$-$C_6$)alkynyl, ($C_3$-$C_{10}$)cycloalkyl, ($C_3$-$C_{10}$)cycloalkenyl, ($C_3$-$C_{10}$)cycloalkyl($C_1$-$C_6$)alkyl, ($C_3$-$C_{10}$)cycloalkenyl($C_1$-$C_6$)alkyl, aryl, aryl($C_1$-$C_6$)alkyl, aryl($C_1$-$C_6$)alkenyl, heterocyclyl, heterocyclyl($C_1$-$C_6$)alkyl, heteroaryl, heteroaryl($C_1$-$C_6$)alkyl, heteroaryl($C_2$-$C_6$)alkenyl, ($C_1$-$C_6$)alkanoyl, aroyl, heterocycloyl, heteroaroyl, cyano($C_1$-$C_6$)alkyl, ($C_1$-$C_6$)alkoxy($C_1$-$C_6$)alkyl, ($C_3$-$C_{10}$)cycloalkoxy($C_1$-$C_6$)alkyl, aryloxy($C_1$-$C_6$)alkyl, ($C_1$-$C_6$)alkylthio($C_1$-$C_6$)alkyl, ($C_3$-$C_{10}$)cycloalkylthio($C_1$-$C_6$)alkyl, arylthio($C_1$-$C_6$)alkyl, ($C_1$-$C_6$)alkylsulfinyl($C_1$-$C_6$)alkyl, ($C_3$-$C_{10}$)cycloalkylsulfinyl($C_1$-$C_6$)alkyl, arylsulfinyl($C_1$-$C_6$)alkyl, ($C_1$-$C_6$)alkylsulfonyl($C_1$-$C_6$)alkyl, ($C_3$-$C_{10}$)cycloalkylsulfonyl($C_1$-$C_6$)alkyl, arylsulfonyl($C_1$-$C_6$)alkyl, ($C_1$-$C_6$)haloalkyl, ($C_2$-$C_6$)haloalkenyl and halo($C_2$-$C_6$)alkynyl.

In one optional embodiment, $R_2$ and $R_3$ together are part of the same fused carbocyclic, heterocyclic, aryl or heteroaryl ring, that is substituted or unsubstituted.

In another optional embodiment, $R_4$ and $R_5$ together are part of the same fused carbocyclic, heterocyclic, aryl or heteroaryl ring, that is substituted or unsubstituted.

In yet another optional embodiment, $R_5$ and $R_6$ together are part of the same fused heterocyclic or heteroaryl ring that is substituted or unsubstituted.

In a preferred aspect, $R_1$ is hydrogen, ($C_1$-$C_6$)alkyl or ($C_1$-$C_6$)alkoxy;

$R_2$ is hydrogen, halo or ($C_1$-$C_6$)haloalkyl;

$R_3$ is hydrogen, halo or ($C_1$-$C_6$)haloalkyl;

$R_2$ and $R_3$ together are part of the same fused carbocyclic, heterocyclic, aryl or heteroaryl ring, which is substituted or unsubstituted;

$R_4$ is hydrogen;

$R_5$ is hydrogen, ($C_1$-$C_6$)alkyl, ($C_3$-$C_{10}$)cycloalkyl or (optionally substituted)aryl; and $R_6$ is selected from the following optionally substituted moieties: ($C_1$-$C_6$)alkyl, ($C_2$-$C_6$)alkenyl, ($C_2$-$C_6$)alkynyl, ($C_3$-$C_{10}$)cycloalkyl, ($C_3$-$C_{10}$)cycloalkenyl, ($C_3$-$C_{10}$)cycloalkyl($C_1$-$C_6$)alkyl, ($C_3$-$C_{10}$)cycloalkenyl($C_1$-$C_6$)alkyl, aryl, aryl($C_1$-$C_6$)alkyl, aryl($C_2$-$C_6$)alkenyl, heterocyclyl($C_1$-$C_6$)alkyl, heteroaryl, heteroaryl($C_1$-$C_6$)alkyl, cyano($C_1$-$C_6$)alkyl, ($C_1$-$C_6$)alkoxy($C_1$-$C_6$)alkyl, aryloxy($C_1$-$C_6$)alkyl, ($C_1$-$C_6$)alkylthio($C_1$-$C_6$)alkyl, ($C_1$-$C_6$)haloalkyl and ($C_2$-$C_6$)haloalkenyl.

In another preferred aspect, $R_1$ is hydrogen, methyl or methoxy;

$R_2$ is hydrogen, fluorine, chlorine or trifluoromethyl;

$R_3$ is hydrogen, fluorine, chlorine, bromine or trifluoromethyl;

$R_2$ and $R_3$ together are part of a methylene dioxy ring;

$R_4$ is hydrogen;

$R_5$ is hydrogen, methyl, ethyl, n-propyl, ipropyl, t-butyl, cyclohexyl or phenyl; and $R_6$ is selected from the group consisting of methyl, ethyl, i-propyl, i-butyl, t-butyl, sec-butyl, —CH($CH_2CH_3$)$_2$, allyl, propargyl, cyclopentyl, cyclohexyl, 3-cyclohexenyl, trans-cinnamyl, —$CH_2CN$, —CH($CH_3$)CN, —($CH_2$)$_2OCH_3$, —$CH_2SCH_3$, —$CH_2CF_3$ or one of:

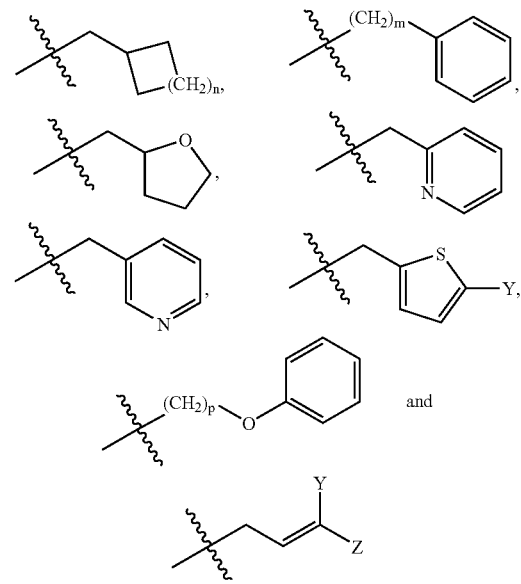

wherein:

n is 0, 2 or 3;

m is 2 or 3;

p is 2;

Y is hydrogen or chlorine; and

Z is chlorine or bromine.

In a more preferred embodiment, $R_1$, $R_2$ and $R_4$ are preferably hydrogen, $R_3$ is independently a halogen, e.g., chlorine, iodine, bromine or fluorine, $R_5$ is independently hydrogen or alkyl, e.g., a substituted or unsubstituted $C_1$ to $C_6$ alkyl or cycloalkyl, including, e.g., methyl, ethyl, n-propyl, isopropyl, n-butyl, isobutyl, cyclohexyl, and the like. $R_5$ is also contemplated to be a substituted or unsubstituted aryl. Preferably, $R_5$ is phenyl or benzyl.

$R_6$ is a substituted or unsubstituted alkyl or aryl. The aryl is preferably a substituted benzyl or substituted phenyl, e.g., including a halo or cyano substituted alkyl, benzyl or phenyl. In particular, $R_6$ is one of the following: 2-methylbutyl, 2-methylpropyl, 2-chlorobenzyl, 4-chlorobenzyl, 2,3-dichlorobenzyl, 2,4-dichlorobenzyl, 4-bromobenzyl, 3,4-dichlorobenzyl, 4-cyanobenzyl, 2,4-difluorobenzyl, 3-chlorophenyl, 4-chlorophenyl, 4-bromophenyl, 4-fluorophenyl, 4-cyanophenyl, 3,4-dichlorophenyl, 2-methylphenyl, 4-methylphenyl, 3-chloro-4-fluorophenyl, 3,4-difluorophenyl, cyanomethyl, propyl, e.g., 1- or 2-propyl, cycloalkyls, including, e.g., cyclopentyl, cyclohexyl, cyclohexylmethyl, 3-cyclohexenyl, alkenyls, e.g., 1 - or 2-propenyl, 3-pentyl, ethyl [single isomer or isomeric mixture of syn(Z) or anti(E) isomer], as well as trihaloaryl moieties, e.g., 2-(trifluoromethyl)benzyl, 3-(trifluoromethyl)benzyl, 4-(trifluoromethyl)benzyl, 2,4-bis(trifluoromethyl)benzyl, and the like.

In a second embodiment, the invention provides for a trifluoromethanesulfonanilide compound of Formula (II):

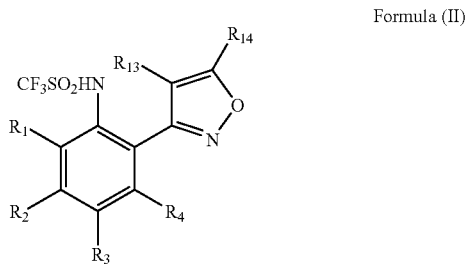

Formula (II)

wherein $R_1$, $R_2$, $R_3$ and $R_4$ are defined as for Formula (I), supra, and $R_{13}$ and $R_{14}$ are independently selected from the following: hydrogen, formyl, carboxyl, cyano, hydroxy, amino, nitro, thiol, halo and the following optionally substituted moieties: alkyl, alkenyl, alkynyl, cycloalkyl, cycloalkenyl, aryl, heterocyclyl, heteroaryl, alkanoyl, aroyl, heterocycloyl, heteroaroyl, alkoxycarbonyl, aryloxycarbonyl, heterocyclyloxycarbonyl, heteroaryloxycarbonyl, alkylaminocarbonyl, arylaminocarbonyl, heterocyclylaminocarbonyl, heteroarylaminocarbonyl, alkoxy, alkenyloxy, cycloalkoxy, cycloalkenyloxy, alkoxyalkoxy, aryloxy, heterocyclyloxy, alkanoate, aryloate, heterocyclyloate, heteroaryloate, alkylsulfonate, arylsulfonate, heterocyclylsulfonate, heteroarylsulfonate, alkylamino, alkenylamino, arylamino, heterocyclylamino, heteroarylamino, alkylcarbonylamino, arylcarbonylamino, heterocyclylcarbonylamino, heteroarylcarbonylamino, alkylthio, alkenylthio, cycloalkylthio, cycloalkenylthio, arylthio, heterocyclylthio, heteroarylthio, alkylsulfinyl, alkenylsulfinyl, cycloalkylsulfinyl, cycloalkenylsulfinyl, arylsulfinyl, heterocyclylsulfinyl, heteroarylsulfinyl, alkylsulfonyl, alkenylsulfonyl, cycloalkylsulfonyl, cycloalkenylsulfonyl, arylsulfonyl, heterocyclylsulfonyl, heteroarylsulfonyl, haloalkyl, haloalkenyl, haloalkynyl, haloalkoxy, haloalkenyloxy, haloalkylsulfonate haloalkylcarbonylamino, haloalkylthio, haloalkylsulfinyl and haloalkylsulfonyl.

Preferably, the above described optionally substituted moieties for $R_{13}$ and $R_{14}$ have the following size ranges: $(C_1-C_{20})$alkyl, $(C_2-C_6)$alkenyl, $(C_2-C_6)$alkynyl, $(C_3-C_{10})$cycloalkyl, $(C_3-C_{10})$cycloalkenyl, aryl, heterocyclyl, heteroaryl, $(C_1-C_6)$alkanoyl, aroyl, heterocycloyl, heteroaroyl, $(C_1-C_6)$alkoxycarbonyl, aryloxycarbonyl, heterocyclyloxycarbonyl, heteroaryloxycarbonyl, $(C_1-C_6)$alkylaminocarbonyl, arylaminocarbonyl, heterocyclylaminocarbonyl, heteroarylaminocarbonyl, $(C_1-C_6)$alkoxy, $(C_2-C_6)$alkenyloxy, $(C_3-C_{10})$cycloalkoxy, $(C_3-C_{10})$cycloalkenyloxy, $(C_1-C_6)$alkoxy$(C_1-C_6)$alkoxy, aryloxy, heterocyclyloxy, $(C_1-C_6)$alkanoate, aryloate, heterocyclyloate, heteroaryloate, $(C_1-C_6)$alkylsulfonate, arylsulfonate, heterocyclylsulfonate, heteroarylsulfonate, $(C_1-C_6)$alkylamino, $(C_2-C_6)$alkenylamino, arylamino, heterocyclylamino, heteroarylamino, $(C_1-C_6)$alkylcarbonylamino, arylcarbonylamino, heterocyclylcarbonylamino, heteroarylcarbonylamino, $(C_1-C_6)$alkylthio, $(C_2-C_6)$alkenylthio, $(C_3-C_{10})$cycloalkylthio, $(C_3-C_{10})$cycloalkenylthio, arylthio, heterocyclylthio, heteroarylthio, $(C_1-C_6)$alkylsulfinyl, $(C_2-C_6)$alkenylsulfinyl, $(C_3-C_{10})$cycloalkylsulfinyl, $(C_3-C_{10})$cycloalkenylsulfinyl, arylsulfinyl, heterocyclylsulfinyl, heteroarylsulfinyl, $(C_1-C_6)$alkylsulfonyl, $(C_2-C_6)$alkenylsulfonyl, $(C_3-C_{10})$cycloalkylsulfonyl, $(C_3-C_{10})$cycloalkenylsulfonyl, arylsulfonyl, heterocyclylsulfonyl, heteroarylsulfonyl, $(C_1-C_6)$haloalkyl, $(C_2-C_6)$haloalkenyl, halo$(C_2-C_6)$alkynyl, $(C_1-C_6)$haloalkoxy, $(C_2-C_6)$haloalkenyloxy, $(C_1-C_6)$haloalkylsulfonate $(C_1-C_6)$haloalkylcarbonylamino, $(C_1-C_6)$haloalkylthio, $(C_1-C_6)$haloalkylsulfinyl and $(C_1-C_6)$haloalkylsulfonyl.

In a third embodiment, the invention provides for a trifluoromethanesulfonanilide oxime ether compound of Formula (III)

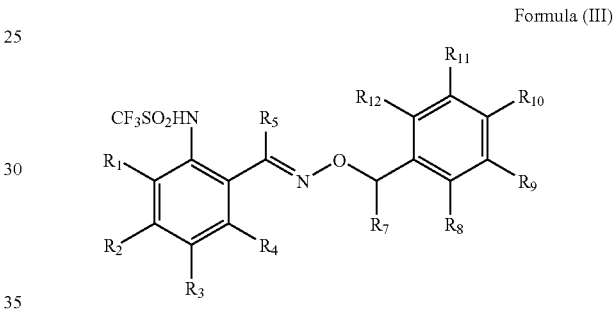

Formula (III)

or a pharmaceutically acceptable salt thereof or a solvate thereof, wherein:

$R_1$ and $R_7$ are independently hydrogen or alkyl, e.g., $(C_1-C_6)$alkyl;

$R_2$ is hydrogen or haloalkyl, e.g., $(C_1-C_6)$haloalkyl;

$R_3$ is hydrogen, halo or haloalkyl, e.g., $(C_1-C_6)$haloalkyl;

$R_4$ is hydrogen;

$R_5$ is hydrogen, alkyl, e.g., $(C_1-C_6)$alkyl, or aryl, e.g., (optionally substituted)aryl;

$R_8$ and $R_{12}$ are independently hydrogen, cyano, halo or haloalkyl, e.g., $(C_1-C_6)$haloalkyl;

$R_9$ and $R_{11}$ are independently hydrogen, (optionally substituted)aryloxy, (optionally substituted)heteroaryloxy, halo or haloalkyl, e.g., $(C_1-C_6)$haloalkyl; and $R_{10}$ is selected from the group consisting of hydrogen, alkyl, e.g., $(C_1-C_6)$alkyl, cycloalkyl, e.g., $(C_3-C_{10})$cycloalkyl, (optionally substituted)aryl, alkoxycarbonyl, e.g., $(C_1-C_6)$alkoxycarbonyl, cyano, alkoxy, e.g., $(C_1-C_6)$alkoxy, nitro, halo and haloalkyl, e.g., $(C_1-C_6)$haloalkyl.

Preferably, $R_1$ and $R_7$ are independently hydrogen or methyl;

$R_2$ is hydrogen or trifluoromethyl;

$R_3$ is hydrogen, chlorine or trifluoromethyl;

$R_4$ is hydrogen;

$R_5$ is hydrogen, methyl, ethyl, n-propyl, i-propyl or phenyl;

$R_8$ is hydrogen, cyano, fluorine, chlorine or trifluoromethyl;

$R_9$ is hydrogen, fluorine, chlorine, bromine, trifluoromethyl or one of:

[Structures: phenoxy group and 5-nitro-2-pyridyloxy group]

$R_{10}$ is hydrogen, t-butyl, cyclohexyl, phenyl, methoxycarbonyl, cyano, methoxy, nitro, fluorine, chlorine, bromine or trifluoromethyl;

$R_{11}$ is hydrogen, fluorine, bromine or trifluoromethyl; and $R_{12}$ is hydrogen, fluorine or chlorine.

In an even more preferred embodiment of Formula (III), $R_1$ through $R_5$ are as defined above for Formula (I). In particular, $R_1$ through $R_5$ are defined as follows: $R_1$, $R_2$ and $R_4$ are preferably hydrogen, $R_3$ is independently a halogen, e.g., chlorine, iodine, bromine or fluorine, $R_5$ is independently hydrogen or alkyl, e.g., a substituted or unsubstituted $C_1$ to $C_6$ alkyl or cycloalkyl, including, e.g., methyl, ethyl, n-propyl, isopropyl, n-butyl, isobutyl, cyclohexyl, and the like. $R_5$ is also contemplated to be a substituted or unsubstituted aryl. Preferably, $R_5$ is phenyl or benzyl. In addition, $R_7$ through $R_{12}$ are defined as follows:

$R_7$ is hydrogen or alkyl, e.g., ($C_1$ to $C_6$)alkyl.

$R_8$ and $R_{12}$ are independently hydrogen, $CF_3$ or halo, e.g., chloro, bromo, fluoro or iodo.

$R_9$ and $R_{11}$ are independently hydrogen or halo, e.g., chloro, bromo, fluoro or iodo.

$R_{10}$ is hydrogen, CN, $CF_3$ or halo, e.g., chloro, bromo, fluoro or iodo.

In a fourth embodiment, the invention provides for a trifluoromethanesulfonanilide oxime ether compound of Formula (IV)

[Structure: Formula (IV)]

or a pharmaceutically acceptable salt thereof or a solvate thereof, wherein:

$R_1$ is hydrogen;

$R_2$ is hydrogen or haloalkyl, e.g., ($C_1$-$C_6$)haloalkyl;

$R_3$ is hydrogen, halo or haloalkyl, e.g., ($C_1$-$C_6$)haloalkyl;

$R_4$ is hydrogen;

$R_5$ is alkyl, e.g., ($C_1$-$C_6$)alkyl, cycloalkyl, e.g., ($C_3$-$C_{10}$)cycloalkyl, or (optionally substituted)aryl;

$R_8$ and $R_{12}$ are independently hydrogen or alkyl, e.g., ($C_1$-$C_6$)alkyl;

$R_9$ and $R_{11}$ are independently hydrogen, halo or haloalkyl, e.g., ($C_1$-$C_6$)haloalkyl; and $R_{10}$ is hydrogen, alkyl, e.g., ($C_1$-$C_6$)alkyl, cyano, halo, haloalkyl, e.g., ($C_1$-$C_6$)haloalkyl or haloalkoxy e.g., ($C_1$-$C_6$)haloalkoxy.

Preferably, $R_1$ is hydrogen;

$R_2$ is hydrogen or trifluoromethyl;

$R_3$ is hydrogen, chlorine or trifluoromethyl;

$R_4$ is hydrogen;

$R_5$ is methyl, ethyl, n-propyl, i-propyl, t-butyl, cyclohexyl or phenyl;

$R_8$ is hydrogen or methyl;

$R_9$ is hydrogen, fluorine, chlorine or trifluoromethyl;

$R_{10}$ is hydrogen, methyl, cyano, fluorine, chlorine, bromine, trifluoromethyl or trifluoromethoxy;

$R_{11}$ is hydrogen; and $R_{12}$ is hydrogen.

In an even more preferred embodiment of Formula (IV), $R_1$ through $R_5$ are as defined above for Formula (I). In particular, $R_1$ through $R_5$ are defined as follows:

$R_1$, $R_2$ and $R_4$ are preferably hydrogen, $R_3$ is independently a halogen, e.g., chlorine, iodine, bromine or fluorine, $R_5$ is independently alkyl, e.g., a substituted or unsubstituted $C_1$ to $C_6$ alkyl or cycloalkyl, including, e.g., methyl, ethyl, n-propyl, isopropyl, n-butyl, isobutyl, cyclohexyl, and the like. $R_5$ is also contemplated to be a substituted or unsubstituted aryl. Preferably, $R_5$ is phenyl or benzyl. In addition, $R_8$ through $R_{12}$ are defined as follows:

$R_8$ and $R_{12}$ are independently hydrogen or alkyl, e.g., ($C_1$-$C_6$)alkyl.

$R_9$ and $R_{11}$ are independently hydrogen, $CF_3$ or halo, e.g., chloro, bromo, fluoro or iodo.

$R_{10}$ is hydrogen, alkyl, e.g., ($C_1$-$C_6$)alkyl, CN, $OCF_3$ or halo, e.g., chloro, bromo, fluoro or iodo.

In a fifth embodiment, the invention provides for a trifluoromethanesulfonanilide oxime ether prodrug compound of Formula (V).

[Structure: Formula (V)]

or a pharmaceutically acceptable salt thereof or a solvate thereof, wherein:

$R_1$, $R_2$, $R_3$, $R_4$, $R_5$ and $R_6$ are defined as for claim 1, and the compound of Formula (V) optionally includes a capping group A that is selected from the group consisting of alkyl, alkenyl, arylalkyl, hydroxyalkyl, alkoxyalkyl, aryloxyalkyl, heterocyclyloxyalkyl, heteroaryloxyalkyl, alkylcarbonyloxyalkyl, arylcarbonyloxyalkyl, heterocyclylcarbonyloxyalkyl, heteroarylcarbonyloxyalkyl, alkoxycarbonyloxyalkyl, aryloxycarbonyloxyalkyl, heterocyclyloxycarbonyloxyalkyl, heteroaryloxycarbonyloxyalkyl, alkylaminocarbonyloxyalkyl, arylaminocarbonyloxyalkyl, heterocyclylaminocarbonyloxyalkyl, heteroarylaminocarbonyloxyalkyl, alkylcarbonylaminoalkyl, arylcarbonylaminoalkyl, heterocyclycarbonylaminoalkyl, heteroarylcarbonylaminoalkyl, alkylsulfonylalkyl, arylsulfonylalkyl, heterocyclylsulfonylalkyl, heteroarylsulfonylalkyl, alkanoyl, aroyl, heterocycloyl, heteroaroyl, alkoxycarbonyl, aryloxycarbonyl, heterocyclyloxycarbonyl, heteroaryloxycarbonyl, alkylaminocarbonyl, arylaminocarbonyl, heterocyclylaminocarbonyl, heteroarylaminocarbonyl, alkylaminothiocarbonyl, arylaminothiocarbonyl, heterocyclylaminothiocarbonyl, heteroarylaminothiocarbonyl, alkylsulfonyl, arylsulfonyl, heterocyclylsulfonyl and heteroarylsulfonyl.

Preferably, the above described moieties for A have the following size ranges: ($C_1$-$C_6$)alkyl, ($C_1$-$C_6$)alkenyl, aryl $(C_1-C_6)$alkyl, hydroxy$(C_1-C_6)$alkyl, $(C_1-C_6)$alkoxy$(C_1-C_6)$alkyl, aryloxy$(C_1-C_6)$alkyl, heterocyclyloxy$(C_1-C_6)$alkyl, heteroaryloxy$(C_1-C_6)$alkyl, $(C_1-C_6)$alkylcarbonyloxy$(C_1-C_6)$alkyl, arylcarbonyloxy$(C_1-C_6)$alkyl, heterocyclylcarbonyloxy$(C_1-C_6)$alkyl, heteroarylcarbonyloxy$(C_1-C_6)$alkyl, $(C_1-C_6)$alkoxycarbonyloxy$(C_1-C_6)$alkyl, aryloxycarbonyloxy$(C_1-C_6)$alkyl, heterocyclyloxycarbonyloxy$(C_1-C_6)$alkyl, heteroaryloxycarbonyloxy$(C_1-C_6)$alkyl, $(C_1-C_6)$alkylaminocarbonyloxy$(C_1-C_6)$alkyl, arylaminocarbonyloxy$(C_1-C_6)$alkyl, heterocyclylaminocarbonyloxy$(C_1-C_6)$alkyl, heteroarylaminocarbonyloxy$(C_1-C_6)$alkyl, $(C_1-C_6)$alkylcarbonylamino$(C_1-C_6)$alkyl, arylcarbonylamino$(C_1-C_6)$alkyl, heterocyclycarbonylamino$(C_1-C_6)$alkyl, heteroarylcarbonylamino$(C_1-C_6)$alkyl, $(C_1-C_6)$alkylsulfonyl$(C_1-C_6)$alkyl, arylsulfonyl$(C_1-C_6)$alkyl, heterocyclylsulfonyl$(C_1-C_6)$alkyl, heteroarylsulfonyl$(C_1-C_6)$alkyl, $(C_1-C_6)$alkanoyl, aroyl, heterocycloyl, heteroaroyl, $(C_1-C_6)$alkoxycarbonyl, aryloxycarbonyl, heterocyclyloxycarbonyl, heteroaryloxycarbonyl, $(C_1-C_6)$alkylaminocarbonyl, arylaminocarbonyl, heterocyclylaminocarbonyl, heteroarylaminocarbonyl, $(C_1-C_6)$alkylaminothiocarbonyl, arylaminothiocarbonyl, heterocyclylaminothiocarbonyl, heteroarylaminothiocarbonyl, $(C_1-C_6)$alkylsulfonyl, arylsulfonyl, heterocyclylsulfonyl and heteroarylsulfonyl.

In particularly preferred embodiments, the invention provides for the 231 compounds enumerated by Tables 8 and 9, infra.

In a fifth embodiment, the invention provides for compositions for delivering the above-described compounds. The inventive compositions comprise an effective amount of the inventive compound or a combination of the inventive compounds, to be employed, together with a suitable carrier. When the inventive compound is employed in the field, in order to treat the ground, structures, food plants, animal care facilities, and the like, the composition will comprise a solid or liquid formulation.

In addition, although the inventive compounds are preferred over previously known agents, in certain optional embodiments they are contemplated to be employed in combination, simultaneously or sequentially, with other art-known agents or combinations of such art-known agents employed for killing or controlling various types of pests. These include, for instance, the organophosphate pesticides, e.g., dicrotophos, terbufos, dimethoate, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion, phosalone, to name but a few such compounds. These also include combinations with carbamate type pesticides, including, e.g., carbaryl, carbofuran, aldicarb, molinate, methomyl, carbofuran, etc., as well as combinations with the organochlorine type pesticides. These further include, for instance, combinations with the biological pesticides, including repellents, the pyrethrins (as well as synthetic variations thereof, e.g., allethrin, resmethrin, permethrin, tralomethrin), and nicotine, e.g., often employed as an acaricide. Other contemplated combinations with other miscellaneous pesticides, e.g., *bacillus thuringensis,* chlorobenzilate, copper compounds, e.g., copper hydroxide, cupric oxychloride sulfate, cyfluthrin, cypermethrin, dicofol, endosulfan, esenfenvalerate, fenvalerate, lambda-cyhalothrin, methoxychlor and sulfur. Combinations with cyclodienes, difluorobenzuron, ryania, and/or older art-known anti-helminth agents, such as, fenbendazole, KT-199, ivermectin, albendazole, etc., are also contemplated.

Solid compositions according to the invention include, for example, a powdered carrier into which an effective amount and concentration of at least one compound according to the invention is admixed. Such solid compositions optionally further include stabilizers, preservatives, coloring agents, perfumes, additional art-known active agents selected to provide synergistic anti-parasite killing activity, and/or agents selected to complement the parasite killing spectrum of the inventive compound or compounds.

Liquid compositions according to the invention include, for example, one or more optional liquid solvents, diluents or carriers that are polar, e.g., based on water, alcohol, or other polar solvent, or a solvent or carrier that is nonpolar, e.g., an organic solvent or the like. An effective amount and concentration of at least one compound according to the invention is admixed, dispersed, emulsified, or dissolved in the liquid carrier. Such liquid compositions optionally further include emulsifiers, detergents, anti-foaming agents, stabilizers, preservatives, coloring agents, perfumes, additional art-known active agents selected to provide synergistic anti-parasite killing activity, and/or agents selected to complement the parasite killing spectrum of the inventive compound or compounds. Such optional diluents or carriers are selected for compatibility with the selected inventive compound, as well as for environmental compatibility and safety, while allowing, for administering the inventive compound or compounds into an area or location of interest, at concentrations effective for the intended purpose.

More preferably, the invention provides for a pharmaceutical composition for treatment of animals infected with parasites that comprises a therapeutically effective dosage amount of the trifluoromethanesulfonanilide oxime ether compound of Formula (I), Formula (II), Formula (III), Formula (IV), Formula (V) and/or combinations thereof, and a pharmaceutically acceptable excipient. The pharmaceutical composition is contemplated to be administered to animals by any art known route, including, e.g., oral, parenteral, topical, and/or rectal, routes of administration.

In a solid form, the pharmaceutical composition includes pharmaceutically acceptable excipients, and carriers, and is prepared as a powder that is optionally dispensed in soluble capsules for oral ingestion, in any art-known tableted form. A solid composition according to the invention is also optionally formulated into a patch for transdermal administration.

In a liquid form, the pharmaceutical composition is provided, together with any optional pharmaceutically acceptable excipients, and carriers, in solution and/or in suspension in a pharmaceutically acceptable liquid composition for administration orally, by infusion or injection and/or by spray or inhalation, and the like.

In a sixth embodiment, the invention provides for methods for killing parasites, both ex vivo, e.g., in the environment, as well as methods of treating a parasite infestation in animals, comprising administering to an animal in need of such treatment an effective amount of a trifluoromethanesulfonanilide oxime ether compound as described above for Formulas (I), (II), (III), (IV), (V) and/or combinations thereof.

Preferably, the above methods and compositions are applied to arthropod and/or helminth parasites. In a further preferred optional embodiment of the invention there are provided methods of preventing or treating parasite infestation in crop plants, stored grain or other stored plant or agricultural products, and people or animals, comprising administering a parasite-suppressive or parasite killing amount of at least one inventive compound or combinations thereof, into an environmental area where parasites of interest are present, or may become present. By "administering"

in this context is meant contacting environmental materials or surfaces with amounts of the inventive compound or with a selected mixture or combination of more than one of the inventive compounds that is effective to kill, suppress and/or repel one or more parasites of interest.

Compositions that include solutions, emulsifications, suspensions and dry forms of the inventive compound(s) are discussed supra. The process of administering such compositions can be achieved by methods well known in the art. These include oral, parenteral, spraying, brushing, dipping, rinsing, washing, dusting, using art-known equipment, in a selected area. The selected area to be treated optionally includes plants, e.g., crops, and/or animals. In a particular embodiment, a composition comprising a compound of the invention is placed on a minor portion of the outer surface of an animal, generally as a line or spot on the animal's back (e.g., as a pour-on application) and the compound migrates over the whole external surface of the animal to protect the animal [see, U.S. Pat. No. 6,492,419 B1, the contents of which are hereby incorporated by reference in their entireties].

Environmental areas contemplated to be treated in this way include, e.g., fields, orchids, gardens and the like, buildings and their environs, including landscaping; storage facilities, transport or fixed storage that contains or analogous structures and structural components, such as walls, floors, roofs, fences, windows and window screens, and the like. Animal living spaces are also included, e.g., animal pens, chicken coops, corals, barns and the like. Human homes and other human residential, business or commercial and educational facilities are also contemplated to be treated or contacted with the inventive compounds or compositions thereof as described above.

These and other aspects of the present invention will be better appreciated by reference to the following drawings and Detailed Description.

DESCRIPTION OF THE INVENTION

Figure 1A:
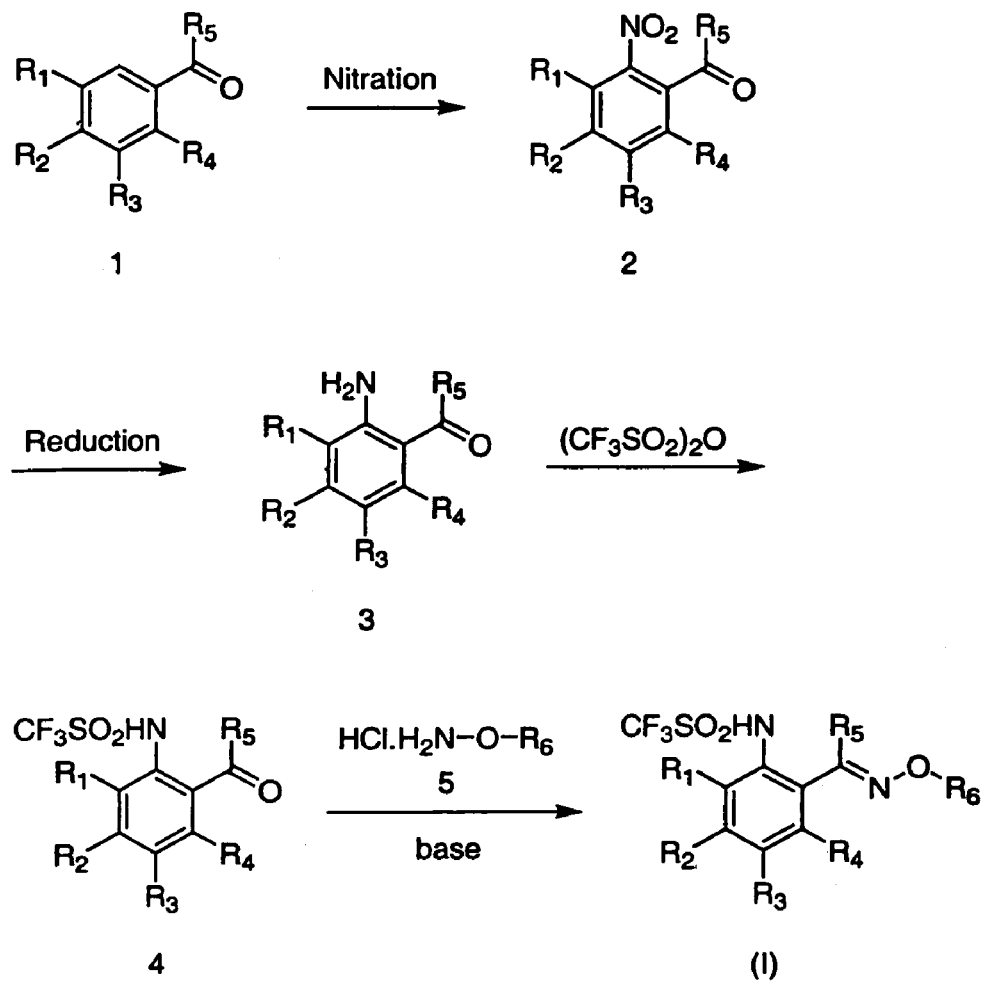
FIG. 1A illustrates reaction scheme 1 for preparing a compound of Formula (I) from a starting compound 1.

Accordingly, the invention provides a series of new trifluoromethanesulfonanilide oxime ether compounds that are highly active against parasites, and having particular activity and utility as endoparasitides, ectoparasiticides, anthelmintics, insecticides and acaricides.

In order to more fully appreciate the description of the invention, the following definitions are provided. As used herein, the following terms are employed as defined below, unless otherwise indicated.

The use of singular terms for convenience in description is in no way intended to be so limiting. Thus, for example, reference to "a parasite" includes reference to one or more of such parasites. As used herein the term "approximately" is used interchangeably with the term "about" and generally signifies that a value is within twenty percent of the indicated value.

An oxime ether is one of a class of compounds with the formula of

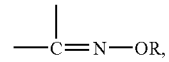

wherein R is a substituted carbon atom.

In this specification "optionally substituted" means that a functional group is either substituted or unsubstituted, at any available position. Substitution can be with one or more functional groups selected from, e.g., alkyl, alkenyl, alkynyl, cycloalkyl, cycloalkenyl, aryl, heterocyclyl, heteroaryl, formyl, alkanoyl, cycloalkanoyl, aroyl, heteroaroyl, carboxyl, alkoxycarbonyl, cycloalkyloxycarbonyl, aryloxycarbonyl, heterocyclyloxycarbonyl, heteroaryloxycarbonyl, alkylaminocarbonyl, cycloalkylaminocarbonyl, arylaminocarbonyl, heterocyclylaminocarbonyl, heteroarylaminocarbonyl, cyano, hydroxy, alkoxy, cycloalkoxy, aryloxy, heterocyclyloxy, heteroaryloxy, alkanoate, cycloalkanoate, aryloate, heterocyclyloate, heteroaryloate, amino, alkylamino, cycloalkylamino, arylamino, heterocyclylamino, heteroarylamino, alkylcarbonylamino, cycloalkylcarbonylamino, arylcarbonylamino, heterocyclylcarbonylamino, heteroarylcarbonylamino, nitro, thiol, alkylthio, cycloalkylthio, arylthio, heterocyclylthio, heteroarylthio, alkylsulfinyl, cycloalkylsulfinyl, arylsulfinyl, heterocyclysulfinyl, heteroarylsulfinyl, alkylsulfinyl, cycloalkylsulfinyl, arylsulfinyl, heterocyclysulfinyl, heteroarylsulfinyl, halo, haloalkyl, haloaryl, haloheterocyclyl, haloheteroaryl, haloalkoxy, and haloalkylsulfonyl, to name but a few such functional groups.

"Alkyl" whether used alone, or in compound words such as alkoxy, alkylthio, alkylamino, dialkylamino or haloalkyl, represents straight or branched chain hydrocarbons ranging in size from one to about 20 carbon atoms, or more. Thus alkyl moieties include, without limitation, moieties ranging in size, for example, from one to about 6 carbon atoms or greater, such as, methyl, ethyl, n-propyl, iso-propyl and/or butyl, pentyl, hexyl, and higher isomers, including, e.g., those straight or branched chain hydrocarbons ranging in size from about 6 to about 20 carbon atoms, or greater.

"Alkenyl" whether used alone, or in compound words such as alkenyloxy or haloalkenyl, represents straight or branched chain hydrocarbons containing at least one carbon-carbon double bond, including, without limitation, moieties ranging in size from two to about 6 carbon atoms or greater, such as, methylene, ethylene, 1-propenyl, 2-propenyl, and/or butenyl, pentenyl, hexenyl, and higher isomers, including, e.g., those straight or branched chain hydrocarbons ranging in size, for example, from about 6 to about 20 carbon atoms, or greater.

"Alkynyl" whether used alone, or in compound words such as alkynyloxy, represents straight or branched chain hydrocarbons containing at least one carbon-carbon triple bond, including, without limitation, moieties ranging in size from, e.g., two to about 6 carbon atoms or greater, such as, ethynyl, 1-propynyl, 2-propynyl, and/or butynyl, pentynyl, hexynyl, and higher isomers, including, e.g., those straight or branched chain hydrocarbons ranging in size from, e.g., about 6 to about 20 carbon atoms, or greater.

"Cycloalkyl" represents a mono- or polycarbocyclic ring system of varying sizes, e.g., from about 3 to about 20 carbon atoms, e.g., cyclopropyl, cyclobutyl, cyclopentyl, cyclohexyl or cycloheptyl. The term cycloalkyloxy represents the same groups linked through an oxygen atom such as cyclopentyloxy and cyclohexyloxy. The term cycloalkylthio represents the same groups linked through a sulfur atom such as cyclopentylthio and cyclohexylthio.

"Cycloalkenyl" represents a non-aromatic mono- or polycarbocyclic ring system, e.g., of about 3 to about 20 carbon atoms containing at least one carbon-carbon double bond, e.g., cyclopentenyl, cyclohexenyl or cycloheptenyl. The term "cycloalkenyloxy" represents the same groups linked through an oxygen atom such as cyclopentenyloxy and cyclohexenyloxy. The term "cycloalkenylthio" represents the same groups linked through a sulfur atom such as cyclopentenylthio and cyclohexenylthio.

The terms, "carbocyclic" and "carbocyclyl" represent a ring system, e.g., of about 3 to about 20 carbon atoms, which may be substituted and/or carry fused rings. Examples of such groups include cyclopentyl, cyclohexyl, or fully or partially hydrogenated phenyl, naphthyl and fluorenyl.

"Aryl" whether used alone, or in compound words such as arylalkyl, aryloxy or arylthio, represents: (i) an optionally substituted mono- or polycyclic aromatic carbocyclic moiety, e.g., of about 6 to about 20 carbon atoms, such as phenyl, naphthyl or fluorenyl; or, (ii) an optionally substituted partially saturated polycyclic carbocyclic aromatic ring system in which an aryl and a cycloalkyl or cycloalkenyl group are fused together to form a cyclic structure such as a tetrahydronaphthyl, indenyl or indanyl ring.

"Heterocyclyl" or "heterocyclic" whether used alone, or in compound words such as heterocyclyloxy represents: (i) an optionally substituted cycloalkyl or cycloalkenyl group, e.g., of about 3 to about 20 ring members, which may contain one or more heteroatoms such as nitrogen, oxygen, or sulfur (examples include pyrrolidinyl, morpholino, thiomorpholino, or fully or partially hydrogenated thienyl, furyl, pyrrolyl, thiazolyl, oxazolyl, oxazinyl, thiazinyl, pyridyl and azepinyl); (ii) an optionally substituted partially saturated polycyclic ring system in which an aryl (or heteroaryl) ring and a heterocyclic group are fused together to form a cyclic structure (examples include chromanyl, dihydrobenzofuryl and indolinyl); or (iii) an optionally substituted fully or partially saturated polycyclic fused ring system that has one or more bridges (examples include quinuclidinyl and dihydro-1,4-epoxynaphthyl).

"Heteroaryl" whether used alone, or in compound words such as heteroaryloxy represents: (i) an optionally substituted mono- or polycyclic aromatic organic moiety, e.g., of about 5 to about 20 ring members in which one or more of the ring members is/are element(s) other than carbon, for example nitrogen, oxygen or sulfur; the heteroatom(s) interrupting a carbocyclic ring structure and having a sufficient number of delocalized pi electrons to provide aromatic character, provided that the rings do not contain adjacent oxygen and/or sulfur atoms. Typical 6-membered heteroaryl groups are pyrazinyl, pyridazinyl, pyrazolyl, pyridyl and pyrimidinyl. All regioisomers are contemplated, e.g., 2-pyridyl, 3-pyridyl and 4-pyridyl. Typical 5-membered heteroaryl rings are furyl, imidazolyl, oxazolyl, isoxazolyl, isothiazolyl, oxadiazolyl, pyrrolyl, 1,3,4-thiadiazolyl, thiazolyl, thienyl and triazolyl. All regioisomers are contemplated, e.g., 2-thienyl and 3-thienyl. Bicyclic groups typically are benzo-fused ring systems derived from the heteroaryl groups named above, e.g., benzofuryl, benzimidazolyl, benzthiazolyl, indolyl, indolizinyl, isoquinolyl, quinazolinyl, quinolyl and benzothienyl; or, (ii) an optionally substituted partially saturated polycyclic heteroaryl ring system in which a heteroaryl and a cycloalkyl or cycloalkenyl group are fused together to form a cyclic structure such as a tetrahydroquinolyl or pyrindinyl ring.

"Formyl" represents a —CHO moiety.

"Alkanoyl" represents a —C(=O)-alkyl group in which the alkyl group is as defined supra. In a particular embodiment, an alkanoyl ranges in size from about $C_2$-$C_{20}$. One example is acyl.

"Aroyl" represents a —C(=O)-aryl group in which the aryl group is as defined supra. In a particular embodiment, an aroyl ranges in size from about $C_7$-$C_{20}$. Examples include benzoyl and 1-naphthoyl and 2-naphthoyl.

"Heterocycloyl" represents a —C(=O)-heterocyclyl group in which the heterocyclic group is as defined supra. In a particular embodiment, an heterocycloyl ranges in size from about $C_4$-$C_{20}$.

"Heteroaroyl" represents a —C(=O)-heteroaryl group in which the heteroaryl group is as defined supra. In a particular embodiment, a heteroaroyl ranges in size from about $C_6$-$C_{20}$. An example is pyridylcarbonyl.

"Carboxyl" represents a —CO₂H moiety.

"Oxycarbonyl" represents a carboxylic acid ester group —CO₂R which is linked to the rest of the molecule through a carbon atom.

"Alkoxycarbonyl" represents an —CO₂-alkyl group in which the alkyl group is as defined supra. In a particular embodiment, an alkoxycarbonyl ranges in size from about $C_2$-$C_6$. Examples include methoxycarbonyl and ethoxycarbonyl.

"Aryloxycarbonyl" represents an —CO₂-aryl group in which the aryl group is as defined supra. Examples include phenoxycarbonyl and naphthoxycarbonyl.

"Heterocyclyloxycarbonyl" represents a —CO₂-heterocyclyl group in which the heterocyclic group is as defined supra.

"Heteroaryloxycarbonyl" represents a —CO₂-heteroaryl group in which the heteroaryl group is as defined supra.

"Aminocarbonyl" represents a carboxylic acid amide group —C(=O)NHR or —C(=O)NR₂ which is linked to the rest of the molecule through a carbon atom.

"Alkylaminocarbonyl" represents a —C(=O)NHR or —C(=O)NR₂ group in which R is an alkyl group as defined supra.

"Arylaminocarbonyl" represents a —C(=O)NHR or —C(=O)NR₂ group in which R is an aryl group as defined supra.

"Heterocyclylaminocarbonyl" represents a —C(=O)NHR or —C(=O)NR₂ group in which R is a heterocyclic group as defined supra. In certain embodiments, NR₂ is a heterocyclic ring, which is optionally substituted.

"Heteroarylaminocarbonyl" represents a —C(=O)NHR or —C(=O)NR$_2$ group in which R is a heteroaryl group as defined supra. In certain embodiments, NR$_2$ is a heteroaryl ring, which is optionally substituted.

"Cyano" represents a —CN moiety, and "hydroxy" represents the —OH moiety.

"Alkoxy" represents an —O-alkyl group in which the alkyl group is as defined supra. Examples include methoxy, ethoxy, n-propoxy, isopropoxy, and the different butoxy, pentoxy, hexyloxy and higher isomers.

"Aryloxy" represents an —O-aryl group in which the aryl group is as defined supra. Examples include, without limitation, phenoxy and naphthoxy.

"Alkenyloxy" represents an —O-alkenyl group in which the alkenyl group is as defined supra. An example is allyloxy.

"Heterocyclyloxy" represents an —O-heterocyclyl group in which the heterocyclic group is as defined supra.

"Heteroaryloxy" represents an —O-heteroaryl group in which the heteroaryl group is as defined supra. An example is pyridyloxy.

"Alkanoate" represents an —OC(=O)—R group in which R is an alkyl group as defined supra.

"Aryloate" represents a —OC(=O)—R group in which R is an aryl group as defined supra.

"Heterocyclyloate" represents an —OC(=O)—R group in which R is a heterocyclic group as defined supra.

"Heteroaryloate" represents an —OC(=O)—R group in which R is a heteroaryl group as defined supra.

"Sulfonate" represents an —OSO$_2$R group that is linked to the rest of the molecule through an oxygen atom.

"Alkylsulfonate" represents an —OSO$_2$-alkyl group in which the alkyl group is as defined supra.

"Arylsulfonate" represents an —OSO$_2$-aryl group in which the aryl group is as defined supra.

"Heterocyclylsulfonate" represents an —OSO$_2$-heterocyclyl group in which the heterocyclic group is as defined supra.

"Heteroarylsulfonate" represents an —OSO$_2$-heteroaryl group in which the heteroaryl group is as defined supra.

"Amino" represents an —NH$_2$ moiety.

"Alkylamino" represents an —NHR or —NR$_2$ group in which R is an alkyl group as defined supra. Examples include, without limitation, methylamino, ethylamino, n-propylamino, iso-propylamino, and the different butylamino, pentylamino, hexylamino and higher isomers.

"Arylamino" represents an —NHR or —NR$_2$ group in which R is an aryl group as defined supra. An example is phenylamino.

"Heterocyclylamino" represents an —NHR or —NR$_2$ group in which R is a heterocyclic group as defined supra. In certain embodiments, NR$_2$ is a heterocyclic ring, which is optionally substituted.

"Heteroarylamino" represents a —NHR or —NR$_2$ group in which R is a heteroaryl group as defined supra. In certain embodiments, NR$_2$ is a heteroaryl ring, which is optionally substituted.

"Carbonylamino" represents a carboxylic acid amide group —NHC(=O)R that is linked to the rest of the molecule through a nitrogen atom.

"Alkylcarbonylamino" represents a —NHC(=O)R group in which R is an alkyl group as defined supra.

"Arylcarbonylamino" represents an —NHC(=O)R group in which R is an aryl group as defined supra.

"Heterocyclylcarbonylamino" represents an —NHC(=O)R group in which R is a heterocyclic group as defined supra.

"Heteroarylcarbonylamino" represents an —NHC(=O)R group in which R is a heteroaryl group as defined supra.

"Nitro" represents a —NO$_2$ moiety.

"Alkylthio" represents an —S-alkyl group in which the alkyl group is as defined supra. Examples include, without limitation, methylthio, ethylthio, n-propylthio, iso-propylthio, and the different butylthio, pentylthio, hexylthio and higher isomers.

"Arylthio" represents an —S-aryl group in which the aryl group is as defined supra. Examples include phenylthio and naphthylthio.

"Heterocyclylthio" represents an —S-heterocyclyl group in which the heterocyclic group is as defined supra.

"Heteroarylthio" represents an —S-heteroaryl group in which the heteroaryl group is as defined supra.

"Sulfinyl" represents an —S(=O)R group that is linked to the rest of the molecule through a sulfur atom.

"Alkylsulfinyl" represents an —S(=O)-alkyl group in which the alkyl group is as defined supra. An example is thioacyl.

"Arylsulfinyl" represents an —S(=O)-aryl group in which the aryl group is as defined supra. An example is thiobenzoyl.

"Heterocyclylsulfinyl" represents an —S(=O)-heterocyclyl group in which the heterocylic group is as defined supra.

"Heteroarylsulfinyl" represents an —S(=O)-heteroaryl group in which the heteroaryl group is as defined supra.

"Sulfonyl" represents an —SO$_2$R group that is linked to the rest of the molecule through a sulfur atom.

"Alkylsulfonyl" represents an —SO$_2$-alkyl group in which the alkl group is as defined supra.

"Arylsulfonyl" represents an —SO$_2$-aryl group in which the aryl group is as defined supra.

"Heterocyclylsulfonyl" represents an —SO$_2$-heterocyclyl group in which the heterocyclic group is as defined supra.

"Heteroarylsulfonyl" represents an —SO$_2$-heteroaryl group in which the heteroaryl group is as defined supra.

The term "halo," whether employed alone or in compound words such as haloalkyl, haloalkoxy or haloalkylsulfonyl, represents fluorine, chlorine, bromine or iodine. Further, when used in compound words such as haloalkyl, haloalkoxy or haloalkylsulfonyl, the alkyl may be partially halogenated or fully substituted with halogen atoms which may be independently the same or different. Examples of haloalkyl include, without limitation, —CH$_2$CH$_2$F, —CF$_2$CF$_3$ and —CH$_2$CHFCl. Examples of haloalkoxy include, without limitation, —OCHF$_2$, —OCF$_3$, —OCH$_2$CCl$_3$, —OCH$_2$CF$_3$ and —OCH$_2$CH$_2$CF$_3$. Examples of haloalkylsulfonyl include, without limitation, —SO$_2$CF$_3$, —SO$_2$CCl$_3$, —SO$_2$CH$_2$CF$_3$ and —SO$_2$CF$_2$CF$_3$.

The term "prodrug" as used herein refers to a compound which is convertible in use, e.g., on an environmental surface and/or in vivo, by metabolic means or other processes (e.g., by hydrolysis) to one of the compounds of the invention, e.g., a compound of Formulas (I), (II), (III), (IV) and/or (V). For example, derivatization of the NH-acidic group of a compound of Formula (I) is contemplated to provide a compound convertible by hydrolysis in vivo to the parent molecule. In certain optional embodiments, delivery of the active compound in prodrug form achieves improved delivery of the inventive compound by improving its physicochemical/pharmacokinetic properties, e.g., by enhancing systemic absorption, delaying clearance or breakdown, in vivo.

Suitable groups for derivatization of the NH-acidic group of compounds of Formula (I) are, for example, alkyl, alkoxyalkyl, alkylcarbonyloxyalkyl, alkanoyl and alkoxycarbonyl.

A parasite "infestation" refers to the presence of parasites in numbers that pose a risk to humans or animals. The presence can be in the environment, e.g., on plants, in animal bedding, on the skin or fur of an animal, etc. When the infestation that is referred to is within an animal, e.g, in the blood or other internal tissues, the term infestation is also intended to be synonymous with. the term, "infection," as that term is generally understood in the art, unless otherwise stated.

An "effective amount," is the amount or quantity of a compound according to the invention that is required to alleviate or reduce parasite numbers in a sample of such parasites, and/or to reduce the numbers of such parasites in and/or on an animal, and/or to inhibit the development of parasite infestation in or on an animal, in whole or in part. This amount is readily determined by observation or detection of the parasite numbers both before and after contacting the sample of parasites with the compound, directly and/or indirectly, e.g., by contacting articles, surfaces, foliage, or animals with the compound. For an in vivo administration of the compound according to the invention, an effective amount is synonymous with a "pharmaceutically effective amount," which is the dose or amount that treats or ameliorates symptoms and/or signs of parasite infection or infestation by the treated animal. This later amount is also readily determined by one of ordinary skill in the art, e.g., by observing or detecting changes in clinical condition or behavior of treated animals, as well as by observing or detecting relative changes in parasite numbers after such treatment. Whether the compound is applied in vivo or ex vivo, the treatment is effective when the parasite count is reduced, after a first application or administration, by an amount ranging from 5% to about 100%. Alternatively, the reduction in parasite count ranges from about 10% to about 95%, relative to the parasite count in an equivalent untreated sample.

Compounds of this invention can exist as one or more stereoisomers. The various stereoisomers include enantiomers, diastereomers and geometric isomers. Those skilled in the art will appreciate that one stereoisomer may be more active than the other(s). In addition, the skilled artisan would know how to separate such stereoisomers. Accordingly, the present invention comprises mixtures, individual stereoisomers, and optically active mixtures of the compounds described herein.

For example, although Formulas (I), (III), (IV), and (V) have been drawn as the anti(E)-isomers, it should be understood that the compounds of the present invention may also exist as syn(Z)-isomers, or mixtures thereof, and therefore, such isomers or mixtures thereof are clearly included within the present invention.

Certain compounds of the present invention will be acidic in nature and can form pharmaceutically acceptable metal, ammonium and organic amine salts. The metal salts include alkali metal (e.g., lithium, sodium and potassium), alkaline earth metal (e.g., barium, calcium and magnesium) and heavy metal (e.g., zinc and iron) salts as well as other metal salts such as aluminium. The organic amine salts include the salts of pharmaceutical acceptable aliphatic (e.g., alkyl), aromatic and heterocyclic amines, as well as those having a mixture of these types of structures.

Amines useful in preparing the salts of the invention can be primary, secondary or tertiary and preferably contain not more than 20 carbon atoms. The salts of the invention are prepared by contacting the acid form with a sufficient amount of the appropriate base to produce a salt in the conventional manner. The acid forms may be regenerated by treating the salt with a suitable dilute aqueous acid solution. The acid forms differ from their respective salt forms somewhat in certain physical properties, such as solubility in polar solvents, but the salts are otherwise equivalent to their respective acid forms for the purposes of the invention.

All such salts are intended to be pharmaceutically acceptable within the scope of the invention and all salts are considered equivalent to the acid form for the purposes of the invention.

The compounds of the present invention can also form stable complexes with solvent molecules that remain intact after the non-complexed solvent molecules are removed from the compounds. These complexes are referred to herein as "solvates". Solvates of the compounds of the present invention are also included in the present invention. In a particular embodiment, the solvent molecule is water (i.e., forming a hydrate).

For all of the methods and new compounds described herein, it is also contemplated that the identified compounds are readily employed in combination with one or more art-known agents for killing or controlling various types of parasites, e.g., including all of the ecto- and endoparasites described herein. Thus, although the inventive compounds and methods are preferred over previously known agents and methods of using previously known agents, in certain optional embodiments they are contemplated to be employed in combination, simultaneously, or sequentially (e.g. in the same composition or in separate compositions), with other art-known agents or combinations of such art-known agents employed for killing or controlling various types of pests.

These additional agents include, for example, art-known anthelmintics, such as, for example, avermectins (e.g. ivermectin, moxidectin, milbemycin), benzimidazoles (e.g. albendazole, triclabendazole), salicylanilides (e.g. closantel, oxyclozanide), substituted phenols (e.g. nitroxynil), pyrimidines (e.g. pyrantel), imidazothiazoles (e.g. levamisole) and praziquantel.

Additional art-known agents for killing or controlling pests include the organophosphate pesticides. This class of pesticides has very broad activity, e.g. as insecticides and, in certain instances, anthelminitic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion, phosalone, to name but a few such compounds. It is also contemplated to include combinations of the inventive methods and compounds with carbamate type pesticides, including, e.g., carbaryl, carbofuran, aldicarb, molinate, methomyl, carbofuran, etc., as well as combinations with the organochlorine type pesticides. It is further contemplated to include combinations with biological pesticides, including e.g. repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *bacillus thuringensis,* chlorobenzilate, formamidines, (e.g. amitaz), copper compounds, e.g., copper hydroxide, cupric oxychloride sulfate, cyfluthrin, cypermethrin, dicofol, endosulfan, esenfenvalerate, fenvalerate, lambda-cyhalothrin, methoxychlor and sulfur.

In addition, for all of the methods and new compounds described herein, it is further contemplated that the identified compounds can be readily employed in combination with syngergists such as piperonyl butoxide (PBO) and triphenyl phosphate (TPP); and/or with Insect Growth Regulators (IGRs) and Juvenile Hormone Analogues (JHAs) such as diflubenzuron, cyromazine, methoprene, etc., thereby providing both initial and sustained control of parasites (at all stages of insect development, including eggs) on the animal subject, as well as within the environment of the animal subject.

Combinations with cyclodienes, ryania, KT-199 and/or older art-known anti-helminth agents, such as avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole), praziquantel and some organophosphates such as naphthalophos and pyraclofos, are also contemplated to be employed in such combinations.

In particular, additional antiparasitic compounds useful within the scope of the present invention are preferably comprised of the class of avermectin compounds. As stated above, the avermectin family of compounds is a series of very potent antiparasitic agents known to be useful against a broad spectrum of endoparasites and ectoparasites in mammals.

A preferred compound for use within the scope of the present invention is ivermectin. Ivermectin is a semi-synthetic derivative of avermectin and is generally produced as a mixture of at least 80% 22,23-dihydroavermectin $B1_a$ and less than 20% 22,23-dihydroavermectin $B1_b$. Ivermectin is disclosed in U.S. Pat. No. 4,199,569, hereby incorporated by reference. Ivermectin has been used as an antiparasitic agent to treat various animal parasites and parasitic diseases since the mid-1980's.

Abamectin is an avermectin that is disclosed as avermectin B1a/B1b in U.S. Pat. No. 4,310,519, which is hereby incorporated by reference in its entirety. Abamectin contains at least 80% of avermectin $B1_a$ and not more than 20% of avermectin $B1_b$.

Another preferred avermectin is Doramectin also known as 25-cyclohexyl-avermectin $B_1$. The structure and preparation of Doramectin, is disclosed in U.S. Pat. No. 5,089,480, which is hereby incorporated by reference in its entirety.

Another preferred avermectin is Moxidectin. Moxidectin, also known as LL-F28249 alpha is known from U.S. Pat. No. 4,916,154, which is hereby incorporated by reference in its entirety.

Another preferred avermectin is Selamectin. Selamectin is 25-cyclohexyl-25-de(1-methylpropyl)-5-deoxy-22,23-dihydro-5-(hydroxyimino)-avermectin $B_1$ monosaccharide.

Milbemycin, or B41, is a substance which is isolated from the fermentation broth of a Milbemycin producing strain of *Streptomyces*. The microorganism, the fermentation conditions and the isolation procedures are more fully described in U.S. Pat. Nos. 3,950,360 and 3,984,564.

Emamectin (4"-deoxy-4"-epi-methylaminoavermectin $B_1$), which can be prepared as described in U.S. Pat. Nos. 5,288,710 or 5,399,717, is a mixture of two homologues, 4"-deoxy-4"-epi-methylaminoavermectin B1a and 4"-deoxy-4"-epi-methylaminoavermectin B1b. Preferably, a salt of Emamectin is used. Non-limiting examples of salts of Emamectin which may be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the Emamectin salt used in the present invention is Emamectin benzoate.

Eprinomectin is chemically known as 4"-epi-Acetylamino-4"-deoxy-avermectin $B_1$. Eprinomectin was specifically developed to be used in all cattle classes and age groups. It was the first avermectin to show broad-spectrum activity against both endo-and ecto-parasites while also leaving minimal residues in meat and milk. It has the additional advantage of being highly potent when delivered topically.

The composition of the present invention optionally comprises combinations of one or more of the following antiparasite compounds.

The antiparasite imidazo[1,2-b]pyridazine compounds as described by U.S. application Ser. No. 11/019,597, filed on Dec. 22, 2004, incorporated by reference herein.

The antiparasite 1-(4-mono and di-halomethylsulphonylphenyl)-2-acylamino-3-fluoropropanol compounds, as described by U.S. application Ser. No. 11/018,156, filed on Dec. 21, 2004, incorporated by reference herein.

The antiparasite phenyl-3-(1H-pyrrol-2-yl)acrylonitrile compounds, as described by U.S. Provisional Application Ser. No. 60/629,699, filed on Nov. 19, 2004, incorporated by reference herein.

The antiparasite n-[(phenyloxy)phenyl]-1,1,1-trifluoromethanesulfonamide and n-[(phenylsulfanyl)phenyl]-1,1,1-trifluoromethanesulfonamide derivatives, as described by U.S. Provisional Application Ser. No. 60/688,898, filed on Jun. 9, 2005, incorporated by reference herein.

The composition of the present invention optionally comprises combinations of one or more of the following antiparasite compounds.

The antiparasite imidazo[1,2-b]pyridazine compounds as described by U.S. application Ser. No. 11/019,597, filed on Dec. 31, 2003, incorporated by reference herein.

The antiparasite 1-(4-fluoromethylsulphonylphenyl)-2-acylamino-3-fluoropropanol compounds, as described by U.S. application Ser. No. 11/018,156, filed on Dec. 31, 2003, incorporated by reference herein.

The antiparasite phenyl-3-(1H-pyrrol-2-yl)acrylonitrile compounds, as described by U.S. Provisional Application Ser. No. 60/612,539, filed on Sep. 23, 2004, incorporated by reference herein.

The antiparasite trifluoromethanesulfonanilide oxime ether compounds, as described by U.S. Provisional Application Ser. No. 60/629,699, filed on Nov. 9, 2004, incorporated by reference herein.

The compositions of the present invention may also further comprise a flukicide. Suitable flukicides include, for example, Triclabendazole, Fenbendazole, Albendazole, Clorsulon and Oxibendazole. It will be appreciated that the above combinations may further include combinations of antibiotic, antiparasitic and anti-fluke active compounds.

In addition to the above combinations, it is also contemplated to provide combinations of the inventive methods and compounds, as described herein, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compounds or methods, e.g., in a combined composition and/or in separate dosage forms.

Art-known antibiotics suitable for this purpose include, for example, those listed hereinbelow.

One useful antibiotic is Florfenicol, also known as D-(threo)-1-(4-methylsulfonylphenyl)-2-dichloroacetamido-3-fluoro-1-propanol. Another preferred antibiotic compound is D-(threo)-1-(4-methylsulfonyphenyl)-2-difluoroacetamido-3-fluoro-1-propanol. Another useful antibiotic is Thiamphenicol. Processes for the manufacture of these antibiotic compounds, and intermediates useful in such processes, are described in U.S. Pat. Nos. 4,311,857; 4,582,918; 4,973,750; 4,876,352; 5,227,494; 4,743,700; 5,567,844; 5,105,009; 5,382,673; 5,352,832; and 5,663,361, hereby incorporated by reference. Other florfenicol analogs and/or prodrugs have been disclosed and such analogs also can be used in the compositions and methods of the present invention [see e.g., U.S. Patent Application Publication No: 2004/0082553, and U.S. patent application Ser. No. 11/016,794, both of which are hereby incorporated by reference in their entireties]. When the antibiotic compound is Florfenicol, the concentration of Florfenicol typically is from about 10% to about 50% w/v, with the preferred level between about 20% and about 40% w/v, even more preferred being at least about 30% w/v.

Another useful antibiotic compound is Tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695, hereby incorporated by reference. Also disclosed in U.S. Pat. No. 4,820,695 is an injectable, aqueous formulation comprising 50% (by volume) propylene glycol, 4% (by volume) benzyl alcohol, and 50 to 500 mg/ml of active ingredient. Tilmicosin may be present as the base or as a phosphate. Tilmicosin has been found to be useful in treatment of respiratory infections, particularly *Pasteurella haemolytica* infections in cattle when administered by injection over a 4 day treatment period. Accordingly, Tilmicosin may be used in treatment of, for example, neonatal calf pneumonia and bovine respiratory disease. When Tilmicosin is present, it is present in an amount of about 1% to about 50%, preferably 10% to about 50%, and in a particular embodiment, 30%.

Another useful antibiotic for use in the present invention is Tulathromycin. Tulathromycin has the following chemical structure.

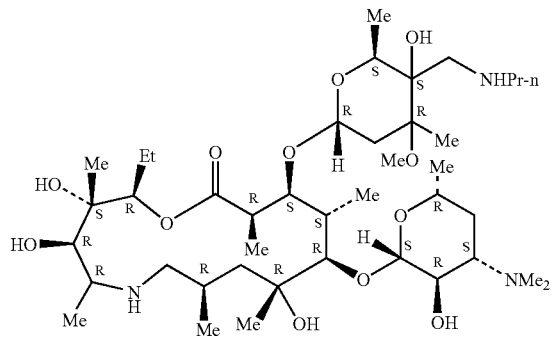

Tulathromycin may be identified as 1-oxa-6-azacyclopentadecan-15-one, 13-[(2,6-dideoxy-3-C-methyl-3-O-methyl-4-C-[(propylamino)methyl]-alpha-L-ribo-hexopyranosyl]oxy]-2-ethyl-3,4,10-trihydroxy-3,5,8,10,12,14-hexamethyl-11-[[3,4,6-trideoxy-3-(dimethylamino)-beta-D-xylo-hexopyranosyl]oxy]-, (2R, 3S, 4R, 5R, 8R, 10R, 11R, 12S, 13S, 14R). Tulathromycin may be prepared in accordance with the procedures set forth in U.S. Patent Publication No. 2003/0064939 A1, which is hereby incorporated by reference in its entirety. Tulathromycin may be present in injectable dosage forms at concentration levels ranging from about 5.0% to about 70% by weight. Tulathromycin is most desirably administered in dosages ranging from about 0.2 mg per kg body weight per day (mg/kg/day) to about 200 mg/kg/day in single or divided doses (i.e., from 1 to 4 doses per day), and more preferably 1.25, 2.5 or 5 mg/kg once or twice weekly, although variations will necessarily occur depending upon the species, weight and condition of the subject being treated. Tulathromycin may be present in injectable dosage forms at concentration levels ranging from about 5.0% to about 70% by weight.

Further antibiotics for use in the present invention include the cephalosporins such as, for example, Ceftiofur, Cefquinome, etc. The concentration of the cephalosporin in the formulation of the present invention optionally varies between about 1 mg/ml to 500 mg/ml.

Another useful antibiotic includes the fluoroquinolones, such as, for example, Enrofloxacin, Danofloxacin, Difloxacin, Orbifloxacin and Marbofloxacin. In the case of Enrofloxacin, it may be administered in a concentration of about 100 mg/ml. Danofloxacin may be present in a concentration of about 180 mg/ml.

Other useful macrolide antibiotics include compounds from the class of ketolides, or, more specifically, the azalides. Such compounds are described in, for example, U.S. Pat. Nos. 6,514,945, 6,472,371, 6,270, 768, 6,437,151 and 6,271,255, and 6,239,112, 5,958,888, and 6,339,063 and 6,054,434, all of which are hereby incorporated by reference in their entireties.

Other useful antibiotics include the tetracyclines, particularly Chlortetracycline and Oxytetracycline. Other antibiotics may include p-lactams such as penicillins, e.g., Penicillin, Ampicillin, Amoxicillin, or a combination of Amoxicillin with Clavulanic acid or other beta lactamase inhibitors Additionally, the present invention optionally includes a composition for the treatment of a microbial and parasitic infection in an animal that comprises one or more of the above-listed antibiotics admixed and/or in combination with one or more of the inventive compounds, and an optional carrier and/or excipient.

Further, it is also contemplated that the inventive methods and compounds be advantageously employed in combination, simultaneously or sequentially, with art-known animal health remedies e.g., trace elements, vitamins, anti-inflammatories, anti-infectives and the like, in the same or different compositions.

Preparation of Inventive Compounds

The compounds of the invention can be prepared by a number of methods. Simply by way of example, and without limitation, the compounds can be prepared using one or more of the reaction schemes and methods described below. Some of the compounds useful in this invention are also exemplified by the following preparative examples, which should not be construed to limit the scope of the disclosure.

The following solvents and reagents may be referred to herein by the abbreviations indicated: acetic acid (AcOH), aluminium trichloride ($AlCl_3$), ammonium chloride ($NH_4Cl$), boron trichloride ($BCl_3$), n-butylamine (n-$BuNH_2$), cuprous chloride (CuCl), 1,2-dichloroethane (DCE), dichloromethane ($CH_2Cl_2$), diethyl azodicarboxylate (DEAD), diethyl ether ($Et_2O$), N,N-dimethylethylenediamine [H$_2$N(CH$_2$)$_2$N(CH$_3$)$_2$], N,N-dimethylformamide (DMF), dimethyl sulfoxide (DMSO), ethanol (EtOH), ethyl acetate (EtOAc), hydrazine monohydrate (N$_2$H$_4$.H$_2$O), hydrochloric acid (HCl), hydrogen (H$_2$), iron powder (Fe), magnesium sulfate (MgSO$_4$), methanol (MeOH), nitric acid (HNO$_3$), petroleum ether; b.p. 40-60° C. (PE), platinum oxide (PtO$_2$), potassium carbonate (K$_2$CO$_3$), potassium permanganate (KMnO$_4$), sodium acetate (NaOAc), sodium carbonate (Na$_2$CO$_3$), sodium hydride (NaH), sodium hydrosulfite (Na$_2$S$_2$O$_4$), sulfuric acid (H$_2$SO$_4$), triethylamine (Et$_3$N), trifluoromethanesulfonic anhydride [(CF$_3$SO$_2$)$_2$O], triphenylphosphine (PPh$_3$), water (H$_2$O). RT is room temperature.

Preferred methods of synthesis of the compounds of Formula (I), wherein R$_1$, R$_2$, R$_3$ and R$_4$ are independently selected from hydrogen, (C$_1$-C$_6$)alkyl, (C$_1$-C$_6$)alkoxy or halo, R$_5$ is (C$_1$-C$_6$)alkyl, and R$_6$ is the same as that set forth above, commence from R$_5$-substituted aryl ketone derivatives of Formula 1 as shown in Scheme 1 of FIG. 1A.

Thus, by way of a nonlimiting example, and with reference to FIG. 1A, the reaction of R$_5$-substituted aryl ketone derivatives of the Formula 1 with a mixture of fuming nitric and concentrated sulfuric acids affords R$_5$-substituted ortho-nitroaryl ketone compounds of Formula 2 using the procedure by Simpson, J. C. E.; Atkinson, C. M.; Schofield, K.; Stephenson, O. *J. Chem. Soc.*, 1945, 646-657. Reduction of the nitro group is preferentially achieved with iron powder in the presence of an acid such as NH$_4$Cl (using the method by Tsuji, K.; Nakamura, K.; Konishi, N.; Okumura, H.; Matsuo, M. *Chem. Pharm. Bull.*, 1992, 40, 2399-2409), or alternatively with PtO$_2$/H$_2$ (using the general method by Leonard, N. J.; Boyd, S. N. *J. Org. Chem.*, 1946, 11, 405-418), to afford R$_5$-substituted ortho-aminoaryl ketone compounds of Formula 3. Compounds of Formula 3 are dissolved in a solvent such as dichloromethane and treated with trifluoromethanesulfonic anhydride to yield trifluoromethanesulfonanilide compounds of Formula 4 (using a modification of the procedure by Harrington, J. K.; Robertson, J. E.; Kvam, D. C.; Hamilton, R. R.; McGurran, K. T.; Trancik, R. J.; Swingle, K. F.; Moore, G. G. I.; Gerster, J. F. *J. Med. Chem.*, 1970, 13,137). Compounds of Formula 4 are dissolved in a solvent such as EtOH and treated with R$_6$-substituted hydroxylamine hydrochloride salts of Formula 5 in the presence of a base such as NaOAc (using the general procedure by Pfeiffer, P. *Chem. Ber.*, 1930, 63, 1811-1814), to afford trifluoromethanesulfonanilide O-substituted oxime ether derivatives of Formula (I). Compounds of Formula (I) are obtained as either single isomers or as a mixture of E- and Z-O-substituted oxime ether derivatives.

A preferred method for preparing compounds of Formula (I), wherein R$_1$, R$_2$, R$_3$, and R$_4$ are independently selected from hydrogen or halo, R$_5$ is hydrogen and R$_6$ is the same as that set forth above, involves commencing from an ortho-nitrobenzaldehyde derivative of Formula 2 (wherein R$_5$ is hydrogen) as shown in Scheme 1 of FIG. 1A. Reduction of the nitro group with Na$_2$S$_2$O$_4$, in the presence of a base such as Na$_2$CO$_3$, affords oilho-aminobenzaldehyde compounds of Formula 3 (using the method of Horner, J. K.; Henry, D. W. *J. Med. Chem.* 1968, 11, 946-949) which are converted in two steps to trifluoromethanesulfonanilide O-substituted oxime ether derivatives of Formula (I) using the methods illustrated in Scheme 1.

A preferred method for preparing compounds Formula (I), wherein R$_1$, R$_2$, R$_3$, and R$_4$ are independently selected from hydrogen or halo, R$_5$ is (optionally substituted)aryl and R$_6$ is the same as that set forth above, involves commencing from an ortho-aminobenzophenone derivative of Formula 3 [wherein R$_5$ is (optionally substituted)aryl] as shown in Scheme 1. Compounds of Formula 3 are then converted in two steps to trifluoromethanesulfonanilide O-substituted oxime ether derivatives of Formula (I) using the methods illustrated in Scheme 1 of FIG. 1A.

Figure 1B:
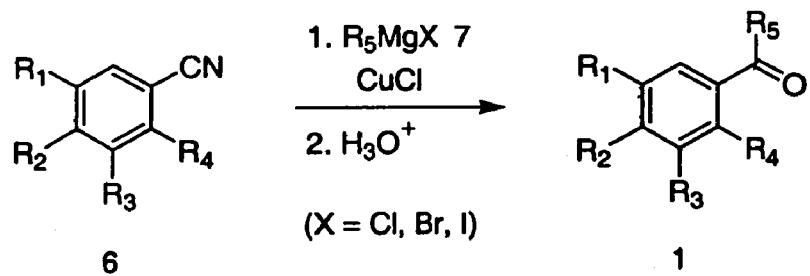
FIG. 1B illustrates reaction scheme 2.

A preferred method for preparing compounds of Formula (I), wherein R$_1$, R$_2$, R$_3$, and R$_4$ are independently selected from hydrogen or halo, R$_5$ is (C$_1$-C$_6$)alkyl, (C$_2$-C$_6$)alkenyl, (C$_3$-C$_{10}$)cycloalkyl, (optionally substituted)aryl, (optionally substituted)aryl(C$_1$-C$_6$)alkyl, (optionally substituted)heteroaryl, (C$_1$-C$_6$)haloalkyl or (C$_2$-C$_6$)haloalkenyl and R$_6$ is the same as that set forth above, involves commencing from arylnitrile derivatives of Formula 6 as shown in Scheme 2 of FIG. 1B.

Thus, by way of a nonlimiting example, reaction of an arylnitrile derivative of Formula 6 with an appropriate organomagnesium halide of Formula 7, in the presence of a catalytic amount of a copper salt such as CuCl, affords R$_5$-substituted aryl ketone derivatives of Formula 1 (using the procedure by Weiberth, F. J.; Hall, S. S. *J. Org. Chem.*, 1987, 52, 3901-3904). Compounds of Formula 1 are then converted in four steps to trifluoromethanesulfonanilide O-substituted oxime ether derivatives of Formula (I) using the methods illustrated in Scheme 1 of FIG. 1A.

Figure 2A:
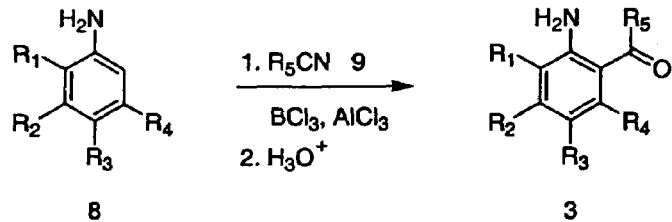
FIG. 2A illustrates reaction scheme 3.

A further preferred method for preparing compounds of Formula (I), wherein R$_1$, R$_2$, R$_3$, and R$_4$ are independently selected from hydrogen or halo, R$_5$ is (C$_1$-C$_6$)alkyl, (C$_2$-C$_6$)alkenyl, (C$_3$-C$_{10}$)cycloalkyl, (optionally substituted)aryl, (optionally substituted)aryl(C$_1$-C$_6$)alkyl, (optionally substituted)heteroaryl, (optionally substituted)heterocyclyl, (C$_1$-C$_6$)haloalkyl or (C$_2$-C$_6$)haloalkenyl, involves commencing from aniline derivatives of Formula 8 as shown in Scheme 3 of FIG. 2A.

Thus, by way of a nonlimiting example, anilines of Formula 8 can be ortho-acylated with an R$_5$-substituted nitrile of Formula 9 in the presence of a stoichiometric amount of BCl$_3$ and AlCl$_3$ (using the method of Sugasawa, T.; Toyoda, T.; Adachi, M.; Sasakura, K. *J. Am. Chem. Soc.*, 1978, 100, 4842-4852). This method gives compounds of Formula 3 which are then converted in two steps to trifluoromethanesulfonanilide O-substituted oxime ether derivatives of Formula (I) using the processes illustrated in Scheme 1 of FIG. 1A.

Figure 2B:
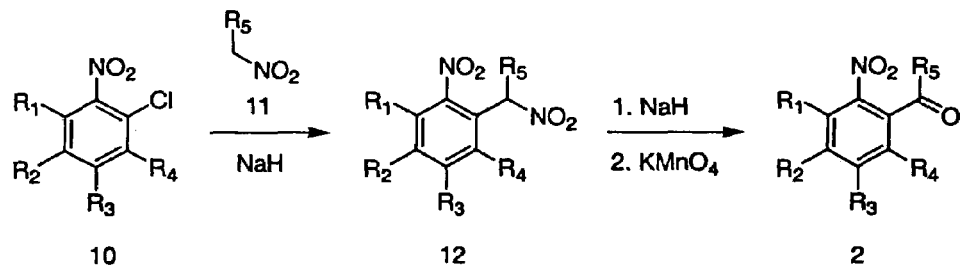
FIG. 2B illustrates reaction scheme 4.

A preferred method for preparing compounds of Formula (I), wherein R$_1$, R$_2$, R$_3$, and R$_4$ are independently selected from hydrogen or (C$_1$-C$_6$)haloalkyl, R$_5$ is (C$_1$-C$_6$)alkyl and R$_6$ is the same as that set forth above, involves commencing from ortho-nitroaryl chloride derivatives of Formula 10 as shown in Scheme 4 of FIG. 2B.

Thus, by way of a nonlimiting example, reaction of an ortho-nitroaryl chloride of Formula 10 with the salt of an appropriate R$_5$-substituted nitroalkane of Formula 11 affords α-aryl R$_5$-substituted nitroalkane derivatives of Formula 12 (using a modification of a procedure by Reid, J. G.; Reny Runge, J. M. *Tetrahedron Lett.*, 1990, 31, 1093-1096). Subjecting compounds of Formula 12 to an oxidative Nef reaction (using the procedure of Kornblum, N.; Erickson, A. S.; Kelly, W. J.; Henggeler, B. *J. Org. Chem.*, 1982, 47,4534-4538) affords compounds of Formula 2, which are then converted in three steps to trifluoromethanesulfonanilide O-substituted oxime ether derivatives of Formula (I) using the methods illustrated in Scheme 1 of FIG. 1A.

Figure 2C:
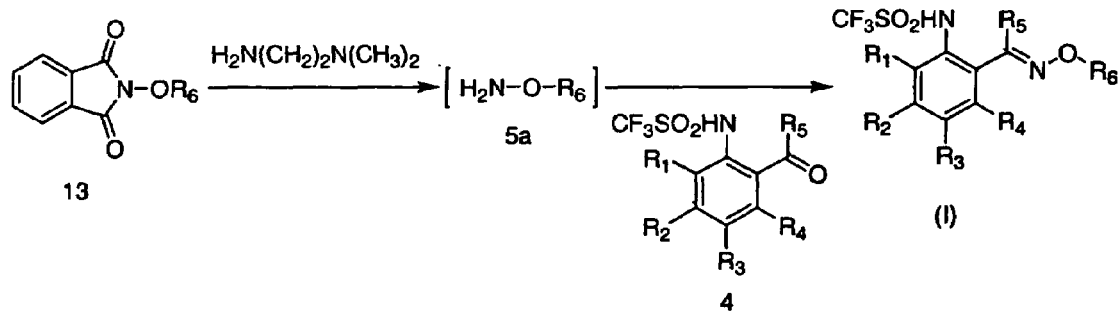
FIG. 2C illustrates reaction scheme 5.

A particularly preferred method of synthesis of compounds of Formula (I), wherein R$_1$, R$_2$, R$_3$, R$_4$, R$_5$ and R$_6$ are the same as that set forth above, is by a one-pot procedure involving the reaction of R$_6$-substituted hydroxylamine derivatives of Formula 5 a with trifluoromethanesulfonanilide compounds of Formula 4 as shown in Scheme 5 of FIG. 2C.

Thus, by way of a nonlimiting example, $R_6$-substituted hydroxylamine compounds of Formula 5a are generated in situ by reaction of $R_6$-substituted O-phthalimide derivatives of Formula 13 with a base such as N,N-dimethylethylenediamine, and subsequently condensed in a one-pot procedure with compounds of Formula 4 to afford trifluoromethanesulfonanilide O-substituted oxime ether derivatives of Formula (I).

Figure 3A:
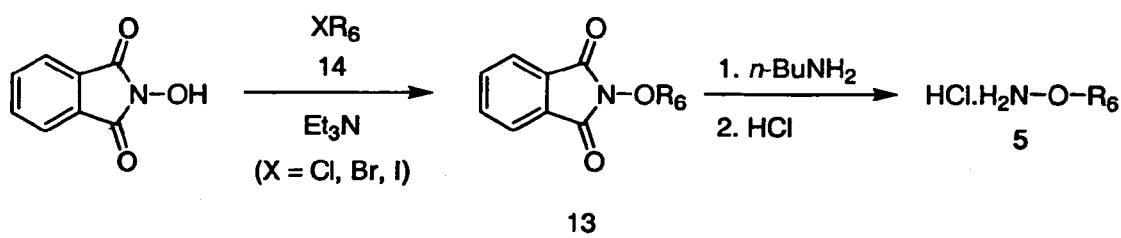
FIG. 3A illustrates reaction scheme 6.

A preferred method of synthesis of O-substituted hydroxylamine hydrochloride salts of Formula 5, wherein $R_6$ is $(C_1-C_6)$alkyl, $(C_2-C_6)$alkenyl, $(C_2-C_6)$alkynyl, $(C_3-C_{10})$cycloalkyl, $(C_3-C_{10})$cycloalkenyl, $(C_3-C_{10})$cycloalkyl$(C_1-C_6)$alkyl, $(C_3-C_{10})$cycloalkenyl$(C_1-C_6)$alkyl, (optionally substituted)aryl$(C_1-C_6)$alkyl, (optionally substituted) aryl$(C_1-C_6)$alkenyl, (optionally substituted)heterocyclyl, (optionally substituted)heterocyclyl$(C_1-C_6)$alkyl, (optionally substituted)heteroaryl$(C_1-C_6)$alkyl, (optionally substituted)heteroaryl$(C_2-C_6)$alkenyl, cyano$(C_1-C_6)$alkyl, $(C_1-C_6)$alkoxy$(C_1-C_6)$alkyl, $(C_3-C_{10})$cycloalkoxy$(C_1-C_6)$alkyl, (optionally substituted)aryloxy$(C_1-C_6)$alkyl, $(C_1-C_6)$alkylthio$(C_1-C_6)$alkyl, $(C_3-C_{10})$cycloalkylthio$(C_1-C_6)$alkyl, (optionally substituted)arylthio$(C_1-C_6)$alkyl, $(C_1-C_6)$alkylsulfinyl$(C_1-C_6)$alkyl, $(C_3-C_{10})$cycloalkylsulfinyl$(C_1-C_6)$alkyl, (optionally substituted)arylsulfinyl$(C_1-C_6)$alkyl, $(C_1-C_6)$alkylsulfonyl$(C_1-C_6)$alkyl, $(C_3-C_{10})$cycloalkylsulfonyl$(C_1-C_6)$alkyl, (optionally substituted)arylsulfonyl$(C_1-C_6)$alkyl, $(C_1-C_6)$haloalkyl or $(C_2-C_6)$haloalkenyl, generally commences from $R_6$-substituted halide derivatives of Formula 14 as shown in Scheme 6 of FIG. 3A.

Thus, by way of a nonlimiting example, $R_6$-substituted halide derivative 14 is dissolved in a solvent such as DMF and reacted with N-hydroxyphthalimide, in the presence of a base such as triethylamine or potassium carbonate, to give $R_6$-substituted O-phthalimide derivatives of Formula 13 (using the general method of McKay, A. F.; Garmaise, D. L.; Paris, G. Y.; Gelblum, S. Can. J. Chem., 1960, 38, 343-358). Compounds of Formula 13 are dissolved in a solvent such as EtOH and treated with an organic base such as n-BuNH$_2$ to liberate the free amine, which is treated with HCl to afford $R_6$-substituted hydroxylamine hydrochloride salt derivatives of Formula 5.

Figure 3B:
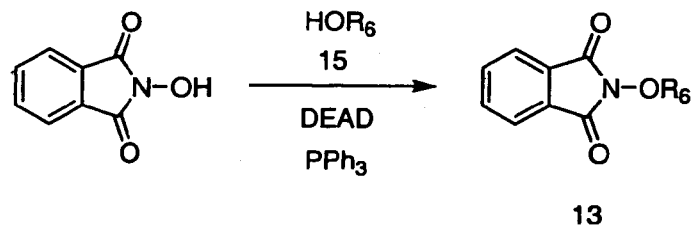
FIG. 3B illustrates reaction scheme 7.

Another preferred method for preparing $R_6$-substituted O-phthalimide derivatives of Formula 13, wherein $R_6$ is the same as that set forth above, is shown in Scheme 7 of FIG. 3B.

Thus, by way of a non-limiting example, compounds of Formula 13 can be prepared from the reaction of N-hydroxyphthalimide with an $R_6$-substituted alcohol of Formula 15 in the presence of a betaine formed between DEAD and PPh$_3$ (using the method of Grochowski, E.; Jurczak, J. Synthesis, 1976, 682-684). Compounds of Formula 13 can then be converted to $R_6$-substituted hydroxylamine hydrochloride salt derivatives of Formula 5 as illustrated in Scheme 6 of FIG. 3A.

Figure 3C:
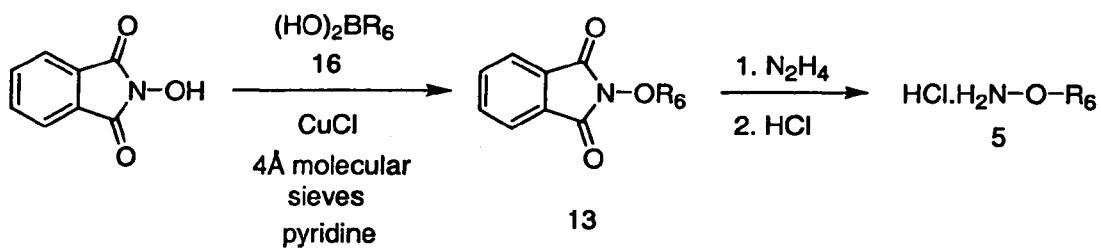
FIG. 3C illustrates reaction scheme 8.

A preferred method for preparing O-substituted hydroxylamine hydrochloride salt derivatives of Formula 5, wherein $R_6$ is (optionally substituted)aryl or (optionally substituted) heteroaryl, is shown in Scheme 8 of FIG. 3C.

Thus, by way of a non-limiting example, an $R_6$-substituted boronic acid 16 and N-hydroxyphthalimide are dissolved in a solvent such as 1,2-DCE and coupled together in the presence of a stoichiometric amount of a copper salt such as CuCl, a base such as pyridine, and a drying agent such as 4 Å molecular sieves, to afford compounds of Formula 13 (using the method of Petrassi, M. H.; Sharpless, K. B.; Kelly, J. W. Org. Lett., 2001, 3,139-142). Compounds of Formula 5 are generated by dissolving $R_6$-substituted O-phthalimide derivative 13 in a solvent such as ethanol and treating with hydrazine monohydrate to give the free amine, which is treated with HCl to afford $R_6$-substituted hydroxylamine hydrochloride salt 5.

Animals to be Treated

The present invention provides compounds and/or compositions for use in the prevention and/or treatment of infestation, diseases and/or related disorders caused by, or as a result of, parasites or other pests that are killed or inhibited (e.g., growth-suppressed) by such compounds and/or compositions. The animal is preferably a vertebrate, and more preferably a mammal, avian or fish. The compound or composition may be administered directly to the animal subject and/or indirectly by applying it to the local environment in which the animal dwells (such as bedding, enclosures, or the like). Appropriate animal subjects include those in the wild, livestock (e.g., raised for meat, milk, butter, eggs, fur, leather, feathers and/or wool), beasts of burden, research animals, companion animals, as well as those raised for/in zoos, wild habitats and/or circuses.

In a particular embodiment, the animal subject is a mammal (including great apes such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites, (e.g., ostriches).

Birds treated or protected by the inventive compounds can be associated with either commercial or noncommercial aviculture. These include e.g., Anatidae, such as swans, geese, and ducks, Columbidae, e.g., doves and pigeons, such as domestic pigeons, Phasianidae, e.g., partridge, grouse and turkeys, Thesienidae, e.g., domestic chickens, Psittacines, e.g., parakeets, macaws, and parrots, e.g., raised for the pet or collector market, among others.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae family, the Serranidae family, the Sparidae family, the Cichlidae family, the Centrarchidae family, the three-Line Grunt (Parapristipoma trilineatum), and the Blue-Eyed Plecostomus (Plecostomus spp), among others.

Other animals are also contemplated to benefit from the inventive compounds, including marsupials (such as kangaroos), reptiles (such as farmed turtles) and other economically important domestic animals for which the inventive compounds are safe and effective in treating or preventing parasite infection or infestation.

CROPS TO BE TREATED

The inventive compounds are also contemplated to be active against agricultural pests that attack plants. In particular, plants include crops of economic or other importance, i.e., in agriculture and related endeavers. Agricultural pests contemplated to be controlled by the inventive compounds include, for example, insect pests. Insect pests include those that can attack stored grains, e.g., *Tribolium* sp., *Tenebrio* sp. Other agricultural pests include spider mites (*Tetranychus* sp.), aphids (*Acyrthiosiphon* sp.), migratory orthopterans such as locusts, and the immature stages of insects that live on plant tissue such as the Southern army worm and Mexican bean beetle larvae.

Further pests of agricultural importance include, e.g., *Acrobasis vaccinii, Agrotis* spp, *Alsophila pometaria, Archips* spp, *Argyrotaenia citrana, A velutinana, Autographa californica, Bacillus thuringiensis, Callopistria floridensis, Choristoneura fumiferana, C occidentalis, C pinus, C rosaceana, Cryptophlebia ombrodelta, Cydia (Laspeyresia) pomonella, C caryana, Dasychira pinicola, Datana ministra, Desmia funeralis, Diatrea saccharalis, Dichocrocis punctiferalis, Dioryctria zimmerman, Ectropis excursaria, Ematurga amitaria, Ennomos subsignaria, Eoreuma loftini, Epiphyas postvittana, Euproctis chrysorrhoea, Grapholita packardi, Hellula rogatalis, Homoeosoma vagella, Hyphantria cunea, Lambdina fiscellaria, Liphophane antennata, Lobesia botrana, Lophocampa maculata, Lymantria dispar, Malacosoma* spp, *Manduca* spp, *Megalopyge opercularis, Mnesampela privata, Orgyia pseudotsugata, O vetusta, Ostrinia nubilalis, Platynota flavedana, P stultana, Pseudaletia unipuncta, Rhopobota naevana, Rhyacionia* spp, *Spodoptera eridania, S exigua, S frugiperda, S omithogalli, Thaumatopoea pityocampa, Thridopteryx ephemeraeformis, Thyrinzeina arnobia,* and others too numerous to mention.

Crops that can be treated in order to kill, remove or present infestation with crop-related pests include, e.g., alfalfa, apples, avocados, blueberries, brassicas, breadfruit, brocolli, bush berries, cabbage, cane berries, cherry, citrus, citrus oil, clover, cole crops, cotton, cucumber, cranberries, currants, apples, eucalyptus, forestry, beet roots and tops, grapes, grapefruit, gooseberries, hay, huckleberries, kiwi fruit, leafy and fruiting vegetables, legumes, lemon, lime, macadamia nuts, mint, orange, ornamentals, peaches, pears, pecans, peppers, plums, pome fruit, potatoes, raspberry, shrubs, soy, starfruit, sugarcane, sunflower, squash, table beets, tangerine, treenuts, trees, turnips, walnuts, the various grain grasses, including corn or maize, wheat, rye, rice, oats, barley, spelt, millet, etc.

Susceptible Parasites

The inventive compounds are broadly described as endectoparasiticides, in that the inventive compounds include those that are active against ectoparasites (arthropods, acarines, etc.) and endoparasites (helminths, e.g., nematodes, trematodes, cestodes, canthocephalans, etc.), including pests that prey on agricultural crops and stored grains (spider mites, aphids, caterpillars, migratory orthopterans such as locusts). Protozoa parasites (*Flagellata, Sarcodina Ciliophora,* and *Sporozoa,* etc.) are also contemplated to be treated by the inventive compounds. The inventive compounds are also active against household pests, and particularly against arthropod pests, such as spiders, mites, and insects, including flies, mosquitoes, ants, termites, silverfish, cockroach, clothes moth, and a myriad of beetles and beetle larvae that impact households.

1. Helminths

The disease or group of diseases described generally as helminthiasis is due to infection of an animal host with parasitic worms known as helminths. Helminthiasis is a prevalent and serious economic problem with domesticated animals such as swine, sheep, horses, cattle, goats, dogs, cats and poultry. Among the Helminths, the group of worms described as nematodes causes widespread and at times serious infection in various species of animals. Nematodes that are contemplated to be treated by the inventive compounds include, without limitation, the following genera:

*Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Heterakis, Lagochilascaris, Loa, Mansonella, Muellerius, Nanophyetus, Necator, Nematodirus, Oesophagostomum, Opisthorchis, Ostertagia, Oxyuris, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichonema, Trichostrongylus, Trichuris, Uncinaria,* and *Wuchereria.*

Of the above, the most common genera of nematodes infecting the animals referred to above are *Haemonchus, Trichostrongylus, Ostertagia, Nemaodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Unicinaria, Toxascaris* and *Parascaris.* Certain of these, such as *Nematodirus, Cooperia* and *Oesophagostomum* attack primarily the intestinal tract while others, such as *Haemonchus* and *Ostertagia,* are more prevalent in the stomach while others such as *Dictyocaulus* are found in the lungs. Still other parasites may be located in other tissues such as the heart and blood vessels, subcutaneous and lymphatic tissue and the like. Table 1A, below, lists a number of these, by Family and Genus, that are of economic (medical and veterinary) importance.

TABLE 1A

| Class | Family | Genus (examples) |
| --- | --- | --- |
| Trematoda | Fasciolidae | *Fasciola* |
| Cestoda | Anoplocephalidae | *Moniezia* |
| " | Dilepididae | *Dipylidium* |
| " | Taeniidae | *Taenia, Echinococcus* |
| Nematoda | Strongyloididae | *Stongyloides* |
| " | Strongylidae | *Strongylus, Oesophagostomum* |
| " | Syngamidae | *Syngamus* |
| " | Trichostrongylidae | *Trichostrongylus, Cooperia, Ostertagia, Haemonchus* |
| " | Heligmonellidae | *Nippostrongylus* |
| " | Dictyocaulidae | *Dictyocaulus* |
| " | Ascarididae | *Ascaris* |
| " | Toxocaridae | *Toxacara* |
| " | Oxyuridae | *Oxyuris* |
| " | Filaridae | *Parafilaria* |
| " | Onchocercidae | *Onchocerca* |
| " | Trichinellidae | *Trichinella* |
| " | Trichuridae | *Trichuris* |
| " | Capillariidae | *Capillaria* |

The most common genera of parasites of the gastrointestinal tract of man are *Ancylostoma, Necator, Ascaris, Strongyloides, Trichinella, Capillaria, Trichuris,* and

*Enterobius*. Other medically important genera of parasites which are found in the blood or other tissues and organs outside the gastrointestinal tract are the filarial worms such as *Wuchereria, Brugia, Onchocerca* and *Loa, Dracunculus* and extra intestinal stages of the intestinal worms *Strongyloides* and *Trichinella*.

Numerous other Helminth genera and species are known to the art, and are also contemplated to be treated by the compounds of the invention. These are enumerated in great detail in TEXTBOOK OF VETERINARY CLINICAL PARASITOLOGY, VOLUME 1, HELMINTHS, by E. J. L. Soulsby, Pubi. F.A. Davis Co., Philadelphia, Pa.; HELMINTHS, ARTHROPODS AND PROTOZOA (Sixth Ed. of MONNIG'S VETERINARY HELMINTHOLOGY AND ENTOMOLOGY) by E. J. L. Soulsby, Publ. The Williams and Wilkins Co., Baltimore, Md., the contents of both of which are incorporated by reference herein in their entireties.

The parasitic infections known as helminthiasis lead to anemia, malnutrition, weakness, weight loss, severe damage to the walls of the intestinal tract and other tissues and organs and, if left untreated, may result in death of the infected host. The compounds described herein have unexpectedly high activity against these parasites, and in addition are also active against *Dirofilaria* in dogs, and *Namatospiroides, Syphacia, Aspiculuris* in rodents. The inventive compounds are also useful as a nematocide for the control of soil nematodes and plant parasites such as *Meloidogyne* spp.

2. Arthropods

It is also contemplated that the inventive compounds are effective against a number of ectoparastides of animals, e.g., arthropod ectoparasites of mammals and birds. Athropods include those summarized in Table 1B, as follows.

TABLE 1B

Summary Of Taxonomy for Important Arthropod Pests

| Subphylum | Class | Order | Examples |
|---|---|---|---|
| Trilobita | | | |
| Cheliceratac | | | |
| helicera and | | | |
| pedipalps | | | |
| | Merostomata | | |
| | Arachnida | | |
| | | Araneae | spiders |
| | | Scorpionida | scorpions |
| | | Acari | mites and ticks |
| Uniramia | | | |
| | Chilopoda | | centipedes |
| | Diplopoda | | millipedes |
| | Pauropoda | | Soft bodied myriapods |
| | Insecta | | |
| | | Hymenoptera | bees, wasps |
| | | Lepidoptera | moths, butterflies |
| | | Hoptera | grasshoppers |
| | | Diptera | true flies |
| | | Hemiptera | true bugs |
| | | Coleoptera | beetles |

Thus, insect pests include, e.g., biting insects, such as flies and mosquitoes, mites, ticks, lice, fleas, true bugs, parasitic maggots, and the like.

Biting insects include, e.g., migrating diperous larvae as *Hypoderma* sp. in cattle, *Gastrophilus* in horses, and *Cuterebra* sp. in rodents, as well as biting flies and mosquitoes of all types. For example, bloodsucking adult flies include, e.g., the horn fly or *Haematobia irritans,* the horse fly or *Tabanus* spp., the stable fly or *Stomoxys calcitrans,* the black fly or *Simulium* spp., the deer fly or *Chrysops* spp., the louse fly or *Melophagus ovinus,* the tsetse fly or *Iossina* spp. Parasitic fly maggots include, e.g., the bot fly (*Oestrus ovis* and *Cuterebra* spp.], the blow fly or *Phaenicia* spp., the screwworm or *Cochliomyia hominivorax,* the cattle grub or *Hypoderma* spp., and the fleeceworm. Mosquitoes, include, for example, *Culex* spp., *Anopheles* spp., and *Aedes* spp.

Mites include *Mesostigmata* spp., e.g., mesostigmatids such as the chicken mite, *Dermanyssus gallinae;* itch or scab mites such as *Sarcoptidae* spp., for example, *Sarcoptes scabiei;* mange mites such as *Psoroptidae* spp., including *Chorioptes bovis* and *Psoroptes ovis;* chiggers, e.g., *Trombiculidae* spp., for example the North American chigger, *Trombicula alfreddugesi.*

Ticks include, e.g., soft-bodied ticks including *Argasidae* spp., for example *Argas* spp. and *Ornithodoros* spp.; hard-bodied ticks including *Ixodidae* spp., for example *Rhipicephalus sanguineus,* and *Boophilus* spp.

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp., such as oriental rat flea (*Xenopsylla cheopis*); and *Pulex* spp., such as human flea (*Pulex irritans*).

True bugs include, e.g., *Cimicidae* or e.g., the common bed bug (*Cimex lectularius*); *Triatominae* spp., including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other arthropod pests and ectoparasites are known to the art, and are also contemplated to be treated by the compounds of the invention. These are enumerated in great detail in MEDICAL AND VETERINARY ENTOMOLOGY, by D. S. Kettle, Publ. John Wiley & Sons, New York and Toronto; CONTROL OF ARTHROPOD PESTS OF LIVESTOCK: A REVIEW OF TECHNOLOGY, by R. O. Drummand, J. E. George, and S. E. Kunz, Publ. CRC Press, Boca Raton, Fla., the contents of both of which are incorporated by reference herein in their entireties.

3. Protozoa

It is also contemplated that the inventive compounds are effective against a number of protozoa endoparasites of animals, including those summarized by Table 1C, as follows.

TABLE 1C

Exemplary Parasitic Protozoa and Associated Human Diseases

| Phylum | Subphylum | Representative Genera | Human Disease or Disorder |
|---|---|---|---|
| Sarcomastigophora (with flagella, pseudopodia, or both) | Mastigophora (Flagella) | *Leishmania* | Visceral, cutaneous and mucocutaneous Infection |
| | | *Trypansoma* | Sleeping sickness Chagas' disease |
| | | *Giardia* | Diarrhea |
| | | *Trichomonas* | Vaginitis |
| | Sarcodina (pseudopodia) | *Entamoeba* | Dysentery, liver Abscess |
| | | *Dientamoeba* | Colitis |
| | | *Naegleria* and | Central nervous |

TABLE 1C-continued

Exemplary Parasitic Protozoa and Associated Human Diseases

| Phylum | Subphylum | Representative Genera | Human Disease or Disorder |
|---|---|---|---|
| | | Acanthamoeba | system and corneal ulcers |
| | | Babesia | Babesiesis |
| Apicomplexa (apical complex) | | Plasmodium | Malaria |
| | | Isospora | Diarrhea |
| | | Sarcocystis | Diarrhea |
| | | Cryptosporidum | Diarrhea |
| | | Toxoplasma | Toxoplasmosis |
| Microspora | | Enterocytozoon | Diarrhea |
| Ciliephora (with cilia) | | Balantidium | Dysentery |
| Unclassified | | Pneumocystis | Pneumonia |

4. Animal Pests, Generally

Livestock pests will include parasites identified above as helminths, arthropods and protozoa. In addition, and simply by way of example, a number of agricultural arthropod pests are summarized by Table 1D, below, in association with exemplary livestock for which these pests are of economic significance.

TABLE 1D

| | |
|---|---|
| Companion animals, e.g., canine and feline. | Flies, fleas, ticks, mites. |
| Horses | Horse bots. |
| | Horse flies and Deer flies. |
| Cattle | Horn flies, Face flies, Pinkeye and lice. |
| Sheep | Sheep keds (biting flies). |
| Poultry | Lesser Mealworms or Litter beetles. |
| General Pests | Rat-tailed maggots. |
| | Moth flies. |
| | Ants, including Allegheny mound ants. |

5. Crop Pests

Simply by way of example, a number of agricultural crop pests are summarized by Table 1E, in association with exemplary crops for which these pests are of economic significance.

TABLE 1E

| Crop | Parasite or Pest |
|---|---|
| Alfalfa | Blister beetles, generally |
| | Clover Root curculio |
| | Potato leafhoppers |
| Corn | Armyworms |
| | Corn borers, e.g, the Common Stalk borer and the European Corn borer |
| | Corn Leaf aphid |
| | Cutworm |
| | Lesser Cornstalk borer |
| | Seedcorn Maggots |
| | Southwestern Corn Borer |
| | Stink bugs |
| | Wireworms |

TABLE 1E-continued

| Crop | Parasite or Pest |
|---|---|
| Soybeans | Beetles, such as the Japanese and the Bean Leaf beetles |
| | Cutworms |
| | Green cloverworm |
| | Seedcorn maggot |
| | Soybean podworm |
| Small Grains | Aphids and Barley Yellow Dwarf |
| | Armyworms generally, e.g., in small grains. |
| | Cereal Leaf beetle |
| | Hessian fly |
| | Wheat Streak Mosaic virus and the Wheat Curl mite |
| Stored Grain | Beetles, such as the Cadelle beetle and Flour beetle |
| | Indianmeal moth |
| | Lesser Grain borer |
| Greenhouse Plants | Cyclamen Mites |
| | Float Plant pests, generally |
| | Springtails |
| General Crop Pests | Aphids |
| | Beet armyworm |
| | Garden fleahopper |
| | Grasshopper, e.g., redlegged, the two-striped, and the differential grasshopper. |
| | Japanese beetles |
| | Seed maggots |
| | Two-Spotted Spider mites |
| | Whiteflies |
| Potatoes | Colorado Potato beetle |
| Peppers | Beet Armyworm |
| | European Corn borer |
| | Pepper Maggot |
| Other Vegetables | Cabbage Webworm |
| | Cabbage insects, generally |
| | Squash Vine Borer and Squash Bug |
| Greenhouse | Float Plant pests, generally |
| | Cyclamen mites (e.g., in a Greenhouse) |
| Tree Fruits | Cherry Fruit flies |
| | Codling moth |
| | European Red mite |
| | Green fruitworms |
| | Leafhoppers (e.g., on Apples) |
| | Leaf rollers |
| | Oriental Fruit moth |
| | Peachtree borer |
| | Rosy Apple aphid |
| | San Jose scale |
| | Woolly Apple aphid |
| | Lesser Peachtree borer |
| | Plum vurculio |
| Nuts | Nut weevils |
| | Pecan Insects |

TABLE 1E-continued

| Crop | Parasite or Pest |
| --- | --- |
| Grapes | Grape Berry moth |
|  | Grape Cane Gallmaker |
|  | Grape Cane Girdler |
|  | Grape Flea beetle |
|  | Grape Insects, generally |
|  | phylloxera, e.g., on grapes |
|  | Grape Root borer |
| Berries | Rednecked and Raspberry Cane Borers |
|  | Root weevils |

6. Household Pests

The inventive compounds are also contemplated to be active against household pests such as the cockroach, *Blatella* sp., clothes moth, *Tineola* sp., carpet beetle, *Attagenus* sp., and the housefly, *Musca domestica*. In particular, susceptable household pests include those that cause sanitary or economic problems in association with residential and office space and materials, as follows.

Ants, including Carpenter ants (*Camponotus* spp), Pavement ants (*Tetramorium caespitum*), Pharaoh ants (*Monomorium pharaonis*), Thief ants (*Solenopsis molesta*), Yellow ants (*Acanthomyops* spp.), Red ants;

Bed Bugs (*Cimex* spp.);

Beetles, e.g., Carpet (*Attagenus* spp.), Longhorned, Flour (*Tribolium* spp.), Drugstore (*Stegobium paniceum*), Elm Leaf, Ladybird (*Harmonia axyridis*);

Old House Borer and Flatheaded Wood Borer, Family Buprestidae., to name but a few;

Boxelder Bug (*Boisea trivittata*);

Carpenter bees;

Centipedes (*Scutigera coleopterata*);

Cockroaches, including, e.g., the American cockroach (*Periplaneta americana*), German cockroach (*Blattella germanica*), Brownbanded cockroach (*Supella longipalpa*), Oriental Cockroach (*Blatta orientalis*), to name but a few.

Earwigs (*Forficula* sp.);

Field crickets;

Flies, including Cluster flies, *Pollenia rudis*; fruit flies, Moth flies, *Psychoda*. spp. gnats, including, e.g., the Fungus gnat, *Sciara* spp. Phorids, Family Phoridae Millipede (*Looceles reclusa*);

Mites, e.g., Clover mites;

Mosquitoes, e.g., *Culex* spp., *Anopheles* spp., *Aedes* spp.;

Moths, including Clothes (*Tineola* sp., *Tinea* sp.); and Indian Meal (*Plodia interpunctella*);

Psocids (*Liposcellis* sp.);

Silverfish (*Lepisma saccharina*);

Sowbugs;

Spiders, including, e.g., the Black Widow, (*Lactrodectus* spp.), and the Orb Weaver;

Springtails, Order Collembola

Ticks, e.g., the American Dog tick, the Lone Star tick (*Amblyomma americanium*); and Wasps, such as the Yellowjacket (*Dolichovespula* spp. and *Vespula* spp.).

Treating and Inhibiting Parasite Infestation of Animals

It will be understood by those of ordinary skill that the methods and compounds of the present invention are useful in treating diseases and disorders that are known to be associated with the presence of helminths and protozoa, including for example, those listed above, that are present in the tissue or body fluids of animals.

For such infections or infestations, systemic administration is preferred, e.g., administration of the inventive compound by a route selected from the oral or rectal route, a parenteral route, e.g., by intraruminal, intramuscular, intravenous, intratracheal, subcutaneous injection or other type of injection or infusion. The administered inventive compound is optionally provided in the form of a pharmaceutically acceptable oral or parenteral composition, or in the feed or water or other liquid composition, as discussed in greater detail, below.

Generally, good results are obtained with the inventive compound by the systemic administration of from about 0.001 to 100 mg per kg of animal body weight, or more particularly, from about 0.01 to 10 mg per kg of animal body weight, such total dose being given at one time or in divided doses over a relatively short period of time such as 1-5 days. With the disclosed inventive compound, excellent control of such parasites is obtained in animals, e.g., by administering from about 0.025 to 50 mg per kg of body weight in a single dose, or more particularly, from about 0.025 to about 5 mg per kg of body weight in a single dose. Repeat treatments are given as required to combat re-infections and are dependent upon the species of parasite and the husbandry techniques being employed. The techniques for administering these materials to animals are known to the artisan. The exact amount of the inventive compound given will of course depend on several factors including the specific compound selected, the animal being treated, the parasite(s) infecting the animal, severity of infection, etc. and all such factors being considered by the artisan in calculating the required effective dose without undue experimentation.

In one preferred embodiment, the inventive compound is administered to animals in an oral unit dosage form, such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. By way of example, drench formulations generally 0.0001 to about 50% by weight of the inventive compound. Preferred drench formulations contain from about 0.001 to about 10% by weight of the inventive compound. More preferred drench formulations contain from about 0.1 to about 5% by weight of the inventive compound. The drench capsules and boluses comprise the active ingredient admixed with a carrier vehicle such as starch, talc, magnesium stearate, or dicalcium phosphate. In certain optional embodiments, e.g., for large animals, such drench formulations are applied topically, and provide a surface concentration on the animal that is effective to kill or suppress parasites, e.g., by providing a concentration of the inventive compound ranging from about 0.001 $\mu g/cm^2$ to about 1000 $\mu g/cm^2$, or more preferably, from about 0.01 $\mu g/cm^2$ to about 100 $\mu g/cm^2$.

In certain other optional embodiments, the inventive compounds may be administered in a controlled release form, e.g., in a subcutaneous slow release formulation, or in the form of a controlled release device affixed to an animal such as a so-called fleacollar. Collars for the controlled release of an insecticide agent for long term protection against flea infestation in a companion animal are art-known, and are described, for example, by U.S. Pat. Nos. 3,852,416, 4,224,901, 5,555,848, and 5,184,573, incorporated herein by reference.

Where it is desired to administer the inventive compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the inventive compound is to be administered via an animal feedstuff, it is intimately dispersed in the feed or used as a top dressing or in the form of pellets which may then be added to the finished feed or optionally fed separately.

Alternatively, the inventive compound may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The selected inventive compound is dissolved or suspended in the parenteral formulation for administration; such formulations generally contain from 0.005 to 5% by weight of the active compound.

The inventive compounds may also be used to prevent and treat diseases caused by other parasites, for example, arthropod parasites such as ticks, lice, fleas, mites and other biting insects in domesticated animals, including poultry. It is also effective in treatment of parasitic diseases that occur in other animals including humans. The optimum amount to be employed for best results will, of course, depend upon the particular compound employed, the species of animal to be treated and the type and severity of parasitic infection or infestation.

When the compound described herein is administered as a component of the feed of the animals, or dissolved or suspended in the drinking water, compositions are provided in which the active compound or compounds are intimately dispersed in an inert carrier or diluent. An inert carrier is one that will not react with the antiparasitic agent and one that may be administered safely to animals. Preferably, a carrier for feed administration is one that is, or may be, an ingredient of the animal ration.

Suitable compositions include feed pre-mixes or supplements in which the active. ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active inventive compounds are intimately dispersed throughout the carrier by methods such as grinding, stirring, milling or tumbling. Compositions containing from about 0.05 to about 5.0%, or from about 0.005 to about 2.0% by weight of the active compound are particularly suitable as feed pre-mixes. Feed supplements, which are fed directly to the animal contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors mentioned supra as well as upon the particular inventive derivative employed, the compound described in this invention is usually fed at concentrations of between about 0.0001 to 0.02% or from about 0.00001 to about 0.002% in the feed in order to achieve the desired antiparasitic result. The compounds of this invention are also useful in combating agricultural pests that inflict damage upon crops while they are growing or while in storage. The compound is applied using known techniques as sprays, dusts, emulsions and the like, to the growing or stored crops to effect protection from such agricultural pests.

Routes of Administration for Animals

As used herein, the terms, "administer" or "administration" refer to the delivery of a compound, salt, solvate, or prodrug of the present invention or of a pharmaceutical composition containing a compound, salt, solvate, or prodrug of this invention to an organism for the purpose of treating or preventing a parasite infestation in animals.

Suitable routes of administration may include, without limitation, oral, rectal, topical, transmucosal, intramuscular, subcutaneous, intramedullary, intrathecal, direct intraventricular, intravenous, intravitreal, intraperitoneal, intranasal, aural or intraocular. The preferred routes of administration are oral and parenteral.

Alternatively, one may administer the compound in a local rather than systemic manner, for example, by preparation as a salve or topically applied formulation that is applied directly to the infected area or by injection of the, compound directly into infected tissue. In either case, a sustained release formulation may be used.

Thus, administration of the compounds of the invention, or their pharmaceutically acceptable salts, in pure form or in an appropriate pharmaceutical composition, can be carried out via any of the accepted modes of administration or agents for serving similar utilities. The routes of administration can be any known to those of ordinary skill. The inventive compounds are given to those in need thereof in any art recognized form, i.e., solid, semi-solid, lyophilized powder, or liquid dosage forms, such as for example, tablets, suppositories, pills, soft elastic and hard gelatin capsules, powders, solutions, suspensions, or aerosols, or the like, in unit or multi-dosage forms suitable for simple administration of precise dosages. The compositions will include a conventional pharmaceutical carrier or excipient and a compound of the invention as the active agent, and, in addition, may include other medicinal agents, pharmaceutical agents, carriers, etc.

For aquatic animal species, e.g., vertebrate fish species, methods of administering the inventive compound(s) include the foregoing, e.g., by injection or by admixing the effective compounds in the feed of farmed fish, and so forth. Method of adminisering to aquatic animal species also include dipping the fish into water comprising an effective concentration of the inventive compound(s), spraying the fish with an effective concentration of the inventive compound(s), while the fish is briefly separated from the water, and so forth.

Composition/Formulation for Animals

Pharmaceutical compositions of the present invention may be manufactured by processes well known in the art, e.g., using a variety of well-known mixing, dissolving, granulating, dragee-making, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen.

For injection, including, without limitation, intravenous, intramusclular and subcutaneous injection, the compounds of the invention may be formulated in aqueous solutions, preferably in physiologically compatible buffers known to those of ordinary skill, as well as other excipients or other materials known to those of ordinary skill. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl-methylcellulose, sodium carboxy-methylcellulose, and/or polyvinylpyrrolidone (PVP). If desired, disintegrating agents may be added, such as cross-linked PVP, agar, or alginic acid. A salt such as sodium alginate may also be used.

Dragee cores are provided with suitable coatings. For this purpose, concentrated sugar-solutions may be used which may optionally contain gum arabic, talc, PVP, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers also may be added in these formulations.

For administration by inhalation, the compounds of the present invention can conveniently be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described supra, the compounds may also be formulated as depot preparations. Such long acting formulations may be administered by implantation (for example, subcutaneously or intramuscularly) or by intramuscular or subcutaneous injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed. Pharmaceutical compositions useful herein also may comprise solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Delivery to Plants/Crops, Facilities, Habitats

The compounds of the invention can be readily formulated by art-known methods for delivery for killing, suppressing or inhibiting endo or ectoparasites in or on plants generally, and particularly in crop plants, e.g., to kill or suppress any of the myriad plant pests enumerated supra. In addition, the compounds of the invention can be applied or distributed into selected environmental areas to kill or suppress endo or ectoparasites where desired. The inventive compounds are readily formulated, by methods known to the art, into compositions suitable for such applications. Such compositions optionally include more than one of the inventive compounds, each selected for an optimal spectrum of activity. In certain optional embodiments, the compositions include other agents, e.g., other art-known antiparasitic agents, pesticides and the like, as enumerated supra, that may provide a useful complementary or synergistic antiparasiticidal effect.

It is further contemplated that the compositions optionally include other useful agents, including weed killers, fertilizers, and the like, for efficient agriculture management.

Compositions for such distribution include solutions, suspensions and dry forms of the inventive compound(s) as discussed supra. This process of administering such compositions can be achieved by methods well known to the art. These include spraying, brushing, dipping, rinsing, washing, dusting, using art-known equipment, in a selected area. The selected area optionally includes plants, e.g., crops, and/or animals.

Thus, environmental areas contemplated to be treated in this way include, e.g., fields, orchids, gardens and the like, buildings and their environs, including landscaping; storage facilities, transport or fixed storage containers or analogous structures and structural components, such as walls, floors, roofs, fences, windows and window screens, and the like. Animal living spaces are also included, e.g., animal pens, chicken coops, corals, barns and the like. Human homes and other human residential, business or commercial and educational facilities are also contemplated to be treated or contacted with the inventive compounds or compositions thereof as described above.

Application can be achieved using art-known spraying devices, e.g., self-pressurized aerosol containers, larger devices employing compressed air or centrifugal distribution, as well as crop dusters, and the like.

EXAMPLES

The following preparative examples of preferred derivatives of the inventive compound serve to provide further appreciation of the invention but are not meant in any way to restrict the effective scope of the invention.

Example 1

Preparation of N-(2-acetyl-4-chlorophenyl)trifluoromethanesulfonamide (Formula 19)

Figure 4:
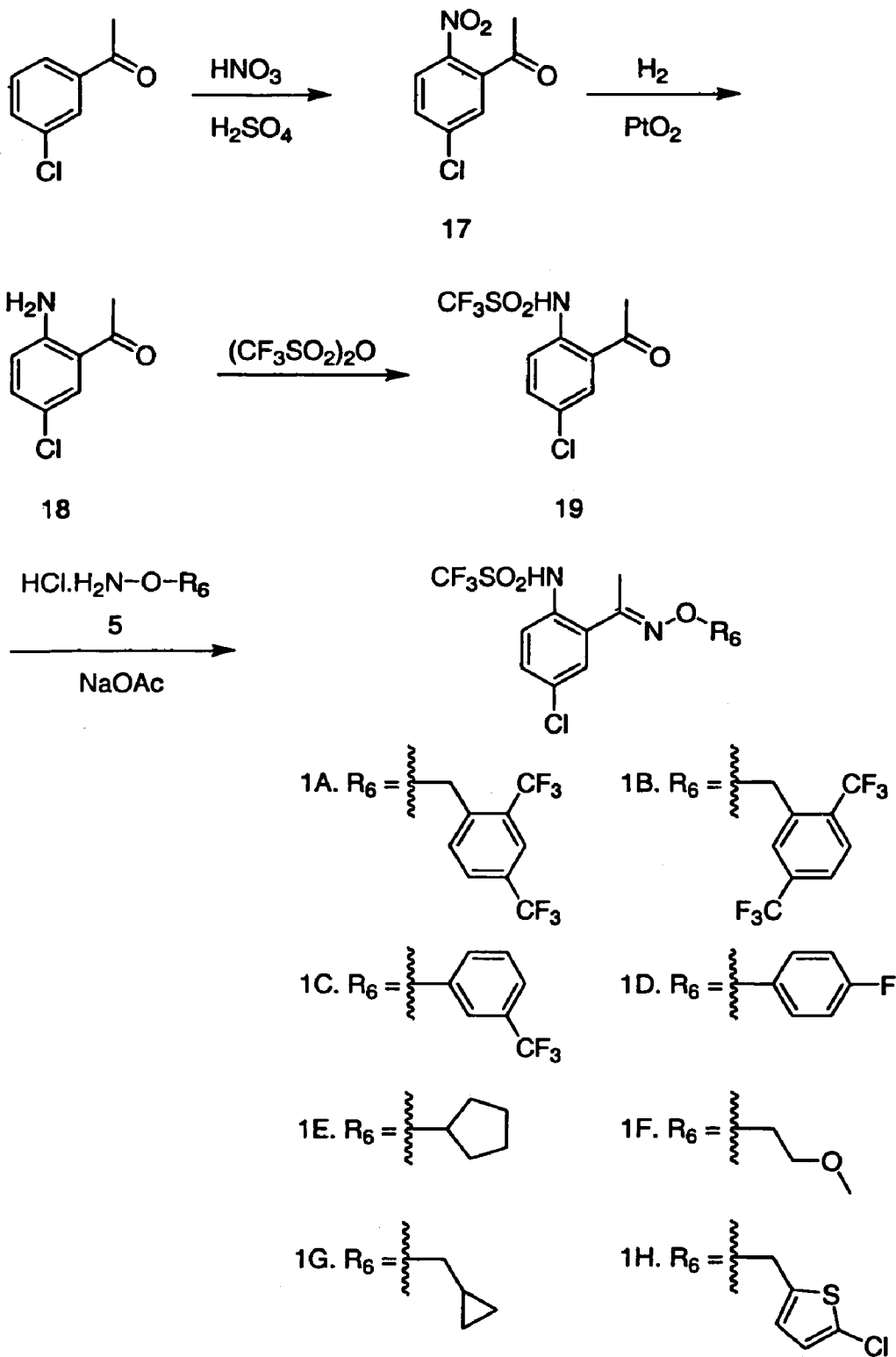
FIG. 4 illustrates the preparative reactions of Examples 1A through 1H.

The following compounds were prepared according to the reaction scheme illustrated by FIG. 4.

a) To a rapidly stirred solution of fuming $HNO_3$ (17 mL) and concentrated $H_2SO_4$ (2.5 mL) at $-20°$ C. was added portionwise 3-chloroacetophenone (5.0 g, 32.34 mmol) over 15 min. The reaction mixture was allowed to warm to $-10°$ C. and stirred for 5 h at this temperature after which ice-water (75 mL) was added and the reaction mixture extracted twice with $CH_2Cl_2$. The organic layers were combined, washed five times with water, dried over $MgSO_4$ and concentrated under reduced pressure. The residue was filtered through a pad of silica (eluting with $CH_2Cl_2$/PE, 4:1) to afford a pale green oil which was recrystallized from $Et_2O$/PE to give 1-(5-chloro-2-nitrophenyl)ethanone 17 (5.45 g, 84%), as pale yellow crystals.

b) A mixture of 1-(5-chloro-2-nitrophenyl)ethanone 17 (4.40 g, 22.05 mmol), $PtO_2$ (40 mg) and charcoal (400 mg) in EtOH (80 mL) was rapidly stirred at RT for 4.5 h under one atmosphere of hydrogen. The reaction mixture was filtered through a pad of celite (the residues washed with $CH_2Cl_2$) and concentrated under reduced pressure. The residue was filtered through a pad of silica (eluting with $CH_2Cl_2$/PE, 4:1) to afford a pale green oil which was recrystallized from $Et_2O$/PE to give 1-(2-amino-5-chlorophenyl)ethanone 18 (3.30 g, 88%), as pale green crystals.

c) To a solution of 1-(2-amino-5-chlorophenyl)ethanone 18 (4.72 g, 27.83 mmol) in anhydrous dichloromethane (150 mL) at 0° C. was added dropwise $(CF_3SO_2)_2O$ (7.0 mL, 41.74 mmol) in anhydrous $CH_2Cl_2$ (30 mL) over 30 min. and the reaction allowed to warm to RT overnight. The reaction mixture was washed with water, dried over $MgSO_4$ and concentrated under vacuum. The residue was filtered through a pad of silica (eluting with $CH_2Cl_2$/PE, 3:7) to afford a yellow oil which was recrystallized from $Et_2O$/PE to give N-(2-acetyl-4-chlorophenyl)trifluoromethanesulfonamide 19 (6.88 g, 82%), as pale yellow crystals. M.p. 36-38° C. $^1$H n.m.r. (200 MHz, $CDCl_3$) δ 12.01, br s, 1H; 7.91, d, J=2.2 Hz, 1H; 7.75, d, J=8.8 Hz, 1H; 7.55, dd, J=2.2 and 8.8 Hz, 1H; 2.71, s, 3H.

Example 1A

Preparation of N-{2-[1-(2,4-bistrifluoromethylbenzyloxyimino)ethyl]-4-chlorophenyl}trifluoromethanesulfonamide (Compound 2)

A solution of N-(2-acetyl-4-chlorophenyl)trifluoromethanesulfonamide 19 (150 mg, 0.50 mmol), O-(2,4-bistrifluoromethylbenzyl)hydroxylamine hydrochloride (154 mg, 0.52 mmol) and anhydrous NaOAc (43 mg, 0.52 mmol) in EtOH (20 mL) was stirred for 15 h at RT. The reaction mixture was concentrated under vacuum and the residue filtered through a pad of silica (eluting with $CH_2Cl_2$/PE, 7:3). Purification by radial thin layer chromatography (eluting with $CH_2Cl_2$/PE, 7.5:92.5 to 1:9) afforded a pale yellow solid which was recrystallized from $CH_2Cl_2$/PE to give N-{2-[1-(2,4-bistrifluoromethylbenzyloxyimino)ethyl]-4-chlorophenyl}trifluoromethanesulfonamide 2 (240 mg, 89%), as a colorless oil. $^1$H n.m.r. (200 MHz, $CDCl_3$) δ 10.96, br s, 1H; 7.96, s, 1H; 7.85, d, J=8.0 Hz, 1H; 7.72, d, J=8.0 Hz, 1H; 7.60, d, J=8.8 Hz, 1H; 7.49, d, J=2.2 Hz, 1H; 7.33, dd, J=2.2 and 8.8 Hz, 1H; 5.46, s, 2H; 2.39, s, 3H. HRMS (M$^+$) 542.0102.

Preparation of O-(2,4-bistrifluoromethylbenzyl)hydroxylamine hydrochloride a) To a solution of N-hydroxyphthalimide (1.33 g, 8.14 mmol) in DMF (7 mL) was added $NEt_3$ (1.25 mL, 8.96 mmol) and 2,4-bis(trifluoromethyl)benzyl bromide (1.53 mL, 8.14 mmol) and the reaction was rapidly stirred for 15 h at RT. MeOH (2 mL) and H$_2$O (20 mL) were added and the reaction mixture was stirred at RT for 1 h, filtered and the solids washed with warm (ca. 40° C.) water and dried under vacuum to afford N-(2,4-bistrifluoromethylbenzyloxy)phthalimide (3.10 g, 98%), as a white solid.

b) A solution of N-(2,4-bistrifluoromethylbenzyloxy)phthalimide (3.10 g, 7.96 mmol) and n-BuNH$_2$ (0.79 mL, 7.96 mmol) was stirred at RT for 15 h. The reaction mixture was concentrated under vacuum, dissolved in CH$_2$Cl$_2$ (100 mL) and warmed with the aid of a heating mantle. 3N HCl (10 mL) was added dropwise to the warm reaction mixture which was stirred for 5 min. The reaction mixture was then stirred at RT for 5 min, filtered and the solids dried under vacuum to afford O-(2,4-bistrifluoromethylbenzyl)hydroxylamine hydrochloride (2.24 g, 95%), as a white solid.

Example 1B

Preparation of N-{2-[1-(2,5-bistrifluoromethylbenzyloxyimino)ethyl]-4-chlorophenyl}trifluoromethanesulfonamide (Compound 120)

A solution of N-(2-acetyl-4-chlorophenyl)trifluoromethanesulfonamide 19 (300 mg, 0.99 mmol), O-(2,5-bistrifluoromethylbenzyl)hydroxylamine hydrochloride (296 mg, 1.0 mmol) and anhydrous NaOAc (53 mg, 0.65 mmol) in MeOH (5 mL) and H$_2$O (15 mL) was adjusted to pH 4.5 with AcOH and heated for 15 h at reflux. The reaction mixture was concentrated under vacuum and the residue filtered through a pad of silica (eluting with CH$_2$Cl$_2$). Purification by radial thin layer chromatography (eluting with CH$_2$Cl$_2$/PE, 1:19 to 1:9) afforded N-{2-[1-(2,5-bistrifluoromethylbenzyloxyimino)ethyl]-4-chlorophenyl}trifluoromethanesulfonamide 120 (100 mg, 19%), as a pale yellow solid. M.p. 73-75° C. $^1$H n.m.r. (200 MHz, CDCl$_3$) δ 10.94, brs, 1H; 7.88-7.71, m, 3H; 7.60, d, J=8.8 Hz, 1H; 7.50, d, J=2.4 Hz, 1H; 7.33, dd, J=2.4 and 8.8 Hz, 1H; 5.46, s, 2H; 2.41, s, 3H.

Preparation of O-(2,5-bistrifluoromethylbenzyl)hydroxylamine hydrochloride a) To a solution of N-hydroxyphthalimide (5.30 g, 32.49 mmol) in DMF (25 mL) was added NEt$_3$ (4.96 mL, 35.58 mmol) and 2,5-bis(trifluoromethyl)benzyl bromide (10.0 g, 32.57 mmol) and the reaction was rapidly stirred for 15 h at RT. MeOH (2 mL) and H$_2$O (100 mL) were added and the reaction mixture was stirred at RT for 1 h, filtered and the solids washed with warm (ca. 40° C.) water and dried under vacuum to afford N-(2,5-bistrifluoromethylbenzyloxy)phthalimide (12.0 g, 95%), as a white solid.

b) A solution of N-(2,5-bistrifluoromethylbenzyloxy)phthalimide (12.0 g, 30.83 mmol) and n-BuNH$_2$ (3.10 mL, 31.31 mmol) was stirred at RT for 15 h. The reaction mixture was concentrated under vacuum, dissolved in CH$_2$Cl$_2$ (200 mL) and warmed with the aid of a heating mantle. 3N HCl (20 mL) was added dropwise to the warm reaction mixture which was stirred for 5 min. The reaction mixture was then stirred at RT for 5 min, filtered and dried under vacuum to afford O-(2,5-bistrifluoromethylbenzyl)hydroxylamine hydrochloride (7.30 g, 80%), as a white solid.

Example 1C

Preparation of N-{4-chloro-2-[1-(3-trifluoromethylphenoxyimino)ethyl]phenyl}trifluoromethanesulfonamide (Compound 134)

A solution of N-(2-acetyl-4-chlorophenyl)trifluoromethanesulfonamide 19 (310 mg, 1.03 mmol), O-(3-trifluoromethylphenyl)hydroxylamine hydrochloride (220 mg, 1.03 mmol) and anhydrous NaOAc (93 mg, 1.13 mmol) in EtOH (18 mL) was stirred for 15 h at RT. The reaction mixture was concentrated under vacuum and the residue filtered through a pad of silica (eluting with CH$_2$Cl$_2$/PE, 3:2). Purification by radial thin layer chromatography (eluting with CH$_2$Cl$_2$/PE, 1:5) afforded N-{4-chloro-2-[1-(3-trifluoromethylphenoxyimino)ethyl]phenyl}trifluoromethanesulfonamide 134 (430 mg, 91%), as a pale yellow solid. M.p. 63-64° C. $^1$H n.m.r. (200 MHz, CDCl$_3$) δ 11.00, br s, 1H; 7.71, d, J=9.0 Hz, 1H; 7.60, d, J=2.2 Hz, 1H; 7.56-7.35, m, 5H; 2.58, s, 3H. O-(3-Trifluoromethylphenyl)hydroxylamine hydrochloride was prepared in two steps by the procedure of Petrassi, M. H.; Sharpless, K. B.; Kelly, J. W. *Org. Lett.*, 2001, 3, 139-142.

Example 1D

Preparation of N-{4-chloro-2-[1-(4-fluorophenoxyimino)ethyl]phenyl}trifluoromethanesulfonamide (Compound 129)

A solution of N-(2-acetyl-4-chlorophenyl)trifluoromethanesulfonamide 19 (350 mg, 1.16 mmol), O-(4-fluorophenyl)hydroxylamine hydrochloride (190 mg, 1.16 mmol) and anhydrous NaOAc (104 mg, 1.27 mmol) in EtOH (16 mL) was stirred for 15 h at RT. The reaction mixture was concentrated under vacuum, the residue filtered through a pad of silica (eluting with CH$_2$Cl$_2$/PE, 3:2) and the solvent removed under reduced pressure. The residue was purified by radial thin layer chromatography (eluting with CH$_2$Cl$_2$/PE, 1:4) to afford N-{4-chloro-2-[1-(4-fluorophenoxyimino)ethyl]phenyl}trifluoromethanesulfonamide 129 (458 mg, 96%), as a pale yellow solid. M.p. 71-73° C. $^1$H n.m.r. (200 MHz, CDCl$_3$) δ 11.23, br s, 1H; 7.69, d, J=9.0 Hz, 1H; 7.59, d, J=2.4 Hz, 1H; 7.40, dd, J=2.4 and 9.0 Hz, 1H; 7.18-7.03, m, 4H; 2.55, s, 3H.

Preparation of O-(4-fluorophenyl)hydroxylamine hydrochloride a) To N-hydroxyphthalimide (1.0 g, 6.12 mmol), CuCl (606 mg, 6.12 mmol), ground freshly activated 4 Å molecular sieves (1.53 g) and 4-fluorophenylboronic acid (1.72 g, 12.29 mmol) was added 1,2-DCE (32 mL) and pyridine (0.544 mL, 6.73 mmol). The green/brown suspension was protected by a CaCl$_2$ guard tube and stirred for 63 h at RT. Silica gel (~20 g) was added and the reaction mixture was concentrated under reduced pressure. The residue was filtered through a pad of silica (eluting with PE; CH$_2$Cl$_2$/PE, 7:3 to 1:4) and the solvent concentrated under vacuum. The residue was purified by preparative chromatography over silica gel (eluting with CH$_2$Cl$_2$/PE, 1:1 to 3:2) to afford N-(4-fluorophenoxy)phthalimide (460 mg, 29%) as a pale yellow solid.

b) To a solution of N-(4-fluorophenoxy)phthalimide (690 mg, 2.68 mmol) in MeOH (2.6 mL) and CHCl$_3$ (23.4 mL) was added N$_2$H$_4$.H$_2$O (390 μL, 8.04 mmol) and the reaction was stirred at RT for 15 h. Silica gel (~6 g) was added and the reaction mixture was concentrated under reduced pressure. The residue was filtered through a pad of silica (eluting with $CH_2Cl_2$/PE, 4:1) and the solvent removed under reduced pressure to afford a dark yellow oil. The free amine was dissolved in $Et_2O$ (15 mL), cooled to 0° C. and acidified with 4N HCl in dioxane (1 mL) to give a white precipitate. The precipitate was washed three times with $Et_2O$ and dried under vacuum to yield O-(4-fluorophenyl)hydroxylamine hydrochloride (400 mg, 91%), as a white solid.

Example 1E

Preparation of N-[4-chloro-2-(1-cyclopentyloxyiminoethyl)phenyl]trifluoromethanesulfonamide (Compound 163)

N,N-Dimethylethylenediamine (254 µL, 2.20 mmol) was added to a solution of N-(cyclopentyloxy)phthalimide (345 mg, 1.50 mmol) in EtOH (5 mL), and the reaction allowed to stir at RT for 15 h. Glacial acetic acid (2 mL) was then added to adjust the mixture to ca. pH 4 followed by a solution of N-(2-acetyl-4-chlorophenyl)trifluoromethanesulfonamide 19 (302 mg, 1.0 mmol) in EtOH (2 mL), and the reaction stirred for 2.25 h at RT. The reaction mixture was concentrated under vacuum, and the residue purified by radial thin layer chromatography (eluting with $CH_2Cl_2$/PE, 1:19) to afford N-[4-chloro-2-(1-cyclopentyloxyiminoethyl)phenyl]trifluoromethanesulfonamide 163 (185 mg, 48%), as a pale yellow solid. $^1$H n.m.r. (400 MHz, $CDCl_3$) δ 12.18, br s, 1H; 7.67, d, J=8.8 Hz, 1H; 7.49, d, J=2.4 Hz, 1H; 7.31, dd, J=2.4 and 8.8 Hz, 1H; 4.80, m, 1H; 2.30, s, 3H; 1.89, m, 4H; 1.74, m, 2H; 1.64, m, 2H. HRMS (M$^+$) 384.0518.

N-(Cyclopentyloxy)phthalimide was prepared by the procedure of Ishikawa, T.; Kamiyama, K.; Matsunaga, N.; Tawada, H.; Iizawa, Y.; Okonogi, K.; Miyake, A. *J. Antibiot.*, 2000, 53,1071-1085.

Example 1F

Preparation of N-{4-chloro-2-[1-(2-methoxyethoxyimino)ethyl]phenyl}trifluoromethanesulfonamide (Compound 185)

N,N-Dimethylethylenediamine (2.54 mL, 22.0 mmol) was added to a solution of N-(2-methoxyethoxy)phthalimide (3.32 g, 15.0 mmol) in EtOH (50 mL), and the reaction allowed to stir at RT for 15 h. Glacial acetic acid (20 mL) was then added to adjust the mixture to Ca. pH 4, followed by the addition of a solution of N-(2-acetyl-4-chlorophenyl)trifluoromethanesulfonamide 19 (3.02 g, 10.0 mmol) in EtOH (2 mL), and the mixture stirred for 65 h at RT. The reaction mixture was concentrated under vacuum and the residue filtered through a pad of silica (eluting with $CH_2Cl_2$/PE, 1:1). Purification by radial thin layer chromatography (eluting with $CH_2Cl_2$/PE, 1:9 to 1:1) afforded N-{4-chloro-2-[1-(2-methoxyethoxyimino)ethyl]phenyl}trifluoromethanesulfonamide 185 (3.0 g, 80%), as a colorless oil. $^1$H n.m.r. (400 MHz, $CDCl_3$) δ 11.40, br s, 1H; 7.65, d, J=8.8 Hz, 1H; 7.47, d, J=2.4 Hz, 1H; 7.33, dd, J=2.4 and 8.8 Hz, 1H; 4.37, m, 2H; 3.71, m, 2H; 3.41, s, 3H; 2.32, s, 3H. HRMS (M$^+$) 374.0308.

N-(2-methoxyethoxy)phthalimide was prepared using an analogous procedure to that described in Example 1A.

Example 1G

Preparation of N-[4-chloro-2-(1-cyclopropylmethoxyiminoethyl)phenyl]trifluoromethanesulfonamide (Compound 187)

N,N-Dimethylethylenediamine (254 µL, 2.20 mmol) was added to a solution of N-(cyclopropylmethoxy)phthalimide (326 mg, 1.50 mmol) in EtOH (5 mL), and the reaction allowed to stir at RT for 15 h. Glacial acetic acid (2 mL) was then added to adjust the mixture to ca. pH 4 followed by a solution of N-(2-acetyl-4-chlorophenyl)trifluoromethanesulfonamide 19 (302 mg, 1.0 mmol) in EtOH (2 mL), and the mixture stirred for 48 h at RT. The reaction mixture was concentrated under vacuum, and the residue purified by column chromatography (eluting with $CH_2Cl_2$/PE, 1:1) to afford N-[4-chloro-2-(1-cyclopropylmethoxyiminoethyl)phenyl]trifluoromethanesulfonamide 187 (300 mg, 81%), as a white solid. M.p. 53-54° C. $^1$H n.m.r. (400 MHz, $CDCl_3$) δ 11.84, br s, 1H; 7.65, d, J=8.8 Hz, 1H; 7.49, d, J=2.4 Hz, 1H; 7.32, dd, J=2.4 and 8.8 Hz, 1H; 4.03, d, J=7.2 Hz, 2H; 2.34, s, 3H; 1.22, m, 1H; 0.64, m, 2H; 0.34, m, 2H.

Preparation of N-(cyclopropylmethoxy)phthalimide

To a suspension of cyclopropyl methanol (562 µl, 6.93 mmol), triphenylphosphine (2.02 g, 7.63 mmol) and N-hydroxyphthalimide (1.28 g, 7.63 mmol) in THF (10 mL) at 0° C. was added dropwise diethylazodicarboxylate (1.20 mL, 7.63 mmol) in THF (10 mL). The reaction mixture was allowed to stir for 15 h after which the solvent was removed under vacuum to dryness. $Et_2O$ (15 mL) was added to triturate the triphenylphosphine oxide and diethylhydrazinedicarboxylate, which was filtered off and washed with a little $Et_2O$. The ethereal solution was concentrated under vacuum to give a residue which was filtered through a pad of silica (eluting with EtOAc/PE, 3:7). Removal of the solvent under reduced pressure afforded a pale yellow solid which was recrystallized from $CH_2Cl_2$/PE to give N-(cyclopropylmethoxy)phthalimide (1.30 g, 86%), as a white solid.

Example 1H

Preparation of N-{4-chloro-2-[1-(5-chlorothiophen-2-ylmethoxyimino)ethyl]phenyl}trifluoromethanesulfonamide (Compound 194)

N,N-Dimethylethylenediamine (178 µL, 1.54 mmol) was added to a solution of N-(5-chlorothiophen-2-ylmethoxy)phthalimide (220 mg, 0.75 mmol) in EtOH (5 mL), and the reaction allowed to stir at RT for 15 h. Glacial acetic acid (1 mL) was then added to adjust the mixture to ca. pH 4 followed by a solution of N-(2-acetyl-4-chlorophenyl)trifluoromethanesulfonamide 19 (211 mg, 0.70 mmol) in EtOH (2 mL), and the mixture stirred for 15 h at RT. The reaction mixture was concentrated under vacuum, and the residue purified by column chromatography (eluting with $CH_2Cl_2$/PE, 1:1) to afford N-{4-chloro-2-[1-(5-chlorothiophen-2-ylmethoxyimino)ethyl]phenyl}trifluoromethanesulfonamide 194 (280 mg, 90%), as white crystals. $^1$H n.m.r. (400 MHz, $CDCl_3$) δ 11.37, br s, 1H; 7.63, d, J=8.8 Hz, 1H; 7.48, d, J=2.4 Hz, 1H; 7.33, dd, J=2.4 and 8.8 Hz, 1H; 6.94, d, J=3.8 Hz; 6.81, d, J=3.8 Hz; 5.24, s, 2H; 2.33, s, 3H. HRMS (M$^+$) 445.9540.

N-(5-Chlorothiophen-2-ylmethoxy)phthalimide was prepared using the procedure reported in U.S. Pat. No. 4,071,533.

The following trifluoromethanesulfonanilide oxime ether compounds, as listed by Tables 8 and 8A, infra, were prepared using similar preparative methods: Compounds 1, 3, 4, 13-23, 25-29, 32, 33, 35, 36, 38-60, 73, 121-127, 132, 135, 137, 140, 141, 143, 144, 147, 149, 151, 158, 160, 161, 172-175, 181, 185, 186, 188-190, 202, 203, 223, 242, 244, 246, 249, 253, 255, 258, 260, 261, 263, 264, 266, 267, 269, 270, 272, 273, 275, 276, 278-280, 282, 283, 285, 286, 288 and 289.

Additional data for the compounds of Example 1, supra, is provided by Table 2, below.

TABLE 2

| Compd # | $^1$H n.m.r. |
| --- | --- |
| 19 | (200MHz, CDCl$_3$) (5:4 mixture of E- and Z-isomers) δ 11.29, br s, 2H; 7.61, d, J=9.0Hz, 1H; 7.49-7.20, m, 11H; 5.34, s, 2H; 5.28, s, 2H; 2.37, s, 3H; 2.26, s, 3H. |
| 21 | (200MHz, CDCl$_3$) δ 11.31, br s, 1H; 7.62, d, J=9.0Hz, 1H; 7.48, d, J=2.4Hz, 1H; 7.43, d, J=2.0Hz, 1H; 7.41-7.25, m, 3H; 5.29, s, 2H; 2.36, s, 3H. |
| 127 | (200MHz, CDCl$_3$) δ 11.17, br s, 1H; 7.70, d, J=9.0Hz, 1H; 7.59, d, J=2.4Hz, 1H; 7.41, dd, J=2.4 and 9.0Hz, 1H; 7.35, d, J=9.0Hz, 2H; 7.11, d, J=9.0Hz, 2H; 2.55, s, 3H. |
| 132 | (200MHz, CDCl$_3$) δ 11.06, br s, 1H; 7.71, d, J=8.8Hz, 1H; 7.59, d, J=2.4Hz, 1H; 7.41, dd, J=2.4 and 8.8Hz, 1H; 7.36-7.04, m, 4H; 2.55, s, 3H. |
| 186 | (400MHz, CDCl$_3$) δ 10.50, br s, 1H; 7.67, d, J=8.8Hz, 1H; 7.49, d, J=2.4Hz, 1H; 7.38, dd, J=2.4 and 8.8Hz, 1H; 4.55, q, $J_{HF}$=8.0Hz, 2H; 2.38, s, 3H. |
| 189 | (400MHz, CDCl$_3$) δ 11.97, br s, 1H; 7.66, d, J=8.8Hz, 1H; 7.49, d, J=2.4Hz, 1H; 7.32, dd, J=2.4 and 8.8Hz, 1H; 4.11, d, J=7.2Hz, 2H; 2.36-2.29, m, 4H; 1.83-1.75, m, 2H; 1.66-1.55, m, 4H; 1.35-1.27, m, 2H. |
| 202 | (400MHz, CDCl$_3$) δ 10.95, br s, 1H; 7.68, d, J=8.8Hz, 1H; 7.47, d, J=2.4Hz, 1H; 7.35, dd, J=2.4 and 8.8Hz, 1H; 4.78, d, J=2.4Hz, 2H; 2.61, t, J=2.4Hz, 1H; 2.33, s, 3H. |
| 223 | (400MHz, CDCl$_3$) δ 12.27, br s, 1H; 7.70, d, J=8.8Hz, 1H; 7.50, d, J=2.4Hz, 1H; 7.31, dd, J=2.4 and 8.8Hz, 1H; 2.32, s, 3H; 1.39, s, 9H. |

Example 2

Preparation of N-(4-chloro-2-propionylphenyl)trifluoromethanesulfonamide (Formula 22)

Figure 5:
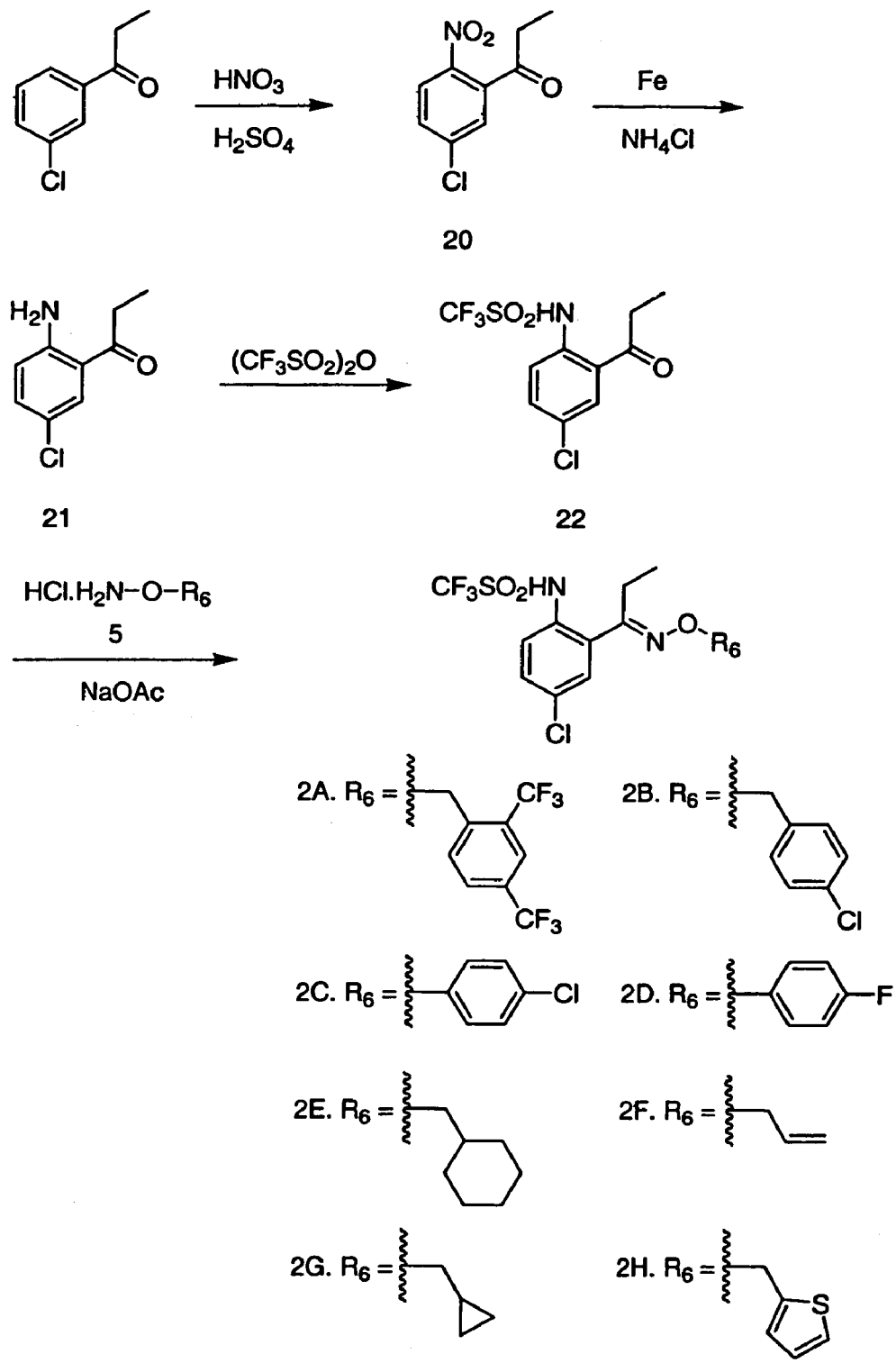
FIG. 5 illustrates the preparative reactions of Examples 2A through 2H.

The following compounds were prepared according to the reaction scheme illustrated by FIG. 5.

a) To a rapidly stirred solution of fuming HNO$_3$ (9 mL) and concentrated H$_2$SO$_4$ (1.3 mL) at −20° C. was added portionwise 3-chloropropiophenone (2.50 g, 14.82 mmol) over 15 min. The reaction mixture was allowed to warm to −10° C. and stirred for 2.25 h at this temperature after which ice-H$_2$O (75 mL) was added and the reaction mixture extracted twice with CH$_2$Cl$_2$. The organic layers were combined, washed five times with water, dried over MgSO$_4$ and concentrated under reduced pressure. The residue was filtered through a pad of silica (eluting with CH$_2$Cl$_2$/PE, 7:3) to afford 1-(5-chloro-2-nitrophenyl)propan-1-one 20 (2.99 g, 94%), as a pale yellow solid.

b) To a mixture of 1-(5-chloro-2-nitrophenyl)propan-1-one 20 (2.49 g, 11.66 mmol) in EtOH (20 mL) and H$_2$O (10 mL) was added iron powder (3.25 g, 58.28 mmol) and NH$_4$Cl (312 mg, 5.83 mmol) and the reaction was rapidly stirred at 90° C. for 30 min. The hot reaction mixture was filtered (the residues were washed with EtOAc) and further EtOAc and H$_2$O added. The EtOAc layer was separated, dried over MgSO$_4$ and concentrated under reduced pressure. The residue was filtered through a pad of silica (eluting with CH$_2$Cl$_2$/PE, 7:3) to afford 1-(2-amino-5-chlorophenyl)propan-1-one 21 (1.95 g, 91%), as a yellow solid.

c) To a solution of 1-(2-amino-5-chlorophenyl)propan-1-one 21 (2.12 g, 11.54 mmol) in anhydrous dichloromethane (80 mL) at 0° C. was added dropwise (CF$_3$SO$_2$)$_2$O (2.91 mL, 17.32 mmol) in anhydrous CH$_2$Cl$_2$ (30 mL) over 30 minutes and the reaction allowed to warm to RT overnight. The reaction mixture was washed with water, dried over MgSO$_4$ and concentrated under vacuum. The residue was filtered through a pad of silica (eluting with CH$_2$Cl$_2$/PE, 3:2) to afford a yellow oil which was recrystallized from Et$_2$O/PE to give N-(4-chloro-2-propionylphenyl)trifluoromethanesulfonamide 22 (3.12 g, 86%), as pale yellow crystals. M.p. 54-55° C. $^1$H n.m.r. (200 MHz, CDCl$_3$) δ 12.06, br s, 1H; 7.93, d, J=2.4 Hz, 1H; 7.75, d, J=9.0 Hz, 1H; 7.54, dd, J=2.4 and 9.0 Hz, 1H; 3.09, q, J=7.2 Hz, 2H; 1.24, t, J=7.2 Hz, 3H.

Example 2A

Preparation of N-{2-[1-(2,4-bistrifluoromethylbenzyloxyimino)propyl]-4-chlorophenyl}trifluoromethanesulfonamide (Compound 76)

A solution of N-(4-chloro-2-propionylphenyl)trifluoromethanesulfonamide 22 (3.21 mg, 10.17 mmol), O-(2,4-bistrifluoromethylbenzyl)hydroxylamine hydrochloride (3.16 mg, 10.68 mmol) and anhydrous NaOAc (876 mg, 10.68 mmol) in EtOH (120 mL) was stirred for 15 h at RT. The reaction mixture was concentrated under vacuum and the residue filtered through a pad of silica (eluting with CH$_2$Cl$_2$/PE, 2:3). Purification by radial thin layer chromatography (eluting with CH$_2$Cl$_2$/PE, 1:9) afforded a pale yellow solid which was recrystallized from CH$_2$Cl$_2$/PE to give N-{2-[1-(2,4-bistrifluoromethylbenzyloxyimino)propyl]-4-chlorophenyl}trifluoromethanesulfonamide 76 (3.70 g, 65%), as a pale yellow oil. $^1$H n.m.r. (200 MHz, CDCl$_3$) δ 10.96, br s, 1H; 7.96, s, 1H; 7.85, d, J=8.4 Hz, 1H; 7.72, d, J=8.4 Hz, 1H; 7.61, d, J=8.8 Hz, 1H; 7.49, d, J=2.4 Hz, 1H; 7.33, dd, J=2.4 and 8.8 Hz, 1H; 5.45, s, 2H; 2.88, q, J=7.6 Hz, 2H; 1.21, t, J=7.6 Hz, 3H. HRMS (M+) 556.0254.

O-(2,4-Bistrifluoromethylbenzyl)hydroxylamine hydrochloride was prepared by the procedure described in Example 1A.

Example 2B

Preparation of N-{4-chloro-2-[1-(4-chlorobenzyloxyimino)propyl]phenyl}trifluoromethanesulfonamide (Compound 11)

A solution of N-(4-chloro-2-propionylphenyl)trifluoromethanesulfonamide 22 (1.75 g, 5.54 mmol), O-(4-chlorobenzyl)hydroxylarmine hydrochloride (1.13 g, 5.82 mmol) and anhydrous NaOAc (477 mg, 5.82 mmol) in EtOH (80 mL) was stirred for 15 h at RT. The reaction mixture was concentrated under vacuum and the residue filtered through a pad of silica (eluting with $CH_2Cl_2$/PE, 3:2). Purification by radial thin layer chromatography (eluting with $CH_2Cl_2$/PE, 1:9) afforded a pale yellow solid which was recrystallized from $CH_2Cl_2$/PE to give N-{4-chloro-2-[1-(4-chlorobenzyloxyimino)propyl]phenyl}trifluoromethanesulfonamide 11 (1.74 mg, 69%), as a white solid. M.p. 54-55° C. $^1$H n.m.r. (200 MHz, $CDCl_3$) δ 11.55, br s, 1H; 7.63, d, J=8.8 Hz, 1H; 7.47, d, J=2.2 Hz, 1H; 7.39-7.29, m, 5H; 5.17, s, 2H; 2.84, q, J=7.6 Hz, 2H; 1.18, t, J=7.6 Hz, 3H.

O-(4-Chlorobenzyl)hydroxylamine hydrochloride was prepared in two steps using an analogous procedure to that described in Example 1A.

Example 2C

Preparation of N-{4-chloro-2-[1-4-chlorophenoxyimino)propyl]phenyl}trifluoromethanesulfonamide (Compound 128)

A solution of N-(4-chloro-2-propionylphenyl)trifluoromethanesulfonamide 22 (450 mg, 1.43 mmol), O-(4-chlorophenyl)hydroxylamine hydrochloride (257 mg, 1.43 mmol) and anhydrous NaOAc (125 mg, 1.52 mmol) in EtOH (23 mL) was stirred for 15 h at RT. The reaction mixture was concentrated under vacuum and the residue filtered through a pad of silica (eluting with $CH_2Cl_2$/PE, 3:2). The residue was purified by radial thin layer chromatography (eluting with $CH_2Cl_2$iPE, 1:5) to afford N-{4-chloro-2-[1-(4-chlorophenoxyimino)propyl]phenyl}trifluoromethanesulfonamide 128 (455 mg, 72%), as a yellow solid. M.p. 87-88° C. $^1$H n.m.r. (200 MHz, $CDCl_3$) δ 11.18, br s, 1H; 7.71, d, J=8.8 Hz, 1H; 7.58, d, J=2.6 Hz, 1H; 7.41, dd, J=2.6 and 8.8 Hz, 1H; 7.35, d, J=8.8 Hz, 2H; 7.11, d, J=8.8 Hz, 2H; 3.02, q, J=7.6 Hz, 2H; 1.30, t, J=7.6 Hz, 3H.

Preparation of O-(4-chlorophenyl)hydroxylamine hydrochloride a) To N-hydroxyphthalimide (1.0 g, 6.12 mmol), CuCl (606 mg, 6.12 mmol), ground freshly activated 4 Å molecular sieves (1.53 g) and 4-chlorophenylboronic acid (1.92 g, 12.28 mmol) was added 1,2-DCE (32 mL) and pyridine (0.544 mL, 6.73 mmol). The green/brown suspension was protected by a $CaCl_2$ guard tube and stirred for 29 hours at RT. Silica gel (~10 g) was added and the reaction mixture was adsorbed by concentration of the solvent under reduced pressure. The residue obtained was purified by preparative chromatography over silica gel (eluting with EtOAc/PE, 1:9) to afford N-(4-chlorophenoxy)phthalimide (1.02 g, 61%), as a white solid.

b) To a solution of N-(4-chlorophenoxy)phthalimide (660 mg, 2.41 mmol) in MeOH (2.5 mL) and $CHCl_3$ (22.5 mL) was added $N_2H_4.H_2O$ (0.35 mL, 7.23 mmol) and the reaction was stirred at RT for 15 hours. Silica gel (~6 g) was added and the reaction mixture was adsorbed by concentration of the solvent under vacuum. The residue was filtered through a pad of silica (eluting with $CH_2Cl_2$/PE, 4:1) and the solvent removed under reduced pressure to afford a dark yellow oil. The free amine was dissolved in $Et_2O$ (15 mL), cooled to 0° C., and acidified with 4N HCl in dibxane (1 mL) to give a white precipitate. The solvent was decanted from the precipitate which was washed twice with $Et_2O$ and dried under vacuum to yield O-(4-chlorophenyl)hydroxylamine hydrochloride (340 mg, 79%), as a white solid.

Example 2D

Preparation of N-{4-chloro-2-[1-(4-fluorophenoxyimino)propyl]phenyl}trifluoromethanesulfonamide (Compound 130)

A solution of N-(4-chloro-2-propionylphenyl)trifluoromethanesulfonamide 22 (386 mg, 1.22 mmol), O-(4-fluorophenyl)hydroxylamine hydrochloride (200 mg, 1.22 mmol) and anhydrous NaOAc (110 mg, 1.34 mmol) in EtOH (18 mL) was stirred for 15 hours at RT. The reaction mixture was concentrated under vacuum and the residue filtered through a pad of silica (eluting with $CH_2Cl_2$/PE, 3:2). The residue was purified by radial thin layer chromatography (eluting with $CH_2Cl_2$/PE, 1:4) to afford N-{4-chloro-2-[1-(4-fluorophenoxyimino)propyl]phenyl}trifluoromethanesulfonamide 130 (420 mg, 81%), as a pale yellow solid. M.p. 47-48° C. $^1$H n.m.r. (200 MHz, $CDCl_3$) δ 11.25, br s, 1H; 7.71, d, J=8.8 Hz, 1H; 7.58, d, J=2.4 Hz, 1H; 7.40, dd, J=2.4 and 8.8 Hz, 1H; 7.18-7.02, m, 4H; 3.02, q, J=7.6 Hz, 2H; 1.31, t, J=7.6 Hz, 3H.

O-(4-Fluorophenyl)hydroxylamine hydrochloride was prepared by the procedure described in Example 1D.

Example 2E

Preparation of N-[4-chloro-2-(1-cyclohexylmethoxyiminopropyl)phenyl]trifluoromethanesulfonamide (Compound 104)

N,N-Dimethylethylenediamine (1.53 mL, 13.18 mmol) was added to a solution of N-(cyclohexylmethoxy)phthalimide (2.33 g, 8.99 mmol) in EtOH (30 mL), and the reaction allowed to stir at RT for 2 hours. Glacial acetic acid (5 mL) was then added to adjust the mixture to ca. pH 4 followed by a solution of N-(4-chloro-2-propionylphenyl)trifluoromethanesulfonamide 22 (1.89 g, 5.99 mmol) in EtOH (10 mL), and the reaction stirred for 15 hours at RT. The reaction mixture was concentrated under vacuum, and the residue dissolved in $Et_2O$ (50 mL) and washed with water, brine, dried over $MgSO_4$ and the solvent removed under reduced pressure. The residue was purified by column chromatography (eluting with $CH_2Cl_2$/PE, 3:4 to 1:3) to afford N-[4-chloro-2-(1-cyclohexylmethoxyiminopropyl)phenyl]trifluoromethanesulfonamide 104 (2.34 g, 91%), as colorless crystals. $^1$H n.m.r. (400 MHz, $CDCl_3$) δ 12.01, br s, 1H; 7.67, d, J=8.8 Hz, 1H; 7.48, d, J=2.4 Hz, 1H; 7.32, dd, J=2.4 and 8.8 Hz, 1H; 4.02, d, J=6 Hz, 2H; 2.81, q, J=7.6Hz, 2H; 1.74, m, 6H; 1.27, m, 3H; 1.19, t, J=7.6Hz, 3H; 1.01, m, 2H. HRMS (M+) 426.0971.

Preparation of N-(cyclohexylmethoxy)phthalimide

To a stirred solution of N-hydroxyphthalimide (10.0 g, 61.30 mmol) in DMF (40 mL) at RT was added NEt$_3$ (9.40 mL, 67.43 mmol) and, in a dropwise fashion, (bromomethyl) cyclohexane (9.41 mL, 67.43 mmol). The reaction was then stirred for 15 hours at 50° C., after which it was allowed to cool to RT and then concentrated under vacuum. The residue was dissolved in Et$_2$O (100 mL) and washed with water, brine, dried over MgSO$_4$ and the solvent removed under reduced pressure. The residue was purified by column chromatography (eluting with CH$_2$Cl$_2$/PE, 1:1 to 3:1) to afford N-(cyclohexylmethoxy)phthalimide (8.40 g, 53%), as a white solid.

Example 2F

Preparation of N-[2-(1-allyloxyiminopropyl)-4-chlorophenyl]trifluoromethanesulfonamide (Compound 156)

A solution of N-(4-chloro-2-propionylphenyl)trifluoromethanesulfonamide 22 (316 mg, 1.0 mmol), O-allylhydroxylamine hydrochloride (119 mg, 1.05 mmol) and anhydrous NaOAc (86 mg, 1.05 mmol) in EtOH (5 mL) was stirred for 15 hours at RT. The reaction mixture was concentrated under vacuum and the residue filtered through a pad of silica (eluting with EtOAc/PE, 1:9). The residue was purified by radial thin layer chromatography (eluting with CH$_2$Cl$_2$/PE, 1:99 to 1:19) to afford N-[2-(1-allyloxyiminopropyl)-4-chlorophenyl]trifluoromethanesulfonamide 156 (116 mg, 31%), as a colorless oil. $^1$H n.m.r. (400 MHz, CDCl$_3$) δ 11.57, br s, 1H; 7.67, d, J=8.8 Hz, 1H; 7.48, d, J=2.4 Hz, 1H; 7.33, dd, J=2.4 and 8.8 Hz, 1H; 6.00, m, 1H; 5.42, d, $^3$J=17.2 Hz, 1H; 5.36, d, $^3$J=10.4 Hz, 1H; 4.68, d, J=6.0 Hz, 2H; 2.83, q, J=7.6 Hz, 2H; 1.19, t, J=7.6 Hz, 3H. HRMS (M$^+$) 370.0350.

Example 2G

Preparation of N-[4-chloro-2-(1-cyclopropylmethoxyiminopropyl)phenyl]trifluoromethanesulfonamide (Compound 196)

N,N-Dimethylethylenediamine (254 μL, 2.20 mmol) was added to a solution of N-(cyclopropylmethoxy)phthalimide (326 mg, 1.50 mmol) in EtOH (5 mL), and the reaction allowed to stir at RT for 15 h. Glacial acetic acid (2 mL) was then added to adjust the mixture to ca. pH 4 followed by the addition of a solution of N-(4-chloro-2-propionylphenyl) trifluoromethanesulfonamide 22 (316 mg, 1.0 mmol) in EtOH (2 mL), and the mixture stirred for 65 h at RT. The reaction mixture was concentrated under vacuum, and the residue purified by column chromatography (eluting with CH$_2$Cl$_2$/PE, 1:1) to afford N-[4-chloro-2-(1-cyclopropylmethoxyiminopropyl)phenyl]trifluoromethanesulfonamide 196 (205 mg, 53%), as a colorless oil. $^1$H n.m.r. (400 MHz, CDCl$_3$) δ 11.88, br s,1H; 7.66, d, J=8.8 Hz, 1H; 7.49, d, J=2.4 Hz, 1H; 7.33, dd, J=2.4 and 8.8 Hz, 1H; 4.02, d, J=7.2 Hz, 1H; 2.83, q, J=7.6 Hz, 2H; 1.22, m, 4H; 0.64, m, 2H; 0.33, m, 2H. HRMS (M$^+$) 384.0515.

N-(cyclopropylmethoxy)phthalimide was prepared by the procedure described in Example 1G.

Example 2H

Preparation of N-{4-chloro-2-[1-(thiophen-2-yl-methoxyimino)propyl] phenyl}trifluoromethanesulfonamide (Compound 207)

N,N-Dimethylethylenediamine (254 μL, 2.20 mmol) was added to a solution of N-(thiophen-2-ylmethoxy)phthalimide (365 mg, 1.50 mmol) in EtOH (5 mL), and the reaction allowed to stir at RT for 15 h. Glacial acetic acid (1 mL) was then added to adjust the mixture to ca. pH 4 followed by a solution of N-(4-chloro-2-propionylphenyl)trifluoromethanesulfonamide 22 (316 mg, 1.0 mmol) in EtOH (2 mL), and the mixture stirred for 15 h at RT. The reaction mixture was concentrated under vacuum, and the residue purified by column chromatography (eluting with CH$_2$Cl$_2$/PE, 1:1) to afford N-{4-chloro-2-[1-(thiophen-2-ylmethoxyimino)propyl]phenyl}trifluoromethanesulfonamide 207 (364 mg, 85%), as a white solid. M.p. 53-54° C. $^1$H n.m.r. (400 MHz, CDCl$_3$) δ 11.49, br s,1H; 7.64, d, J=8.8 Hz, 1H; 7.47, d, J=2.4 Hz, 1H; 7.33, m, 2H; 7.16, m, 1H; 7.01, m, 1H; 2.82, q, J=7.6 Hz, 2H; 1.17, t, J=7.6 Hz, 3H. HRMS (M$^+$) 426.0065.

Preparation of N-(thiophen-2-ylmethoxy)phthalimide

To a suspension of 2-thiophenemethanol (4.15 mL, 43.64 mmol), triphenylphosphine (12.59 g, 48.01 mmol) and N-hydroxyphthalimide (7.83 g, 48.01 mmol) in THF (120 mL) at 0° C. was added dropwise diethylazodicarboxylate (7.56 mL, 48.01 mmol) in THF (20 mL). The reaction mixture was allowed to stir for 15 h after which the solvent was removed under vacuum to dryness. Et$_2$O (50 mL) was added to triturate the triphenylphosphine oxide and diethylhydrazinedicarboxylate, which was filtered off and washed with a little Et$_2$O. The ethereal solution was concentrated under vacuum to give a residue which was filtered through a pad of silica (eluting with EtOAc/PE, 3:7). Removal of the solvent under reduced pressure afforded N-(thiophen-2-ylmethoxy)phthalimide (1.50 g, 13%), as a pale yellow solid.

The following trifluoromethanesulfonanilide oxime ether compounds, as listed by Tables 8 and 8A, were prepared using similar preparative methods: Compounds 5-10, 12, 34, 37, 72, 74, 75, 77, 79, 84-86, 91, 93, 94, 103, 105-107, 109, 131, 133, 136, 138, 139, 142, 145, 146, 148, 150, 152-157, 159, 170, 171, 183, 184, 197, 204-206, 207, 208, 224, 243, 245, 247, 248, 250, 254, 256, 257, 259, 262, 265, 268, 271, 274, 277, 281, 284, 287 and 290.

Additional data for compounds of Example 2 are provided by Table 3, below.

TABLE 3

| Compd # | $^1$H n.m.r. |
|---|---|
| 9 | (200MHz, CDCl$_3$) δ 11.41, br s, 1H; 7.67-7.60, m, 3H; 7.53-7.48, m, 3H; 7.32, dd, J=2.2 and 8.8Hz, 1H; 5.26, s, 2H; 2.86, q, J=7.6Hz, 2H; 1.20, t, J=7.6Hz, 3H. |
| 72 | (200MHz, CDCl$_3$) δ 11.34, br s, 1H; 7.63, d, J=9.2Hz, 1H; 7.50-7.45, m, 2H; 7.39-7.20, m, 3H; 5.32, s, 2H; 2.86, q, J=7.6Hz, 2H; 1.20, t, J=7.6Hz, 3H. |

TABLE 3-continued

| Compd # | $^1$H n.m.r. |
|---|---|
| 131 | (200MHz, CDCl$_3$) δ 11.07, br s, 1H; 7.71, d, J=8.8Hz, 1H; 7.57, d, J=2.4Hz, 1H; 7.40, dd, J=2.4 and 8.8Hz, 1H; 7.34-7.03, m, 4H; 3.00, q, J=7.6Hz, 2H; 1.29, t, J=7.6Hz, 3H. |
| 138 | (200MHz, CDCl$_3$) δ 11.15, br s, 1H; 7.72, d, J=9.2Hz, 1H; 7.58, m, 1H; 7.49, d, J=8.8Hz, 2H; 7.42, m, 1H; 7.06, d, J=8.8Hz, 2H; 3.02, q, J=7.6Hz, 2H; 1.31, t, J=7.6Hz, 3H. |
| 155 | (400MHz, CDCl$_3$) δ 12.19, br s, 1H; 7.68, d, J=8.8Hz, 1H; 7.48, d, J=2.4Hz, 1H; 7.32, dd, J=2.4 and 8.8Hz, 1H; 4.79, m, 1H; 2.79, q, J=7.6Hz, 2H; 1.95-1.82, m, 4H; 1.74, m, 2H; 1.63, m, 2H; 1.17, t, J=7.6Hz, 3H. |
| 205 | (400MHz, CDCl$_3$) δ 11.27, br s, 1H; 7.62, d, J=8.8Hz, 1H; 7.44, d, J=2.4Hz, 1H; 7.32, dd, J=2.4 and 8.8Hz, 1H; 4.20, m, 3H; 3.83-3.95, m, 2H; 2.71-2.88, m, 2H; 2.04, m, 1H, 1.90, m, 2H; 1.58, m, 1H; 1.18, t, J=8.0Hz, 3H. |
| 208 | (400MHz, CDCl$_3$) δ 10.94, br s, 1H; 7.70, d, J=8.8Hz, 1H; 7.47, d, J=2.4Hz, 1H; 7.35, dd, J=2.4 and 8.8Hz, 1H; 4.76, d, J=2.4Hz, 2H; 2.82, q, J=7.6Hz, 2H; 2.61, t, J=2.4Hz, 1H; 1.18, J=7.6Hz, 3H. |
| 224 | (400MHz, CDCl$_3$) δ 12.26, br s, 1H; 7.71, d, J=8.8Hz, 1H; 7.50, d, J=2.4Hz, 1H; 7.31, dd, J=2.4 and 8.8Hz, 1H; 2.81, q, J=7.6Hz, 2H; 1.38, s, 9H; 1.17, J=7.6Hz, 3H. |

Example 3

Preparation of N-(4-chloro-2-formylphenyl)trifluoromethanesulfonamide (Formula 24)

Figure 6:
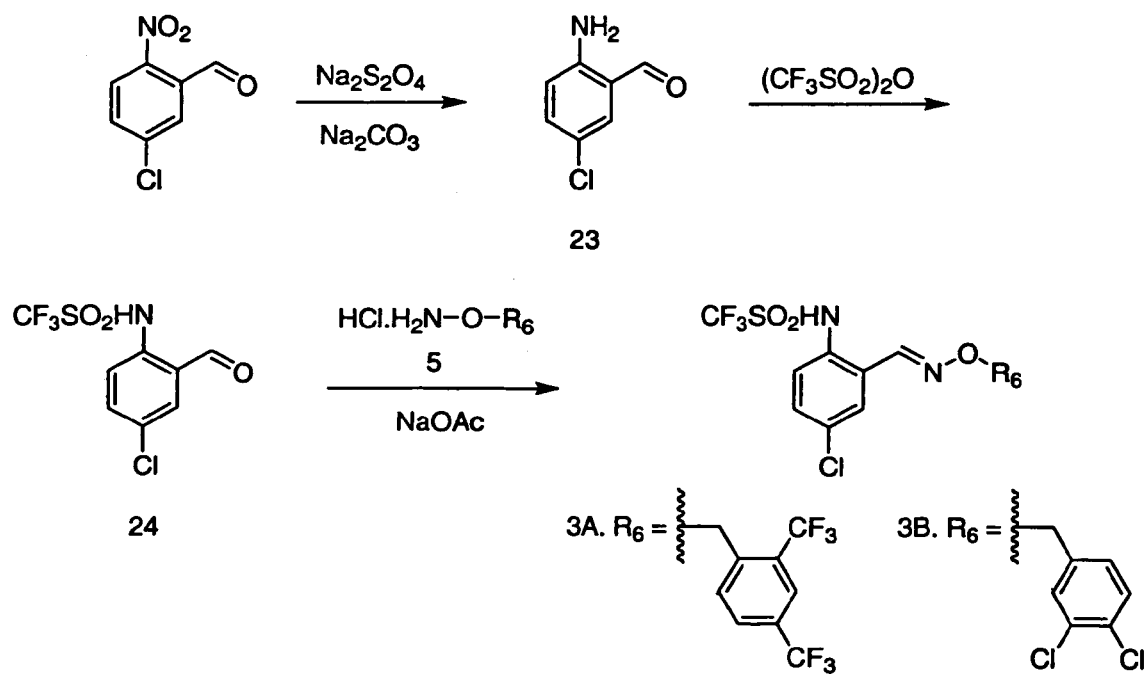
FIG. 6 illustrates the preparative reactions of Examples 3A and 3B.

The following compounds were prepared according to the reaction scheme illustrated by FIG. 6.

a) To a solution of Na$_2$S$_2$O$_4$ (tech., ~85%) (29.72 g, 145.09 mmol) and Na$_2$CO$_3$ (12.98 g, 122.46 mmol) in H$_2$O (500 mL) at 45° C. was added dropwise 5-chloro-2-nitrobenzaldehyde (tech., ~80%) (5.31 g, 22.89 mmol) in MeOH (100 mL) over 25 min. The reaction mixture was heated to 65° C., allowed to cool to RT and extracted three times with CH$_2$Cl$_2$. The combined organics were washed with H$_2$O, dried and the solvent concentrated under reduced pressure. The residue was filtered through a pad of silica (eluting with CH$_2$Cl$_2$/PE, 4:1) and the solvent concentrated under reduced pressure to afford 2-amino-5-chlorobenzaldehyde 23 (2.12 g, 60%), as a yellow oil.

b) To a solution of 2-amino-5-chlorobenzaldehyde 23 (2.12 g, 13.62 mmol) and Et$_3$N (1.99 mL, 14.31 mmol) in anhydrous dichloromethane (120 mL) at −78° C. was added dropwise (CF$_3$SO$_2$)$_2$O (2.41 mL, 14.31 mmol) in anhydrous CH$_2$Cl$_2$ (30 mL) over 10 min. The reaction mixture was allowed to warm to RT over 15 h, washed with water, dried over MgSO$_4$ and concentrated under vacuum. The residue was filtered through a pad of silica (eluting with CH$_2$Cl$_2$/PE, 3:7 to 100% CH$_2$Cl$_2$) to afford N-(4-chloro-2-formylphenyl)trifluoromethanesulfonamide 24 (938 mg, 24%), as a brown oil. $^1$H n.m.r. (200 MHz, CDCl$_3$) δ 11.11, br s, 1H; 9.89, s, 1H; 7.79-7.74, m, 2H; 7.62, dd, J=2.4 and 8.8 Hz, 1H. HRMS (M$^+$) 286.9629.

Example 3A

Preparation of N-{2-[(2,4-bistrifluoromethylbenzyloxyimino)methyl]-4-chlorophenyl}trifluoromethanesulfonamide (Compound 65)

A solution of N-(4-chloro-2-formylphenyl)trifluoromethanesulfonamide 24 (180 mg, 0.63 mmol), O-(2,4-bistrifluoromethylbenzyl)hydroxylamine hydrochloride (342 mg, 1.16 mmol) and anhydrous NaOAc (141 mg, 1.72 mmol) in EtOH (10 mL) was stirred for 15 hours at RT. The reaction mixture was concentrated under vacuum and the residue filtered through a pad of silica (eluting with CHCl$_3$). Purification by radial thin layer chromatography (eluting with CH$_2$Cl$_2$/PE, 1:9 to 3:7) afforded N-{2-[(2,4-bistrifluoromethylbenzyloxyimino)methyl]-4-chlorophenyl}-trifluoromethanesulfonamide 65 (192 mg, 58%), as a yellow solid. M.p. 65-67° C. $^1$H n.m.r. (200 MHz, CDCl$_3$) δ 10.38, br s, 1H; 8.20, s, 1H; 7.97, s, 1H; 7.86, d, J=8.0 Hz, 1H; 7.75, d, J=8.0 Hz, 1H; 7.65, d, J=8.8 Hz, 1H; 7.35, dd, J=2.4 and 8.8 Hz, 1H; 7.28, d, J=2.4 Hz, 1H; 5.44, s, 2H.

O-(2,4-Bistrifluoromethylbenzyl)hydroxylamine hydrochloride was prepared by the procedure described in Example 1A.

Example 3B

Preparation of N-{4-chloro-2-[(3,4-dichlorobenzyloxyimino)methyl]phenyl}trifluoromethanesulfonamide (Compound 97)

A solution of N-(4-chloro-2-formylphenyl)trifluoromethanesulfonamide 24 (163 mg, 0.57 mmol), O-(3,4-dichlorobenzyl)hydroxylamine hydrochloride (130 mg, 0.57 mmol) and anhydrous NaOAc (77 mg, 0.94 mmol) in EtOH (10 mL) was stirred for 15 hours at RT. The reaction mixture was concentrated under vacuum and the residue filtered through a pad of silica (eluting with CHCl$_3$). Purification by radial thin layer chromatography (eluting with CH$_2$Cl$_2$/PE, 1:9) afforded N-{4-chloro-2-[(3,4-dichlorobenzyloxyimino)methyl]phenyl}trifluoromethanesulfonamide 97 (172 mg, 66%), as a colorless oil. $^1$H n.m.r. (200 MHz, CDCl$_3$) δ 10.65, br s, 1H; 8.14, s, 1H; 7.66, d, J=8.8 Hz, 1H; 7.51-7.45, m, 2H; 7.35, dd, J=2.4 and 8.8 Hz, 1H; 7.27-7.22, m, 2H; 5.12, s, 2H. HRMS (M$^+$) 459.9422.

O-(3,4-Dichlorobenzyl)hydroxylamine hydrochloride was prepared in two steps using an analogous procedure to that described in Example 1A.

The following trifluoromethanesulfonanilide oxime ether compounds, as listed by Tables 8 and 8A, infra, were prepared using similar preparative methods: Compounds 67, 70, 81, 95 and 96.

Additional data for compounds of Example 3 is provided by Table 4, below.

TABLE 4

| Compd # | $^1$H n.m.r. (200MHz, CDCl$_3$) |
|---|---|
| 95 | δ 10.63, br s, 1H; 8.16, s, 1H; 7.66, d, J=8.6Hz, 1H; 7.48, dd, J=2.0 and 8.0Hz, 1H; 7.41-7.31, m, 2H; 7.28-7.20, m, 2H; 5.32, s, 2H. |
| 96 | δ 8.11, s, 1H; 7.66, d, J=9.0Hz, 1H; 7.53, d, J=8.4Hz, 2H; 7.36-7.24, m, 4H; 5.13, s, 2H. |

Example 4

Preparation of N-(2-benzoyl-4-chlorophenyl)trifluoromethanesulfonamide (Formula 25)

Figure 7:
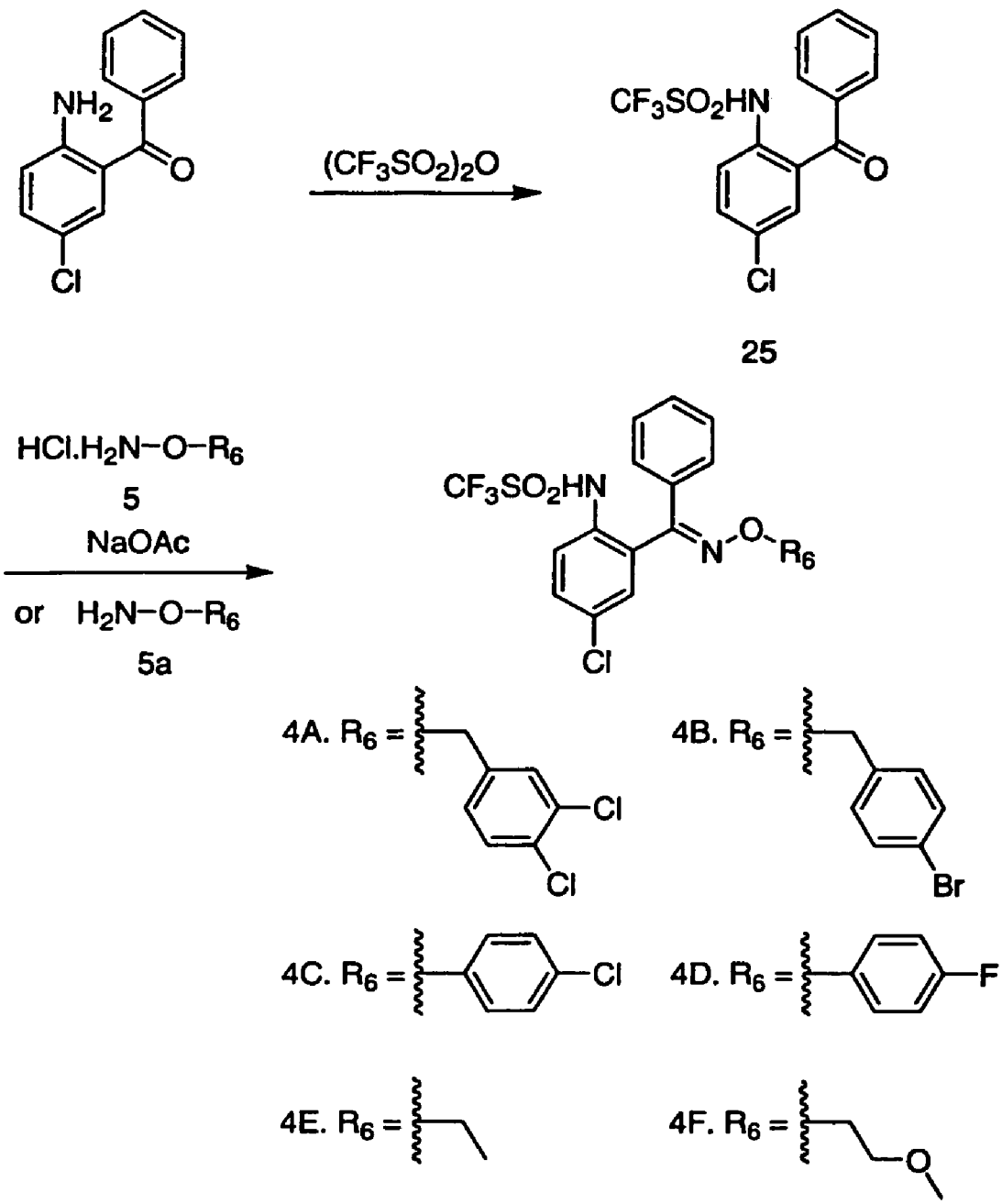
FIG. 7 illustrates the preparative reactions of Examples 4A through 4F.

The following compounds were prepared according to the reaction scheme illustrated by FIG. 7.

To a solution of 2-amino-5-chlorobenzophenone (500 mg, 2.16 mmol) in anhydrous CH$_2$Cl$_2$ (30 mL) at 0° C. was added dropwise (CF$_3$SO$_2$)$_2$O (545 µL, 3.24 mmol) in anhydrous CH$_2$Cl$_2$ (10 mL) over 10 min and the reaction allowed to warm to RT over 15 hours. The reaction mixture was washed with water, dried over MgSO$_4$ and concentrated under vacuum. The residue was filtered through a pad of silica (eluting with CH$_2$Cl$_2$/PE, 7:3) to afford N-(2-benzoyl-4-chlorophenyl)trifluoromethanesulfonamide 25 (710 mg, 90%), as a pale yellow solid. $^1$H n.m.r. (200 MHz, CDCl$_3$) δ 7.80-7.69, m, 3H; 7.66-7.51, m, 5H. HRMS (M$^+$) 362.9928.

Example 4A

Preparation of N-{4-chloro-2-[(3,4-dichlorobenzyloxyimino)phenylmethyl]phenyl}trifluoromethanesulfonamide (Compound 87)

A solution of N-(2-benzoyl-4-chlorophenyl)trifluoromethanesulfonamide 25 (710 mg, 1.95 mmol), O-(3,4-dichlorobenzyl)hydroxylamine hydrochloride (468 mg, 2.05 mmol) and anhydrous NaOAc (168 mg, 2.05 mmol) in EtOH (50 mL) was stirred for 15 hours at RT. The reaction mixture was concentrated under vacuum, the residue filtered through a pad of silica (eluting with CH$_2$Cl$_2$/PE, 3:2) and the solvent removed under reduced pressure. An isomeric mixture of E- and Z-oxime ether derivatives was obtained, which were separated by radial thin layer chromatography (eluting with CH$_2$Cl$_2$/PE, 7.5:92.5 to 1:5). The major isomer was obtained as a pale yellow solid which was recrystallized from CH$_2$Cl$_2$/PE to give N-{4-chloro-2-[(3,4-dichlorobenzyloxyimino)phenylmethyl]phenyl}trifluoromethanesulfonamide 87 (535 mg, 51%), as pale yellow crystals. M.p. 87-88° C. $^1$H n.m.r. (200 MHz, CDCl$_3$) δ 11.18, br s, 1H; 7.65, d, J=8.8 Hz, 1H; 7.55-7.40, m, 5H; 7.34-7.14, m, 4H; 6.88, d, J=2.2 Hz, 1H; 5.09, s, 2H. The minor isomer was obtained as a pale yellow solid (315 mg, 30%).

O-(3,4-Dichlorobenzyl)hydroxylamine hydrochloride was prepared in two steps using an analogous procedure to that described in Example 1A.

Example 4B

Preparation of N-{2-[(4-bromobenzyloxyimino)phenylmethyl]-4-chlorophenyl}trifluoromethanesulfonamide (Compound 64)

A solution of N-(2-benzoyl-4-chlorophenyl)trifluoromethanesulfonamide 25 (370 mg, 1.02 mmol), O-(4-bromobenzyl)hydroxylamine hydrochloride (270 mg, 1.13 mmol) and anhydrous NaOAc (90 mg, 1.10 mmol) in EtOH (20 mL) was stirred for 15 hours at RT. The reaction mixture was concentrated under vacuum and the residue filtered through a pad of silica (eluting with CH$_2$Cl$_2$/PE, 3:2). Purification by radial thin layer chromatography (eluting with CH$_2$Cl$_2$/PE, 1:9) afforded N-{2-[(4-bromobenzyloxyimino)phenylmethyl]-4-chlorophenyl}trifluoromethanesulfonamide 64 (210 mg, 38%), as a yellow solid. M.p. 55-56° C. $^1$H n.m.r. (200 MHz, CDCl$_3$) δ 11.32, br s, 1H; 7.66, d, J=9.0 Hz, 1H; 7.55-7.48, m, 5H; 7.33-7.20, m, 5H; 6.88, d, J=2.4 Hz, 1H; 5.11, s, 2H.

O-(4-Bromobenzyl)hydroxylamine hydrochloride was prepared in two steps using an analogous procedure to that described in Example 1A.

Example 4C

Preparation of N-{4-chloro-2-[(4-chlorophenoxyimino)phenylmethyl]phenyl}trifluoromethanesulfonamide (Compound 164)

N,N-Dimethylethylenediamine (82 µL, 0.75 mmol) was added to a suspension of O-(4-chlorophenyl)hydroxylamine hydrochloride (141 mg, 0.51 mmol) in EtOH (15 mL), and the reaction allowed to stir at RT for 15 hours. Glacial acetic acid (3 mL) was then added to adjust the mixture to ca. pH 4 followed by a solution of N-(2-benzoyl-4-chlorophenyl)trifluoromethanesulfonamide 25 (170 mg, 0.47 mmol) in EtOH (5 mL), and the reaction stirred for 63 hours at RT. The reaction mixture was concentrated under vacuum, and the residue dissolved in CH$_2$Cl$_2$ (50 mL), washed with water (twice), brine, dried over MgSO$_4$ and the solvent evaporated under reduced pressure. The residue was filtered through a pad of silica (eluting with CH$_2$Cl$_2$/PE, 3:7) and purified by radial thin layer chromatography (eluting with CH$_2$Cl$_2$/PE, 1:19 to 1:4) to afford N-{4-chloro-2-[(4-chlorophenoxyimino)phenylmethyl]phenyl}trifluoromethanesulfonamide 164 (140 mg, 61%), as a orange-brown solid. M.p. 86-87° C. $^1$H n.m.r. (200 MHz, CDCl$_3$) δ 10.99, br s, 1H; 7.73, d, J=8.8 Hz, 1H; 7.54, m, 3H; 7.43-7.27, m, 5H; 7.07, m, 1H; 7.01, m, 2H. O-(4-Chlorophenyl)hydroxylamine hydrochloride was prepared by the procedure described in Example 2C.

Example 4D

Preparation of N-{4-chloro-2-[(4-fluorophenoxyimino)phenylmethyl]phenyl}trifluoromethanesulfonamide (Compound 165)

N,N-Dimethylethylenediamine (121 µL, 1.10 mmol) was added to a suspension of O-(4-chlorophenyl)hydroxylamine hydrochloride (194 mg, 0.76 mmol) in EtOH (15 mL), and the reaction allowed to stir at RT for 15 hours. Glacial acetic acid (4 mL) was then added to adjust the mixture to ca. pH 4 followed by a solution of N-(2-benzoyl-4-chlorophenyl)

trifluoromethanesulfonamide 25 (250 mg, 0.69 mmol) in EtOH (5 mL), and the reaction stirred for 48 hours at RT. The reaction mixture was concentrated under vacuum, and the residue dissolved in $CH_2Cl_2$ (50 mL), washed with water (twice), brine, dried over $MgSO_4$ and the solvent evaporated under reduced pressure. The residue was filtered through a pad of silica (eluting with $CH_2Cl_2$/PE, 1:1) and purified by radial thin layer chromatography (eluting with $CH_2Cl_2$/PE, 1:9) to afford N-{4-fluoro-2-[(4-chlorophenoxyimino)phenylmethyl]phenyl}trifluoromethanesulfonamide 165 (110 mg, 34%), as a orange-brown solid. M.p. 90-93° C. $^1$H n.m.r. (200 MHz, $CDCl_3$) δ 11.05, br s, 1H; 7.73, d, J=8.8 Hz, 1H; 7.55, m, 3H; 7.43-7.34, m, 3H; 7.07, s, 2H; 7.04, d, J=3.0 Hz, 2H; 7.00, d, J=2.6 Hz, 1H.

O-(4-Fluorophenyl)hydroxylamine hydrochloride was prepared by the procedure described in Example 1D.

Example 4E

Preparation of N-[4-chloro-2-(ethoxyiminophenylmethyl)phenyl]trifluoromethanesulfonamide (Compound 177)

N,N-Dimethylethylenediamine (254 μL, 2.20 mmol) was added to a solution of N-ethoxyphthalimide (287 mg, 1.50 mmol) in EtOH (5 mL), and the reaction allowed to stir at RT for 15 hours. Glacial acetic acid (2 mL) was then added to adjust the mixture to ca. pH 4, followed by the addition of N-(2-benzoyl-4-chlorophenyl)trifluoromethanesulfonamide 25 (364 mg, 1.0 mmol), and the reaction stirred for 22 hours at RT. The reaction mixture was concentrated under vacuum, and the residue dissolved in $Et_2O$ (50 mL) and washed with water, brine, dried over $MgSO_4$ and the solvent removed under reduced pressure. The residue was purified by radial thin layer chromatography (eluting with $CH_2Cl_2$/PE, 1:99 to 1:9) to afford a single syn(Z) or anti(E)-isomer of N-[4-chloro-2-(ethoxyiminophenylmethyl)phenyl]trifluoromethanesulfonamide 177 (48 mg, 12%), as a colorless oil. $^1$H n.m.r. (400 MHz, $CDCl_3$) δ 11.70, br s, 1H; 7.70, d, J=8.8 Hz, 1H; 7.50, m, 3H; 7.32, dd, J=2.4 and 8.8 Hz, 1H; 7.26, m, 2H; 4.25, q, J=7.2 Hz, 2H; 1.32, t, J=7.2 Hz, 3H. HRMS (M$^+$) 406.0358.

An isomeric mixture of syn(Z) and anti(E)-N-[4-chloro-2-(ethoxyiminophenylmethyl)phenyl]trifluoromethanesulfonamide (compound 178) was also isolated (360 mg, 88%), as a colorless oil.

N-ethoxyphthalimide was prepared using an analogous procedure to that described in Example 1A.

Example 4F

Preparation of N-{4-chloro-[(2-methoxyethoxyimino)phenylmethyl]phenyl}trifluoromethanesulfonamide (Compound 234)

N,N-Dimethylethylenediamine (254 μL, 2.20 mmol) was added to a solution of N-(2-methoxyethoxy)phthalimide (332 mg, 1.50 mmol) in EtOH (5 mL), and the reaction allowed to stir at RT for 7 hours. Glacial acetic acid (2 mL) was then added to adjust the mixture to ca. pH 4, followed by the addition of N-(2-benzoyl-4-chlorophenyl)trifluoromethanesulfonamide 25 (364 mg, 1.0 mmol), and the reaction stirred for 15 hours at 30° C. The reaction mixture was concentrated under vacuum, and the residue dissolved in $Et_2O$ (50 mL) and washed with water, brine, dried over $MgSO_4$ and the solvent removed under reduced pressure. The residue was purified by radial thin layer chromatography (eluting with $CH_2Cl_2$/PE, 1:19) to afford N-{4-chloro-[(2-methoxyethoxyimino)phenylmethyl]phenyl}trifluoromethanesulfonamide 234 (324 mg, 74%), as a colorless oil. $^1$H n.m.r. (400 MHz, $CDCl_3$) (2:1 mixture of E- and Z-isomers) δ 11.06, br s, 1H; 8.87, br s, 1H; 7.67, d, J=8.8 Hz, 1H; 7.54-7.31, m, 13H; 7.10, d, J=2.4 Hz, 1H; 6.92, d, J=2.4 Hz, 1H; 4.33, m, 4H; 3.67, m, 4H; 3.46, s, 3H; 3.38, s, 3H. HRMS (M$^+$) 436.0465.

N-(2-methoxyethoxy)phthalimide was prepared using an analogous procedure to that described in Example 1A.

The following trifluoromethanesulfonanilide oxime ether compounds, as listed by Tables 8 and 8A, infra, were prepared using similar preparative methods: Compounds 24, 30, 31, 61-63, 66, 68, 69, 71, 78, 80, 82, 83, 88-90, 162, 176, 178-180, 232, 233, 251 and 252.

Additional data for compounds of Example 4 is provided by Table 5, below.

TABLE 5

| Compd # | $^1$H n.m.r. |
|---|---|
| 61 | (200MHz, $CDCl_3$) δ 11.14, br s, 1H; 7.65, d, J=8.8Hz, 1H; 7.55-7.48, m, 3H; 7.42, d, J=1.8Hz, 1H; 7.33, d, J=2.6Hz, 1H; 7.30-7.23, m, 4H; 6.89, d, J=2.2Hz, 1H; 5.23, s, 2H. |
| 63 | (200MHz, $CDCl_3$) δ 11.33, br s, 1H; 7.67, d, J=8.8Hz, 1H; 7.57-7.50, m, 3H; 7.38-7.23, m, 7H; 6.90, d, J=2.4Hz, 1H; 5.13, s, 2H. |
| 176 | (400MHz, $CDCl_3$) δ 11.82, br s, 1H; 7.71, d, J=8.8Hz, 1H; 7.48, m, 3H; 7.31, dd, J=2.4 and 8.8Hz, 1H; 7.26, m, 2H; 6.91, d, J=2.4Hz, 1H; 4.47, septet, J=6.4Hz, 1H; 1.29 d, J=6.4Hz, 6H. |
| 232 | (400MHz, $CDCl_3$) δ 11.54, br s, 1H; 7.69, d, J=8.8Hz, 1H; 7.51, m, 3H; 7.33, dd, J=2.4 and 8.8Hz, 1H; 7.26, m, 2H; 6.91, d, J=2.4Hz, 1H; 4.00, s, 3H. |
| 251 | (400MHz, $CDCl_3$) δ 11.71, br s, 1H; 7.70, d, J=8.8Hz, 1H; 7.50, m, 3H; 7.32, dd, J=2.4 and 8.8Hz, 1H; 7.27, m, 2H; 6.92, d, J=2.4Hz, 1H; 4.15, t, J=6.4Hz, 2H; 1.72, m, 2H; 0.91, t, J=7.2Hz, 3H. |

Example 5

Figure 8:
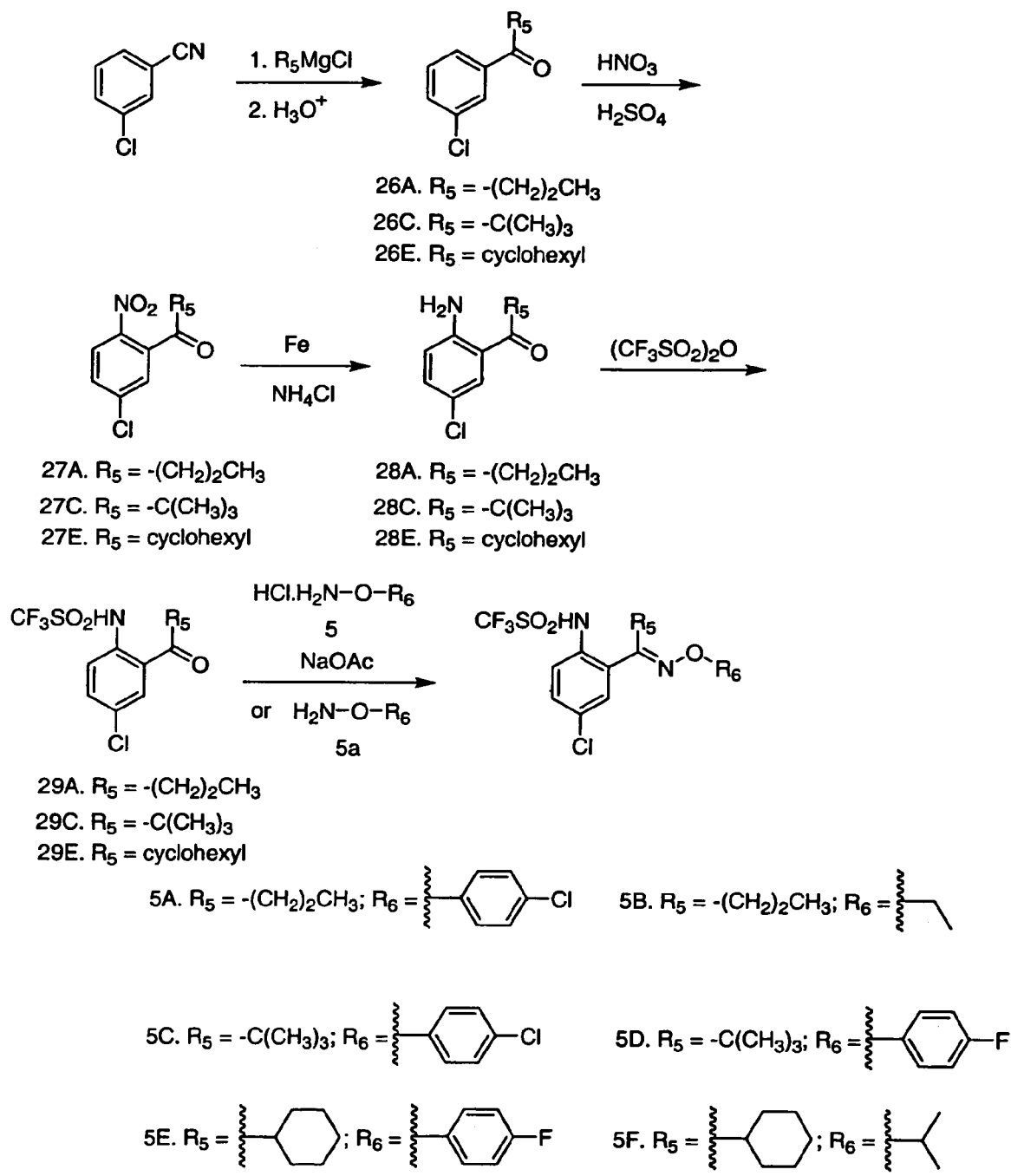
FIG. 8 illustrates the preparative reactions of Examples 5A through 5F.

The following compounds were prepared according to the reaction scheme illustrated by FIG. 8.

Example 5A

Preparation of N-{4-chloro-2-[1-(4-chlorophenoxyimino)butyl]phenyl}trifluoromethanesulfonamide (Compound 166)

A solution of N-(2-butyryl-4-chlorophenyl)trifluoromethanesulfonamide 29A (333 mg, 1.0 mmol), O-(4-chlorophenyl)hydroxylamine hydrochloride (200 mg, 1.10 mmol) and anhydrous NaOAc (91 mg, 1.10 mmol) in EtOH (30 mL) was stirred for 15 hours at RT. The reaction mixture was concentrated under vacuum, the residue filtered through a pad of silica (eluting with $CH_2Cl_2$/PE, 1:4) and the solvent removed under reduced pressure. The residue was purified by radial thin layer chromatography (eluting with $CH_2Cl_2$/PE, 1:19 to 3:7) to afford N-{4-chloro-2-[1-(4-chlorophenoxyimino)butyl]phenyl}trifluoromethanesulfonamide 166 (283 mg, 62%), as a yellow solid. M.p. 62.5-64.5° C. $^1$H n.m.r. (200 MHz, $CDCl_3$) δ 11.27, br s, 1H; 7.72, d, J=8.8 Hz, 1H; 7.57, d, J=2.4 Hz, 1H; 7.41, dd, J=2.4 and 8.8 Hz, 1H; 7.35, d, J=8.8 Hz, 2H; 7.11, d, J=8.8 Hz, 2H; 2.98, m, 2H; 1.71, sextet, 2H; 1.09, t, J=7.4 Hz, 3H.

Preparation of N-(2-butyryl-4-chlorophenyl)trifluoromethanesulfonamide (Formula 29A)

a) To a stirred solution of 3-chlorobenzonitrile (2.0 g, 14.54 mmol) and n-propylmagnesium chloride (2M in $Et_2O$) (8.0 mL, 15.99 mmol) in THF (40 mL) was added CuCl (29 mg, 0.29 mmol), and the mixture was refluxed for 30 minutes. After cooling to RT, cold 1N HCl (10 mL) was added cautiously, the THF removed under reduced pressure, further 1N HCl (30 mL) added and the reaction heated at 90° C. for 1 hour. To the cooled reaction mixture was added water (20 mL) and $CH_2Cl_2$ (50 mL), the phases separated, and the aqueous phase again extracted with $CH_2Cl_2$. The combined organics were washed with water, dried over $MgSO_4$ and the solvent evaporated under vacuum. The residue was filtered through a pad of silica (eluting with $CH_2Cl_2$) to afford 1-(3-chlorophenyl)butan-1-one 26A (3.14 g, 97%), as a yellow liquid.

b) To rapidly stirred 1-(3-chlorophenyl)butan-1-one 26A (2.86 g, 15.66 mmol) at ca. −20° C. was added dropwise a mixture of fuming $HNO_3$ (11 mL) and concentrated $H_2SO_4$ (1.5 mL) that had been cooled to −20° C. The reaction mixture was allowed to warm to −10° C., stirred for 2 hours at this temperature after which it was poured into ice-water (75 mL) and extracted twice with $CH_2Cl_2$. The combined organic layers were washed three times with water, once with brine, dried over $MgSO_4$ and concentrated under reduced pressure. The residue was filtered through a pad of silica (eluting with $CH_2Cl_2$/PE, 3:2) to afford 1-(5-chloro-2-nitrophenyl)butan-1-one 27A (3.40 g, 95%), as a pale green solid.

c) To a mixture of 1-(5-chloro-2-nitrophenyl)butan-1-one 27A (3.40 g, 14.94 mmol) in EtOH (40 mL) and $H_2O$ (20 mL) was added iron powder (4.17 9, 74.68 mmol) and $NH_4Cl$ (400 mg, 7.47 mmol), and the reaction was rapidly stirred at 90° C. for 30 minutes. The hot reaction mixture was filtered, the residues rinsed with EtOAc, and further $H_2O$ added. The phases were separated and the organics were washed with water, brine, dried over $MgSO_4$ and concentrated under reduced pressure to afford 1-(2-amino-5-chlorophenyl)butan-1-one 28A (2.81 g, 95%), as a yellow solid.

d) To a solution of 1-(2-amino-5-chlorophenyl)butan-1-one 28A (2.819, 14.22 mmol) in anhydrous dichloromethane (50 mL) at 0° C. was added dropwise $(CF_3SO_2)_2O$ (3.59 mL, 21.32 mmol) in anhydrous $CH_2Cl_2$ (15 mL) over 30 minutes, and the reaction allowed to warm to RT over 15 hours. The reaction mixture was washed with water, brine, dried over $MgSO_4$ and concentrated under vacuum. The residue was filtered through a pad of silica (eluting with $CH_2Cl_2$/PE, 3:7) to afford N-(2-butyryl-4-chlorophenyl)trifluoromethanesulfonamide 29A (3.89 g, 83%), as a yellow solid. $^1H$ n.m.r. (200 MHz, $CDCl_3$) δ 12.05, br s, 1H; 7.93, d, J=2.4 Hz, 1H; 7.76, d, J=8.8 Hz, 1H; 7.54, dd, J=2.4 and 8.8 Hz, 1H; 3.02, t, J=7.0 Hz, 2H; 1.78, sextet, 1H; 1.02, t, J=7.4 Hz, 3H. HRMS ($M^+$) 329.0098.

O-(4-Chlorophenyl)hydroxylamine hydrochloride was prepared by the procedure described in Example 2C.

Example 5B

Preparation of N-[4-chloro-2-(1-ethoxyiminobutyl) phenyl]trifluoromethanesulfonamide (Compound 193)

N,N-Dimethylethylenediamine (254 μL, 2.20 mmol) was added to a solution of N-ethoxyphthalimide (287 mg, 1.50 mmol) in EtOH (5 mL), and the reaction allowed to stir at RT for 15 hours. Glacial acetic acid (2 mL) was then added to adjust the mixture to ca. pH 4, followed by the addition of N-(2-butyryl-4-chlorophenyl)trifluoromethanesulfonamide 29A (330 mg, 1.0 mmol), and the reaction stirred for 15 hours at RT. The reaction mixture was concentrated under vacuum, and the residue dissolved in $Et_2O$ (50 mL) and washed with water, brine, dried over $MgSO_4$ and the solvent removed under reduced pressure. The residue was filtered through a pad of silica (eluting with $CH_2Cl_2$/PE, 1:1), the solvent evaporated under reduced pressure and the residue purified by radial thin layer chromatography (eluting with $CH_2Cl_2$/PE, 1:19) to afford N-[4-chloro-2-(1-ethoxyiminobutyl)phenyl]trifluoromethanesulfonamide 193 (82 mg, 22%), as a colorless oil. $^1H$ n.m.r. (400 MHz, $CDCl_3$) δ 12.10, br s, 1H; 7.67, d, J=8.8 Hz, 1H; 7.47, d, J=2.4 Hz, 1H; 7.32, dd, J=2.4 and 8.8 Hz, 1H; 4.27, q, J=7.2 Hz, 2H; 2.78, m, 2H; 1.59, sextet, 2H; 1.37, t, J=7.2 Hz, 3H; 1.02, t, J=7.6 Hz, 3H. HRMS ($M^+$) 372.0514.

N-(2-butyryl-4-chlorophenyl)trifluoromethanesulfonamide 29A was prepared by the procedure described in Example 5A.

N-ethoxyphthalimide was prepared using an analogous procedure to that described in Example 1A.

Example 5C

Preparation of N-{4-chloro-2-[1-(4-chlorophenoxyimino)2,2-dimethylpropyl] phenyl}trifluoromethanesulfonamide (Compound 182)

A solution of N-[4-chloro-2-(2,2-dimethylpropionyl)phenyl]trifluoromethanesulfonamide 29C (300 mg, 0.87 mmol), O-(4-chlorophenyl)hydroxylamine hydrochloride (173 mg, 0.96 mmol) and anhydrous NaOAc (80 mg, 0.96 mmol) in EtOH (20 mL) was stirred for 40 hours at RT. The reaction mixture was concentrated under vacuum, the residue filtered through a pad of silica (eluting with $CH_2Cl_2$/PE, 3:7) and the solvent removed under reduced pressure. The residue was purified by recrystallization from $CH_2Cl_2$/PE to afford N-{4-chloro-2-[1-(4-chlorophenoxyimino)butyl] phenyl}trifluoromethanesulfonamide 182 (40 mg, 10%), as a yellow solid. M.p. 69-70° C. $^1H$ n.m.r. (200 MHz, $CDCl_3$) δ 7.52, d, J=8.8 Hz, 1H; 7.43, dd, J=2.2 and 8.8 Hz, 1H; 7.25, d, J=9.2 Hz, 2H; 7.18, d, J=2.2 Hz, 1H; 7.01, d, J=9.2 Hz, 2H; 6.43, br s, 1H; 1.33, s, 9H.

Preparation of N-[4-chloro-2-(2,2-dimethylpropionyl)phenyl]trifluoromethanesulfonamide (Formula 29C)

a) To a stirred solution of 3-chlorobenzonitrile (2.0 g, 14.54 mmol) and tert-butylmagnesium chloride (1M in THF) (15.99 mL, 15.99 mmol) in THF (10 mL) was added CuCl (29 mg, 0.29 mmol), and the mixture was refluxed for 20 hours. After cooling to RT, cold 1N HCl (10 mL) was added cautiously, the THF removed under reduced pressure, further 1N HCl (20 mL) added and the reaction heated at 90° C. for 1 hour. To the cooled reaction mixture was added water (20 mL) and $CH_2Cl_2$ (50 mL), the phases separated, and the aqueous phase again extracted with $CH_2Cl_2$. The combined organics were washed with water, dried over $MgSO_4$ and the solvent evaporated under vacuum to afford 1-(3-chlorophenyl)2,2-dimethylpropan-1-one 26C (2.50 g, 87%), as a brown oil.

b) To rapidly stirred 1-(3-chlorophenyl2,2-dimethylpropan-1-one 26C (2.50 g, 12.71 mmol) at ca. −20° C. was added dropwise a mixture of fuming $HNO_3$ (10 mL) and concentrated $H_2SO_4$ (1.0 mL) that had been cooled to −20° C.

The reaction mixture was allowed to warm to −10° C., stirred for 2 hours at this temperature after which it was poured into ice-water (75 mL) and extracted twice with $CH_2Cl_2$. The combined organic layers were washed three times with water, once with brine, dried over $MgSO_4$ and concentrated under reduced pressure. The residue was filtered through a pad of silica (eluting with $CH_2Cl_2$/PE, 3:2) to afford 1-(5-chloro-2-nitrophenyl)2,2-dimethylpropan-1-one 27C (2.6 g, 85%), as a pale yellow solid.

c) To a mixture of 1-(5-chloro-2-nitrophenyl)2,2-dimethylpropan-1-one 27C (1.50 g, 6.21 mmol) in EtOH (10 mL) and $H_2O$ (5 mL) was added iron powder (1.73 g, 31.03 mmol) and $NH_4Cl$ (166 mg, 3.10 mmol), and the reaction was rapidly stirred at 90° C. for 30 minutes. The hot reaction mixture was filtered, the residues rinsed with EtOAc, and further $H_2O$ added. The phases were separated and the organics were washed with water, brine, dried over $MgSO_4$ and concentrated under reduced pressure to afford 1-(2-amino-5-chlorophenyl)2,2-dimethylpropan-1-one 28C (920 mg, 70%), as a pale yellow solid.

d) To a solution of 1-(2-amino-5-chlorophenyl)2,2-dimethylpropan-1-one 28C (920 mg, 4.35 mmol) in anhydrous dichloromethane (20 mL) at 0° C. was added dropwise $(CF_3SO_2)_2O$ (1.10 mL, 6.52 mmol) in anhydrous $CH_2Cl_2$ (5 mL) over 30 minutes, and the reaction allowed to warm to RT over 15 hours. The reaction mixture was washed with water, brine, dried over $MgSO_4$ and concentrated under vacuum. The residue was filtered through a pad of silica (eluting with $CH_2Cl_2$/PE, 3:7) to afford N-[4-chloro-2-(2,2-dimethylpropionyl)phenyl]trifluoromethanesulfonamide 29C (1.44 g, 96%), as a yellow solid. $^1$H n.m.r. (200 MHz, $CDCl_3$) δ 10.05, br s, 1H; 7.87, d, J=2.4 Hz, 1H; 7.69, d, J=8.8 Hz, 1H; 7.49, dd, J=2.4 and 8.8 Hz, 1H; 1.40, s, 9H.

O-(4-Chlorophenyl)hydroxylamine hydrochloride was prepared by the procedure described in Example 2C.

Example 5D

Preparation of N-{4-chloro-2-[1-(4-fluorophenoxyimino)2,2-dimethylpropyl]phenyl}trifluoromethanesulfonamide (Compound 198)

A solution of N-[4-chloro-2-(2,2-dimethylpropionyl)phenyl]trifluoromethanesulfonamide 29C (280 mg, 0.82 mmol), O-(4-fluorophenyl)hydroxylamine hydrochloride (200 mg, 1.22 mmol) and anhydrous NaOAc (100 mg, 1.22 mmol) in EtOH (20 mL) was stirred for 48 hours at RT. The reaction mixture was concentrated under vacuum and the residue purified by column chromatography (eluting with $CH_2Cl_2$/PE, 1:4 to 2:3) to afford N-{4-chloro-2-[1-(4-fluorophenoxyimino)2,2-dimethylpropyl]phenyl}trifluoromethanesulfonamide 198 (40 mg, 11%), as an orange oil. 1H n.m.r. (200 MHz, $CDCl_3$) δ 7.52, d, J=8.8 Hz, 1H; 7.42, dd, J=2.2 and 8.8 Hz, 1H; 7.19, d, J=2.2 Hz, 1H; 7.00, m, 4H; 6.49, br s, 1H; 1.32, s, 9H. HRMS (M$^+$) 452.0576.

N-[4-chloro-2-(2,2-dimethylpropionyl)phenyl]trifluoromethanesulfonamide 29C was prepared by the procedure described in Example 5C.

O-(4-Fluorophenyl)hydroxylamine hydrochloride was prepared by the procedure described in Example 1D.

Example 5E

Preparation of N-{4-chloro-2-[(4-fluorophenoxyimino)cyclohexylmethyl]phenyl}trifluoromethanesulfonamide (Compound 169)

A solution of N-(4-chloro-2-cyclohexanecarbonylphenyl)trifluoromethanesulfonamide 29E (410 mg, 1.11 mmol), O-(4-fluorophenyl)hydroxylamine hydrochloride (200 mg, 1.22 mmol) and anhydrous NaOAc (100 mg, 1.22 mmol) in EtOH (20 mL) was stirred for 15 hours at RT. The reaction mixture was concentrated under vacuum and the residue purified by column chromatography (eluting with $CH_2Cl_2$/PE, 3:7 to $CH_2Cl_2$) to afford N-{4-chloro-2-[(4-flurophenoxyimino)cyclohexylmethyl]phenyl}trifluoromethanesulfonamide 169 (200 mg, 38%), as a white solid. $^1$H n.m.r. (200 MHz, $CDCl_3$) δ 7.54, d, J=8.8 Hz, 1H; 7.43, dd, J=2.2 and 8.8 Hz, 1H; 7.24, d, J=2.2 Hz, 1H; 7.12-6.95, m, 5H; 2.56, m, 1H; 2.14, m, 1H; 1.93-1.65, m, 5H; 1.29, m, 4H.

Preparation of N-(4-chloro-2-cyclohexanecarbonylphenyl)trifluoromethanesulfonamide (Formula 29E)

a) To a stirred solution of 3-chlorobenzonitrile (2.0 g, 14.54 mmol) and cyclohexylmagnesium chloride (2M in $Et_2O$) (8.0 mL, 15.99 mmol) in THF (20 mL) was added CuCl (29 mg, 0.29 mmol), and the mixture was refluxed for 30 minutes. After cooling to RT, cold 1N HCl (10 mL) was added cautiously, the THF removed under reduced pressure, further 1N HCl (30 mL) added and the reaction heated at 90° C. for 1 hour. To the cooled reaction mixture was added water (20 mL) and $CH_2Cl_2$ (50 mL), the phases separated, and the aqueous phase again extracted with $CH_2Cl_2$. The combined organics were washed with water, dried over $MgSO_4$ and the solvent evaporated under vacuum. The residue was filtered through a pad of silica (eluting with $CH_2Cl_2$) to afford (3-chlorophenyl)cyclohexylmethanone 26E (3.14 g, 97%), as a yellow liquid.

b) To rapidly stirred (3-chlorophenyl)cyclohexylmethanone 26E (3.14 g, 14.10 mmol) at ca. −20° C. was added dropwise a mixture of fuming $HNO_3$ (12 mL) and concentrated $H_2SO_4$ (1.6 mL) that had been cooled to −20° C. The reaction mixture was allowed to warm to −10° C., stirred for 2 hours at this temperature after which it was poured into ice-water (75 mL) and extracted twice with $CH_2Cl_2$. The combined organic layers were washed three times with water, once with brine, dried over $MgSO_4$ and concentrated under reduced pressure. The residue was filtered through a pad of silica (eluting with $CH_2Cl_2$/PE, 3:2) and recrystallized from $CH_2Cl_2$/PE to afford (5-chloro-2-nitrophenyl)cyclohexylmethanone 27E (2.50 g, 66%), as a pale yellow solid.

c) To a mixture of (5-chloro-2-nitrophenyl)cyclohexylmethanone 27E (580 mg, 2.17 mmol) in EtOH (6 mL) and $H_2O$ (3 mL) was added iron powder (605 mg, 10.83 mmol) and $NH_4Cl$ (58 mg, 1.08 mmol), and the reaction was rapidly stirred at 90° C. for 30 minutes. The hot reaction mixture was filtered, the residues rinsed with EtOAc, and further $H_2O$ added. The phases were separated and the organics were washed with water, brine, dried over MgSO₄ and the solvent removed under reduced pressure. The residue was filtered through a pad of silica (eluting with EtOAc/PE; 1:1) to afford (2-amino-5-chlorophenyl)cyclohexylmethanone 28E (470 mg, 91%), as a yellow solid.

d) To a solution of (2-amino-5-chlorophenyl)cyclohexylmethanone 28E (470 mg, 1.98 mmol) in anhydrous dichloromethane (10 mL) at 0° C. was added dropwise $(CF_3SO_2)_2O$ (499 µL, 2.97 mmol) in anhydrous $CH_2Cl_2$ (3 mL) over 30 minutes, and the reaction allowed to warm to RT over 60 hours. The reaction mixture was washed with water, brine, dried over MgSO₄ and concentrated under vacuum. The residue was filtered through a pad of silica (eluting with $CH_2Cl_2$/PE, 2:3) to afford N-(4-chloro-2-cyclohexanecarbonylphenyl)trifluoromethanesulfonamide 29E (340 mg, 47%), as a white solid. ¹H n.m.r. (200 MHz, CDCl₃) δ 11.95, br s, 1H; 7.89, d, J=2.4 Hz, 1H; 7.75, d, J=8.8 Hz, 1H; 7.54, dd, J=2.4 and 8.8 Hz, 1H; 3.25, m, 1H; 1.95-1.70, m, 5H; 1.53-1.28, m, 5H.

O-(4-Fluorophenyl)hydroxylamine hydrochloride was prepared by the procedure described in Example 1D.

Example 5F

Preparation of N-[4-chloro-2-(cyclohexylisopropoxyiminomethyl)phenyl]trifluoromethanesulfonamide (Compound 210)

N,N-Dimethylethylenediamine (254 µL, 2.20 mmol) was added to a solution of N-isopropoxyphthalimide (308 mg, 1.50 mmol) in EtOH (5 mL), and the reaction allowed to stir at RT for 15 hours. Glacial acetic acid (2 mL) was then added to adjust the mixture to ca. pH 4, followed by the addition of N-(4-chloro-2-cyclohexanecarbonylphenyl)-trifluoromethanesulfonamide 29E (370 mg, 1.0 mmol), and the reaction stirred for 15 hours at RT. The reaction mixture was concentrated under vacuum, and the residue dissolved in Et₂O (50 mL) and washed with water, brine, dried over MgSO₄ and the solvent removed under reduced pressure. The residue was purified by column chromatography (eluting with $CH_2Cl_2$/PE, 1:1) to afford N-[4-chloro-2-(cyclohexylisopropoxyiminomethyl)phenyl]trifluoromethanesulfonamide 210 (390 mg, 91%), as a colorless oil. ¹H n.m.r. (400 MHz, CDCl₃) (1:1 mixture of E- and Z-isomers) δ 10.59, br s, 1H; 8.11, br s, 1H; 7.61, d, J=8.8 Hz, 1H; 7.49, d, J=8.8 Hz, 1H; 7.46, d, J=2.4 Hz, 1H; 7.42, dd, J=2.4 and 8.8 Hz, 1H; 7.30, dd, J=2.4 and 8.8 Hz, 1H; 7.24, d, J=2.4 Hz, 1H; 4.49, m, 1H; 4.39, m, 1H; 2.97, m, 1H; 2.45, m, 1H; 1.97-1.71, m, 14H; 1.34-1.24, m, 18H. HRMS (M⁺) 426.0983.

N-(4-chloro-2-cyclohexanecarbonylphenyl)trifluoromethanesulfonamide 29E was prepared by the procedure described in Example 5E.

N-isopropoxyphthalimide was prepared by the procedure of Ishikawa, T.; Kamiyama, K.; Matsunaga, N.; Tawada, H.; Iizawa, Y.; Okonogi, K.; Miyake, A. *J. Antibiot.*, 2000, 53, 1071-1085.

The following trifluoromethanesulfonanilide oxime ether compounds, as listed by Tables 8 and 8A, infra, were prepared using similar preparative methods: Compounds 168, 191, 192, 195, 209 and 211-213.

Additional data for compounds of Example 5 is provided by Table 6, below.

TABLE 6

| Compd # | ¹H n.m.r. |
|---|---|
| 168 | (200MHz, CDCl₃) δ 11.34, br s, 1H; 7.71, d, J=9.0Hz, 1H; 7.57, d, J=2.4Hz, 1H; 7.40, dd, J=2.4 and 9.0Hz, 1H; 7.17-7.03, m, 4H; 2.97, m, 2H; 1.72, m, 2H; 1.09, t, J=7.8Hz, 3H. |
| 191 | (400MHz, CDCl₃) δ 12.26, br s, 1H; 7.69, d, J=8.8Hz, 1H; 7.48, d, J=2.4Hz, 1H; 7.31, dd, J=2.4 and 8.8Hz, 1H; 4.46, m, 1H; 2.78, m, 2H; 1.60, m, 2H; 1.34, d, J=6.4Hz, 6H; 1.01, t, J=7.6Hz, 3H. |
| 195 | (400MHz, CDCl₃) δ 12.30, br s, 1H; 7.69, d, J=8.8Hz, 1H; 7.47, d, J=2.4Hz, 1H; 7.31, dd, J=2.4 and 8.8Hz, 1H; 4.78, m, 1H; 2.76, m, 2H; 1.88, m, 4H; 1.78-1.54, m, 6H; 1.00, t, J=7.2Hz, 3H. |
| 211 | (400MHz, CDCl₃) (1:1 mixture of E- and Z-isomers) δ 10.71, br s, 1H; 7.96, br s, 1H; 7.61, d, J=8.8Hz, 1H; 7.46, m, 2H; 7.37, dd, J=2.4 and 8.8Hz, 1H; 7.30, dd, J=2.4 and 8.8Hz, 1H; 7.23, d, J=2.4Hz, 1H; 4.79, m, 1H; 4.71, m, 1H; 2.92, m, 1H; 2.45, m, 1H; 1.98-1.59, m, 30H; 1.36-1.20, m, 6H. |

Example 6

Figure 9:
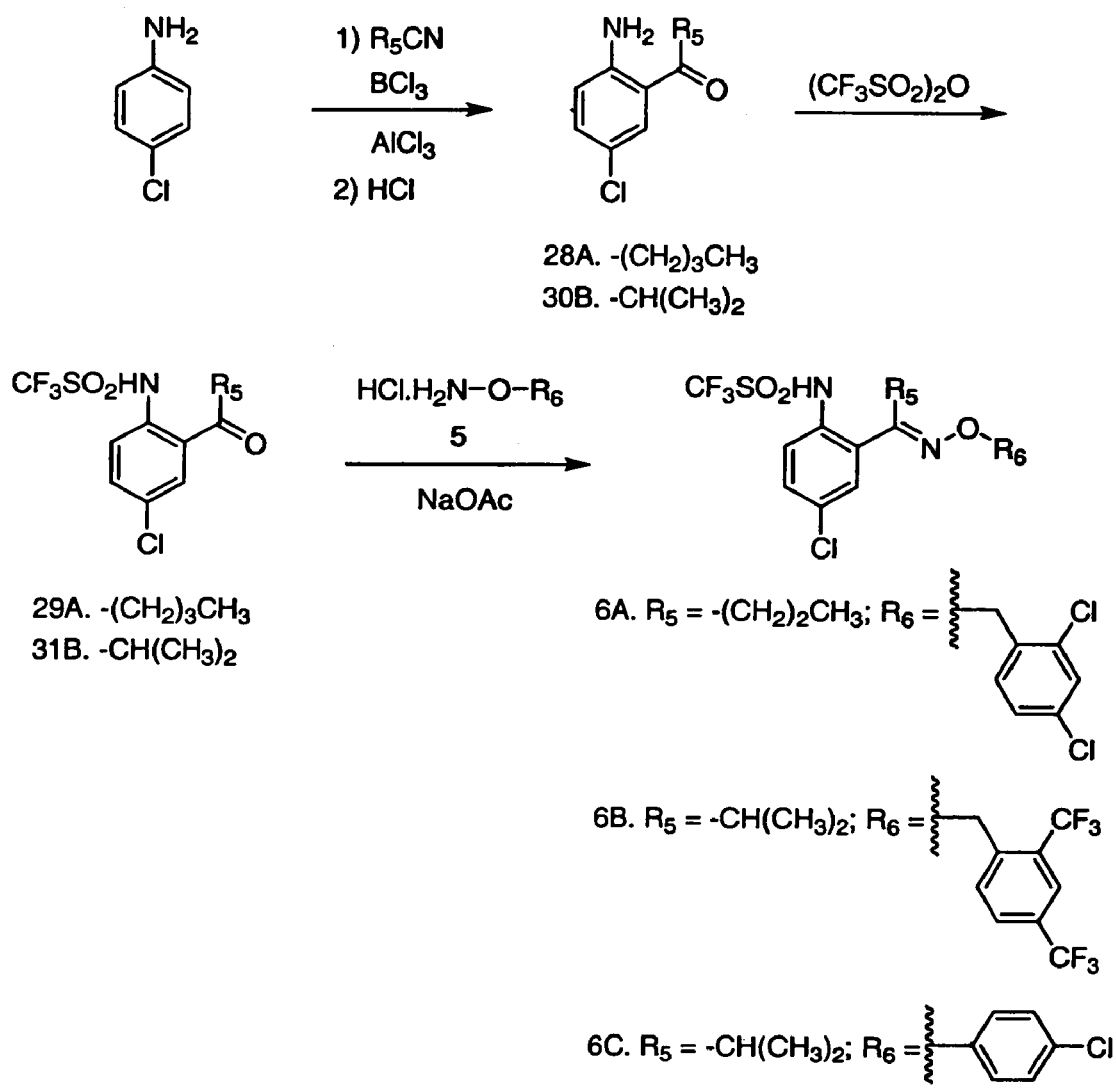
FIG. 9 illustrates the preparative reactions of Examples 6A through 6C.

The following compounds were prepared according to the reaction scheme illustrated by FIG. 9.

Example 6A

Preparation of N-{4-chloro-2-[1-(2,4-dichlorobenzyloxyimino)butyl]}trifluoromethanesulfonamide (Compound 100)

a) To BCl₃ (1 M in $CH_2Cl_2$) (37.62 mL, 37.62 mmol) and 1,2-DCE (30 mL) at 0° C. was added dropwise 4-chloroaniline (7.38 g, 57.90 mmol) in 1,2-DCE (30 mL) and the ice-cold solution allowed to stir for 30 min. Butyronitrile (2.52 mL, 28.93 mmol) and AlCl₃ (5.02 g, 37.62 mmol) were added in succession and the reaction mixture stirred at 0° C. for 30 min, and heated at 90° C. for 24 h. The solution was cooled to 0° C., 2N HCl (60 mL) added and was then heated at 90° C. for 30 minutes. The reaction mixture was extracted three times with $CH_2Cl_2$, dried over MgSO₄ and the solvent concentrated under vacuum. The residue was filtered through a pad of silica (eluting with $CH_2Cl_2$/PE, 9:1) and the solvent concentrated to afford 1-(2-amino-5-chlorophenyl)butan-1-one 28A (2.68 g, 47%), as a yellow solid.

b) N-(2-butyryl-4-chlorophenyl)trifluoromethanesulfonamide 29A was prepared by the procedure described in Example 5A.

c) A solution of N-(2-butyryl-4-chlorophenyl)trifluoromethanesulfonamide 29A (243 mg, 0.74 mmol), O-(2,4-dichlorobenzyl)hydroxylamine hydrochloride (176 mg, 0.77 mmol) and anhydrous NaOAc (86 mg, 1.05 mmol) in EtOH (10 mL) was stirred for 15 hours at RT. The reaction mixture was concentrated under vacuum and the residue filtered through a pad of silica (eluting with CHCl₃). Purification by radial thin layer chromatography (eluting with $CH_2Cl_2$/PE, 7.5:82.5 to 3:17) afforded N-{4-chloro-2-[1-(2-chloro-4-methylbenzyloxyimino)butyl]}trifluoromethanesulfonamide 100 (189 mg, 51%) as a pale yellow solid. M.p. 65-66° C. ¹H n.m.r. (200 MHz, CDCl₃) δ 11.45, br s, 1H; 7.63, d, J=9.0 Hz, 1H; 7.46, d, J=2.6 Hz, 1H; 7.44, d, J=1.8 Hz, 1H; 7.41-7.34, m, 2H; 7.30-7.25, m, 2H; 5.27, s, 2H; 2.80, m, 2H; 1.60, m, 2H; 1.02, t, J=7.4 Hz, 3).

O-(2,4-Dichlorobenzyl)hydroxylamine hydrochloride was prepared in two steps using an analogous procedure to that described in Example 1A.

Example 6B

Preparation of N-{2-[1-(2,4-bistrifluoromethylbenzyloxyimino)-2-methylpropyl]-4-chlorophenyl}trifluoromethanesulfonamide (Compound 116)

a) To $BCl_3$ (1 M in $CH_2Cl_2$) (37.62 mL, 37.62 mmol) and 1,2-DCE (30 mL) at 0° C. was added dropwise 4-chloroaniline (7.38 g, 57.90 mmol) in 1,2-DCE (30 mL) and the ice-cold solution allowed to stir for 30 min. Isobutyronitrile (2.63 mL, 28.94 mmol) and $AlCl_3$ (5.02 g, 37.62 mmol) were added in succession and the reaction mixture stirred at 0° C. for 30 min, and heated at 90° C. for 24 hours. The solution was cooled to 0° C., 2N HCl (60 mL) added and was then heated at 90° C. for 30 min. The reaction mixture was extracted three times with $CH_2Cl_2$, dried over $MgSO_4$ and the solvent concentrated under vacuum. The residue was filtered through a pad of silica (eluting with $CH_2Cl_2$/PE, 4:1) and the solvent concentrated to afford 1-(2-amino-5-chlorophenyl)-2-methylpropan-1-one 30B (2.08 g, 36%), as a yellow solid.

b) To a solution of 1-(2-amino-5-chlorophenyl)-2-methylpropan-1-one 30B (2.08 g, 10.52 mmol) and $Et_3N$ (1.54 mL, 11.05 mmol) in anhydrous $CH_2Cl_2$ (100 mL) at 0° C. was added dropwise $(CF_3SO_2)_2O$ (1.86 mL, 11.05 mmol) in anhydrous $CH_2Cl_2$ (50 mL) over 30 min. The reaction mixture was allowed to warm to RT over 15 hours, washed with water, dried over $MgSO_4$ and concentrated under vacuum. The residue was filtered through a pad of silica (eluting with $CH_2Cl_2$/PE, 4:1) to afford N-(4-chloro-2-isobutyrylphenyl)trifluoromethanesulfonamide 31B (2.93 g, 84%), as a pale yellow solid. $^1$H n.m.r. (200 MHz, $CDCl_3$) δ 11.91, br s, 1H; 7.92, d, J=2.6 Hz, 1H; 7.76, d, J=9.1 Hz, 1H; 7.55, dd, J=2.6 and 9.1 Hz, 1H, 3.58, quintet, J=7.0 Hz, 1H; 1.24, d, J=7.0 Hz, 6H. HRMS (M$^+$) 329.0093.

c) A solution of N-(4-chloro-2-isobutyrylphenyl)trifluoromethanesulfonamide 31B (300 mg, 0.91 mmol), O-(2,4-bistrifluoromethylbenzyl)hydroxylamine hydrochloride (270 mg, 0.91 mmol) and anhydrous NaOAc (75 mg, 0.91 mmol) in EtOH (20 mL) was stirred for 15 h at RT. The reaction mixture was concentrated under vacuum and the residue filtered through a pad of silica (eluting with $CH_2Cl_2$/PE, 9:1). Purification by radial thin layer chromatography (eluting with $CH_2Cl_2$/PE, 1:19) afforded N-{2-[1-(2,4-bistrifluoromethylbenzyloxyimino)-2-methylpropyl]-4-chlorophenyl}trifluoromethanesulfonamide 116 (120 mg, 23%), as a pale yellow oil. $^1$H n.m.r. (200 MHz, $CDCl_3$) δ 9.43, br s, 1H; 7.98, s, 1H; 7.89, d, J=8.0 Hz, 1H; 7.74, d, J=8.0 Hz, 1H; 7.56, d, J=8.8 Hz, 1H; 7.44, d, J=2.4 Hz, 1H; 7.33, dd, J=2.4 and 8.8 Hz, 1H; 5.45, s, 2H; 3.47, quintet, J=7.0 Hz, 1H; 1.37, d, J=7.0 Hz, 6H. HRMS (M$^+$) 570.0417.

O-(2,4-Bistrifluoromethylbenzyl)hydroxylamine hydrochloride was prepared by the procedure described in Example 1A.

Example 6C

Preparation of N-{4-chloro-2-[1-(4-chlorophenoxyimino)-2-methylpropyl]phenyl}trifluoromethanesulfonamide (Compound 215)

A solution of N-(4-chloro-2-isobutyrylphenyl)trifluoromethanesulfonamide 31B (244 mg, 1.11 mmol), O-(4-Chlorophenyl)hydroxylamine hydrochloride (200 mg, 0.91 mmol) and anhydrous NaOAc (91 mg, 1.11 mmol) in EtOH (10 mL) was stirred for 48 h at RT. The reaction mixture was concentrated under vacuum, and the residue purified by column chromatography (eluting with $CH_2Cl_2$/PE, 3:7) to afford N-{4-chloro-2-[1-(4-chlorophenoxyimino)-2-methylpropyl]phenyl}trifluoromethanesulfonamide 215 (80 mg, 24%), as an orange oil. $^1$H n.m.r. (200 MHz, $CDCl_3$) δ 7.56, d, J=8.8 Hz, 1H; 7.45, dd, J=2.4 and 8.8 Hz, 1H; 7.27, d, J=9.0 Hz, 2H; 7.23, d, J=2.4 Hz, 1H; 7.07, d, J=9.0 Hz, 2H; 2.94, m, 1H; 1.37, s, 3H; 1.19, s, 3H.

An isomeric mixture of syn(Z) and anti(E)-N-{4-chloro-2-[1-(4-chlorophenoxyimino)-2-methylpropyl]phenyl}trifluoromethanesulfonamide was also isolated (210 mg, 62%), as an orange oil.

N(4-chloro-2-isobutyrylphenyl)trifluoromethanesulfonamide 31B was prepared by the procedure described in Example 6B.

O-(4-Chlorophenyl)hydroxylamine hydrochloride was prepared by the procedure described in Example 2C.

The following trifluoromethanesulfonanilide oxime ether compounds, as listed by Tables 8 and 8A, infra, were prepared using similar preparative methods: Compounds 92, 98, 99, 101, 102, 108, 110-115, 117-119, 121 and 216.

Additional data for compounds of Example 6 is provided by Table 7, below.

TABLE 7

| Compd # | $^1$H n.m.r.(200 MHz, $CDCl_3$) |
|---|---|
| 92 | δ 11.48, br s, 1H; 7.67–7.60, m, 3H; 7.50, d, J=8.0Hz, 2H; 7.46, d, J=2.2Hz, 1H; 7.32, dd, J=2.2 and 8.6Hz, 1H; 5.25, s, 2H; 2.82, m, 2H; 1.61, m, 2H; 1.00, t, J=7.2Hz, 3H. |
| 98 | δ 11.03, br s, 1H; 7.96, s, 1H; 7.86, d, J=8.2Hz, 1H; 7.72, d, J=8.2Hz, 1H; 7.62, d, J=8.8Hz, 1H; 7.47, d, J=2.4Hz, 1H; 7.32, dd, J=2.4 and 8.8Hz, 1H; 5.45, s, 2H; 2.84, m, 2H; 1.62, m, 2H; 1.04, t, J=7.2Hz, 3H. |
| 108 | δ 9.75, br s, 1H; 7.66, d, J=8.0Hz, 2H; 7.58–7.47, m, 3H; 7.43, d, J=2.2Hz, 1H; 7.31, dd, J=2.2 and 8.8Hz, 1H; 5.23, s, 2H; 3.42, septet, J=7.3Hz, 1H; 1.35, d, J=7.3Hz, 6H. |
| 119 | (250 MHz, $CDCl_3$) δ 9.79, br s, 1H; 7.56, d, J=7.0Hz, 1H; 7.44, d, J=1.4Hz, 1H; 7.41, d, J=1.8Hz, 1H; 7.36–7.26, m, 3H; 5.23, s, 2H; 3.37, septet, J=5.8Hz, 1H; 1.32, d, J=5.8Hz, 6H. |

TABLE 7-continued

| Compd # | $^1$H n.m.r.(200 MHz, CDCl$_3$) |
|---|---|
| 121 | δ 10.73, br s, 1H; 7.97, s, 1H; 7.86, d, J=8.2Hz, 1H; 7.74, d, J=8.2Hz, 1H; 7.63, dd, J=9.2Hz and J$_{HF}$=5.2Hz, 1H; 7.23, dd, J=3.4Hz and J$_{HF}$=10.2Hz, 1H; 7.13–7.03, m, 1H; 5.48, s, 2H; 2.39, s, 3H. |

Example 7

Figure 10:
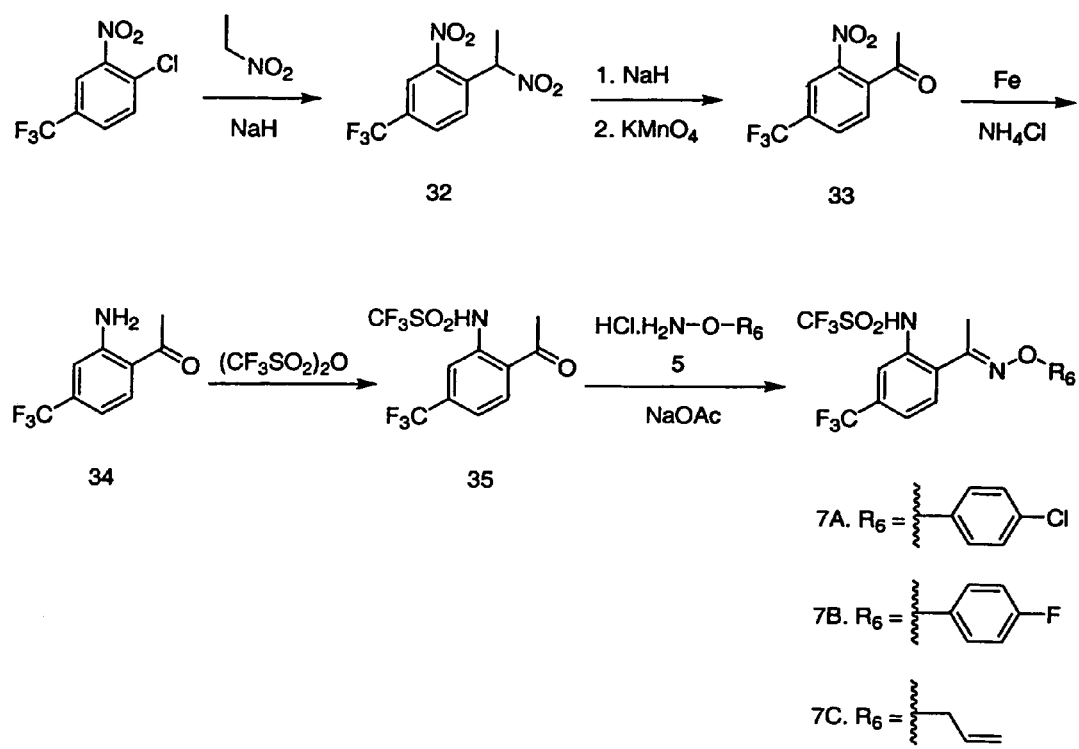
FIG. 10 illustrates the preparative reactions of Examples 7A through 7C.

The following compounds were prepared according to the reaction scheme illustrated by FIG. 10.

Example 7A

Preparation of N-{2-[1-(4-chlorophenoxyimino) ethyl]-5-trifluoromethylphenyl}trifluoromethanesulfonamide (Compound 199)

A solution of N-(2-acetyl-5-trifluoromethylphenyl)trifluoromethanesulfonamide 35 (250 g, 0.75 mmol), O-(4-chlorophenyl)hydroxylamine hydrochloride (148 mg, 0.82 mmol) and anhydrous NaOAc (67 mg, 0.82 mmol) in EtOH (15 mL) was stirred for 20 hours at RT. The reaction mixture was concentrated under vacuum, the residue filtered through a pad of silica (eluting with CH$_2$Cl$_2$) and the solvent removed under reduced pressure. The residue was purified by recrystallization from CH$_2$Cl$_2$/PE to afford N-{2-[1-(4-chlorophenoxyimino)ethyl]-5-trifluoromethylphenyl}trifluoromethanesulfonamide 199 (310 mg, 90%), as a pale yellow solid. M.p. 89-90° C. $^1$H n.m.r. (200 MHz, CDCl$_3$) δ 11.41, br s, 1H; 8.02, s, 1H; 7.76, d, J=8.6 Hz, 1H; 7.56, m, 1H; 7.36, d, J=9.2 Hz, 2H; 7.12, d, J=9.2 Hz, 2H; 2.60, s, 3H.

Preparation of N-(2-acetyl-5-trifluoromethylphenyl) trifluoromethanesulfonamide 35 a) To a suspension of sodium hydride (1.60 g, 66.50 mmol) in DMSO (60 mL) was added dropwise a mixture of nitroethane (1.91 mL, 26.60 mmol) and 4-chloro-3-nitrobenzotrifluoride (3.0 g, 13.30 mmol) dissolved in DMSO (20 mL), and the reaction mixture was stirred for 2 hours at RT. Glacial acetic acid/water (1:1) was added to bring the mixture to ca. pH 4 and EtOAc (50 mL) was added, the phases separated, and the aqueous phase again extracted with EtOAc. The combined organics were twice washed with water, dried over MgSO$_4$ and the solvent removed under vacuum. The residue was filtered through a pad of silica (eluting with CH$_2$Cl$_2$/PE; 1:1) to afford 2-nitro-1-(1-nitroethyl)-4-trifluoromethylbenzene 32 (3.05 g, 87%), as an orange oil.

b) To sodium hydride (313 mg, 13.02 mmol) in 2-methyl-2-propanol (20 mL) was added 2-nitro-1-(1-nitroethyl)-4-trifluoromethylbenzene 32 (1.72 g, 6.51 mmol), and the reaction mixture was stirred for 30 minutes at 40° C. Cold EtOAc (60 mL) was added, the reaction cooled to 0° C. and ice (~30 g) and a cold solution of potassium permanganate (1.03 g, 6.51 mmol) and boric acid (403 mg, 6.51 mmol) in water (40 mL) was added. After 1 hour of vigorous stirring at 0° C., sodium metabisulfite (1M, 14 mL) and sulfuric acid (1N, 26 mL) was added and the reaction mixture extracted twice with EtOAc. The combined organics were washed with water, brine, dried and the solvent removed under vacuum. The residue was filtered through a pad of silica (eluting with CH$_2$Cl$_2$/PE; 1:1) to afford 1-(2-nitro-4-trifluoromethylphenyl) ethenone 33 (607 mg, 40%), as a yellow solid.

c) To a mixture of 1-(2-nitro-4-trifluoromethylphenyl) ethenone 33 (1.44 g, 6.18 mmol) in EtOH (30 mL) and H$_2$O (15 mL) was added iron powder (1.72 g, 30.88 mmol) and NH$_4$Cl (165 mg, 3.09 mmol), and the reaction was rapidly stirred at 90° C. for 30 minutes. The hot reaction mixture was filtered, the residues rinsed with EtOAc, and further H$_2$O added. The phases were separated and the organics were washed with water, brine, dried over MgSO$_4$ and the solvent removed under reduced pressure. The residue was filtered through a pad of silica (eluting with EtOAc/PE; 1:1) to afford 1-(2-amino-4-trifluoromethylphenyl)ethanone 34 (1.20 g, 96%), as a yellow solid.

d) To a solution of 1-(2-amino-4-trifluoromethylphenyl) ethanone 34 (1.21 g, 5.96 mmol) in anhydrous dichloromethane (50 mL) at 0° C. was added dropwise (CF$_3$SO$_2$)$_2$O (2.0 mL, 11.91 mmol) in anhydrous CH$_2$Cl$_2$ (25 mL) over 30 minutes, and the reaction allowed to warm to RT over 60 hours. The reaction mixture was washed with water, brine, dried over MgSO$_4$ and concentrated under vacuum. The residue was filtered through a pad of silica (eluting with CH$_2$Cl$_2$) to afford N-(2-acetyl-5-trifluoromethylphenyl)trifluoromethanesulfonamide 35 (1.23 g, 62%), as a yellow solid. $^1$H n.m.r. (200 MHz, CDCl$_3$) δ 12.15, brs, 1H; 8.09, m, 2H; 7.53, m, 1H; 2.77, s, 3H.

O-(4-Chlorophenyl)hydroxylamine hydrochloride was prepared by the procedure described in Example 2C.

Example 7B

Preparation of N-{2-[1-(4-fluorophenoxyimino) ethyl]-5-trifluoromethylphenyl}trifluoromethanesulfonamide (Compound 200)

A solution of N-(2-acetyl-5-trifluoromethylphenyl)trifluoromethanesulfonamide 35 (280 mg, 0.84 mmol), O-(4-fluorophenyl)hydroxylamine hydrochloride (150 mg, 0.92 mmol) and anhydrous NaOAc (75 mg, 0.92 mmol) in EtOH (15 mL) was stirred for 24 hours at RT. The reaction mixture was concentrated under vacuum, the residue purified by column chromatography (eluting with CH$_2$Cl$_2$/PE; 1:1 to 4:1) and the solvent removed under reduced pressure. Recrystallization from CH$_2$Cl$_2$/PE afforded N-{2-[1-(4-fluorophenoxyimino)ethyl]-5-trifluoromethylphenyl}trifluoromethanesulfonamide 200 (300 mg, 81%), as colorless crystals. M.p. 95-96° C. $^1$H n.m.r. (200 MHz, CDCl$_3$) δ 11.48, br s, 1H; 8.01, s, 1H; 7.76, d, J=8.4 Hz, 1H; 7.55, m, 1H; 7.19–7.04, m, 4H; 2.60, s, 3H.

O-(4-Fluorophenyl)hydroxylamine hydrochloride was prepared by the procedure described in Example 1D.

Example 7C

Preparation of N-[2-(1-allyloxyiminoethyl)-5-trifluoromethylphenyl]trifluoromethanesulfonamide (Compound 241)

A solution of N-(2-acetyl-5-trifluoromethylphenyl)trifluoromethanesulfonamide 35 (168 mg, 0.50 mmol), O-allylhydroxylamine hydrochloride (60mg, 0.53 mmol) and anhydrous NaOAc (43 mg, 0.53 mmol) in EtOH (3 mL) was stirred for 15 hours at RT. The reaction mixture was concentrated under vacuum, and the residue purified by radial thin layer chromatography (eluting with $CH_2Cl_2$/PE, 1:99) to afford N-[2-(1-allyloxyiminoethyl)-5-trifluoromethylphenyl]trifluoromethanesulfonamide 241 (155 mg, 80%), as a colorless oil. $^1H$ n.m.r. (400 MHz, $CDCl_3$) δ 11.82, br s, 1H; 7.98, s, 1H; 7.65, d, J=8.2Hz, 1H; 7.49, d, J=8.2Hz, 1H; 6.02, m, 1H; 5.44, d, $^3J$=17.2 Hz, 1H; 5.37, d, $^3J$=10.4 Hz, 1H; 4.72, d, J=6.0 Hz, 2H; 2.38, s, 3H. HRMS ($M^+$) 390.0465.

The following trifluoromethanesulfonanilide oxime ether compounds, as listed in Tables 8 and 8A, infra, were prepared using similar preparative methods: Compounds 201, 214, 217-222 and 235-240.

Additional data for compounds of Example 7 is provided by Table 10, below.

TABLE 10

| Compd # | $^1H$ n.m.r.(400 MHz, $CDCl_3$) |
|---|---|
| 235 | δ 12.40, br s, 1H; 7.99, s, 1H; 7.66, d, J=8.2Hz, 1H; 7.47, d, J=8.2Hz, 1H; 4.50, m, 1H; 2.37, s, 3H; 1.37, d, J=6.4Hz, 6H. |

Example 8

Figure 11:
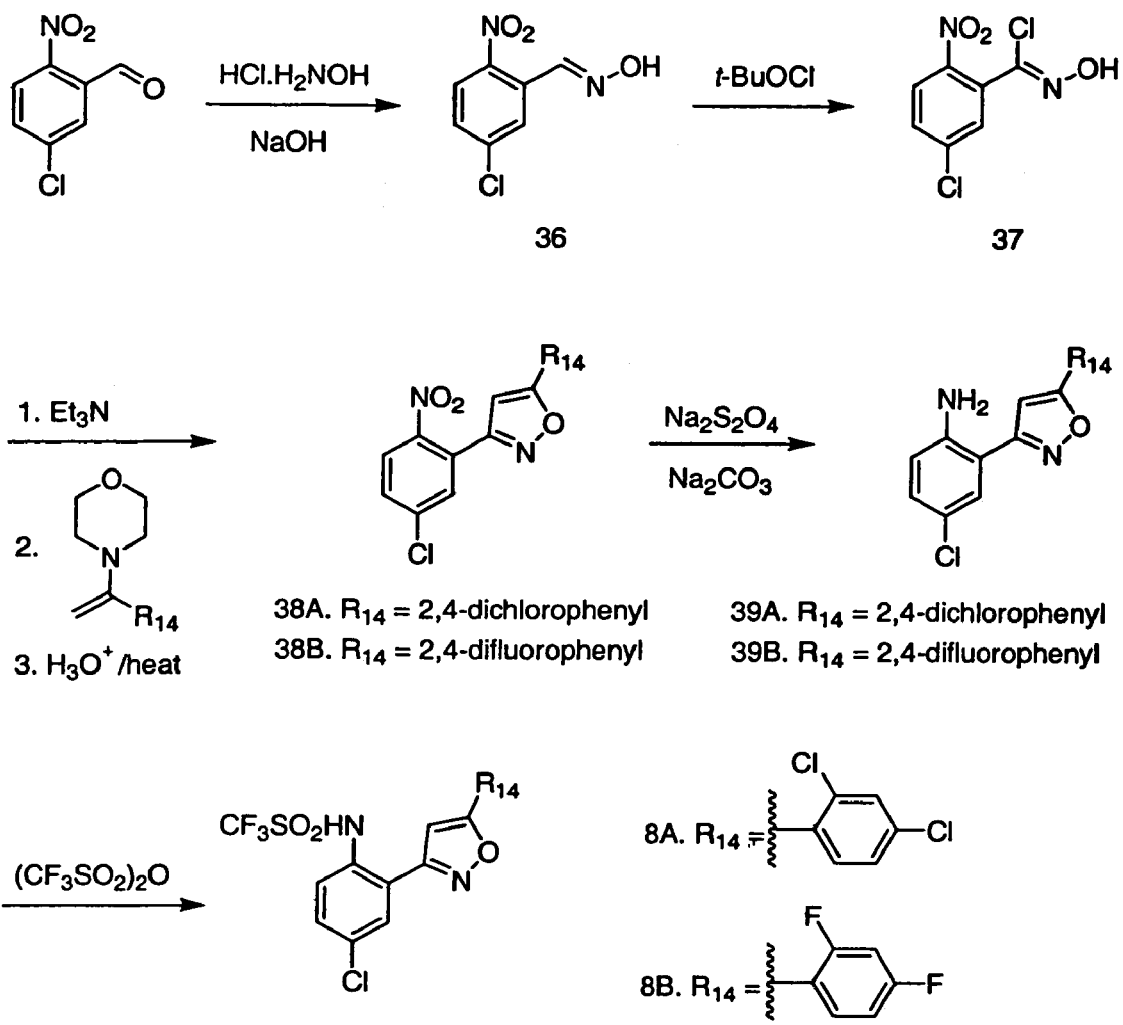
FIG. 11 illustrates the preparative reactions of Examples 8A and 8B.

The following compounds were prepared according to the reaction scheme illustrated by FIG. 11.

Example 8A

Preparation of N-{4-chloro-2-[5-(2,4-dichlorophenyl)isoxazol-3-yl]phenyl}trifluoromethanesulfonamide (Compound 229)

a) To a solution of 4-[1-(2,4-dichlorophenyl)vinyl]morpholine (1.23 g, 4.77 mmol) and $Et_3N$ (731 µL, 5.25 mmol) in anhydrous $CHCl_3$ (30 mL) was added dropwise a solution of 5-chloro-2-nitrobenzohydroximoyl chloride 37 (1.18 g, 5.02 mmol) in anhydrous $CHCl_3$ (15 mL), and the reaction allowed to stir for 24 h at RT. The reaction mixture was then washed with $H_2O$ (2×30 mL), dried over $MgSO_4$ and concentrated under reduced pressure. The residue was then dissolved in THF (22 mL), 2N HCl (42 mL) was added, and the mixture was heated at 75° C. for 8 h. Once the reaction mixture had cooled, 5% $Na_2CO_3$ (110 mL) was added, and it was extracted with $CH_2Cl_2$ (2×75 mL). The combined organics were washed with $H_2O$ (75 mL), dried over $MgSO_4$ and concentrated under reduced pressure. The residue was filtered through a pad of silica (eluting with $CH_2Cl_2$/PE, 3:2) and the solvent concentrated under reduced pressure to afford 3-(5-chloro-2-nitrophenyl)-5-(2,4-dichlorophenyl)isoxazole 38A (1.23 g, 66%), as a white solid. $^1H$ n.m.r. (200 MHz, $CDCl_3$) δ 8.04, d, J=8.8 Hz, 1H; 7.96, d, J=8.6 Hz, 1H; 7.75, d, J=2.2 Hz, 1H; 7.63, dd, J=2.2 and 8.6 Hz, 1H; 7.56, d, J=2.2 Hz, 1H; 7.43, dd, J=2.2 and 8.8 Hz, 1H; 7.06, s, 1H.

b) A suspension of 3-(5-chloro-2-nitrophenyl)-5-(2,4-dichlorophenyl)isoxazole 38A (919 mg, 2.49 mmol) in MeOH (90 mL) was stirred for 1 h at RT, and for 30 min at 65° C. To this was added $Na_2CO_3$ (1.32 g, 12.43 mmol), followed by dropwise addition of a solution of $Na_2S_2O_4$ (2.49 g, 12.43 mmol) in $H_2O$ (35 mL) over 15 min. The temperature was raised to 70° C. and the reaction mixture was stirred for a further 30 min. EtOAc (120 mL) was added and the reaction mixture was allowed to cool to RT. The solids were removed by filtration and washed with further EtOAc. The organic phase was partitioned and washed with $H_2O$, dried over $MgSO_4$ and then filtered through a pad of silica (eluting with EtOAc/PE, 1:1). The solvent was concentrated under reduced pressure to afford 4-chloro-2-[5-(2,4-dichlorophenyl)isoxazol-3-yl]phenylamine 39A (554 mg, 68%), as a yellow solid. $^1H$ n.m.r. (200 MHz, $CDCl_3$) δ 7.93, d, J=8.8 Hz, 1H; 7.58, d, J=2.2 Hz, 1H; 7.50, d, J=2.2 Hz, 1H; 7.42, dd, J=2.2 and 8.8 Hz, 1H; 7.27, s, 1H; 7.17, dd, J=2.2 and 8.8 Hz, 1H; 6.75, d, J=8.8 Hz, 1H.

c) To a solution of 4-chloro-2-[5-(2,4-dichlorophenyl)isoxazol-3-yl]phenylamine 39A (84 mg, 0.25 mmol) in anhydrous dichloromethane (25 mL) at 0° C. was added dropwise $(CF_3SO_2)_2O$ (62 µL, 0.37 mmol) in anhydrous $CH_2Cl_2$ (10 mL) over 10 min, and the reaction allowed to warm to RT overnight. The reaction mixture was washed with $H_2O$ and then brine, dried over $MgSO_4$ and concentrated under vacuum. The residue was filtered through a pad of silica (eluting with $CH_2Cl_2$/PE, 4:1) and the solvent removed under reduced pressure. The residue was purified by radial thin layer chromatography (eluting with $CH_2Cl_2$/PE, 1:9 to 1:4) to afford N-{4-chloro-2-[5-(2,4-dichlorophenyl)isoxazol-3-yl]phenyl}trifluoromethanesulfonamide 229 (54 mg, 46%), as a white solid. M.p. 142-144° C. $^1H$ n.m.r. (200 MHz, $CDCl_3$) δ 10.46, br s, 1H; 7.96, d, J=8.4 Hz, 1H; 7.79, d, J=9.0 Hz, 1H; 7.70, d, J=2.4 Hz, 1H; 7.61, d, J=1.8 Hz, 1H; 7.46, m, 2H; 7.34, s, 1H.

Preparation of 5-chloro-2-nitrobenzohydroximoyl chloride 37 a) To a solution of 5-chloro-2-nitrobenzaldehyde (2.85 g, 15.40 mmol) in EtOH (10 mL) was added sequentially $H_2O$ (10 mL), ice (~7 mL), hydroxylamine hydrochloride (1.12 g, 16.18 mmol), 50% NaOH (307 µL, 3.84 mmol) and EtOH (50 mL). The reaction was allowed to stir for 1 h at RT, after which $H_2O$ (10 mL) was added and the mixture extracted with $Et_2O$ (2×75 mL). The combined organics were dried over $MgSO_4$ and concentrated under reduced pressure to ca. 10 mL. $H_2O$ (50 mL) was then quickly added which formed a precipitate, and this was collected by filtration to afford 5-chloro-2-nitrobenzaldehyde oxime 36 (2.65 g, 86%), as a yellow solid.

b) To a solution of 5-chloro-2-nitrobenzaldehyde oxime 36 (1.0 g, 4.99 mmol) in 1,2-DCE (25 mL) and 2-PrOH (6.3 mL) at ca. −10° C. was added all at once t-butyl hypochlorite (780 µL, 6.48 mmol), and the reaction allowed to rapidly stir for 30 min at RT. The solvent was removed under reduced pressure (at 50° C.) to afford 5-chloro-2-nitrobenzohydroximoyl chloride 37 (1.11 g, 95%), as a white solid. $^1H$ n.m.r. (200 MHz, $CDCl_3$) δ 8.56, br s, 1H; 7.96, d, J=8.4 Hz, 1H; 7.59, m, 2H.

Example 8B

Preparation of N-{4-chloro-2-[5-(2,4-difluorophenyl)isoxazol-3-yl]phenyl}trifluoromethanesulfonamide (Compound 231)

a) To a solution of 4-[1-(2,4-dichlorophenyl)vinyl]morpholine (500 mg, 2.22 mmol) and $Et_3N$ (340 μL, 2.44 mmol) in anhydrous $CHCl_3$ (20 mL) was added dropwise a solution of 5-chloro-2-nitrobenzohydroximoyl chloride 37 (548 mg, 2.33 mmol) in anhydrous $CHCl_3$ (10 mL), and the reaction allowed to stir for 24 h at RT. The reaction mixture was then washed with $H_2O$ (2×30 mL), dried over $MgSO_4$ and concentrated under reduced pressure. The residue was then dissolved in THF (10 mL), 2N HCl (20 mL) was added, and the mixture was heated at 75° C. for 7 h. Once the reaction mixture had cooled, 5% $Na_2CO_3$ (50 mL) was added, and it was extracted with $CH_2Cl_2$ (2×50 mL). The combined organics were washed with $H_2O$ (50 mL), dried over $MgSO_4$ and concentrated under reduced pressure. The residue was filtered through a pad of silica (eluting with $CH_2Cl_2$/PE, 3:2) and the solvent concentrated under reduced pressure to afford 3-(5-chloro-2-nitrophenyl)-5-(2,4-difluorophenyl)isoxazole 38B (465 mg, 62%), as a white solid. $^1H$ n.m.r. (200 MHz, $CDCl_3$) δ 8.01, m, 2H; 7.73, d, J=2.2 Hz, 1H; 7.62, dd, J=2.2 and 8.4 Hz, 1H; 7.12-6.93, m, 2H; 6.77, d, J=3.6 Hz, 1H.

b) A suspension of 3-(5-chloro-2-nitrophenyl)-5-(2,4-difluorophenyl)isoxazole 38B (250 mg, 0.74 mmol) in MeOH (25 mL) was stirred for 1 h at RT, and for 30 min at 65° C. To this was added $Na_2CO_3$ (394 mg, 3.71 mmol), followed by dropwise addition of a solution of $Na_2S_2O_4$ (760 mg, 3.71 mmol) in $H_2O$ (10 mL) over 15 min. The temperature was raised to 70° C. and the reaction mixture was stirred for a further 30 min. EtOAc (30 mL) was added and the reaction mixture was allowed to cool to RT. The solids were removed by filtration and washed with further EtOAc. The organic phase was partitioned and washed with $H_2O$, dried over $MgSO_4$ and then filtered through a pad of silica (eluting with EtOAc/PE, 1:1). The solvent was concentrated under reduced pressure to afford 4-chloro-2-[5-(2,4-difluorophenyl)isoxazol-3-yl]phenylamine 39B (71 mg, 34%), as a yellow solid. $^1H$ n.m.r. (200 MHz, $CDCl_3$) δ 7.99, m, 1H; 7.50, d, J=2.4 Hz, 1H; 7.17, dd, J=2.4 and 8.8 Hz, 1H; 7.11-6.95, m, 3H; 6.74, d, J=8.8 Hz, 1H.

c) To a solution of 4-chloro-2-[5-(2,4-difluorophenyl)isoxazol-3-yl]phenylamine 39B (71 mg, 0.23 mmol) in anhydrous dichloromethane (10 mL) at 0° C. was added dropwise $(CF_3SO_2)_2O$ (43 μL, 0.26 mmol) in anhydrous $CH_2Cl_2$ (5 mL) over 10 min, and the reaction allowed to warm to RT overnight. The reaction mixture was washed with $H_2O$ and then brine, dried over $MgSO_4$ and concentrated under vacuum. The residue was filtered through a pad of silica (eluting with $CH_2Cl_2$/PE, 4:1) and the solvent removed under reduced pressure. The residue was purified by radial thin layer chromatography (eluting with $CH_2Cl_2$/PE, 1:9 to 3:7) to afford N-{4-chloro-2-[5-(2,4-difluorophenyl)isoxazol-3-yl]phenyl}trifluoromethanesulfonamide 231 (33 mg, 32%), as a pale yellow solid. M.p. 117-119° C. $^1H$ n.m.r. (200 MHz, $CDCl_3$) δ 10.46, br s, 1H; 8.02, m, 1H; 7.79, d, J=8.8 Hz, 1H; 7.70, d, J=2.4 Hz, 1H; 7.46, dd, J=2.4 and 8.8 Hz, 1H; 7.15-6.98, m, 3H.

The following trifluoromethanesulfonanilide oxime ether compounds, as listed in Tables 9 and 9A, infra, were prepared using similar preparative methods: Compounds 225-228, 230 and 291-295.

Additional data for compounds of Example 8 is provided by Table 11, below.

TABLE 11

| Compd # | $^1H$ n.m.r.(400 MHz, $CDCl_3$) |
|---|---|
| 291 | δ 10.67, br s, 1H; 7.75, d, J=8.8Hz, 1H; 7.58, d, J=2.4Hz, 1H; 7.41, dd, J=2.4 and 8.8Hz, 1H; 6.39, s, 1H; 2.85, m, 2H; 1.76, m, 2H; 1.44, m, 2H; 0.98, t, J=7.2Hz, 3H. |
| 293 | δ 10.47, br s, 1H; 8.57, d, J=1.6Hz, 1H; 7.78, d, J=8.8Hz, 1H; 7.62, d, J=2.4Hz, 1H; 7.45, dd, J=2.4 and 8.8Hz, 1H; 6.79, d, J=1.6Hz, 1H. |

Example 9

Figure 12:
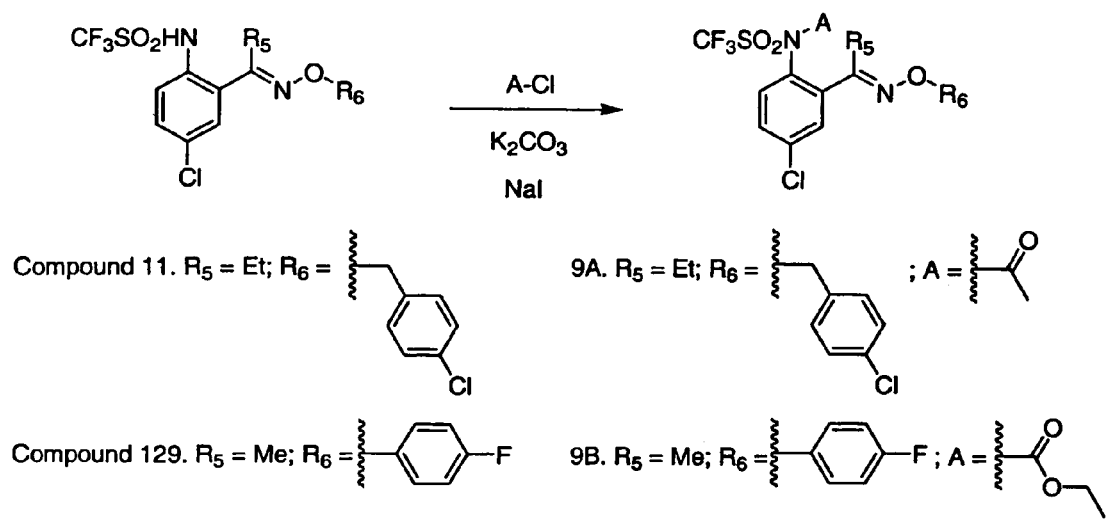
FIG. 12 illustrates the preparative reaction of Examples 9A and 9B.

The following compounds were prepared according to the reaction scheme illustrated by FIG. 12.

Example 9A

Preparation of N-acetyl-N-{4-chloro-2-[1-(4-chlorobenzyloxyimino)propyl]phenyl}trifluoromethanesulfonamide (Compound 307)

To a mixture of N-{4-chloro-2-[1-(4-chlorobenzyloxyimino)propyl]phenyl}trifluoromethanesulfonamide (compound 11) (150 mg, 0.33 mmol) and $K_2CO_3$ (137 mg, 0.99 mmol) in acetone (5 mL) was added acetyl chloride (70 μL, 0.99 mmol), and the reaction allowed to stir at RT for 2 hours. The reaction mixture was concentrated under vacuum and the residue dissolved in $CHCl_3$ (20 mL), washed with $H_2O$ (15 mL), dried over $MgSO_4$ and concentrated under reduced pressure. The residue was purified by radial thin layer chromatography (eluting with EtOAc/PE, 1:19) to afford N-acetyl-N-{4-chloro-2-[1-(4-chlorobenzyloxyimino)propyl]phenyl}trifluoromethanesulfonamide 307 (156 mg, 95%), as a pale yellow solid. M.p. 64-66° C. $^1H$ n.m.r. (400 MHz, $CDCl_3$) δ 7.51, d, J=2.4 Hz, 1H; 7.42, dd, J=2.4 and 8.8 Hz, 1H; 7.30, m, 4H; 7.23, d, J=2.4 Hz, 1H; 5.12, m, 2H; 2.83, m, 1H; 2.67, m, 1H; 1.91, s, 3H; 1.18, t, J=7.6 Hz, 3H.

Example 9B

Preparation of N-carbonylethoxy-N-{4-chloro-2-[1-(4-fluorophenoxyimino)ethyl]phenyl}trifluoromethanesulfonamide (Compound 310)

To a mixture of N{4-chloro-2-[1-(4-fluorophenoxyimino)ethyl]phenyl}trifluoromethanesulfonamide (compound 129) (150 mg, 0.37 mmol) and $K_2CO_3$ (151 mg, 1.10 mmol) in acetone (5 mL) was added ethyl chloroformate (105 μL, 1.10 mmol), and the reaction allowed to stir at RT for 21 hours. The reaction mixture was concentrated under vacuum and the residue dissolved in $Et_2O$ (50 mL), washed with $H_2O$ (40 mL) then brine (40 mL), dried over $Na_2SO_4$ and concentrated under reduced pressure. The residue was purified by radial thin layer chromatography (eluting with EtOAc/PE, 1:19) to afford N-carbonylethoxy-N-{4-chloro-2-[1-(4-fluorophenoxyimino)ethyl]phenyl}trifluoromethanesulfonamide 310 (85 mg, 63% based on recovered starting material), as a pale yellow oil. $^1H$ n.m.r. (400 MHz, $CDCl_3$) δ

7.52, d, J=2.4 Hz, 1H; 7.45, dd, J=2.4 and 8.8 Hz, 1H; 7.26, d, J=2.4 Hz, 1H; 7.14, m, 2H; 6.98, m, 2H; 4.24, m, 1H; 4.15, m, 1H; 2.41,s, 3H; 1.15, t, J=7.2 Hz, 3H. HRMS (M⁺) 482.0316.

The following trifluoromethanesulfonanilide oxime ether compounds, as listed in Table 13, infra, were prepared using similar preparative methods: Compounds 296-306, 308, 309 and 311-323.

Additional data for compounds of Example 9 is provided by Table 12, below.

TABLE 12

| Compd # | $^1$H n.m.r.(400 MHz, CDCl$_3$) |
|---|---|
| 308 | δ 7.56, d, J=2.4Hz, 1H; 7.49, dd, J=2.4 and 8.8Hz, 1H; 7.26, d, J=8.8Hz, 1H; 7.09, m, 2H; 7.00, m, 2H; 2.43, s, 3H; 2.17, s, 3H. |
| 312 | δ 7.49, d, J=2.4Hz, 1H; 7.42, dd, J=2.4 and 8.8Hz, 1H; 7.35, d, J=8.8Hz, 1H; 7.14, m, 2H; 7.02, m, 2H; 2.43, s, 3H; 2.34, m, 2H; 1.66, m, 2H; 0.95, t, J=7.2Hz, 3H. |

Example 10

Listing of Exemplified Compounds

A total of 323 compounds have been prepared according to the methods of Examples 1-9, as described above. These are summarized by Tables 8, 8A, 9, 9A and 13, hereinbelow, as follows.

Abbreviations for Tables 8, 8A, 9, 9A and 13

"C#" is the compound number; "[M⁺]" is the mass reading by high resolution mass spectroscopy; and "MP" is the melting point of the compound, in ° C., where available.

Solely for convenience, all of the compounds in these tables have been drawn as single anti(E)-isomers about the C=N bond. However, the compounds of the present invention are not meant to be so limited, but rather, the structures depicted are meant also to represent stereoisomers, and/or mixtures thereof, etc., as discussed supra.

Table 8 provides compounds 1-224, based on Formula (I) supra.

TABLE 8

| C# | Compound structure | Mp(° C.) | [M⁺] |
|---|---|---|---|
| 1 | 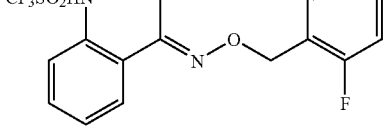 | | |
| 2 | 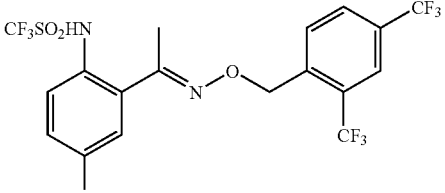 | | 542.0102 |
| 3 | 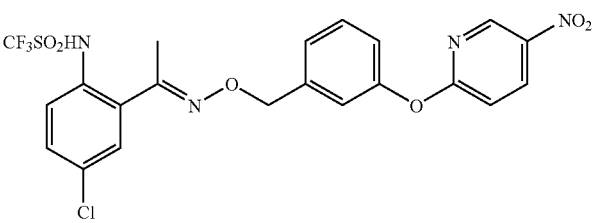 | | |
| 4 | 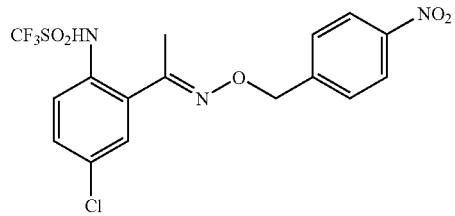 | | 95-96 |

TABLE 8-continued

| C# | Compound structure | Mp(° C.) | [M+] |
|---|---|---|---|
| 5 | 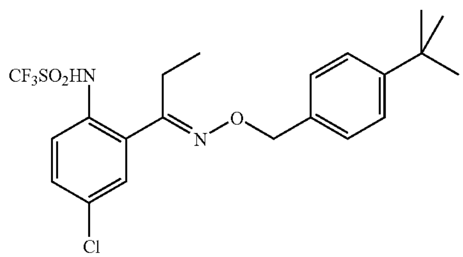 | 73-74 | |
| 6 | 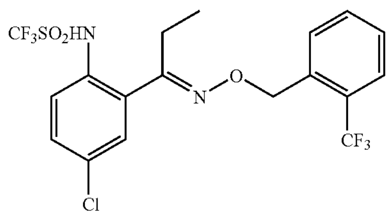 | 49-51 | |
| 7 | 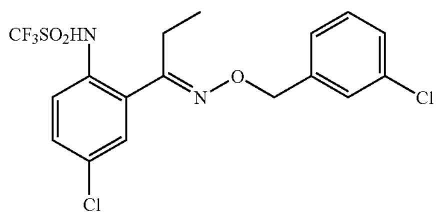 | 60-61 | |
| 8 | 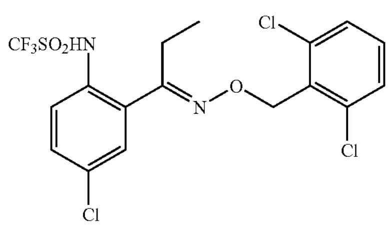 | 113-115 | |
| 9 | 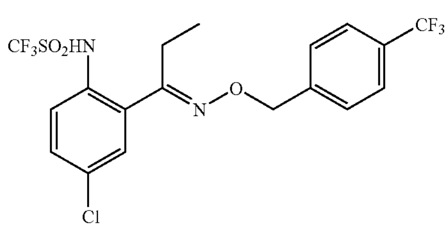 | 76-77 | |
| 10 | 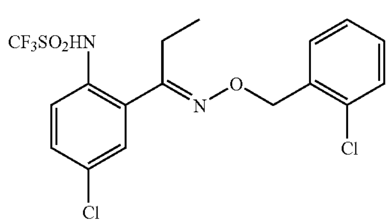 | 60-61 | |

TABLE 8-continued

| C# | Compound structure | Mp(° C.) | [M+] |
|---|---|---|---|
| 11 | 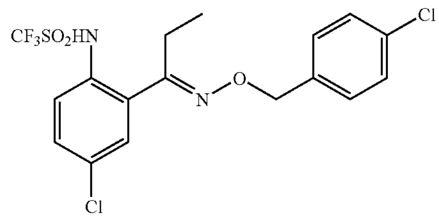 | 54-55 | |
| 12 | 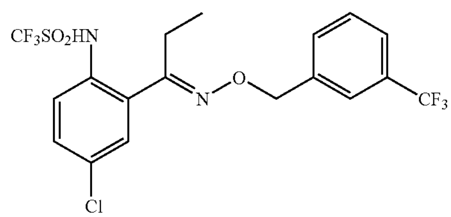 | | |
| 13 | 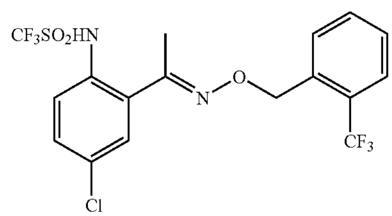 | 99-100 | |
| 14 | 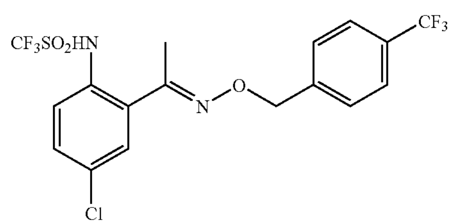 | 69-70 | |
| 15 | 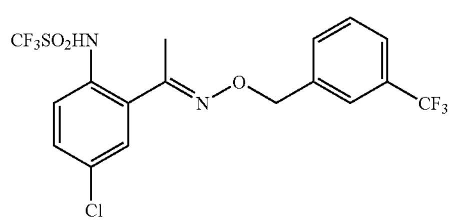 | 83-85 | |
| 16 | 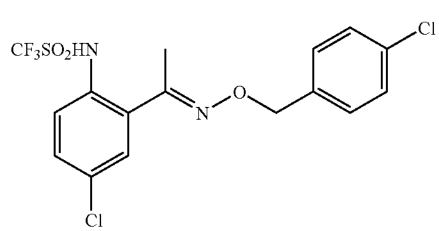 | 86-87 | |
| 17 | 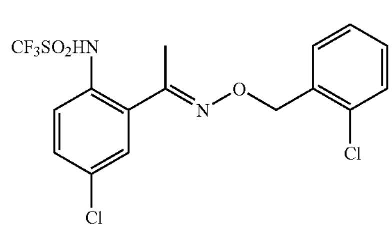 | 69-71 | |

TABLE 8-continued

| C# | Compound structure | Mp(° C.) | [M+] |
|----|-------------------|----------|------|
| 18 | CF₃SO₂HN—(4-Cl-phenyl)-C(CH₃)=N-O-CH₂-(3-Cl-phenyl) | 49-50 | |
| 19 | CF₃SO₂HN—(4-Cl-phenyl)-C(CH₃)=N-O-CH₂-(2,3-diCl-phenyl) | 50-52 | |
| 20 | CF₃SO₂HN—(4-Cl-phenyl)-C(CH₃)=N-O-CH₂-(2,6-diCl-phenyl) | 129-130 | |
| 21 | CF₃SO₂HN—(4-Cl-phenyl)-C(CH₃)=N-O-CH₂-(2,4-diCl-phenyl) | 108-109 | |
| 22 | CF₃SO₂HN—(4-Cl-phenyl)-C(CH₃)=N-O-CH₂-phenyl | 107-108 | |
| 23 | CF₃SO₂HN—(4-Cl-phenyl)-C(CH₃)=N-O-CH₂-(4-Br-phenyl) | 80-81 | |

TABLE 8-continued

| C# | Compound structure | Mp(° C.) | [M+] |
|---|---|---|---|
| 24 | (structure: 2-(CF₃SO₂HN)-5-Cl-phenyl phenyl ketone O-(4-CF₃-benzyl)oxime) | | |
| 25 | (structure: 2-(CF₃SO₂HN)-phenyl methyl ketone O-(3,3-dichloroallyl)oxime) | | 389.9812 |
| 26 | (structure: 2-(CF₃SO₂HN)-phenyl methyl ketone O-(4-chlorobenzyl)oxime) | | |
| 27 | (structure: 2-(CF₃SO₂HN)-phenyl methyl ketone O-(cyanomethyl)oxime) | 97-99 | |
| 28 | (structure: 2-(CF₃SO₂HN)-phenyl methyl ketone O-(2-cyanobenzyl)oxime) | | |
| 29 | (structure: 2-(CF₃SO₂HN)-phenyl methyl ketone O-ethyloxime) | | 310.0599 |
| 30 | (structure: 2-(CF₃SO₂HN)-phenyl phenyl ketone O-methyloxime) | | |
| 31 | (structure: 2-(CF₃SO₂HN)-phenyl phenyl ketone O-ethyloxime) | | |

TABLE 8-continued

| C# | Compound structure | Mp(° C.) | [M+] |
|---|---|---|---|
| 32 | 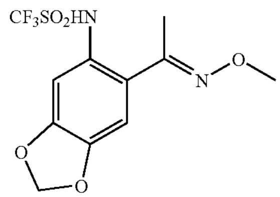 | 84-86 | |
| 33 | 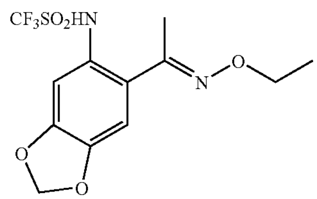 | | |
| 34 | 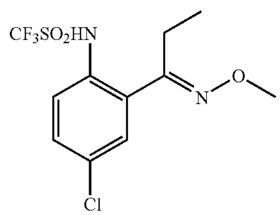 | 40-42 | |
| 35 | 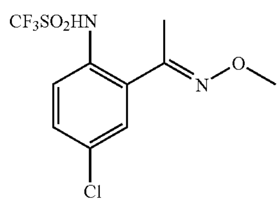 | 71-73 | |
| 36 | 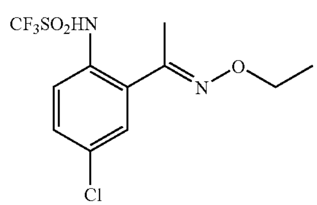 | 55-57 | |
| 37 | 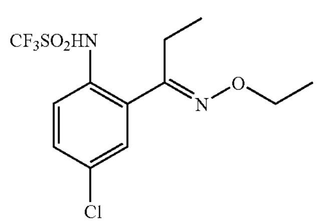 | | 358.0357 |
| 38 | 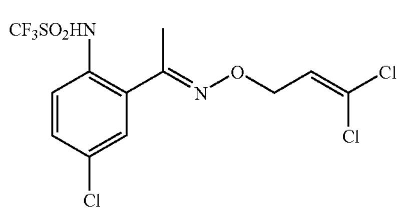 | 61-62 | |

TABLE 8-continued

| C# | Compound structure | Mp(° C.) | [M+] |
|---|---|---|---|
| 39 | 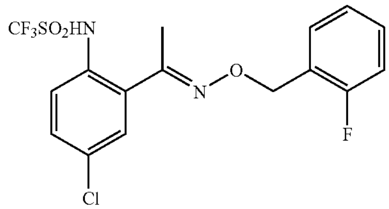 | 105-106 | |
| 40 | 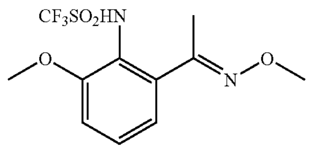 | | |
| 41 | 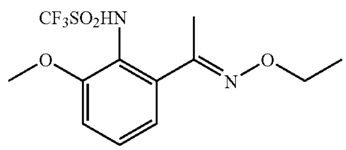 | | |
| 42 | 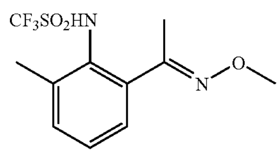 | | |
| 43 | 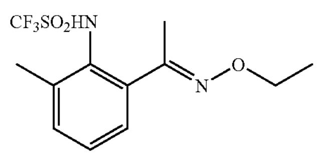 | | |
| 44 | 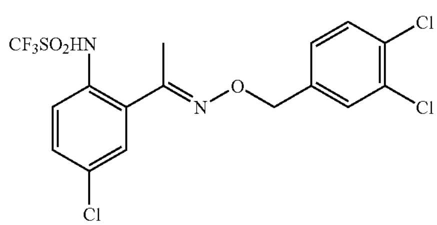 | | |
| 45 | 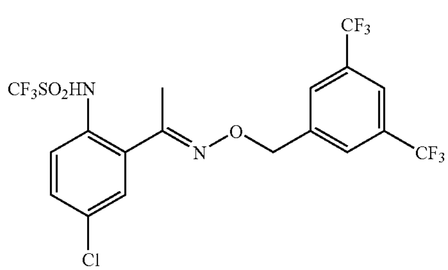 | | |
| 46 | 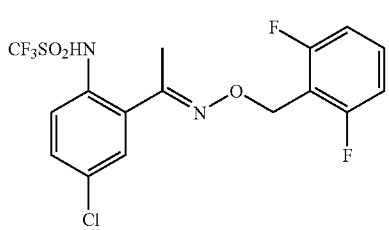 | | |

TABLE 8-continued

| C# | Compound structure | Mp(° C.) | [M+] |
|---|---|---|---|
| 47 | 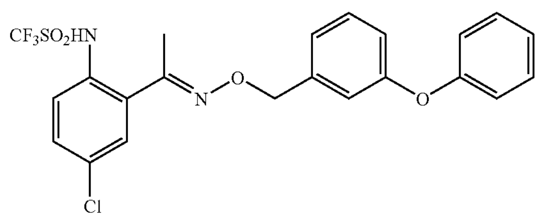 | | |
| 48 | 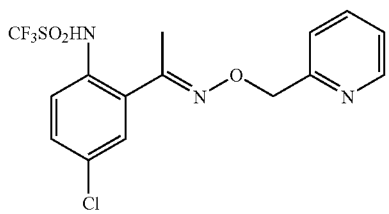 | 120-122 | |
| 49 | 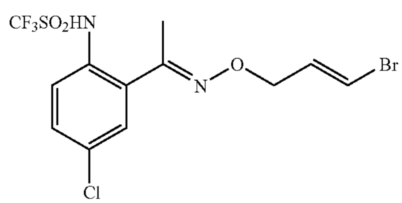 | | |
| 50 | 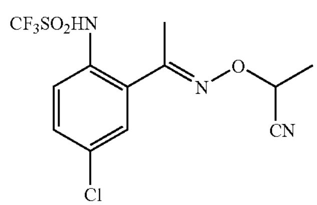 | | |
| 51 | 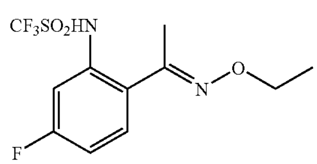 | 84-86 | |
| 52 | 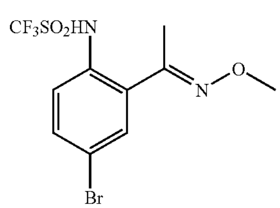 | 68-70 | |
| 53 | 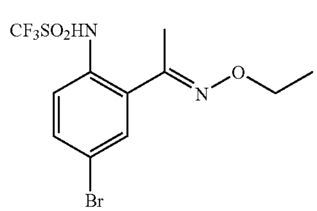 | 52-54 | |

TABLE 8-continued
| C# | Compound structure | Mp(° C.) | [M⁺] |
|---|---|---|---|
| 54 | 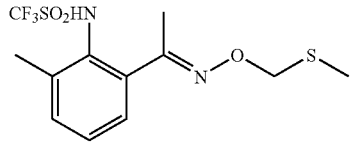 | | 356.0455 |
| 55 | 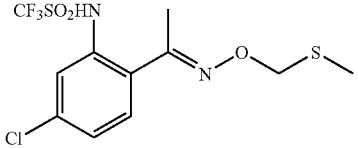 | | |
| 56 | 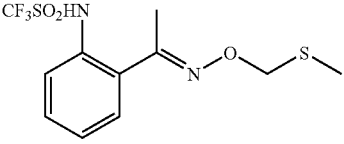 | 83-85 | |
| 57 | 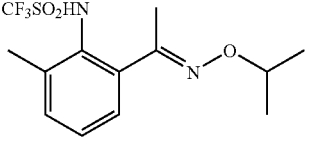 | | |
| 58 | 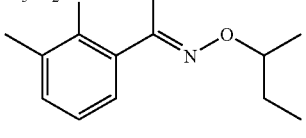 | | |
| 59 | 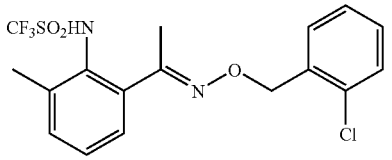 | | |
| 60 | 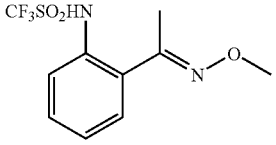 | | |
| 61 | 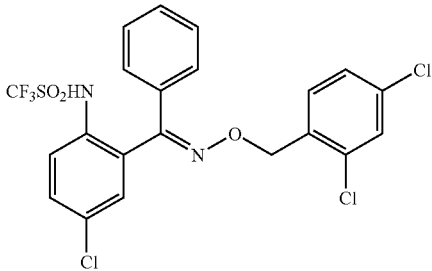 | 92-93 | |

TABLE 8-continued

| C# | Compound structure | Mp(° C.) | [M+] |
|---|---|---|---|
| 62 | 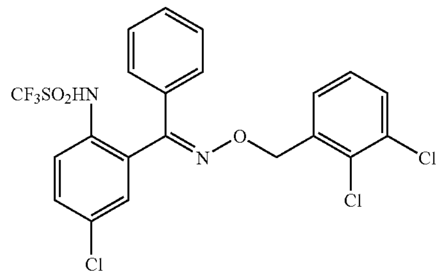 | | |
| 63 | 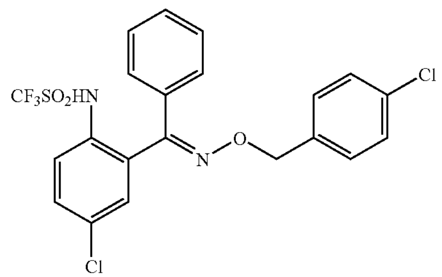 | 68-70 | |
| 64 | 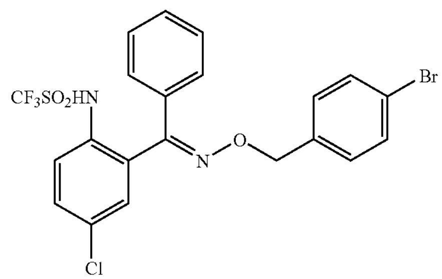 | 55-56 | |
| 65 | 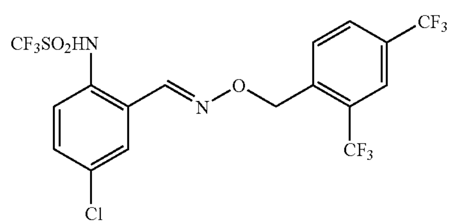 | 65-67 | |
| 66 | 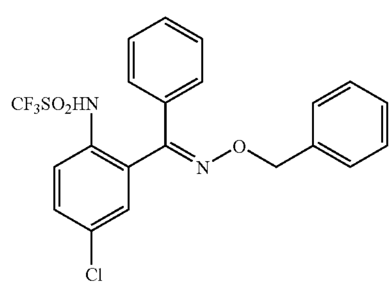 | | |
| 67 | 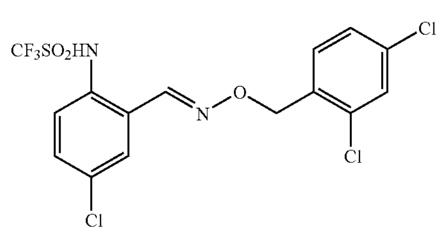 | | |

TABLE 8-continued

| C# | Compound structure | Mp(° C.) | [M+] |
|---|---|---|---|
| 68 | 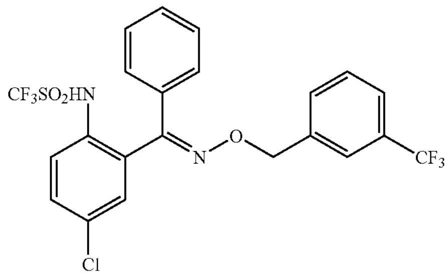 | 65-66 | |
| 69 | 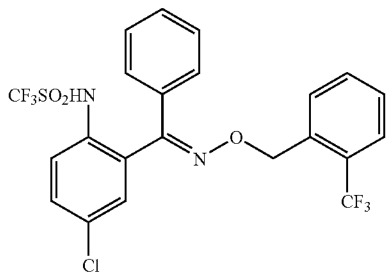 | 42-44 | |
| 70 | 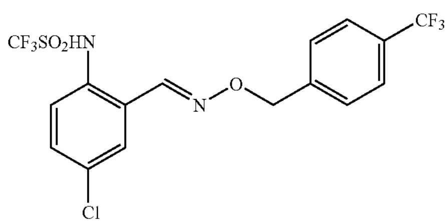 | 83-84 | |
| 71 | 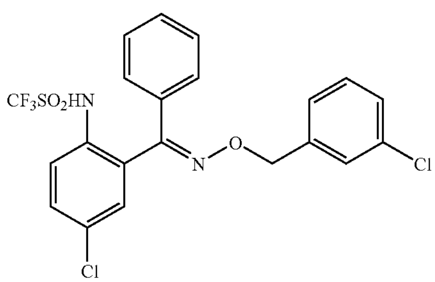 | | |
| 72 | 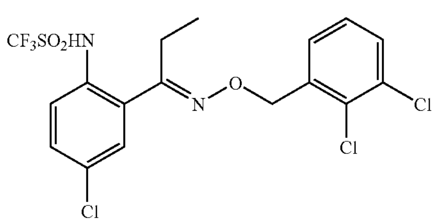 | 53-55 | |
| 73 | 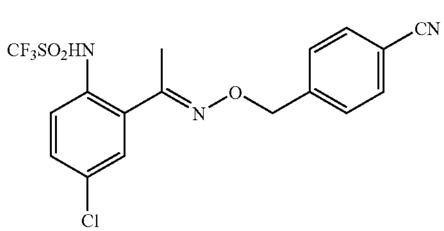 | 91-92 | |

TABLE 8-continued

| C# | Compound structure | Mp(° C.) | [M+] |
|---|---|---|---|
| 74 | 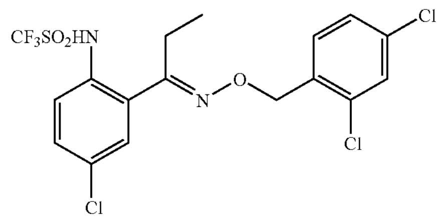 | | |
| 75 | 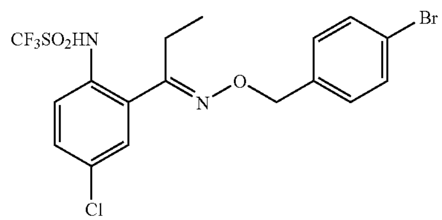 | 48-51 | |
| 76 | 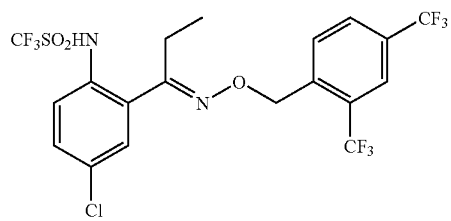 | | 556.0254 |
| 77 | 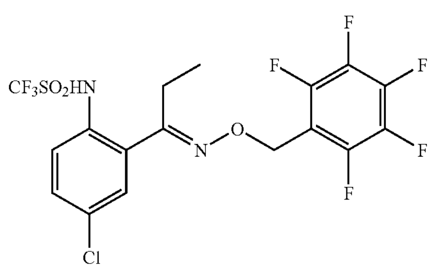 | | |
| 78 | 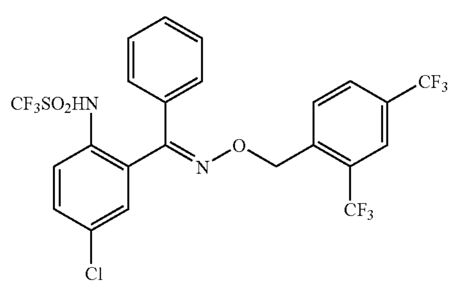 | | |
| 79 | 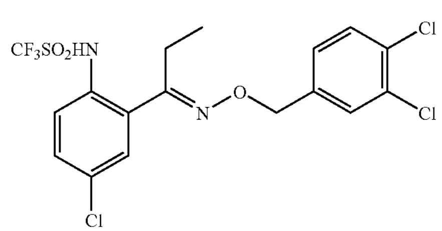 | | 487.9726 |

TABLE 8-continued

| C# | Compound structure | Mp(° C.) | [M+] |
|---|---|---|---|
| 80 | 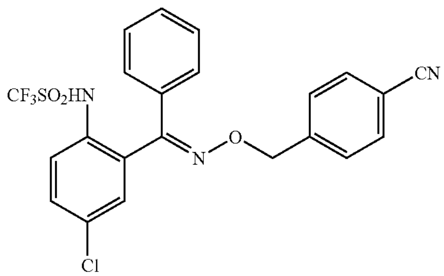 | 122-123 | |
| 81 | 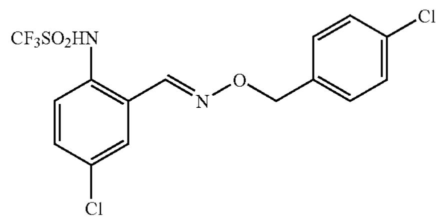 | | |
| 82 | 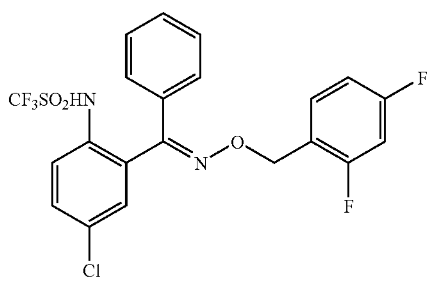 | 79-81 | |
| 83 | 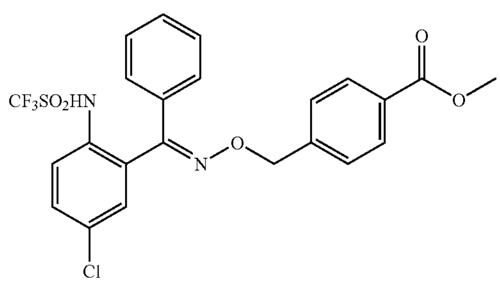 | | |
| 84 | 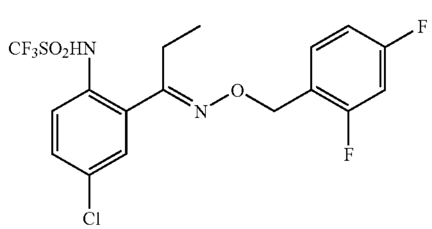 | | 456.0327 |
| 85 | 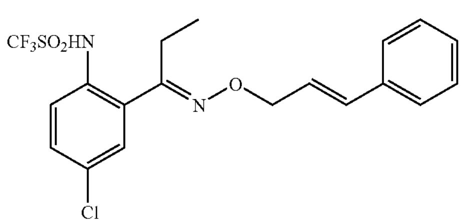 | 46-48 | |

TABLE 8-continued

| C# | Compound structure | Mp(° C.) | [M+] |
|---|---|---|---|
| 86 | 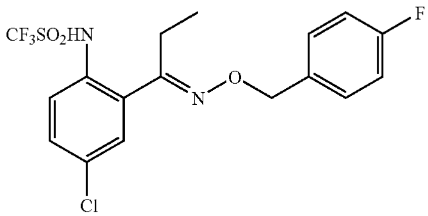 | 36-38 | |
| 87 | 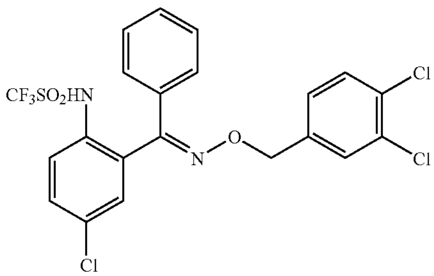 | 87-88 | |
| 88 | 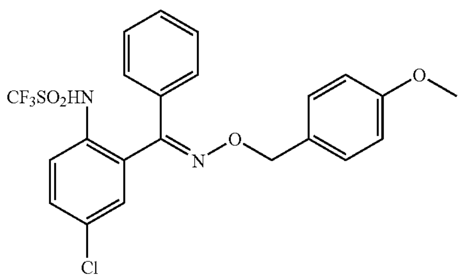 | 89-91 | |
| 89 | 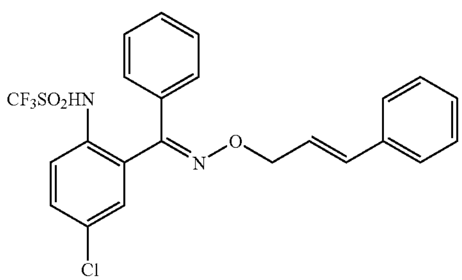 | | |
| 90 | 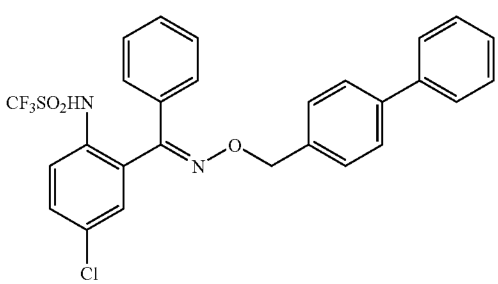 | | |
| 91 | 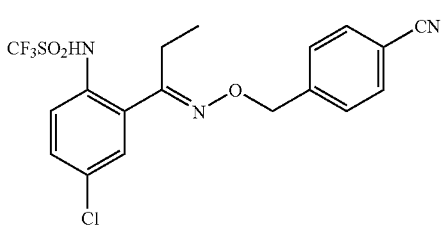 | 47-49 | |

TABLE 8-continued

| C# | Compound structure | Mp(° C.) | [M+] |
|---|---|---|---|
| 92 | 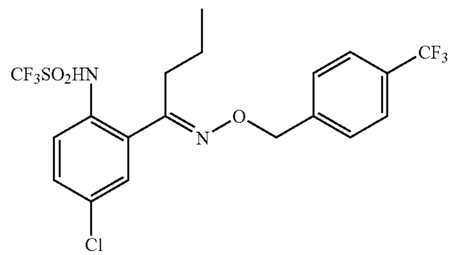 | 78-79 | |
| 93 | 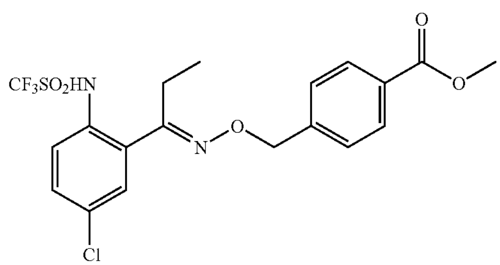 | 63-65 | |
| 94 | 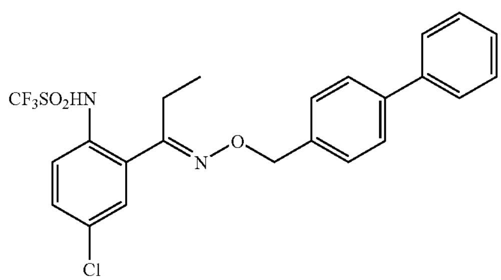 | | |
| 95 | 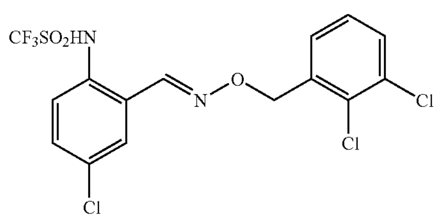 | 86-88 | |
| 96 | 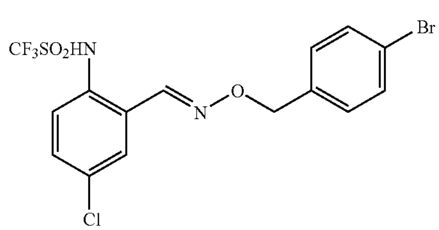 | | 469.9316 |
| 97 | 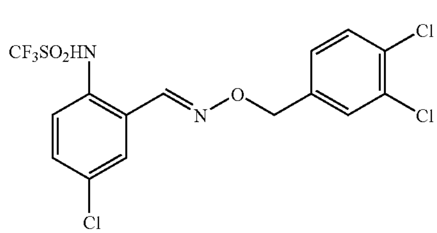 | | 459.9422 |

TABLE 8-continued

| C# | Compound structure | Mp(° C.) | [M+] |
|---|---|---|---|
| 98 | 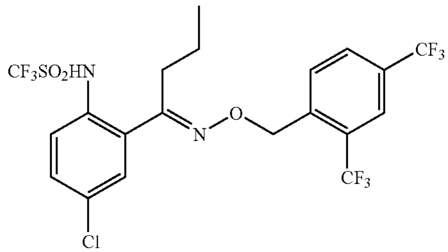 | | 570.0426 |
| 99 | 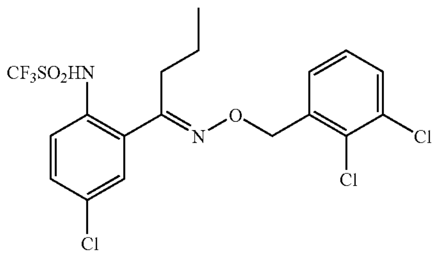 | | |
| 100 | 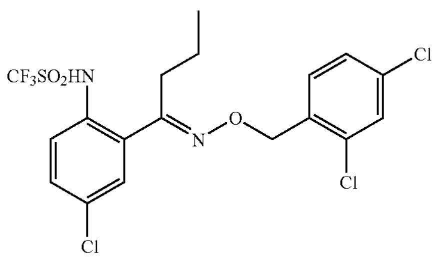 | 65-66 | |
| 101 | 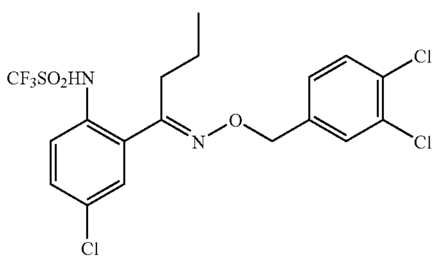 | | |
| 102 | 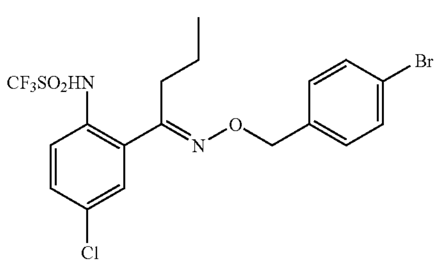 | | |
| 103 | 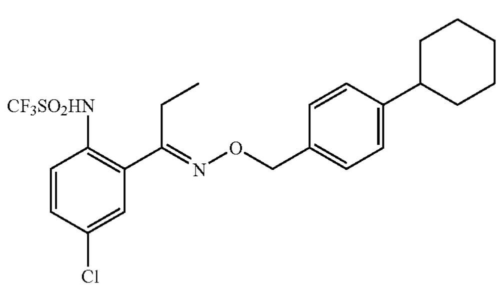 | | |

TABLE 8-continued

| C# | Compound structure | Mp(° C.) | [M+] |
|---|---|---|---|
| 104 | 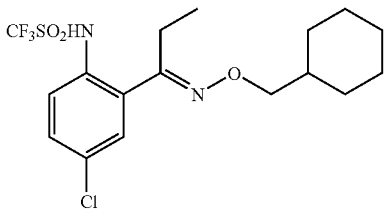 | 65.5-67 | |
| 105 | 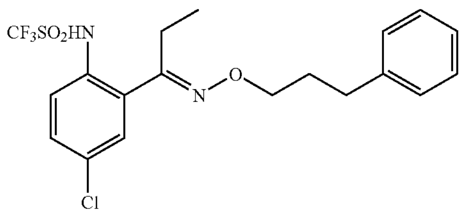 | | |
| 106 | 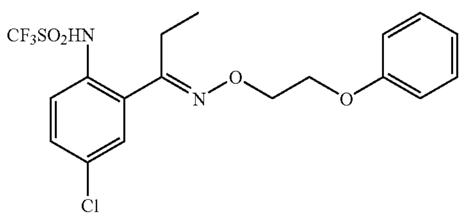 | | |
| 107 | 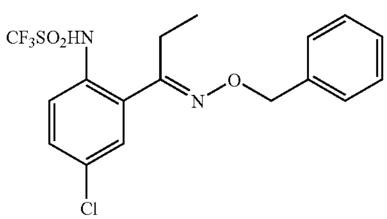 | | |
| 108 | 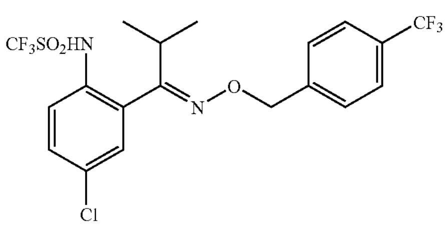 | | 502.0551 |
| 109 | 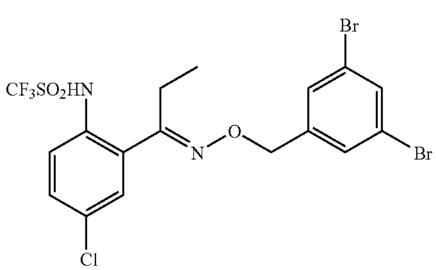 | | |

TABLE 8-continued

| C# | Compound structure | Mp(° C.) | [M+] |
|---|---|---|---|
| 110 | 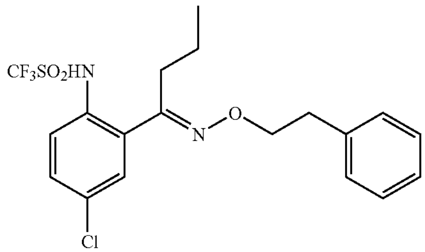 | | |
| 111 | 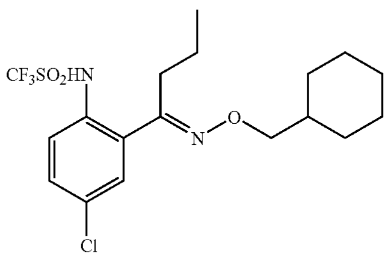 | | 440.1145 |
| 112 | 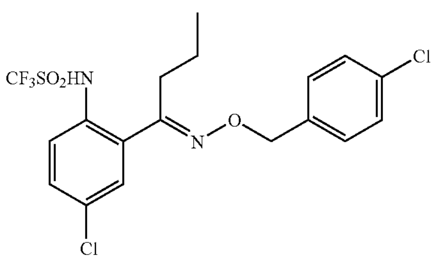 | 44-46 | |
| 113 | 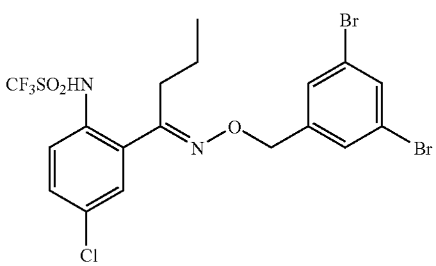 | | |
| 114 | 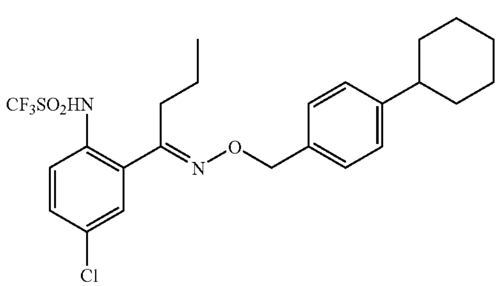 | | |
| 115 | 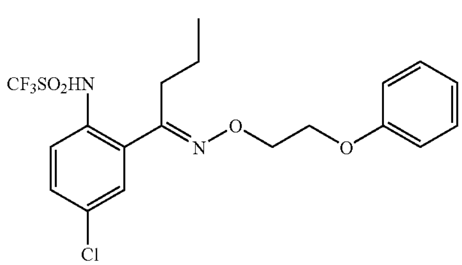 | | |

TABLE 8-continued

| C# | Compound structure | Mp(° C.) | [M⁺] |
|---|---|---|---|
| 116 | 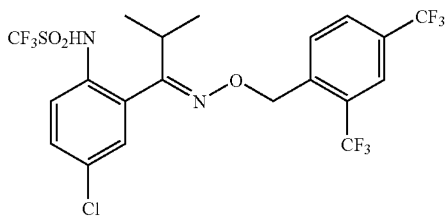 | | 570.0417 |
| 117 | 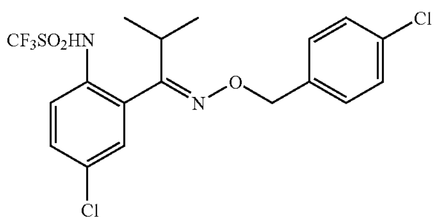 | | |
| 118 | 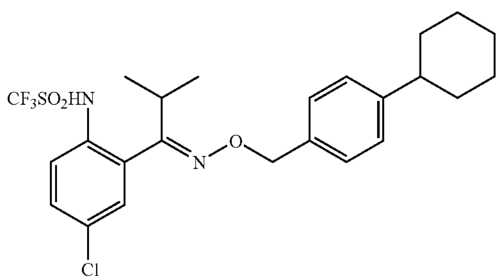 | | |
| 119 | 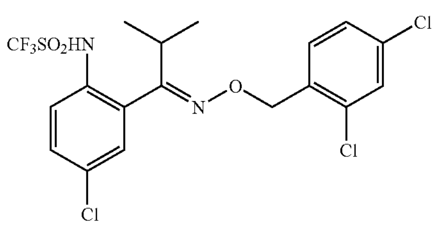 | | 501.9889 |
| 120 | 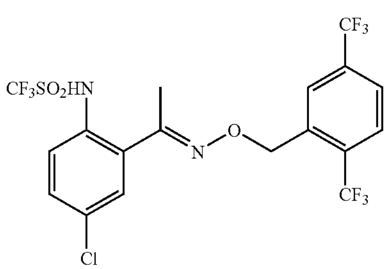 | 73-75 | |
| 121 | 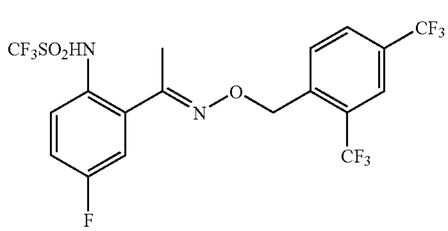 | | 526.0409 |

TABLE 8-continued

| C# | Compound structure | Mp(° C.) | [M+] |
|---|---|---|---|
| 122 | 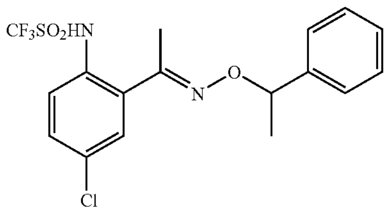 | | |
| 123 | 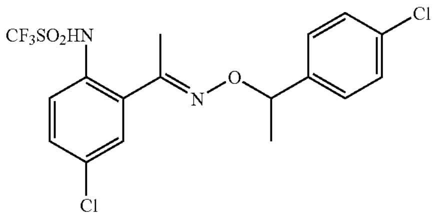 | | |
| 124 | 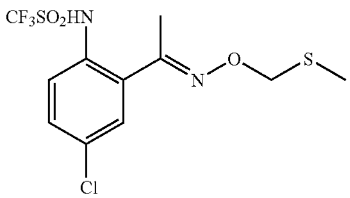 | 84-86 | |
| 125 | 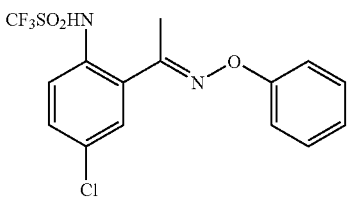 | 86-87 | |
| 126 | 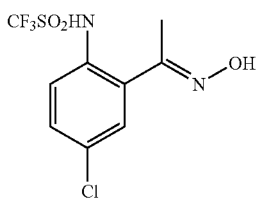 | | |
| 127 | 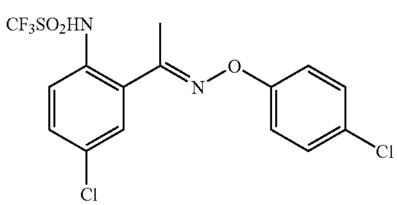 | 102-103 | |
| 128 | 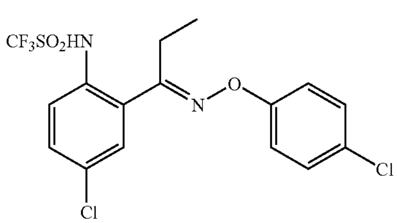 | 87-88 | |

TABLE 8-continued

| C# | Compound structure | Mp(° C.) | [M+] |
|---|---|---|---|
| 129 | 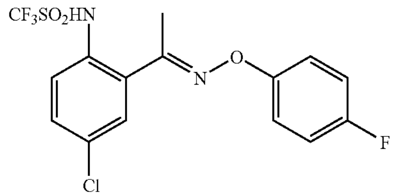 | 71-73 | |
| 130 | 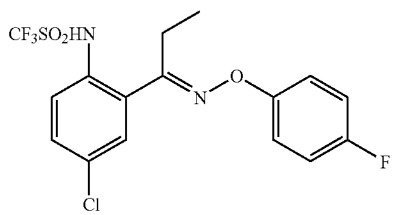 | 47-48 | |
| 131 | 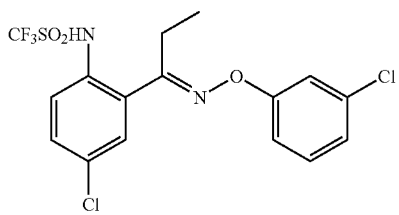 | 61-62 | |
| 132 | 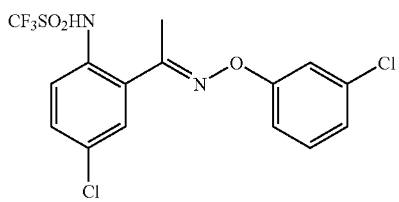 | 83-84 | |
| 133 | 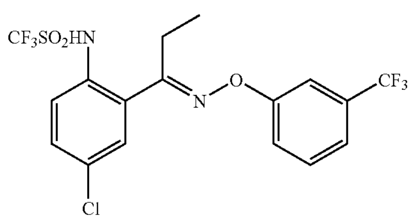 | 62-63 | |
| 134 | 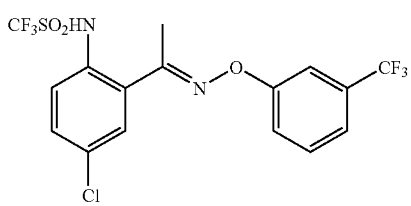 | 63-64 | |
| 135 | 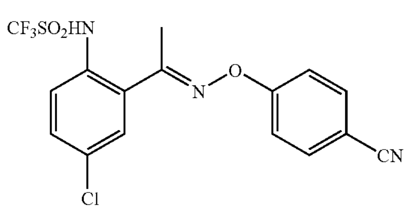 | 141-142 | |

TABLE 8-continued

| C# | Compound structure | Mp(° C.) | [M+] |
|---|---|---|---|
| 136 | 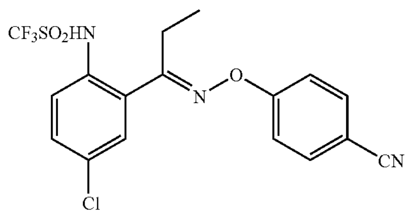 | 117-119 | |
| 137 | 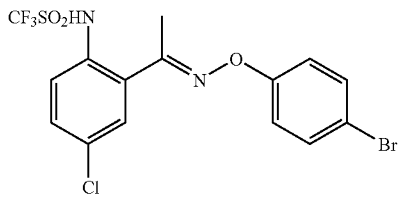 | 106-107 | |
| 138 | 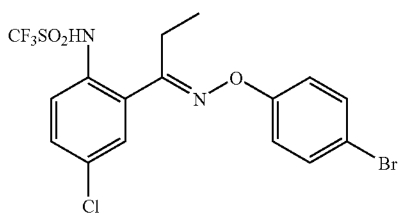 | 103-105 | |
| 139 | 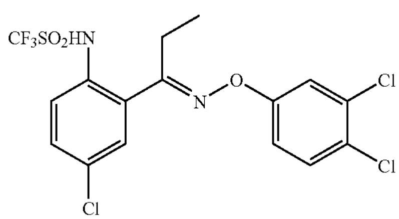 | 70-71 | |
| 140 | 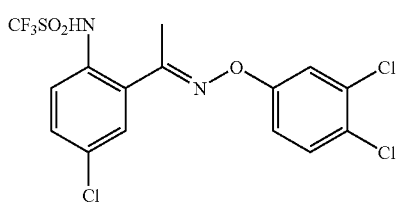 | 94-95 | |
| 141 | 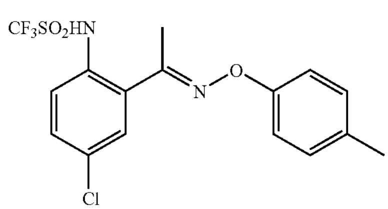 | 116-117 | |
| 142 | 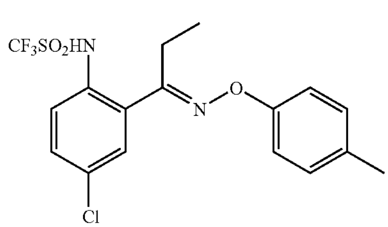 | 67-68 | |

TABLE 8-continued

| C# | Compound structure | Mp(° C.) | [M+] |
|---|---|---|---|
| 143 | 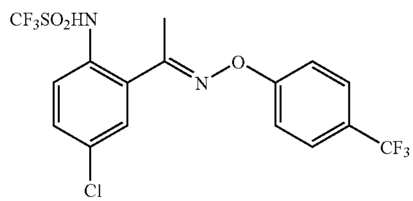 | 102-103 | |
| 144 | 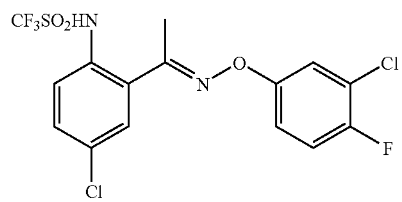 | 80-81 | |
| 145 | 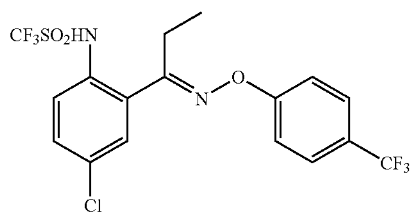 | 85-85 | |
| 146 | 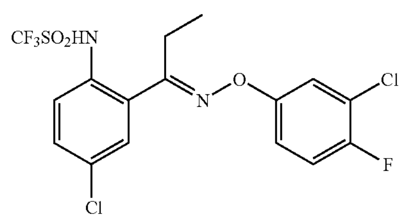 | 60-61 | |
| 147 | 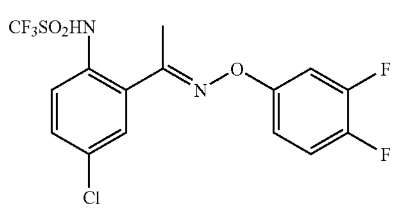 | 64-65 | |
| 148 | 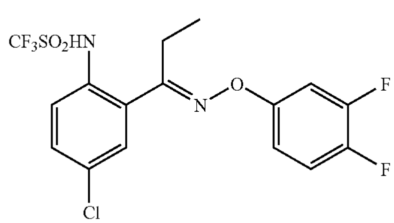 | 68-69 | |
| 149 | 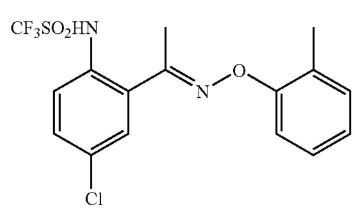 | 89.5-90.5 | |

TABLE 8-continued

| C# | Compound structure | Mp(° C.) | [M+] |
|---|---|---|---|
| 150 | 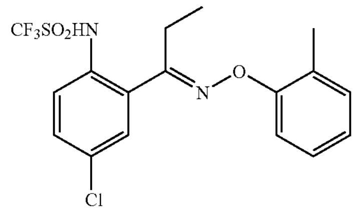 | 93—95 | |
| 151 | 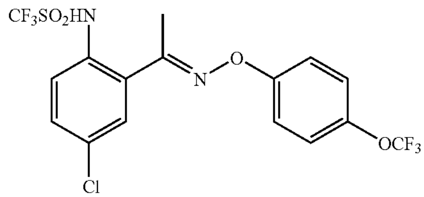 | 55-57 | |
| 152 | 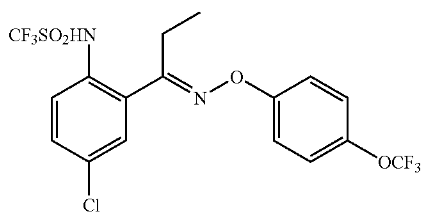 | 49 | |
| 153 | 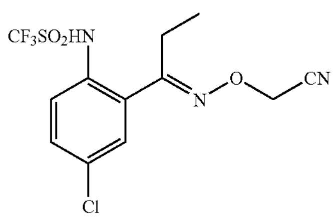 | | 369.0148 |
| 154 | 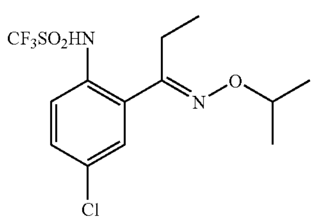 | | 372.0511 |
| 155 | 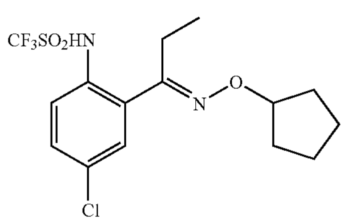 | | 398.0671 |
| 156 | 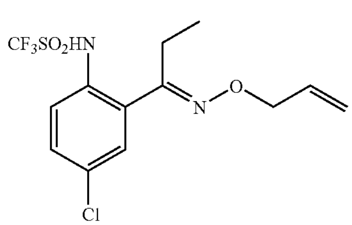 | | 370.035 |

TABLE 8-continued

| C# | Compound structure | Mp(° C.) | [M+] |
|---|---|---|---|
| 157 | 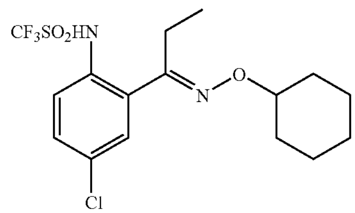 | | 412.0822 |
| 158 | 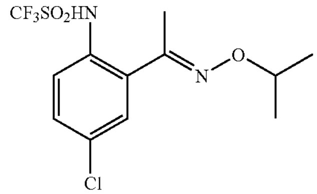 | | 358.0358 |
| 159 | 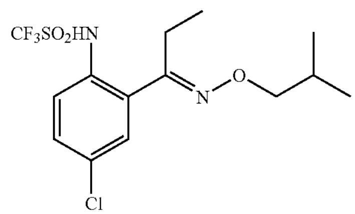 | | 386.0658 |
| 160 | 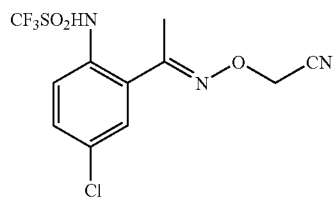 | | 354.9997 |
| 161 | 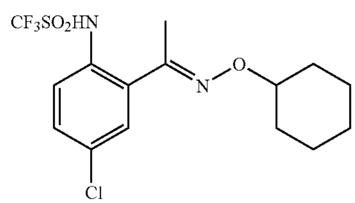 | | 398.0667 |
| 162 | 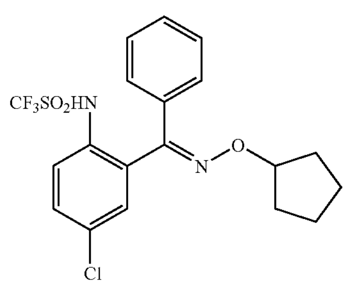 | | 420.0513 |
| 163 | 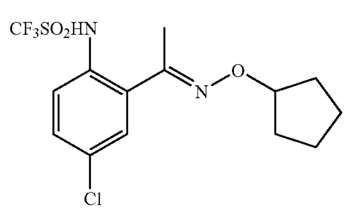 | | 384.0518 |

TABLE 8-continued

| C# | Compound structure | Mp(° C.) | [M+] |
|---|---|---|---|
| 164 | 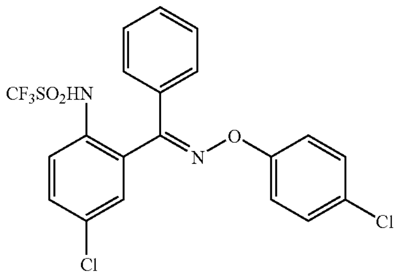 | 86-87 | |
| 165 | 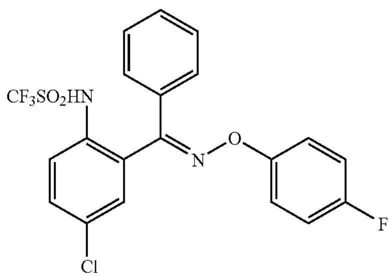 | 90-93 | |
| 166 | 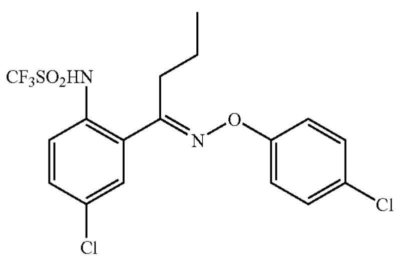 | 62.5-64.5 | |
| 167 | 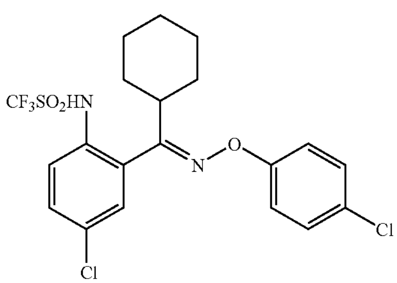 | 102-104 | |
| 168 | 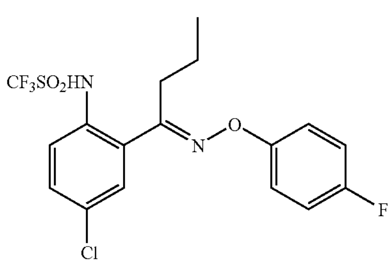 | 69-70 | |

TABLE 8-continued

| C# | Compound structure | Mp(° C.) | [M+] |
|---|---|---|---|
| 169 | 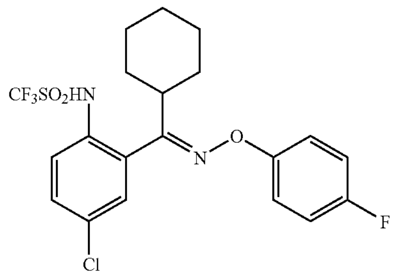 | 98-100 | |
| 170 | 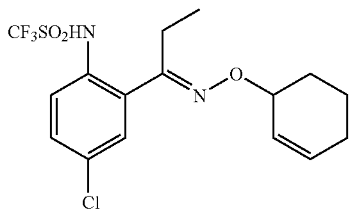 | | 410.0669 |
| 171 | 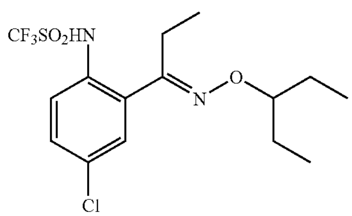 | | 400.0825 |
| 172 | 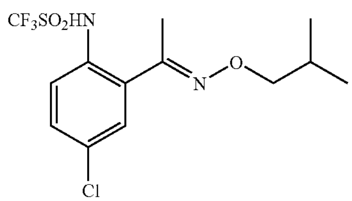 | | 372.0512 |
| 173 | 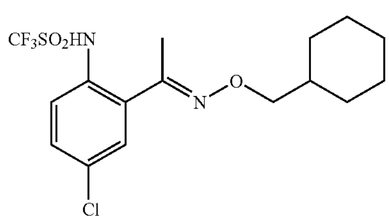 | | 412.0822 |
| 174 | 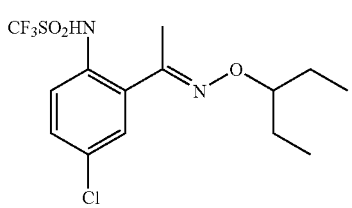 | | 386.0663 |
| 175 | 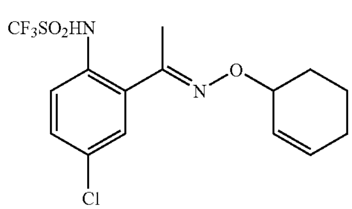 | | 396.0516 |

TABLE 8-continued

| C# | Compound structure | Mp(° C.) | [M+] |
|---|---|---|---|
| 176 | 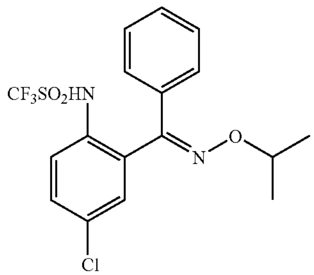 | | 420.0513 |
| 177* | 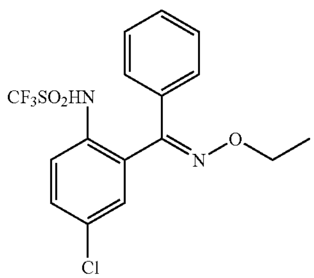 | | 406.0358 |
| 178** | 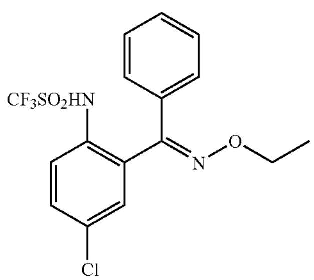 | | |
| 179 | 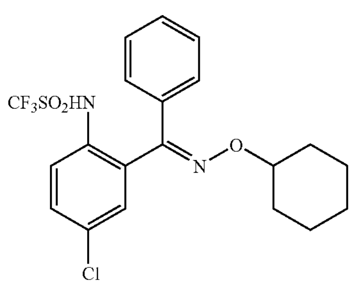 | | 460.0828 |
| 180 | 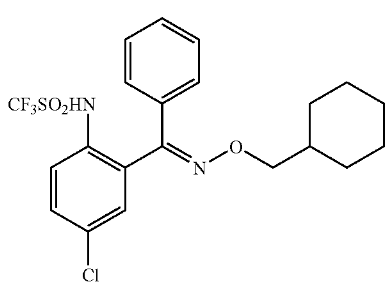 | | 474.0977 |

TABLE 8-continued

| C# | Compound structure | Mp(° C.) | [M+] |
|---|---|---|---|
| 181 | 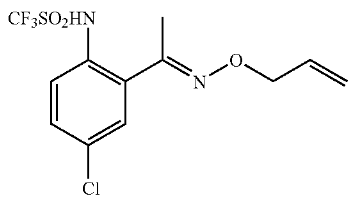 | | 356.0202 |
| 182 | 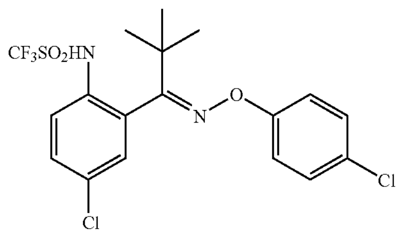 | | |
| 183 | 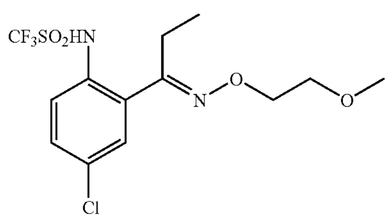 | | 388.0463 |
| 184 | 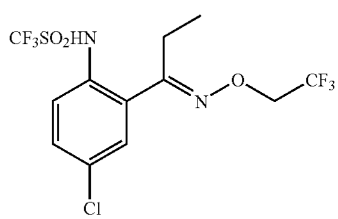 | | 412.0065 |
| 185 | 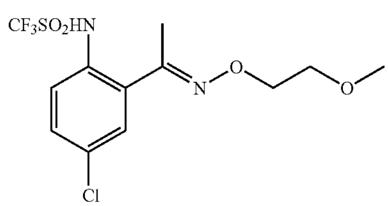 | | 374.0308 |
| 186 | 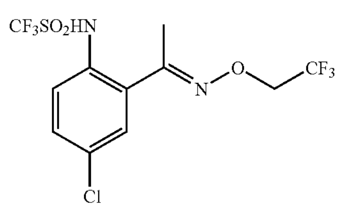 | 85-86 | 397.9923 |
| 187 | 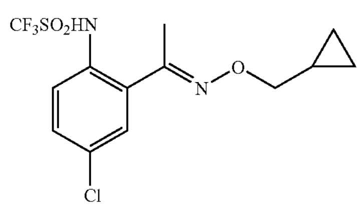 | 53-54 | |

TABLE 8-continued

| C# | Compound structure | Mp(° C.) | [M+] |
|---|---|---|---|
| 188 | 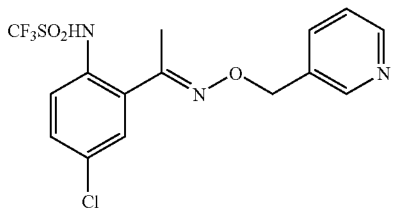 | 123.5-124.5 | |
| 189 | 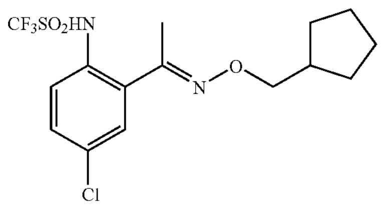 | | 398.0678 |
| 190 | 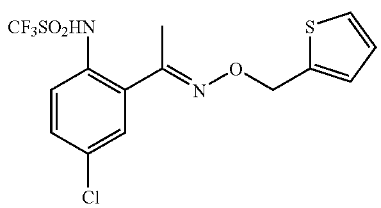 | 101-103 | |
| 191 | 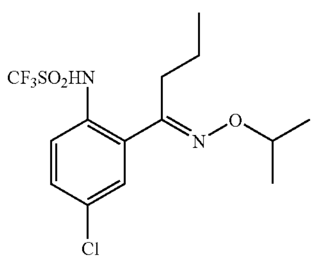 | | 380.9760 |
| 192 | 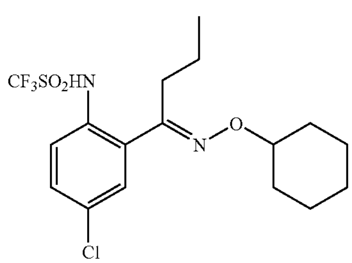 | | 426.0990 |
| 193 | 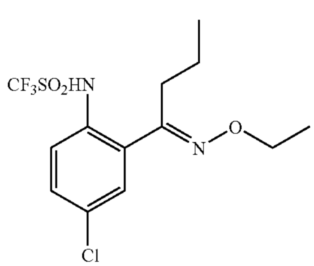 | | 372.0514 |

TABLE 8-continued
| C# | Compound structure | Mp(° C.) | [M+] |
|---|---|---|---|
| 194 | 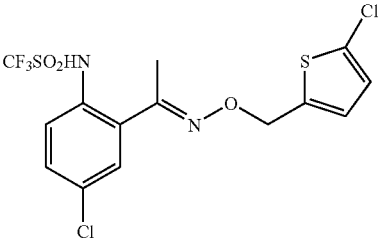 | | 445.9520 |
| 195 | 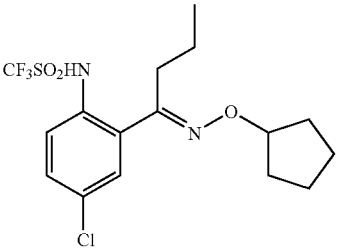 | | 412.0834 |
| 196 | 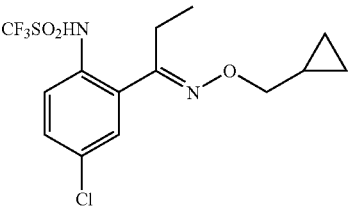 | | 384.0515 |
| 197 | 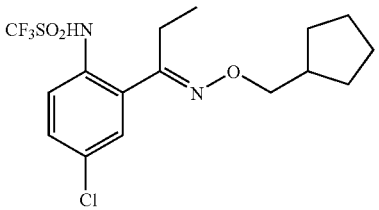 | | 412.0830 |
| 198 | 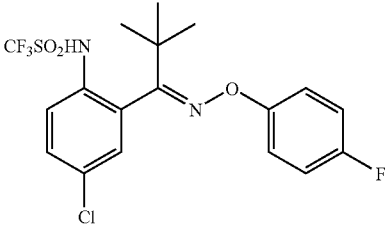 | 89-91 | |
| 199 | 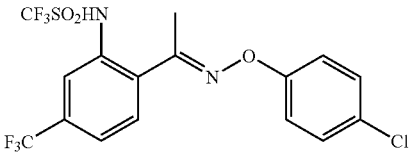 | 94-96 | |
| 200 | 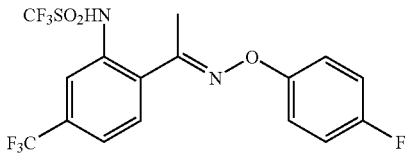 | 95-96 | |

TABLE 8-continued

| C# | Compound structure | Mp(° C.) | [M+] |
|---|---|---|---|
| 201 | 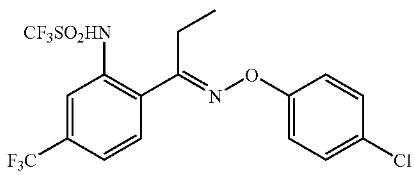 | 99-100 | |
| 202 | 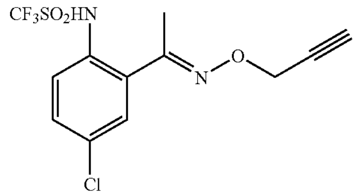 | | 354.0043 |
| 203 | 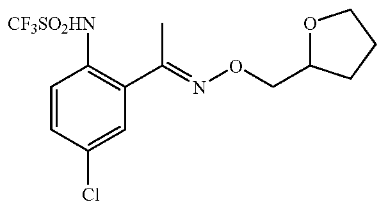 | | 400.0457 |
| 204 | 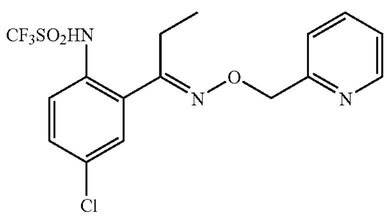 | | 421.0464 |
| 205 | 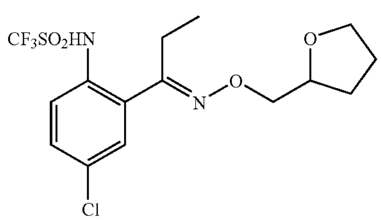 | | 414.0612 |
| 206 | 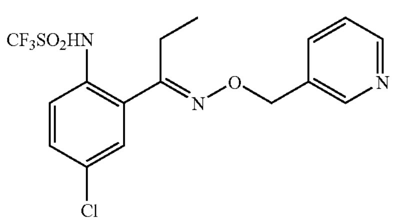 | | 421.0469 |
| 207 | 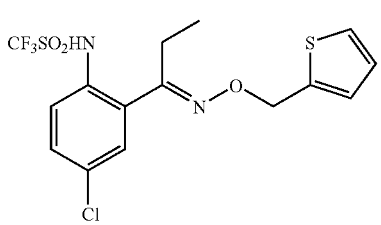 | 53-54 | 426.0065 |

TABLE 8-continued

| C# | Compound structure | Mp(° C.) | [M+] |
|---|---|---|---|
| 208 | 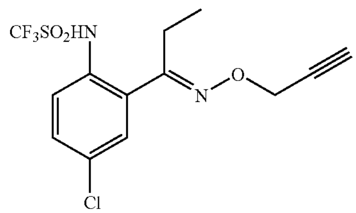 | | 368.0202 |
| 209 | 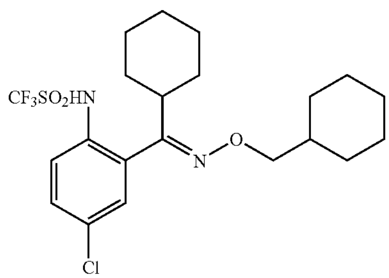 | | 480.1444 |
| 210 | 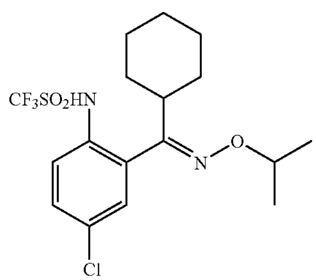 | | 426.0983 |
| 211 | 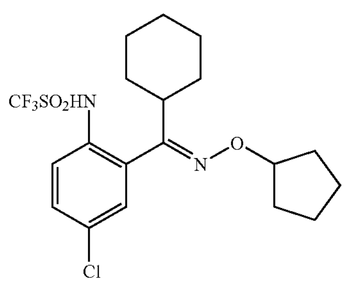 | | 452.1137 |
| 212 | 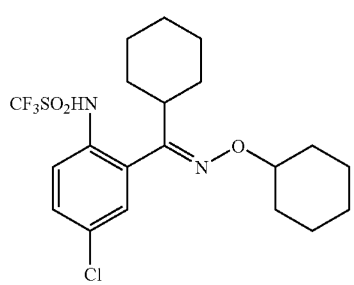 | | 466.1293 |

TABLE 8-continued

| C# | Compound structure | Mp(° C.) | [M+] |
|---|---|---|---|
| 213 | 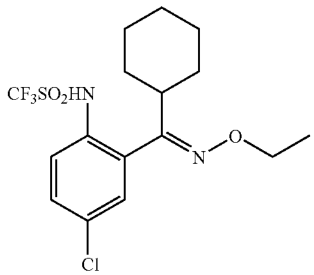 | | 412.0818 |
| 214 | 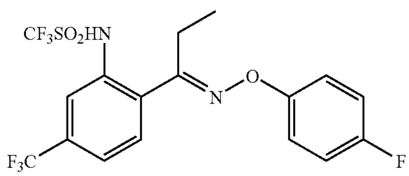 | 94-96 | |
| 215 | 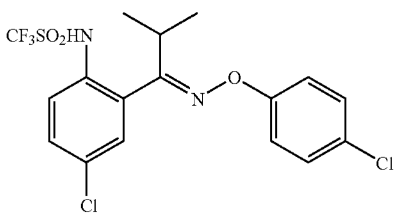 | 68-70 | |
| 216 | 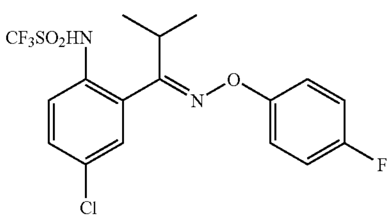 | 74-76 | |
| 217 | 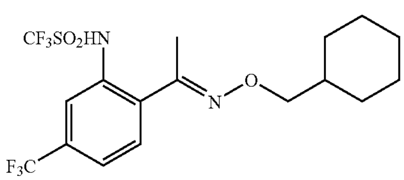 | | 446.1112 |
| 218 | 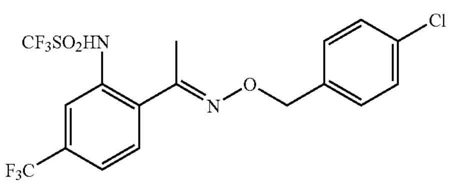 | 86-88 | |
| 219 | 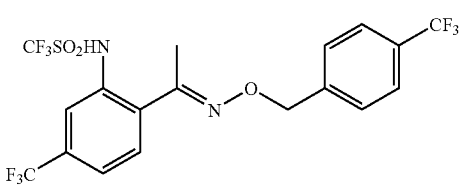 | 68-69 | |

TABLE 8-continued

| C# | Compound structure | Mp(° C.) | [M⁺] |
|---|---|---|---|
| 220 | (CF₃SO₂HN, F₃C-phenyl)-C(Et)=N-O-CH₂-(4-Cl-phenyl) | 70.5-71.5 | |
| 221 | (CF₃SO₂HN, F₃C-phenyl)-C(Et)=N-O-CH₂-(4-CF₃-phenyl) | 48-49 | |
| 222 | (CF₃SO₂HN, F₃C-phenyl)-C(Et)=N-O-CH₂-cyclohexyl | 72-73 | |
| 223 | (CF₃SO₂HN, 4-Cl-phenyl)-C(Me)=N-O-t-Bu | 67-68 | 372.0516 |
| 224 | (CF₃SO₂HN, 4-Cl-phenyl)-C(Et)=N-O-t-Bu | 76-77.5 | 386.0674 |

*Compound 177 exists as either a single syn(Z) or anti(E) isomer.
**Compound 178 exists as a mixture of syn(Z) and anti(E) isomers.

Table 8A provides compounds 232-290, based on Formula (I) supra.

TABLE 8A

| C# | Compound structure | Mp (° C.) | [M⁺] |
|---|---|---|---|
| 232* | (CF₃SO₂HN, 4-Cl-phenyl)-C(Ph)=N-O-Me | | 392.0205 |

TABLE 8A-continued

| C# | Compound structure | Mp (° C.) | [M+] |
|---|---|---|---|
| 233* | 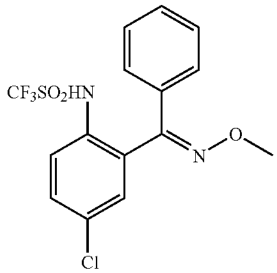 | | 392.0201 |
| 234 | 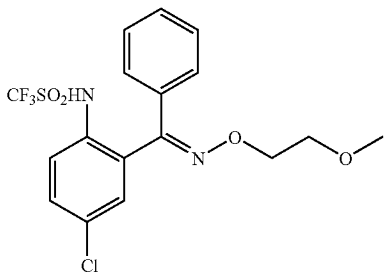 | | 436.0465 |
| 235 | 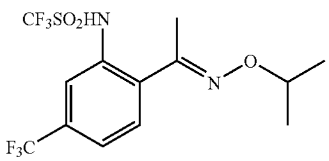 | | 392.0621 |
| 236 | 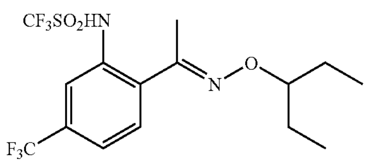 | | 420.0942 |
| 237 | 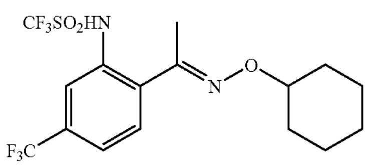 | | 432.0940 |
| 238 | 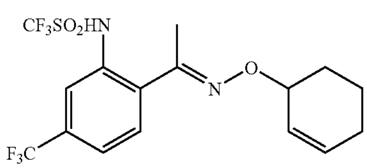 | | 430.0787 |
| 239 | 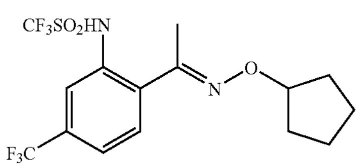 | | 418.0782 |
| 240 | 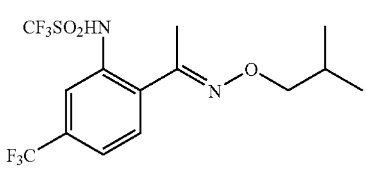 | | 406.0782 |

TABLE 8A-continued

| C# | Compound structure | Mp (° C.) | [M⁺] |
|---|---|---|---|
| 241 | 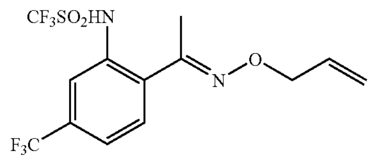 | | 390.0465 |
| 242 | 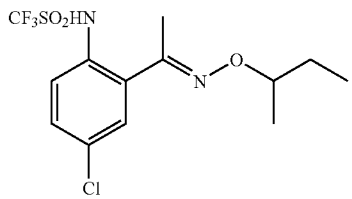 | | 372.0498 |
| 243 | 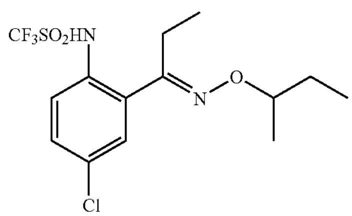 | | 386.0670 |
| 244 | 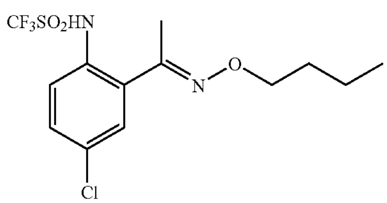 | | 372.0507 |
| 245 | 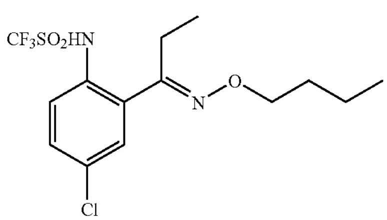 | | 386.0670 |
| 246 | 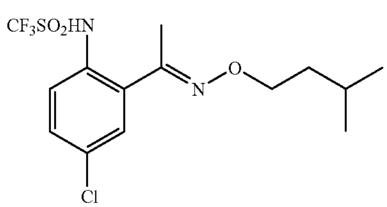 | | 386.0668 |
| 247* | 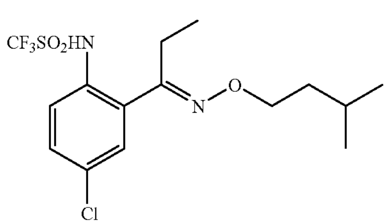 | | 400.0832 |

TABLE 8A-continued

| C# | Compound structure | Mp (° C.) | [M+] |
|---|---|---|---|
| 248* | (structure) | | |
| 249 | (structure) | | 384.0514 |
| 250 | (structure) | | 398.0665 |
| 251* | (structure) | | 420.0515 |
| 252* | (structure) | | |
| 253 | (structure) | | 384.0516 |

TABLE 8A-continued

| C# | Compound structure | Mp (° C.) | [M+] |
|---|---|---|---|
| 254 | 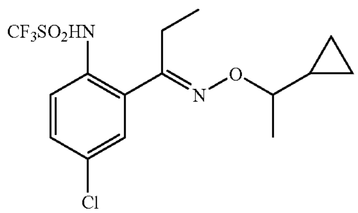 | | 398.0669 |
| 255 | 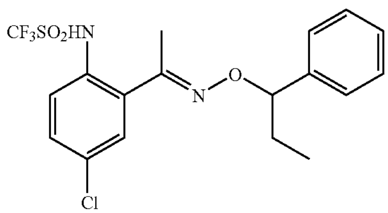 | | 434.0665 |
| 256 | 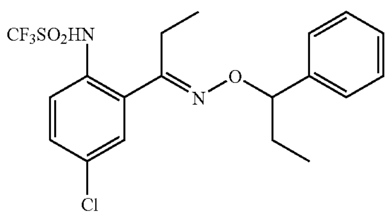 | | |
| 257 | 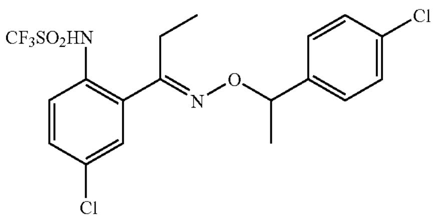 | | 468.0277 |
| 258 | 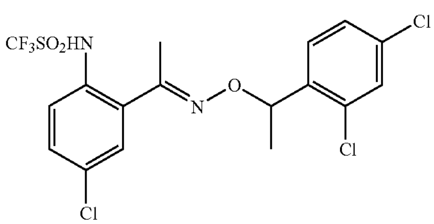 | | |
| 259 | 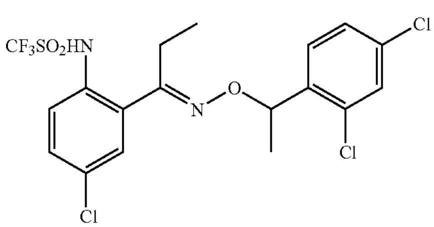 | | |
| 260 | 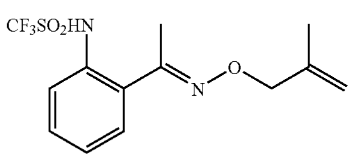 | | |

TABLE 8A-continued

| C# | Compound structure | Mp (° C.) | [M+] |
|---|---|---|---|
| 261 | 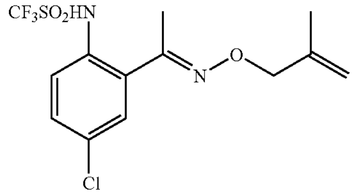 | | |
| 262 | 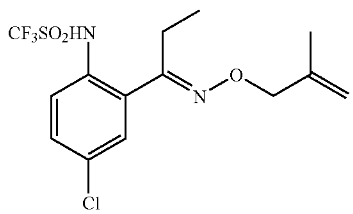 | | |
| 263 | 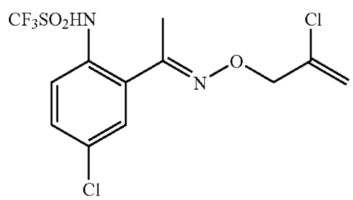 | | |
| 264 | 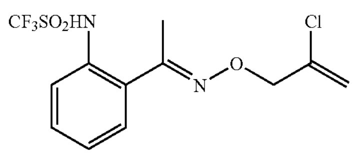 | | |
| 265 | 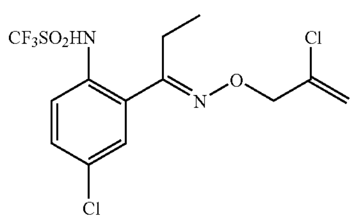 | | |
| 266 | 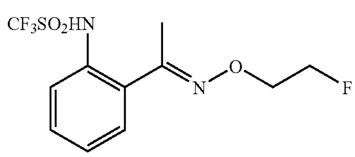 | | |
| 267 | 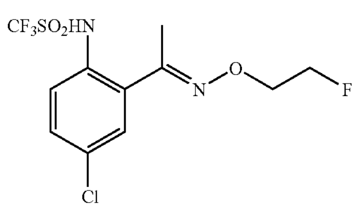 | | |
| 268 | 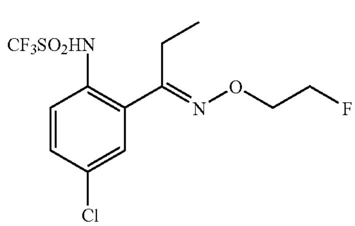 | | |

TABLE 8A-continued

| C# | Compound structure | Mp (° C.) | [M+] |
|---|---|---|---|
| 269 | CF₃SO₂HN-C₆H₄-C(CH₃)=N-O-CH₂CH₂-O-CH₂CH₃ | | |
| 270 | CF₃SO₂HN-C₆H₃(Cl)-C(CH₃)=N-O-CH₂CH₂-O-CH₂CH₃ | | |
| 271 | CF₃SO₂HN-C₆H₃(Cl)-C(C₂H₅)=N-O-CH₂CH₂-O-CH₂CH₃ | | |
| 272 | CF₃SO₂HN-C₆H₄-C(CH₃)=N-O-CH₂-C≡C-CH₂CH₃ | | |
| 273 | CF₃SO₂HN-C₆H₃(Cl)-C(CH₃)=N-O-CH₂-C≡C-CH₂CH₃ | | |
| 274 | CF₃SO₂HN-C₆H₃(Cl)-C(C₂H₅)=N-O-CH₂-C≡C-CH₂CH₃ | | |
| 275 | CF₃SO₂HN-C₆H₄-C(CH₃)=N-O-CH₂CH₂-C(F)=CF₂ | | |
| 276 | CF₃SO₂HN-C₆H₃(Cl)-C(CH₃)=N-O-CH₂CH₂-C(F)=CF₂ | | |

TABLE 8A-continued

| C# | Compound structure | Mp (° C.) | [M+] |
|---|---|---|---|
| 277 | 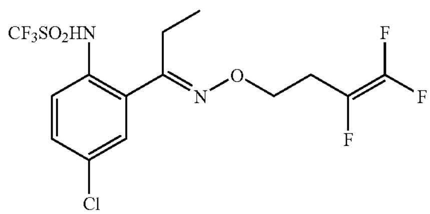 | | |
| 278 | 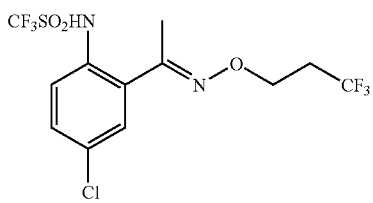 | | |
| 279 | 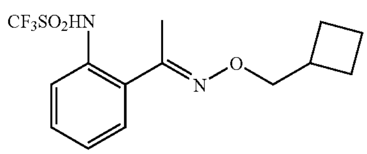 | | |
| 280 | 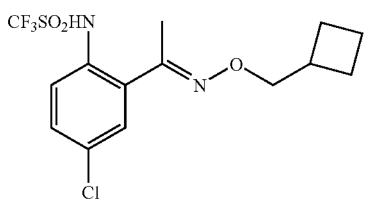 | | |
| 281 | 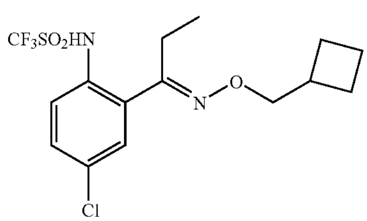 | | |
| 282 | 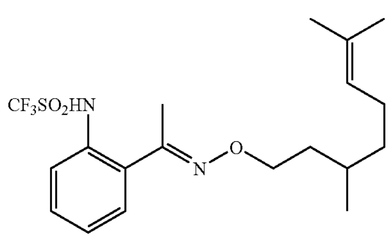 | | |
| 283 | 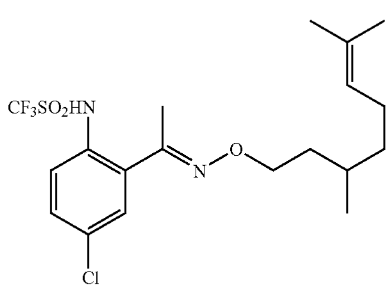 | | |

TABLE 8A-continued

| C# | Compound structure | Mp (° C.) | [M+] |
|---|---|---|---|
| 284 | 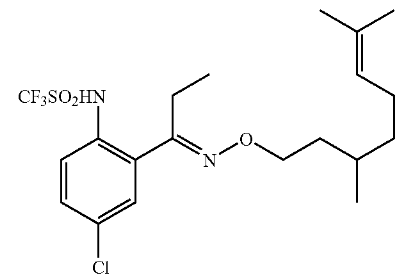 | | |
| 285 | | + | |
| 286 | | + | |
| 287 | | + | |

TABLE 8A-continued

| C# | Compound structure | Mp (° C.) | [M+] |
|---|---|---|---|
| 288 | CF₃SO₂HN—[2-substituted phenyl]—C(CH₃)=N—O—CH₂—CH=CH—CH₃ | | |
| 289 | CF₃SO₂HN—[2-substituted, 4-Cl phenyl]—C(CH₃)=N—O—CH₂—CH=CH—CH₃ | | |
| 290 | CF₃SO₂HN—[2-substituted, 4-Cl phenyl]—C(CH₂CH₃)=N—O—CH₂—CH=CH—CH₃ | | |

*Compound 232 exists as either a single syn(Z) or anti(E) isomer.
*Compound 233 exists as either a single syn(Z) or anti(E) isomer.
*Compound 247 exists as either a single syn(Z) or anti(E) isomer.
*Compound 248 exists as either a single syn(Z) or anti(E) isomer.
*Compound 251 exists as either a single syn(Z) or anti(E) isomer.
*Compound 252 exists as either a single syn(Z) or anti(E) isomer.

Table 9 illustrates compounds 225-231, based on Formula (II) supra.

TABLE 9

| C# | Compound structure | Mp (° C.) |
|---|---|---|
| 225 | CF₃SO₂HN—[2-substituted, 4-Cl phenyl]-3-isoxazolyl-5-phenyl | 115–117 |
| 226 | CF₃SO₂HN—[2-substituted, 4-Cl phenyl]-3-isoxazolyl-5-CO₂Et | 105–106 |
| 227 | CF₃SO₂HN—[2-substituted, 4-Cl phenyl]-3-isoxazolyl-5-(4-Cl-phenyl) | 140–142 |
| 228 | CF₃SO₂HN—[2-substituted, 4-Cl phenyl]-3-isoxazolyl-5-(4-F-phenyl) | 167–168 |

TABLE 9-continued

| C# | Compound structure | Mp (° C.) |
|---|---|---|
| 229 | (structure) | 144–146 |
| 230 | (structure) | 142–144 |
| 231 | (structure) | 117–119 |

Table 9A illustrates compounds 291-295, based on Formula (II) supra.

TABLE 9A

| C# | Compound structure | Mp (° C.) | [M+] |
|---|---|---|---|
| 291 | (structure) | | 382.0360 |

TABLE 9A-continued

| C# | Compound structure | Mp (° C.) | [M+] |
|---|---|---|---|
| 292 | (structure) | 114–116 | |
| 293 | (structure) | | |
| 294 | (structure) | | |
| 295 | (structure) | | |

Table 13 illustrates compounds 296-323, based on Formula (V) supra.

TABLE 13

| C# | Compound structure | Mp (° C.) | [M+] |
|---|---|---|---|
| 296 | 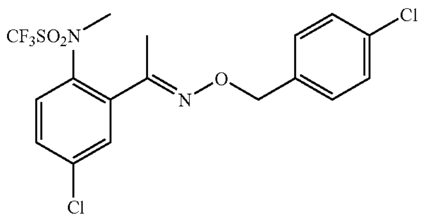 | | |
| 297 | 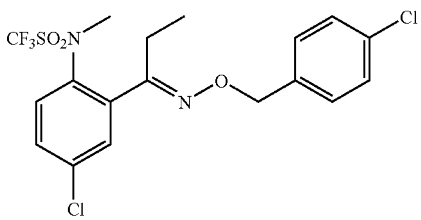 | | |
| 298 | 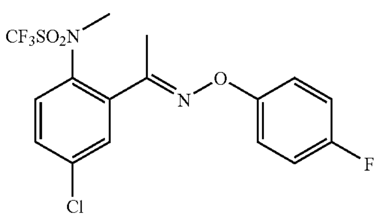 | | |
| 299 | 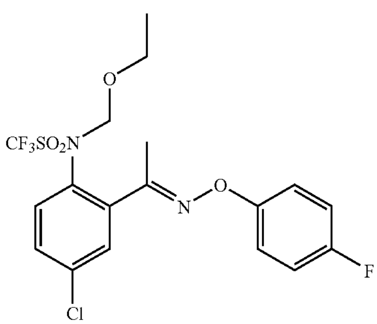 | | |
| 300 | 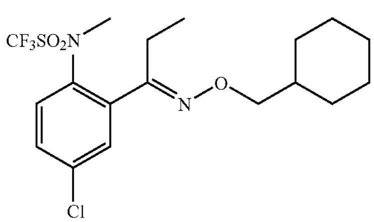 | | |
| 301 | 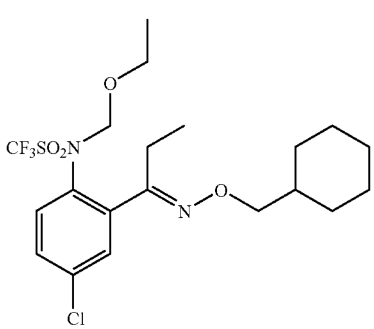 | | |

TABLE 13-continued

| C# | Compound structure | Mp (° C.) | [M+] |
|---|---|---|---|
| 302 | 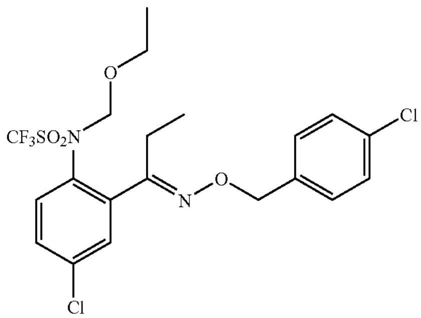 | | |
| 303 | 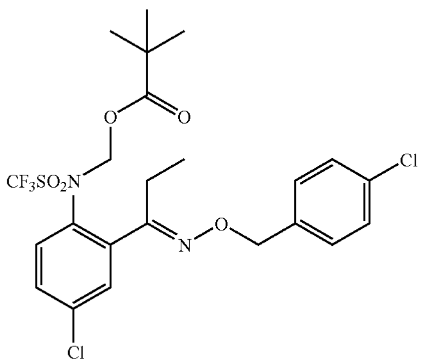 | | |
| 304 | 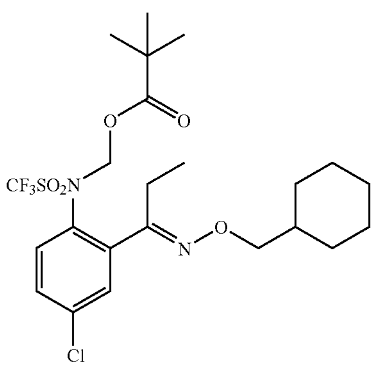 | | |
| 305 | 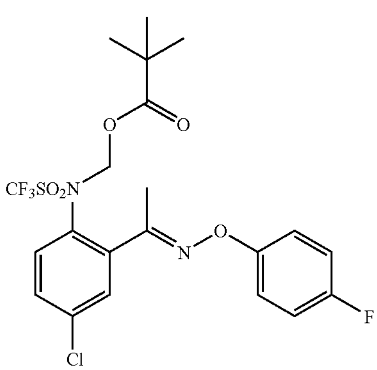 | | |

TABLE 13-continued

| C# | Compound structure | Mp (° C.) | [M+] |
|---|---|---|---|
| 306 | 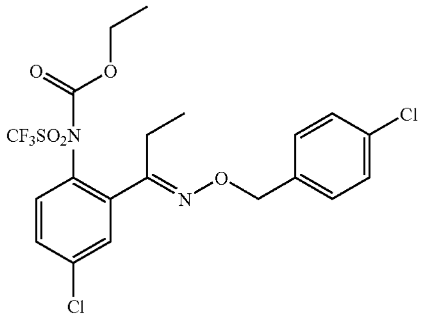 | | |
| 307 | 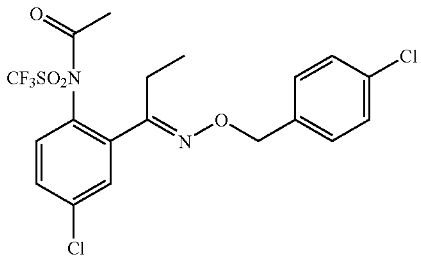 | 67–69 | |
| 308 | 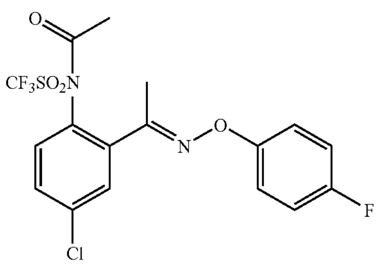 | 105–107 | |
| 309 | 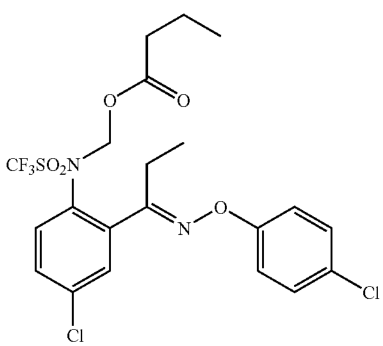 | | |
| 310 | 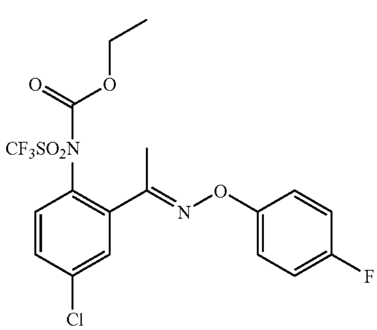 | | 482.0316 |

TABLE 13-continued

| C# | Compound structure | Mp (° C.) | [M+] |
|---|---|---|---|
| 311 | 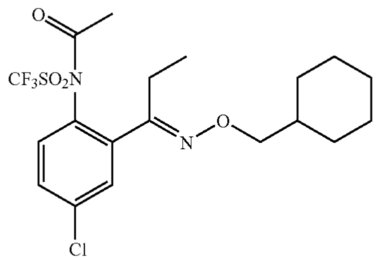 | | |
| 312 | 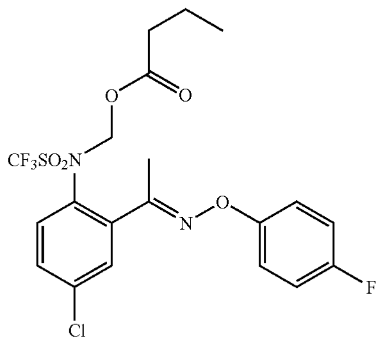 | | |
| 313 | 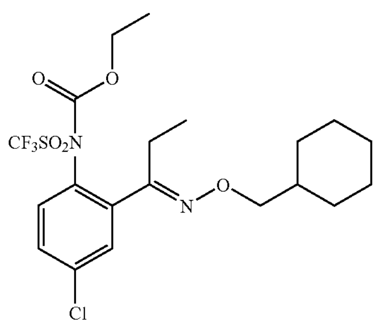 | | |
| 314 | 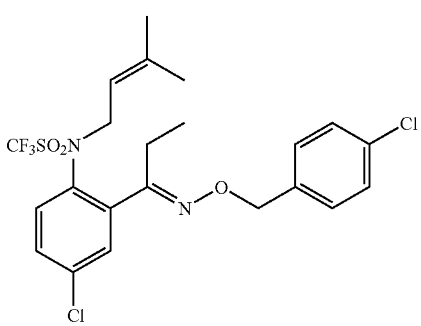 | | |
| 315 | 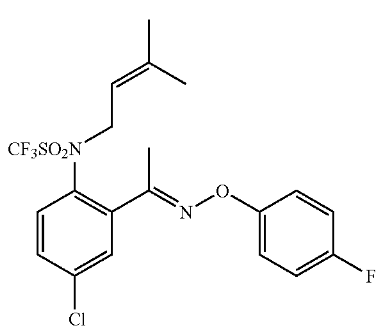 | | |

TABLE 13-continued

| C# | Compound structure | Mp (° C.) | [M+] |
|---|---|---|---|
| 316 | 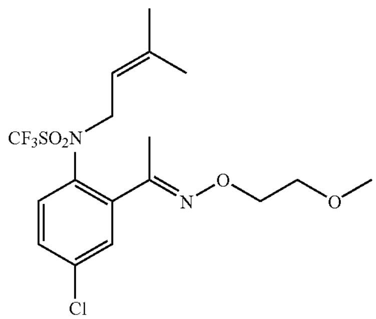 | | |
| 317 | 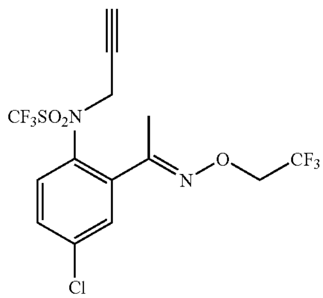 | | |
| 318 | 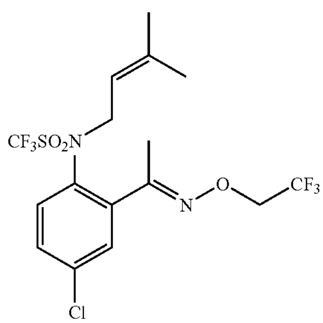 | | |
| 319 | 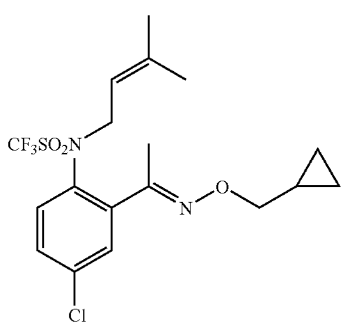 | | |
| 320 | 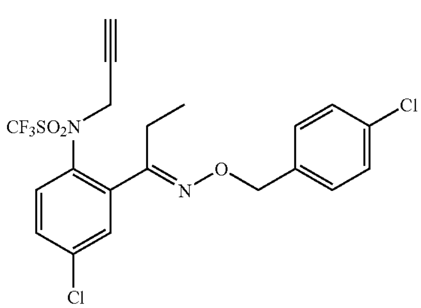 | | |

TABLE 13-continued

| C# | Compound structure | Mp (° C.) | [M+] |
|---|---|---|---|
| 321 | 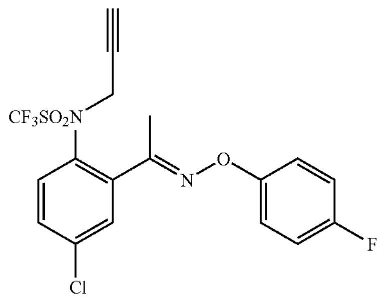 | | |
| 322 | 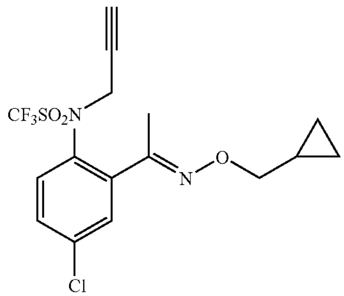 | | |
| 323 | 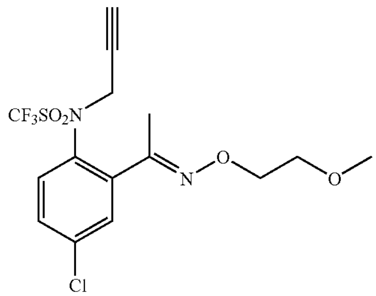 | | |

Example 11

The following assays were used to determine the parasiticidal activity of the compounds of the invention. The compounds tested were prepared according to Examples 1-9, above. In certain cases, one or more of the assays were performed by two different laboratories, labeled as Laboratory 1 and Laboratory 2. Due to the nature of the assays, in certain instances the results are better taken qualitatively rather than quantitatively. However, the ultimate effectiveness of the compounds may still be established.

a) *Haemonchus Contortus* Larvacidal Assay:

The effect of compounds on larval development was determined in the assay described by Gill et al. (1995, *International Journal of Parasitology* 25:463-470). Briefly, in this assay, nematode eggs were applied to the surface of an agar matrix containing the test compound and then allowed to develop through to the L3, infective stage (6 days). The wells for each dilution of every compound (from highest to lowest concentration) were inspected to determine the well number corresponding to the lowest concentration at which development was inhibited in 99% of the nematode larvae present ($LD_{99}$). Because well numbers correspond to a two-fold serial dilution of each compound, a titre (dilution factor) is generated as $2^{n-1}$, where n is the well number. By dividing the highest concentration tested by the titre an $LD_{99}$ value can be obtained, representing the concentration required to inhibit development in 99% of the nematode larvae present. The compounds supplied as solid and viscous liquids were dissolved in DMSO. Twelve serial one-half dilutions in DMSO solution were prepared from the stock solution, each of which was then diluted ⅕ with water. Aliquots (10 μl) of each dilution were transferred to the bioassay plates to give a final concentration range of 0.024 to 50 μg/ml.

b) *Ctenocephalides felis* Adulticide Assay: *C. felis* Single Dose Screen

The purpose of this example was to confirm that sample compounds or formulations exhibit significant insecticidal activity against cat fleas contacted with a treated glass surface. Mortality of fleas was the primary endpoint in the assay. Fleas were considered dead if they didn't move or were on their sides and unable to walk or right themselves. In the screening assay a single concentration of a test compound was selected to demonstrate insecticidal activity. The concentration chosen (1.26 μg/cm²) was higher than that known to kill 90% of cat fleas ($LC_{90}$) using the reference compound, permethrin.

The test species was the cat flea (*Ctenocephalides felis*). The strain used was obtained from external suppliers as pupae and held in the laboratory under testing conditions until the adults had emerged. Fifteen (15) fleas were used in a minimum of four replicates against a single concentration level (approximately 60 fleas). The insects were selected to be in the adult life stage, aged between 3 and 7 days post emergence.

The compounds to be tested were supplied as solids and were prepared in acetone as described below prior to testing. Samples were stored in a refrigerator (5±1° C.) unless otherwise specified.

During the mortality testing, the temperature was maintained at 25±1° C. Humidity was maintained at 75±5%. The base (area=159 mm$^2$) of a 100 mL glass Erlenmeyer (conical) flask provided the treatment surface. Flasks were pretreated with Coatasil™ glass treatment to maximise bio-availability of test compounds by preventing them from binding to glass the surface. The base of the 100 mL Erlenmeyer flask was treated with 0.5 mL of test sample in acetone and gently swirled. This volume was sufficient to cover the base of the flask. Flasks were left to dry for 24 hours before flea exposure.

Adult cat fleas were placed into a sorting chamber, which allowed fleas to jump into the Erlenmeyer flasks. Fifteen (15) adult cat fleas were collected in each flask. The top of the flasks were then covered in Parafilm™ and small holes were made to allow gas exchange. A 0.5 mL volume of acetone as a solvent control was applied to the base of an Erlenmeyer flask and the testing proceeded in the same manner described above. Cat fleas in the treatment containers were held under testing conditions for 8, 24 and/or 48 hours. Mortality was recorded at 8, 24, 8 and 24, or 24 and 48 hours. Pooled 8, 24, 8 and 24, and 24 and 48 hour mortality data were converted to percentages and are summarized by Tables 14, 14A and 14B, below.

c) *Ctenocephalides felis* Adulticide Assay: *C. felis* Dose Response

The purpose of this example was to determine the LC$_{50}$ when cat fleas were contacted with a glass surface treated with sample compounds or formulations prepared as described above. Mortality of fleas was defined as follows: fleas were considered dead if they didn't move or were on their sides and unable to walk or right themselves. LC$_{50}$: Lethal Concentration 50—concentration of glass surface treatment at which 50% of the cat fleas were killed. The test species was the cat flea (*Ctenocephalides felis*). The strain used was obtained from external suppliers as pupae and held in the laboratory under testing conditions until the adults had emerged. Fifteen (15) fleas were used in a minimum of four replicates for each dose level (total of 60 fleas per dose level). The insects were selected to be in the adult life stage, aged between 3 and 7 days post emergence.

The compounds to be tested were dissolved in acetone just prior to testing. Samples of compounds were stored in a refrigerator (5±1° C.) unless otherwise specified. During the mortality testing, the temperature was maintained at 25+1° C. Humidity was maintained at 75±5%. The base (area=159 mm$^2$) of a 100 mL glass Erlenmeyer (conical) flask provided the treatment surface. Flasks were pretreated with Coatasil™ glass treatment to maximise bio-availability of test compounds by preventing them from binding to the glass surface.

Six dose levels (concentrations) of test sample, in the form of a serial dilution, were derived from a pilot study and covered a range that produced very low to very high mortality. The base of the 100 mL Erlenmeyer flask was treated with 0.5 mL of test sample in acetone and gently swirled. This volume was sufficient to cover the base of the flask. Flasks were left to dry for 24 hours before flea exposure. Adult cat fleas were lightly anaesthetised by cooling and then placed into a sorting chamber, which allowed fleas to revive and jump into the Erlenmeyer flasks. Fifteen (15) adult cat fleas were collected in each flask. The top of the flasks were then covered in Parafilm™ and small holes made to allow gas exchange. A 0.5 mL volume of acetone was applied to the base of an Erlenmeyer flask and the testing proceeded in the same manner described above. Cat fleas in the treatment containers were held under testing conditions for 24 hours. Mortality resulting from the treatments was recorded at 8 and 24 hours. Pooled 24 hour mortality data were subjected to probit analysis to obtain concentration response data (LC$_{50}$) (Finney, D. J., 1971. *Probit Analysis*. 3rd ed. Cambridge Univ. Press, London).

d) Rapid Screening Protocol for Topical Application on Brown Dog Ticks (*Rhipicephalus sanguineus*)

The aim of the test was to determine the presence of significant acaricidal activity in sample compounds or formulations when applied topically on brown dog ticks. A tick was defined as dead if it gave no apparent response when touched lightly and observed for 1 minute. To assess the experimental compound for acaricidal activity, a single dose level was chosen based on known results from previous experiments with a commercially available active reference compound. Both permethrin and fipronil were employed as reference compounds. The insect species tested was the Brown Dog Tick (*Rhipicephalus sanguineus*). Mixed sex adult ticks were used for tests. The strain used was cultured by von Berky Veterinary Services, Woody Point, QLD, AU and supplied as unfed adult ticks (mixed sex). Ticks were maintained in controlled conditions (temp. 18°+2° C., humidity 75±5% RH).

Test compounds (formulations or active ingredients) were stored in a refrigerator (5±1° C.) unless otherwise specified. Temperature was maintained at 25±1° C. and the humidity was ambient. The screening dose chosen was higher than that known to kill 90% of insects (LD$_{90}$) using the reference compound. In the case of topical application of active compounds on adult ticks, the reference compound was fipronil and the dose chosen was 10 μg of active per tick (=10 μg of fipronil/1 μl of acetone). Ticks were each treated on the abdomen with 1 μL of a single dose level of test sample in acetone; ten ticks were treated with solvent only (acetone) in each test. Tests were replicated 4 times (total of 40 ticks treated). Ticks were held in recovery containers maintained under appropriate rearing conditions for 24 hours. Mortality resulting from the treatments was recorded at 24 hours. Pooled 24 hour mortality data were converted to percentages.

e) Dose response protocol for topical application on brown dog ticks (*Rhipicephalus sanguineus*): The test determines the level of insecticidal activity of sample compounds or formulations when applied topically on brown dog ticks. Sample compounds were stored prior to use in a freezer (−5±1° C.), unless otherwise specified.

DEFINITIONS

Mortality: A tick is defined as dead after it gives no apparent response when touched lightly or gently breathed upon, while observed for 30 seconds.

LD50 (Lethal Dose 50): The dose of a topically applied treatment at which 50% of the dog ticks are killed.

Reference compound: To assess an experimental compound for significant acaricidal activity a single dose level is chosen, which is based upon known results from previous experiments using a commercially available active i.e., a reference compound. The reference compound selected is one in common use, and one that has a similar mode of action against the Brown Dog Tick (i.e., the test species).

Recovery container: A recovery container consists of a 500 ml round plastic container measuring 115 mm diameter and 70 mm height, with a tight fitting lid that has 10 small (~1 mm) holes inserted for air exchange. A 90 mm diameter piece of filter paper was placed on the bottom of the container and moistened with 1 mL of de-stilled water.

Adult, mixed sex, Brown Dog Ticks (*Rhipicephalus sanguineus*) were reared as follows: (i) cultured, (ii) transferred unfed, to a testing laboratory, and (iii) then maintained under controlled conditions (i.e., temp. 18°±2° C., humidity 75±5% RH). The ticks used were selected for vigor prior to testing, i.e., capable of actively walking and responsive to being touched or gently breathed upon.

During the testing, the temperature was maintained at 25±1° C., and the humidity was ambient. Seven dose levels (concentrations) of sample compound, in the form of serial dilutions in acetone, were derived from a pilot study and covered a range that produced very low to very high mortality. Groups of ten ticks were treated topically (on the abdomen) with 1 µL of a single dose level of the sample compound. Each test was replicated four times, i.e., employing a total of 40 ticks per dose level of each sample compound. As a control, ten ticks were treated with solvent only (acetone) for each test. Following the treatment, the ticks were held in recovery containers maintained under appropriate rearing conditions for 24 hours. Mortality resulting from the treatments was recorded at 24 hours. Pooled 24 hour mortality data were subjected to probit analysis to obtain concentration response data ($LC_{50}$) [see, Finney, D. J., *Probit Analysis* $3^{rd}$ ed., Cambridge Univ. Press, London (1971).]

All equipment that was not disposed of was decontaminated by soaking overnight in a 1% (minimum) solution of PYRONEG™ detergent. PYRONEG™ is a pyrogenically negative cleaner containing 60% alkaline salts. Surfaces were lightly scrubbed after soaking and double rinsed before re-use.

In Tables 14A, 14B and 14C, provided below, are listed the *Haemonchus contortus* $LD_{99}$ values (measured in micrograms/mL), the *Ctenocephalides felis* rapid screening values (measured in % mortality), the *Ctenocephalides felis* $LC_{50}$ values (measured in micrograms/$cm^2$), the *Rhipicephalus sanguineus* rapid screening values (measured in % mortality) and the *Rhipicephalus sanguineus* $LD_{50}$ values (measured in micrograms/tick) for selected compounds in accordance with the present invention. The tabulated data confirm that the inventive compounds have significant antiparasite activity for both endo and ectoparasites, as shown.

TABLE 14

| Cd # | C. felis Mortality (%) 8 h[A] | C. felis Mortality (%) 24 h[A] | C. felis Mortality (%) 48 h[B] | C. felis $LC_{50}$ (µg/$cm^2$)[C] | R. sanguineus Mortality (%) 24 h[E] | R. sanguineus Mortality (%) 48 h[F] | R. sanguineus $LD_{50}$ (µg/tick) | Haemonchus contortus $LD_{99}$ (µg/mL) |
|---|---|---|---|---|---|---|---|---|
| 1 | | | | | | | | |
| 2 | 2 | | | | | | | 0.1 |
| 3 | | | | | | | | |
| 4 | | | | | | | | 2.5 |
| 5 | 8 | | | | | | | 3.3 |
| 6 | 69 | 96 | | 0.1, 0.03[D] | 31, 17[F] | 82 | | 1.3 |
| 7 | | | | | | | | 1.6 |
| 8 | | | | | | | | 13 |
| 9 | 86 | 98 | | 0.1, 0.01[D] | 90, 42[F] | 95 | 2.7 | 0.6 |
| 10 | 56 | 73 | | 0.3 | | | | 2.7 |
| 11 | 87 | 100 | | 0.1, 0.01[D] | 83, 30[F] | 97 | 2.5 | 0.7 |
| 12 | | | | | | | | 1.7 |
| 13 | | | | | | | | 3 |
| 14 | 2 | | | | | | | 0.9 |
| 15 | | | | | | | | 2.7 |
| 16 | 90[B] | 100[B] | | | 72 | | | 1.3 |
| 17 | | | | | | | | 3.5 |
| 18 | | | | | | | | 3.7 |
| 19 | | | | | | | | 0.7 |
| 20 | | | | | | | | 12 |
| 21 | 5 | | | | | | | 0.7 |
| 22 | | | | | | | | 6 |
| 23 | | | | | | | | 0.8 |
| 24 | | 43 | | 0.8[D] | | | | 2.5 |
| 25 | | 100 | | | | | | |
| 26 | | | | | | | | |
| 27 | | 95 | | | | | | |
| 28 | | | | | | | | |
| 29 | | 92 | | | | | | |
| 30 | | 62 | | | | | | |
| 31 | | 74 | | | | | | |
| 32 | | 100 | | | | | | |
| 33 | | | | | | | | |
| 34 | | 100 | | | | | | |
| 35 | | 100 | | | | | | |
| 36 | | 100 | | | | | | |
| 37 | | 29 | | | 100 | | | |
| 38 | 8 | | | | | | | 0.9 |
| 39 | | | | | | | | 7 |
| 40 | | 45 | | | | | | |
| 41 | | 45 | | | | | | |

TABLE 14-continued

| Cd # | C. felis Mortality (%) 8 h[A] | C. felis Mortality (%) 24 h[A] | C. felis Mortality (%) 48 h[B] | C. felis LC$_{50}$ (μg/cm$^2$)[C] | R. sanguineus Mortality (%) 24 h[E] | R. sanguineus Mortality (%) 48 h[F] | R. sanguineus LD$_{50}$ (μg/tick) | Haemonchus contortus LD$_{99}$ (μg/mL) |
|---|---|---|---|---|---|---|---|---|
| 42 |  | 72 |  |  |  |  |  |  |
| 43 |  | 86 |  |  |  |  |  |  |
| 44-46 |  |  |  |  |  |  |  |  |
| 47 |  |  |  |  |  |  |  | 1.5 |
| 48 |  | 94 |  |  |  |  |  |  |
| 49-50 |  |  |  |  |  |  |  |  |
| 51 |  | 100 |  |  |  |  |  |  |
| 52 |  | 100 |  |  |  |  |  |  |
| 53 |  | 100 |  |  |  |  |  |  |
| 54 |  | 93 |  |  |  |  |  |  |
| 55 |  |  |  |  |  |  |  |  |
| 56 |  | 100 |  |  |  |  |  |  |
| 57 |  | 77 |  |  |  |  |  |  |
| 58 |  | 25 |  |  |  |  |  |  |
| 59-60 |  |  |  |  |  |  |  |  |
| 61 | 17 |  |  |  |  |  |  | 1.7 |
| 62 |  |  |  |  |  |  |  | 3 |
| 63 |  |  |  |  |  |  |  | 1.6 |
| 64 |  |  |  |  |  |  |  | 1.4 |
| 65 | 10 |  |  |  |  |  |  | 0.3 |
| 66 |  |  |  |  |  |  |  | 13 |
| 67 | 12 |  |  |  |  |  |  | 0.9 |
| 68 |  |  |  |  |  |  |  | 3.5 |
| 69 |  |  |  |  |  |  |  | 2.7 |
| 70 |  |  |  |  |  |  |  | 3 |
| 71 |  |  |  |  |  |  |  | 3 |
| 72 | 13 | 63 |  | 0.5 |  |  |  | 0.3 |
| 73 | 1 |  |  |  |  |  |  | 5 |
| 74 | 94 |  |  | 0.2 |  |  |  | 0.4 |
| 75 | 37 | 78 |  | 0.3 | 58, 10[F] |  | 77 | 0.9 |
| 76 | 100 |  |  | 0.2, 0.05[D] | 88, 7[F] |  | 80 | 0.3 |
| 77 | 3 |  |  |  |  |  |  | 2.5 |
| 78 | 21 |  |  |  |  |  |  | 1.8 |
| 79 | 73 | 100 |  | 0.6 |  |  |  | 0.6 |
| 80 |  |  |  |  |  |  |  | 3.5 |
| 81 |  |  |  |  |  |  |  | 1.7 |
| 82 |  |  |  |  |  |  |  | 3.3 |
| 83 |  |  |  |  |  |  |  |  |
| 84 | 95 |  |  |  |  |  |  | 3.3 |
| 85 | 6 |  |  |  |  |  |  | 1.6 |
| 86 |  |  |  |  |  |  |  | 3.5 |
| 87 | 5 |  |  |  |  |  |  | 1.3 |
| 88 |  |  |  |  |  |  |  | 15 |
| 89-90 |  |  |  |  |  |  |  |  |
| 91 |  | 67 |  |  |  |  |  | 13 |
| 92 | 36 |  |  |  |  |  |  | 1.6 |
| 93 |  |  |  |  |  |  |  |  |
| 94 |  |  |  |  |  |  |  | 7.5 |
| 95 |  |  |  |  |  |  |  | 0.8 |
| 96 |  | 21 |  |  |  |  |  | 0.7 |
| 97 |  | 42 |  |  |  |  |  | 0.6 |
| 98 | 79 |  |  |  |  |  |  | 1.4 |
| 99 |  |  |  |  |  |  |  | 2.5 |
| 100 | 58 | 88 |  | 0.4 |  |  |  | 1.8 |
| 101 |  |  |  |  |  |  |  | 1.9 |
| 102 |  |  |  |  |  |  |  | 1.9 |
| 103 |  |  |  |  |  |  |  |  |
| 104 |  | 100 |  | 0.3, 1.6[D] | 100, 57[F] |  | 100 | 10 |
| 105 |  |  |  |  |  |  |  | 3.5 |
| 106 |  | 48 |  | 1.0 |  |  |  | 11 |
| 107 |  |  |  |  |  |  |  | 10 |
| 108 | 12 |  |  |  |  |  |  | 1.3 |
| 109 | 3 |  |  |  |  |  |  | 2.8 |
| 110 |  |  |  |  |  |  |  | 5 |
| 111 | 9[B] | 70[B] |  |  |  |  |  | 5 |
| 112 |  |  |  |  |  |  |  | 3 |
| 113 |  |  |  |  |  |  |  | 3.8 |
| 114 |  |  |  |  |  |  |  |  |
| 115 |  |  |  |  |  |  |  | 7.5 |
| 116 | 10 |  |  |  |  |  |  | 0.9 |
| 117 |  |  |  |  |  |  |  | 3.5 |
| 118 |  |  |  |  |  |  |  | 10 |
| 119 |  |  |  |  |  |  |  | 1.2 |
| 120 | 2 |  |  |  |  |  |  | 0.5 |
| 121 | 3 |  |  |  |  |  |  | 0.6 |

TABLE 14-continued

| Cd # | C. felis Mortality (%) 8 h$^A$ | C. felis Mortality (%) 24 h$^A$ | C. felis Mortality (%) 48 h$^B$ | C. felis LC$_{50}$ (μg/cm$^2$)$^C$ | R. sanguineus Mortality (%) 24 h$^E$ | R. sanguineus Mortality (%) 48 h$^F$ | R. sanguineus LD$_{50}$ (μg/tick) | Haemonchus contortus LD$_{99}$ (μg/mL) |
|---|---|---|---|---|---|---|---|---|
| 122 | | | | | | | | 7 |
| 123 | 11 | | | 1.2, 0.3$^D$ | | | | 0.9 |
| 124 | | 100 | | | | | | |
| 125 | 6 | | | | | | | 5.5 |
| 126 | | | | | | | | |
| 127 | | 90 | | 0.3 | | | | 0.4 |
| 128 | | 100 | | 0.08, 0.05$^D$ | 95, 50$^F$ | 85 | | 0.4 |
| 129 | | 100 | | 0.05, 0.02$^D$ | 100, 82$^F$ | | 1.3 | 1.9 |
| 130 | | 100 | | 0.2, 0.03$^D$ | 90, 92$^F$ | 100 | 1.5 | 1.5 |
| 131 | | 100 | | 0.7 | | | | 1.6 |
| 132 | | 100 | | 0.2 | 33, 47$^F$ | 80 | | 1.6 |
| 133 | | 71 | | | | | | 0.9 |
| 134 | | 96 | | 0.4 | | | | 0.4 |
| 135 | | 47 | | | | | | 3 |
| 136 | | 74 | | | | | | 2.5 |
| 137 | | 91 | | | | | | 0.4 |
| 138 | | 78 | | | | | | 1.7 |
| 139 | | 64 | | 0.3$^D$ | | | | 0.9 |
| 140 | | 71 | | | | | | 0.7 |
| 141 | | 41 | | | | | | |
| 142 | | 72 | | | | | | |
| 143 | | 7 | | | | | | |
| 144 | | 15 | | | | | | |
| 145 | | 9 | | | | | | |
| 146 | | 11 | | | | | | |
| 147 | | 4 | | | | | | |
| 148 | | 38 | | | | | | |
| 149 | | 17 | | | | | | |
| 150 | | 48 | | | | | | |
| 151 | | 62 | | | | | | |
| 152 | | 61 | | | | | | |
| 153 | | 77 | | | 65 | | | |
| 154 | | 100 | | | 100 | | | |
| 155 | | 100 | | 0.2, 0.02$^D$ | 100, 92$^F$ | 92 | 1.5 | |
| 156 | | 100 | | 0.4, 0.02$^D$ | 100, 92$^F$ | 95 | 0.6 | |
| 157 | | 100 | | 0.3 | 100 | | 5.7 | |
| 158 | | 100 | | 0.2 | 95 | | | |
| 159 | | 100 | | 0.2 | 100 | | | |
| 160 | | 42 | | | 77 | | | |
| 161 | | 100 | | 0.2 | | | | |
| 162 | | 14 | | | | | | |
| 163 | | 100 | | 0.1 | | | | |
| 164 | | 19 | | | | | | |
| 165 | | 21 | | | | | | |
| 166 | | 17 | | | | | | |
| 167 | | 3 | | | | | | |
| 168 | | 36 | | | | | | |
| 169 | | 9 | | | | | | |
| 170 | | 97 | | 0.2 | 100 | | | |
| 171 | | 100 | | 0.4 | 100 | | | |
| 172 | | 100 | | 0.06 | 100 | | | |
| 173 | | 96 | | | 100 | | | |
| 174 | | 100 | | 0.1 | 100 | | 2.9 | |
| 175 | | 100 | | 0.1 | 100 | | 4.0 | |
| 176 | | 52 | | | 87 | | | |
| 177 | | 100 | | 0.3 | 95 | | 17.6 | |
| 178 | | 96 | | 0.3 | 87, 50$^F$ | 85 | | |
| 179 | | 12 | | | 45 | | | |
| 180 | | 8 | | | 52 | | | |
| 181 | | 100 | | 0.1 | 100 | | | |
| 182 | | 28 | | | | | | |
| 183 | 100$^B$ | 100$^B$ | | | 95$^F$ | 100 | | |
| 184 | 100$^B$ | 100$^B$ | | | 80$^F$ | 92 | | |
| 185 | 100$^B$ | 100$^B$ | | 0.2, 0.01$^D$ | 100$^F$ | 100 | 0.7 | |
| 186 | 100$^B$ | 100$^B$ | | 0.1, 0.006$^D$ | 82$^F$ | 100 | 0.9 | |
| 187 | 100$^B$ | 100$^B$ | | 0.1, 0.005$^D$ | 100$^F$ | 100 | 1.0 | |
| 188 | 98$^B$ | 98$^B$ | | | 10$^F$ | 40 | | |
| 189 | 91$^B$ | 97$^B$ | | 0.01$^D$ | 100$^F$ | 100 | 2.2 | |
| 190 | 98$^B$ | 100$^B$ | | | 32$^F$ | 75 | | |
| 191 | 52$^B$ | 100$^B$ | | | 90$^F$ | 92 | | |
| 192 | 18$^B$ | 43$^B$ | | | | | | |
| 193 | 88$^B$ | 100$^B$ | | 0.01$^D$ | 95$^F$ | 95 | 1.2 | |
| 194 | 100$^B$ | 100$^B$ | | 0.02$^D$ | 75$^F$ | 100 | 2.0 | |
| 195 | 33$^B$ | 100$^B$ | | | 87$^F$ | 97 | | |
| 196 | 96$^B$ | 100$^B$ | | 0.008$^D$ | 100$^F$ | 100 | 1.2 | |

TABLE 14-continued

| Cd # | C. felis Mortality (%) 8 h[A] | C. felis Mortality (%) 24 h[A] | C. felis Mortality (%) 48 h[B] | C. felis LC$_{50}$ (μg/cm$^2$)[C] | R. sanguineus Mortality (%) 24 h[E] | R. sanguineus Mortality (%) 48 h[F] | R. sanguineus LD$_{50}$ (μg/tick) | Haemonchus contortus LD$_{99}$ (μg/mL) |
|---|---|---|---|---|---|---|---|---|
| 197 | 80[B] | 97[B] | | | 90[F] | 100 | | |
| 198 | 16[B] | 92[B] | | | 12[F] | 35 | | |
| 199 | 82[B] | 100[B] | | | 0[F] | 5 | | |
| 200 | 93[B] | 100[B] | | | 2[F] | 17 | | |
| 201 | 85[B] | 100[B] | | | 17[F] | 22 | | |
| 202 | 100[B] | 100[B] | | 0.01[D] | 100[F] | 100 | 0.9 | |
| 203 | 98[B] | 98[B] | | | 60[F] | 95 | | |
| 204 | 100[B] | 100[B] | | | 32[F] | 87 | | |
| 205 | 97[B] | 98[B] | | 0.02[D] | 65[F] | 100 | 3.1 | |
| 206 | 97[B] | 100[B] | | | 27[F] | 52 | | |
| 207 | 98[B] | 100[B] | | 0.007[D] | 70[F] | 100 | 2.5 | |
| 208 | 100[B] | 100[B] | | 0.02[D] | 100[F] | 100 | 0.8 | |
| 209 | 38[B] | 93[B] | | | 2[F] | 22 | | |
| 210 | 66[B] | 100[B] | | 0.1[D] | 97[F] | 100 | 2.7 | |
| 211 | 46[B] | 100[B] | | | 27[F] | 90 | | |
| 212 | 24[B] | 100[B] | | | 10[F] | 57 | | |
| 213 | 53[B] | 100[B] | | | 70[F] | 90 | | |
| 214 | 98[B] | 100[B] | | | 7[F] | 20 | | |
| 215 | 82[B] | 100[B] | | 0.07[D] | 65[F] | 87 | 1.7 | |
| 216 | 97[B] | 100[B] | | | 42[F] | 72 | | |
| 217 | 46[B] | 90[B] | | | 12[F] | 30 | | |
| 218 | 90[B] | 100[B] | | | 27[F] | 75 | | |
| 219 | 69[B] | 100[B] | | | 20[F] | 60 | | |
| 220 | 54[B] | 100[B] | | | 25[F] | 62 | | |
| 221 | 44[B] | 100[B] | | | 35[F] | 67 | | |
| 222 | 27[B] | 96[B] | | | 17[F] | 32 | | |
| 223 | 92[B] | 100[B] | | 0.04[D] | 92[F] | 97 | 1.4 | |
| 224 | 83[B] | 100[B] | | 0.04[D] | 90[F] | 95 | 1.5 | |
| 232 | | 96[B] | 100 | | 40 | | | |
| 233 | | 15[B] | 96 | | | | | |
| 234 | | 64[B] | 100 | | | | | |
| 235 | | 100[B] | 100 | 0.2[D] | 100 | | 2.3 | |
| 236 | | 69[B] | 100 | | | | | |
| 237 | | 4[B] | 36 | | | | | |
| 238 | | 61[B] | 84 | | | | | |
| 239 | | 86[B] | 100 | | 90 | | | |
| 240 | | 64[B] | 98 | | | | | |
| 241 | | 100[B] | 100 | 0.1[D] | 100 | | 1.9 | |
| 242 | | 100[B] | 100 | 0.1[D] | 100 | | 3.1 | |
| 243 | | 100[B] | 100 | 0.1[D] | 100 | | 3.8 | |
| 244 | | 100[B] | 100 | 0.07[D] | 100 | | 3.0 | |
| 245 | | 100[B] | 100 | 0.09[D] | 100 | | 3.9 | |
| 246 | | 98[B] | 100 | | 97 | | | |
| 247 | | 100[B] | 100 | 0.1[D] | 100 | | 4.6 | |
| 248 | | 96[B] | 100 | | 92 | | | |
| 249 | | 100[#] | 100 | 1.3[D] | 100 | | 3.3 | |
| 250 | | 97[B] | 100 | | 97 | | | |
| 251 | | 32[B] | 100 | | | | | |
| 252 | | 15[B] | 100 | | | | | |
| 253 | | 100[B] | 100 | 1.2[D] | 100 | | 3.4 | |
| 254 | | 84[B] | 100 | | 95 | | | |
| 255 | 1[B] | 100[B] | | | 22* | | | |
| 256 | 0[B] | 84[B] | | | | | | |
| 257 | 5[B] | 96[B] | | | 40* | | | |
| 258 | 8[B] | 88[B] | | | | | | |
| 259 | 0[B] | 71[B] | | | | | | |

[A]Laboratory 1 A data.
[B]Laboratory 2 B data.
[C]Laboratory 1 C data.
[D]Laboratory 2 D data.
[E]Laboratory 1 E data.
[F]Laboratory 2 F data.
*Dose rate of 5 μg/tick.

Additional compounds 225-231 and 291-295 provided the following results, as shown by Table 14A.

TABLE 14A

| Cd # | Ctenocephalides felis Mortality (%) 8 h[A] | Ctenocephalides felis Mortality (%) 24 h[A] | Rhipicephalus sanguineus Mortality (%) 24 h[E] | Haemonchus contortus LD$_{99}$ (μg/mL) |
|---|---|---|---|---|
| 225 | | | | 3.2 |
| 226 | | | | |
| 227 | 7 | 9 | | 0.1 |
| 228 | 3 | 3 | | 0.4 |
| 229 | 2 | 7 | | 0.09 |
| 230 | 8 | 15 | | 0.4 |
| 231 | | 7 | | 0.6 |
| 291 | 91[B] | 100[B] | 67 | |
| 292 | 15[B] | 92[B] | | |
| 293 | 60[B] | 100[B] | 80 | |
| 294 | 3[B] | 40[B] | | |
| 295 | 0[B] | 44[B] | | |

[A]Laboratory 1 A data.
[B]Laboratory 2 B data.
[E]Laboratory 1 E data.

Additional compounds 296-313 provided the following results, as shown by Table 14B.

TABLE 14B

| Cd # | Ctenocephalides felis Mortality (%) 8 h[A] | Ctenocephalides felis Mortality (%) 24 h[A] | Ctenocephalides felis Mortality (%) 48 h[B] | Rhipicephalus sanguineus Mortality (%) 24 h[E] |
|---|---|---|---|---|
| 296 | | 0 | 19 | |
| 297 | | 1 | 28 | |
| 298 | | 1 | 12 | |
| 299 | | 0 | 56 | |
| 300 | | 0 | 9 | |
| 301 | | 1 | 19 | |
| 302 | | 3 | 82 | 5 |
| 303 | | 0[B] | 76 | 2 |
| 304 | | 0[B] | 81 | |
| 305 | | 1[B] | 21 | |
| 306 | | 0[B] | 48 | |
| 307 | | 10[B] | 98 | 5 |
| 308 | 29[B] | 100[B] | | 7 |
| 309 | 3[B] | 86[B] | | |
| 310 | 56[B] | 100[B] | | 52 |
| 311 | 14[B] | 76[B] | | |
| 312 | 11[B] | 89[B] | | |
| 313 | 0[B] | 59[B] | | |

[A]Laboratory 1 A data.
[B]Laboratory 2 B data.
[E]Laboratory 1 E data.

CONCLUSION

A substantial number of the tested compounds exhibited effective killing of most or all of the test organisms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A trifluoromethanesulfonanilide oxime ether compound of Formula (I)

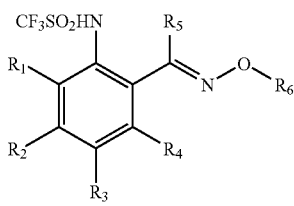

or a pharmaceutically acceptable salt thereof or a solvate thereof, wherein:

$R_1$, $R_2$, $R_3$ and $R_4$ are independently selected from the group consisting of hydrogen, formyl, carboxyl, cyano, hydroxy, amino, nitro, thiol, halo and the following optionally substituted moieties: alkyl, alkenyl, alkynyl, cycloalkyl, cycloalkenyl, aryl, heterocyclyl, heteroaryl, alkanoyl, aroyl, heterocycloyl, heteroaroyl, alkoxycarbonyl, aryloxycarbonyl, heterocyclyloxycarbonyl, heteroaryloxycarbonyl, alkylaminocarbonyl, arylaminocarbonyl, heterocyclylaminocarbonyl, heteroarylaminocarbonyl, alkoxy, alkenyloxy, cycloalkoxy, cycloalkenyloxy, alkoxy, aryloxy, alkanoate, aryloate, heterocycloate, heteroaroate, alkylsulfonate, arylsulfonate, heterocyclylsulfonate, heteroarylsulfonate, alkylamino, alkenylamino, arylamino, heterocyclylamino, heteroarylamino, alkylcarbonylamino, arylcarbonylamino, heterocyclylcarbonylamino, heteroarylcarbonylamino, alkylthio, alkenylthio, cycloalkylthio, cycloalkenylthio, arylthio, heterocyclylthio, heteroarylthio, alkylsulfinyl, alkenylsulfinyl, cycloalkylsulfinyl, cycloalkenylsulfinyl, arylsulfinyl, heterocyclylsulfinyl, heteroarylsulfinyl, alkylsulfonyl, alkenylsulfonyl, cycloalkylsulfonyl, cycloalkenylsulfonyl, arylsulfonyl, heterocyclylsulfonyl, heteroarylsulfonyl, haloalkyl, haloalkenyl, haloalkynyl, haloalkoxy, haloalkenyloxy, haloalkylsulfonate, haloalkylcarbonylamino, haloalkylthio, haloalkylsulfinyl and haloalkylsulfonyl;

$R_5$ is selected from hydrogen, halogen, cyano and the following optionally substituted moieties: alkyl, alkenyl, alkynyl, cycloalkyl, cycloalkenyl, cycloalkylalkyl, cycloalkenylalkyl, aryl, arylalkyl, heterocyclyl, haloalkyl, haloalkenyl and haloalkynyl; and $R_6$ is selected from hydrogen and the following optionally substituted moieties: alkyl, alkenyl, alkynyl, cycloalkyl, cycloalkenyl, cycloalkylalkyl, cycloalkenylalkyl, aryl, arylalkyl, arylalkenyl, heterocyclyl, heterocyclylalkyl, heteroaryl, heteroarylalkyl, heteroarylalkenyl, alkanoyl, aroyl, heterocycloyl, heteroaroyl, cyanoalkyl, alkoxyalkyl, cycloalkoxyalkyl, aryloxyalkyl, alkylthioalkyl, cycloalkylthioalkyl, arylthioalkyl, alkylsulfinylalkyl, cycloalkylsulfinylalkyl, arylsulfinylalkyl, alkylsulfonylalkyl, cycloalkylsulfonylalkyl, arylsulfonylalkyl, haloalkyl, haloalkenyl and haloalkynyl.

2. The trifluoromethanesulfonanilide oxime ether compound of claim 1 wherein $R_2$ and $R_3$ together are part of the same fused carbocyclic, heterocyclic, aryl or heteroaryl ring, that is substituted or unsubstituted.

3. The trifluoromethanesulfonanilide oxime ether compound of claim 1 wherein $R_4$ and $R_5$ together are part of the same fused carbocyclic, heterocyclic, aryl or heteroaryl ring, that is substituted or unsubstituted.

4. The trifluoromethanesulfonanilide compound of claim 1 wherein $R_5$ and $R_6$ together are part of the same fused heterocyclic or heteroaryl ring, that is substituted or unsubstituted.

5. The trifluoromethanesulfonanilide oxime ether compound of claim 1, wherein:

$R_1$ is hydrogen, $(C_1$-$C_6)$alkyl or $(C_1$-$C_6)$alkoxy;

$R_2$ is hydrogen, halo or $(C_1$-$C_6)$haloalkyl;

$R_3$ is hydrogen, halo or $(C_1$-$C_6)$haloalkyl;

$R_2$ and $R_3$ together are part of the same fused carbocyclic, heterocyclic, aryl or heteroaryl ring, which is substituted or unsubstituted;

$R_4$ is hydrogen;

$R_5$ is hydrogen, $(C_1$-$C_6)$alkyl, $(C_3$-$C_{10})$cycloalkyl or (optionally substituted)aryl; and $R_6$ is selected from the group consisting of $(C_1$-$C_6)$alkyl, $(C_2$-$C_6)$alkenyl, $(C_2$-$C_6)$alkynyl, $(C_3$-$C_{10})$cycloalkyl, $(C_3$-$C_{10})$cycloalkenyl, $(C_3$-$C_{10})$cycloalkyl$(C_1$-$C_6)$alkyl, $(C_3$-$C_{10})$cycloalkenyl$(C_1$-$C_6)$alkyl, and the following optionally substituted moieties: aryl, aryl$(C_1$-$C_6)$alkyl, aryl$(C_2$-$C_6)$alkenyl, heterocyclyl$(C_1$-$C_6)$alkyl, heteroaryl, heteroaryl$(C_1$-$C_6)$alkyl, cyano$(C_1$-$C_6)$alkyl, $(C_1$-$C_6)$alkoxy$(C_1$-$C_6)$alkyl, aryloxy$(C_1$-$C_6)$alkyl, $(C_1$-$C_6)$alkylthio$(C_1$-$C_6)$alkyl, $(C_1$-$C_6)$haloalkyl and $(C_2$-$C_6)$haloalkenyl.

6. The trifluoromethanesulfonanilide oxime ether compound of claim 1, wherein:

$R_1$ is hydrogen, methyl or methoxy;

$R_2$ is hydrogen, fluorine, chlorine or trifluoromethyl;

$R_3$ is hydrogen, fluorine, chlorine, bromine or trifluoromethyl;

$R_2$ and $R_3$ together are part of a methylene dioxy ring;

$R_4$ is hydrogen;

$R_5$ is hydrogen, methyl, ethyl, n-propyl, i-propyl, t-butyl, cyclohexyl or phenyl; and $R_6$ is selected from the group consisting of methyl, ethyl, i-propyl, i-butyl, t-butyl, sec-butyl, —CH(CH$_2$CH$_3$)$_2$, allyl, propargyl, cyclopentyl, cyclohexyl, 3-cyclohexenyl, trans-cinnamyl, —CH$_2$CN, —CH(CH$_3$)CN, —(CH$_2$)$_2$OCH$_3$, —CH$_2$SCH$_3$, —CH$_2$CF$_3$ or one of:

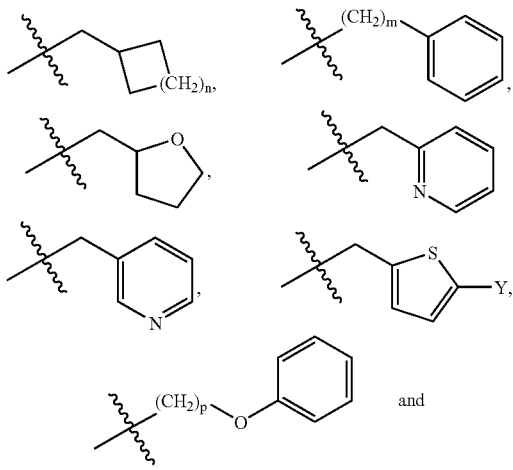

and

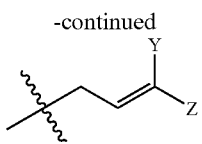

wherein:
n is 0, 2 or 3;
m is 2 or 3;
p is 2;
Y is hydrogen or chlorine; and
Z is chlorine or bromine.

7. A trifluoromethanesulfonanilide oxime ether compound corresponding to

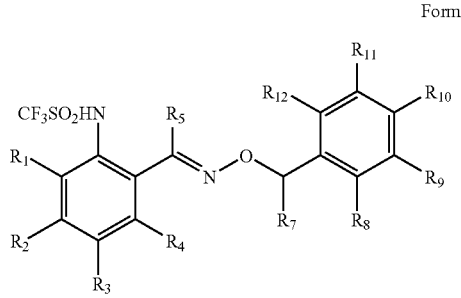

Formula (III)

or a pharmaceutically acceptable salt thereof or a solvate thereof,
wherein:
$R_1$ and $R_7$ are independently hydrogen or $(C_1-C_6)$alkyl;
$R_2$ is hydrogen or $(C_1-C_6)$haloallyl;
$R_3$ is hydrogen, halo or $(C_1-C_6)$haloalkyl;
$R_4$ is hydrogen;
$R_5$ is hydrogen, $(C_1-C_6)$alkyl or (optionally substituted) aryl;
$R_8$ and $R_{12}$ are independently hydrogen, cyano, halo or $(C_1-C_6)$haloalkyl;
$R_9$ and $R_{11}$ are independently hydrogen, (optionally substituted)aryloxy, (optionally substituted)heteroaryloxy, halo or $(C_1-C_6)$haloalkyl; and
$R_{10}$ is selected from the group consisting of hydrogen, $(C_1-C_6)$alkyl, $(C_3-C_{10})$cycloalkyl, (optionally substituted)aryl, $(C_1-C_6)$alkoxycarbonyl, cyano, $(C_1-C_6)$alkoxy, nitro, halo and $(C_1-C_6)$haloalkyl.

8. The trifluoromethanesulfonanilide oxime ether compound of claim 7,
wherein:
$R_1$ and $R_7$ are independently hydrogen or methyl;
$R_2$ is hydrogen or trifluoromethyl;
$R_3$ is hydrogen, chlorine or trifluoromethyl;
$R_4$ is hydrogen;
$R_5$ is hydrogen, methyl, ethyl, n-propyl, i-propyl or phenyl;
$R_8$ is hydrogen, cyano, fluorine, chlorine or trifluoromethyl;
$R_9$ is hydrogen, fluorine, chlorine, bromine, trifluoromethyl or one of:

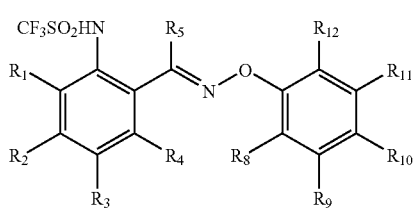

$R_{10}$ is hydrogen, t-butyl, cyclohexyl, phenyl, methoxycarbonyl, cyano, methoxy, nitro, fluorine, chlorine, bromine or trifluoromethyl;
$R_{11}$ is hydrogen, fluorine, bromine or trifluoromethyl; and
$R_{12}$ is hydrogen, fluorine or chlorine.

9. A trifluoromethanesulfonanilide oxime ether compound corresponding to

Formula (IV)

or a pharmaceutically acceptable salt thereof or a solvate thereof,
wherein:
$R_1$ is hydrogen;
$R_2$ is hydrogen or $(C_1-C_6)$haloalkyl;
$R_3$ is hydrogen, halo or $(C_1-C_6)$haloalkyl;
$R_4$ is hydrogen;
$R_5$ is $(C_1-C_6)$alkyl, $(C_3-C_{10})$cycloalkyl, or (optionally substituted)aryl;
$R_8$ and $R_{12}$ are independently hydrogen or $(C_1-C_6)$alkyl;
$R_9$ and $R_{11}$ are independently hydrogen, halo or $(C_1-C_6)$haloalkyl; and
$R_{10}$ is hydrogen, $(C_1-C_6)$alkyl, cyano, halo, $(C_1-C_6)$haloalkyl or $(C_1-C_6)$haloalkoxy.

10. The trifluoromethanesulfonanilide oxime ether compound of claim 8,
wherein:
$R_1$ is hydrogen;
$R_2$ is hydrogen or trifluoromethyl;
$R_3$ is hydrogen, chlorine or trifluoromethyl;
$R_4$ is hydrogen;
$R_5$ is methyl, ethyl, n-propyl, i-propyl, t-butyl, cyclohexyl or phenyl;
$R_8$ is hydrogen or methyl;
$R_9$ is hydrogen, fluorine, chlorine or trifluoromethyl;
$R_{10}$ is hydrogen, methyl, cyano, fluorine, chlorine, bromine, trifluoromethyl or trifluoromethoxy;
$R_{11}$ is hydrogen; and
$R_{12}$ is hydrogen.

11. A trifluoromethanesulfonanilide oxime ether prodrug compound corresponding to Formula (V)

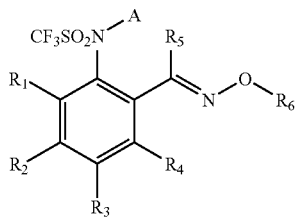

or a pharmaceutically acceptable salt thereof or a solvate thereof, wherein:

$R_1$, $R_2$, $R_3$, $R_4$, $R_5$ and $R_6$ are defined as for claim 1, and

A is selected from the following optionally substituted moieties: alkyl, alkenyl, arylalkyl, hydroxyalkyl, alkoxyalkyl, aryloxyalkyl, heterocyclyloxyalkyl, heteroaryloxyalkyl, alkylcarbonyloxyalkyl, arylcarbonyloxyalkyl, heterocyclylcarbonyloxyalkyl, heteroarylcarbonyloxyalkyl, alkoxycarbonyloxyalkyl, aryloxycarbonyloxyalkyl, heterocyclyloxycarbonyloxyalkyl, heteroaryloxycarbonyloxyalkyl, alkylaminocarbonyloxyalkyl, arylaminocarbonyloxyalkyl, heterocyclylaminocarbonyloxyalkyl, heteroarylaminocarbonyloxyalkyl, alkylcarbonylaminoalkyl, arylcarbonylaminoalkyl, heterocyclycarbonylaminoalkyl, heteroarylcarbonylaminoalkyl, alkylsulfonylalkyl, arylsulfonylalkyl, heterocyclylsulfonylalkyl, heteroarylsulfonylalkyl, alkanoyl, aroyl, heterocycloyl, heteroaroyl, alkoxycarbonyl, aryloxycarbonyl, heterocyclyloxycarbonyl, heteroaryloxycarbonyl, alkylaminocarbonyl, arylaminocarbonyl, heterocyclylaminocarbonyl, heteroarylaminocarbonyl, alkylaminothiocarbonyl, arylaminothiocarbonyl, heterocyclylaminothiocarbonyl, heteroarylaminothiocarbonyl, alkylsulfonyl, arylsulfonyl, heterocyclylsulfonyl and heteroarylsulfonyl.

12. The trifluoromethanesulfonanilide oxime ether compound of claim 1 that is selected from the compounds listed in the table below:

| | Compound structure |
|---|---|
| 1 | 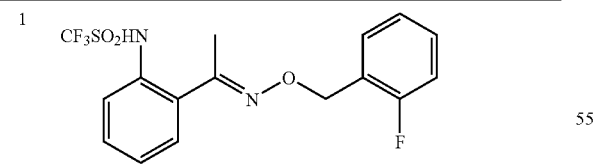 |
| 2 | 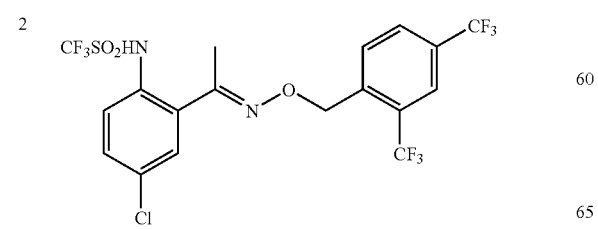 |

-continued

| | Compound structure |
|---|---|
| 3 | 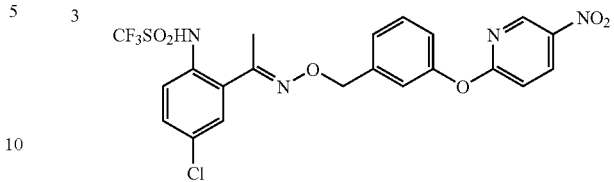 |
| 4 | 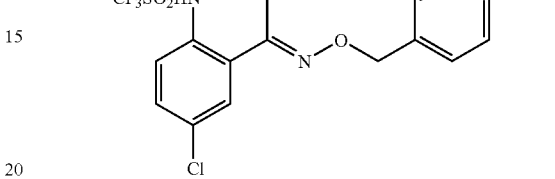 |
| 5 | 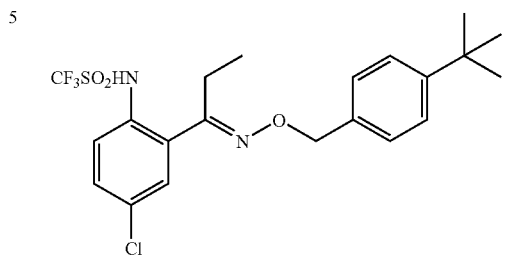 |
| 6 | 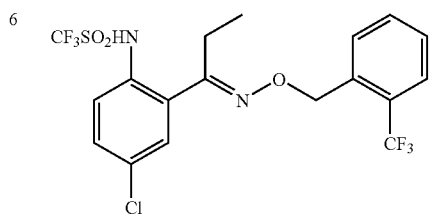 |
| 7 | 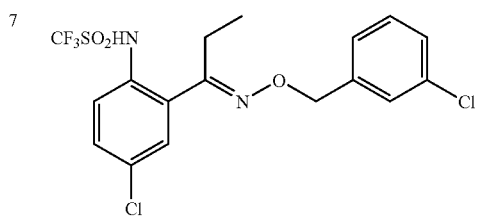 |
| 8 | 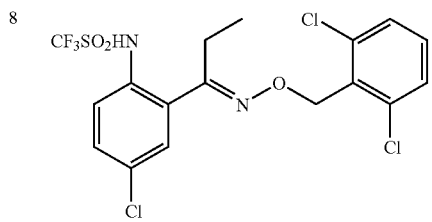 |
| 9 | 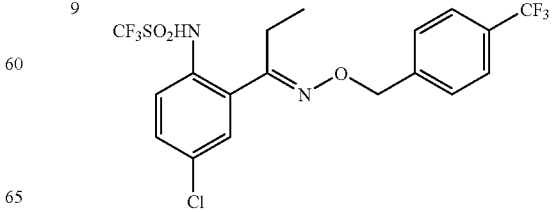 |

-continued
| Compound structure |
|---|
| 10 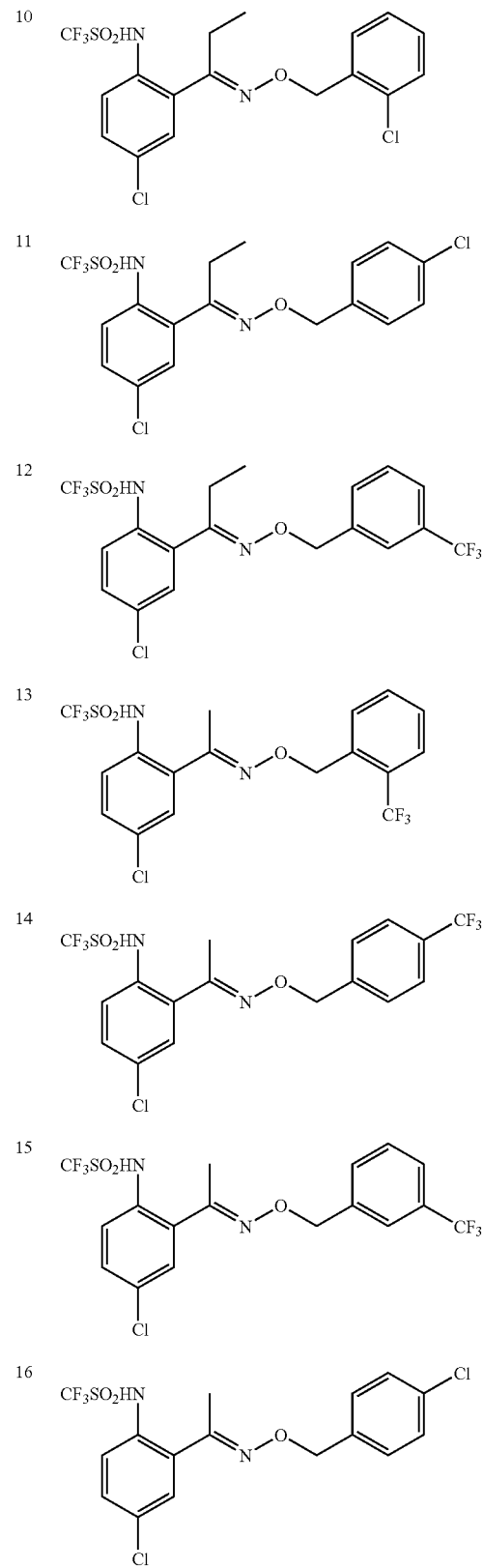 |
| 11 |
| 12 |
| 13 |
| 14 |
| 15 |
| 16 |
-continued
| Compound structure |
|---|
| 17 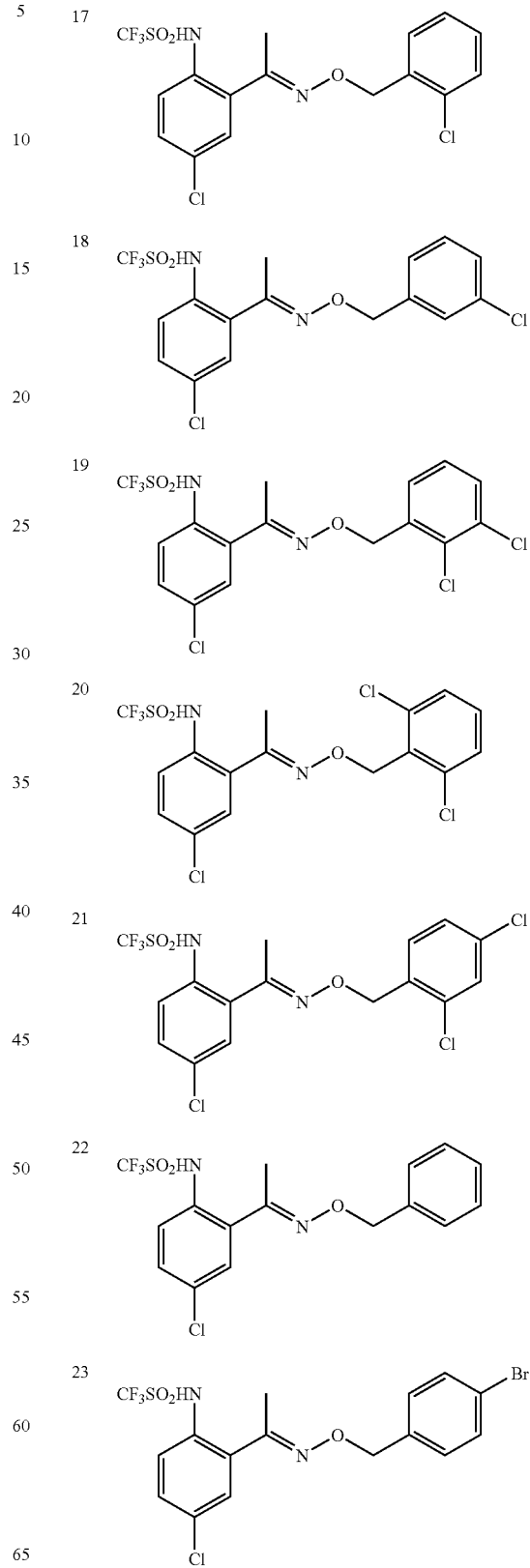 |
| 18 |
| 19 |
| 20 |
| 21 |
| 22 |
| 23 |

|Compound structure|
|---|
|24 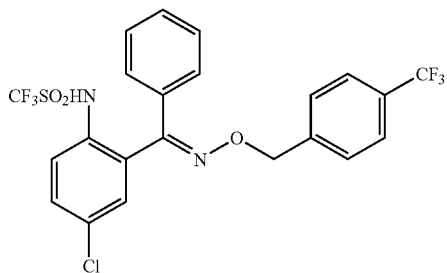|
|25 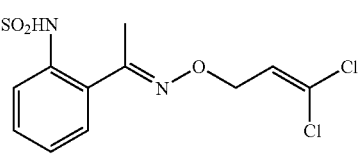|
|26 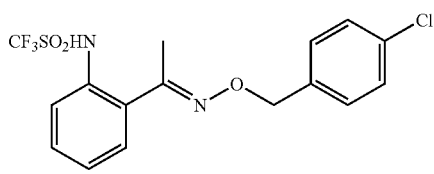|
|27 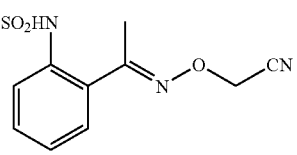|
|28 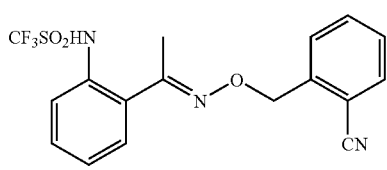|
|29 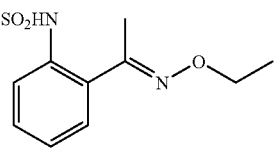|
|30 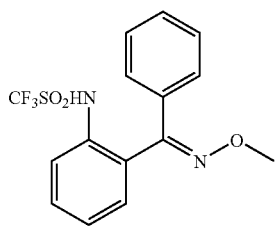|
|31 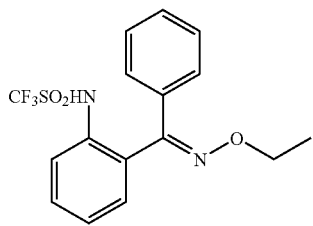|
|Compound structure|
|---|
|32 |
|33 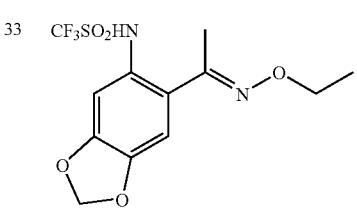|
|34 |
|35 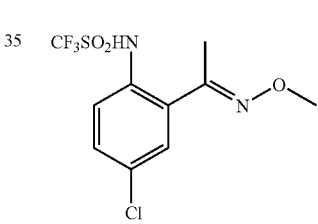|
|36 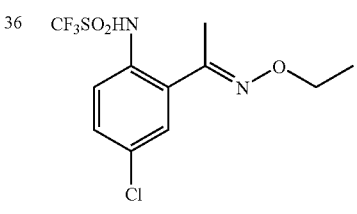|
|37 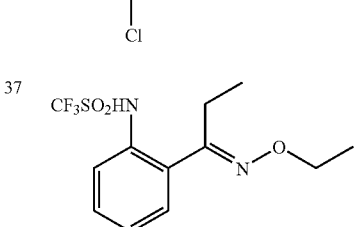|
|38 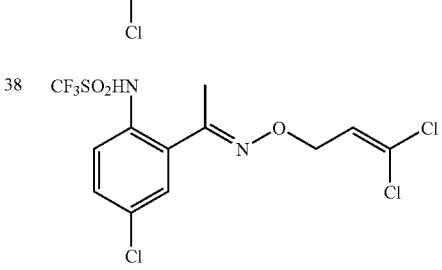|

-continued
| | Compound structure |
|---|---|
| 39 | 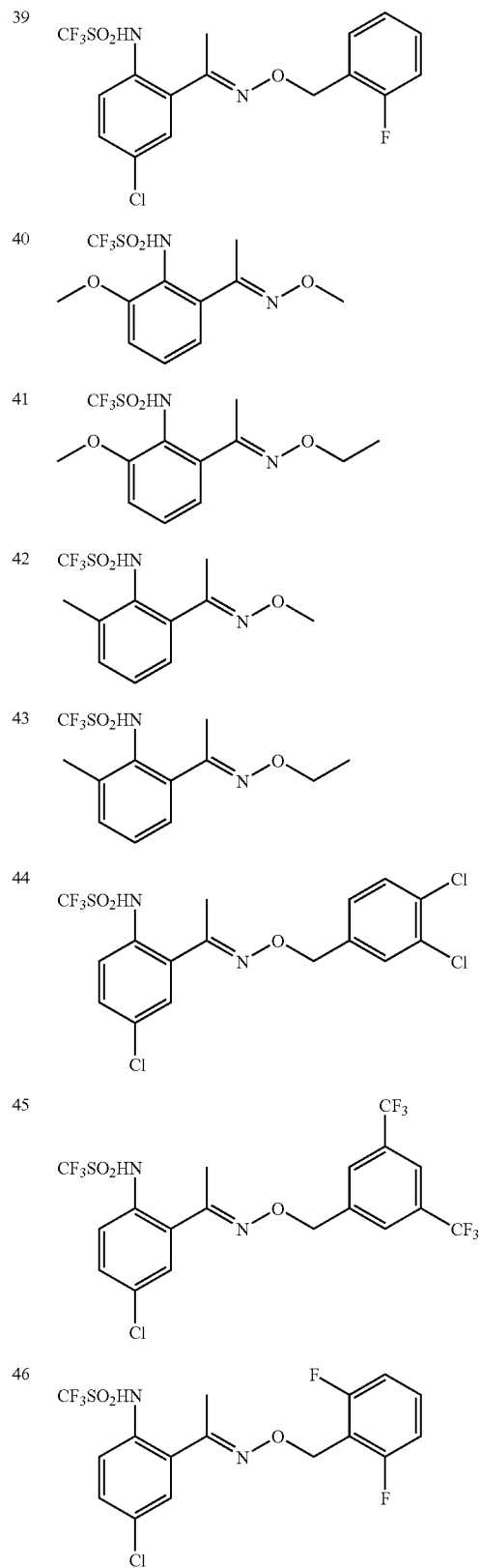 |
| 40 | |
| 41 | |
| 42 | |
| 43 | |
| 44 | |
| 45 | |
| 46 | |
-continued
| | Compound structure |
|---|---|
| 47 | 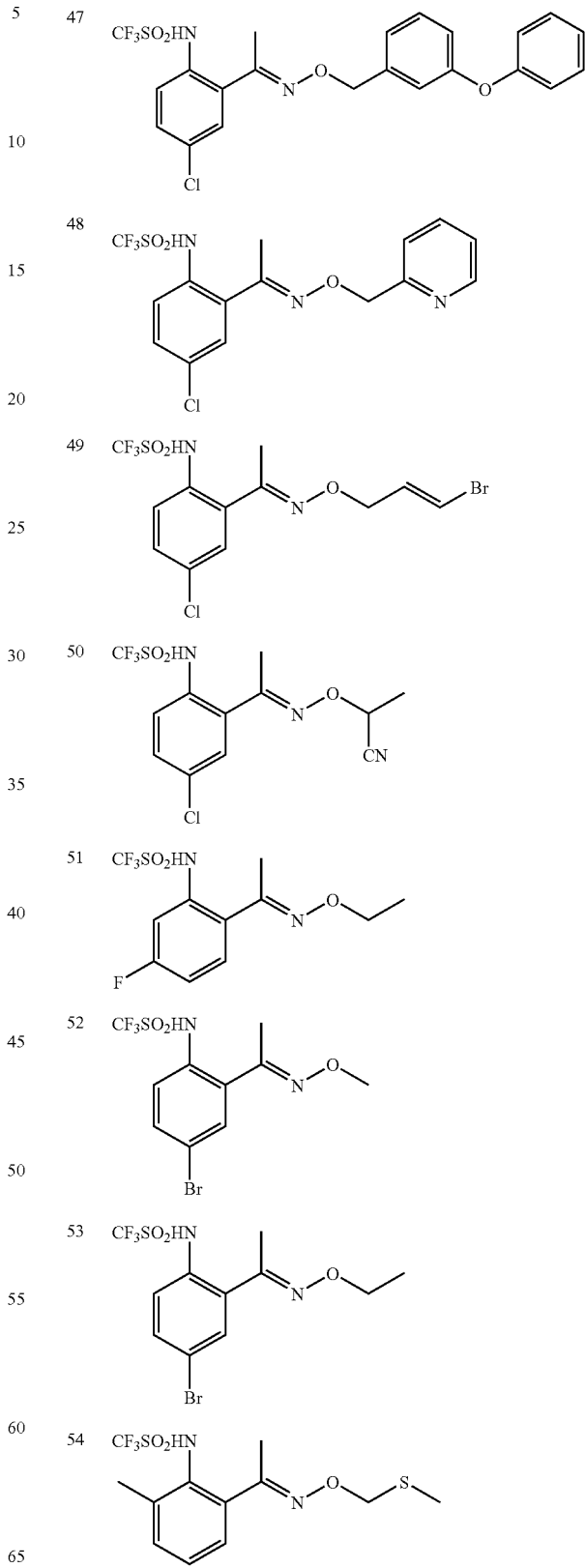 |
| 48 | |
| 49 | |
| 50 | |
| 51 | |
| 52 | |
| 53 | |
| 54 | |

| | Compound structure |
|---|---|
| 55 | (CF₃SO₂HN, chloro-substituted phenyl) C(CH₃)=N-O-CH₂-S-CH₃ |
| 56 | (CF₃SO₂HN-phenyl) C(CH₃)=N-O-CH₂-S-CH₃ |
| 57 | (CF₃SO₂HN, methyl-substituted phenyl) C(CH₃)=N-O-CH(CH₃)₂ |
| 58 | (CF₃SO₂HN, methyl-substituted phenyl) C(CH₃)=N-O-CH(CH₃)CH₂CH₃ |
| 59 | (CF₃SO₂HN, methyl-substituted phenyl) C(CH₃)=N-O-CH₂-(2-chlorophenyl) |
| 60 | (CF₃SO₂HN-phenyl) C(CH₃)=N-O-CH₃ |
| 61 | (CF₃SO₂HN, chloro-substituted phenyl)(phenyl) C=N-O-CH₂-(2,4-dichlorophenyl) |
| 62 | (CF₃SO₂HN, chloro-substituted phenyl)(phenyl) C=N-O-CH₂-(2,3-dichlorophenyl) |
| 63 | (CF₃SO₂HN, chloro-substituted phenyl)(phenyl) C=N-O-CH₂-(4-chlorophenyl) |
| 64 | (CF₃SO₂HN, chloro-substituted phenyl)(phenyl) C=N-O-CH₂-(4-bromophenyl) |
| 65 | (CF₃SO₂HN, chloro-substituted phenyl) CH=N-O-CH₂-(2,4-bis(CF₃)phenyl) |
| 66 | (CF₃SO₂HN, chloro-substituted phenyl)(phenyl) C=N-O-CH₂-phenyl |
| 67 | (CF₃SO₂HN, chloro-substituted phenyl) CH=N-O-CH₂-(2,4-dichlorophenyl) |
| 68 | (CF₃SO₂HN, chloro-substituted phenyl)(phenyl) C=N-O-CH₂-(3-CF₃-phenyl) |

201
-continued
| | Compound structure |
|---|---|
| 69 | 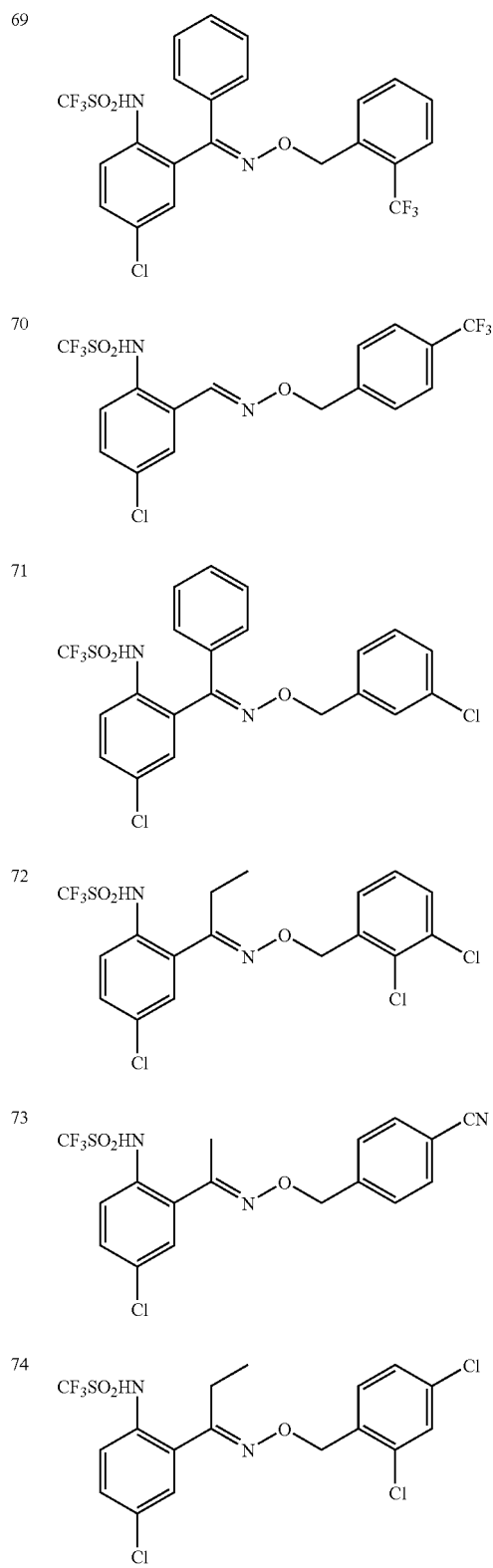 |
| 70 | |
| 71 | |
| 72 | |
| 73 | |
| 74 | |
202
-continued
| | Compound structure |
|---|---|
| 75 | 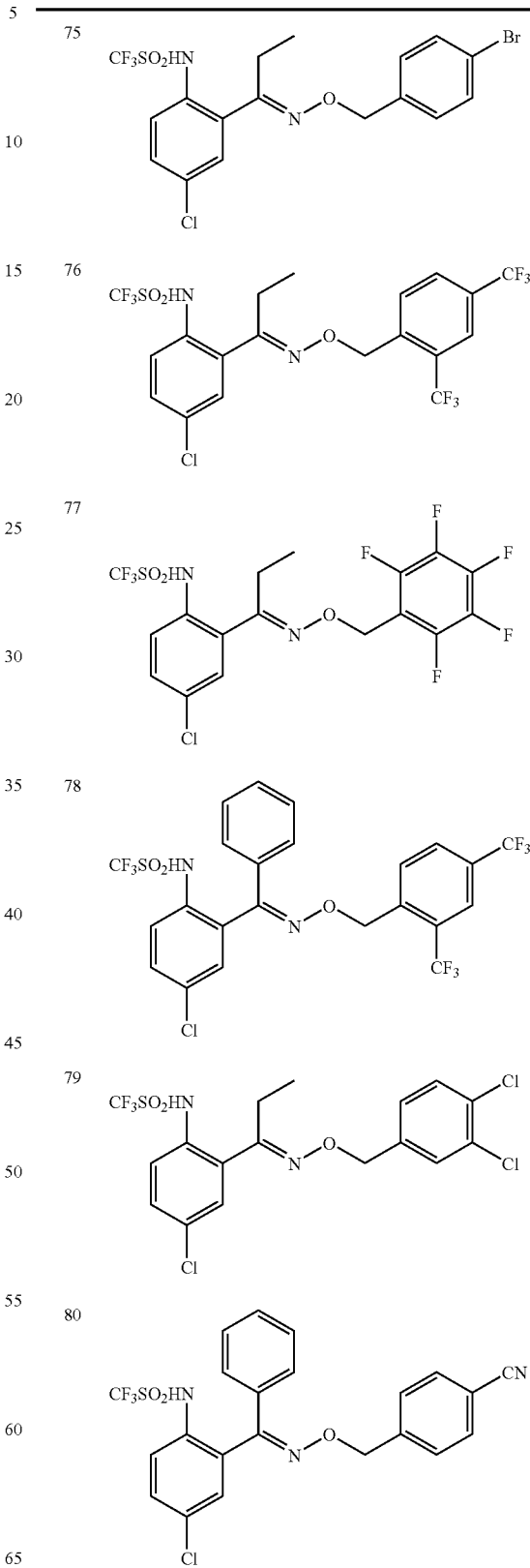 |
| 76 | |
| 77 | |
| 78 | |
| 79 | |
| 80 | |

| Compound structure |
|---|
| 81 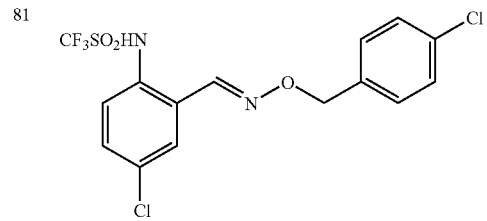 |
| 82 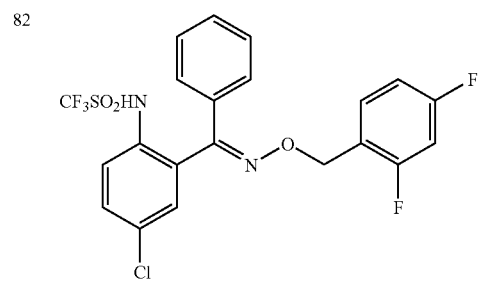 |
| 83 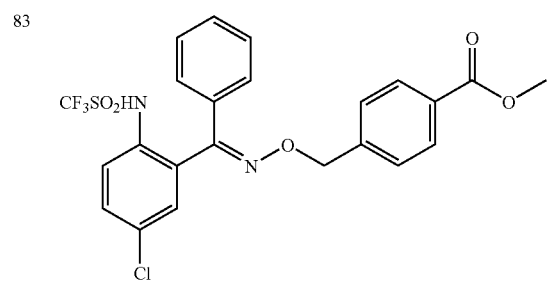 |
| 84 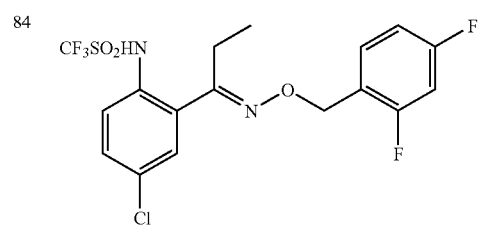 |
| 85 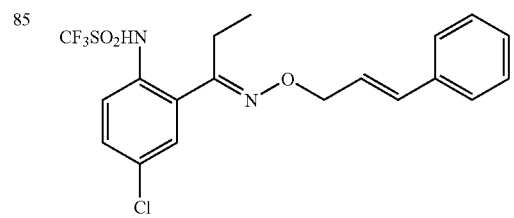 |
| 86 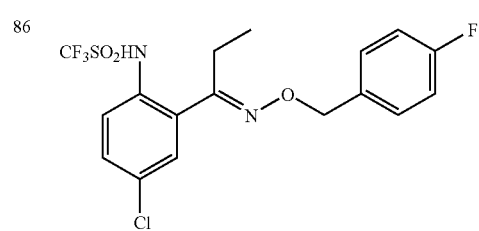 |
| Compound structure |
|---|
| 87 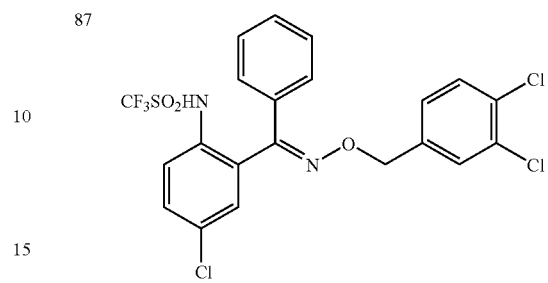 |
| 88 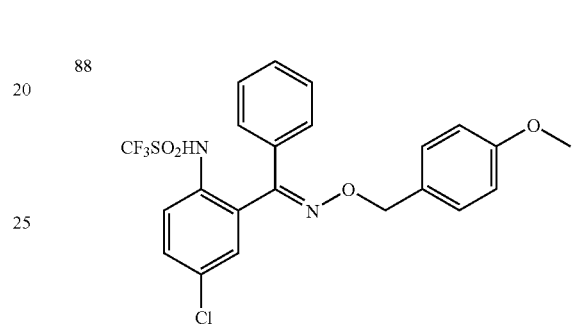 |
| 89 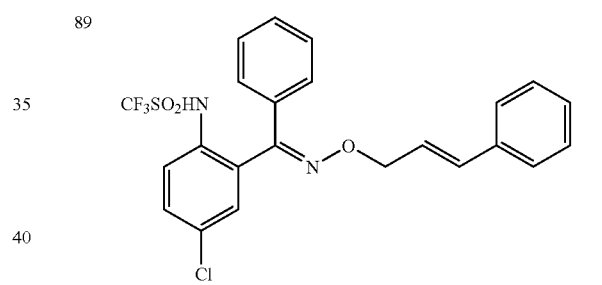 |
| 90 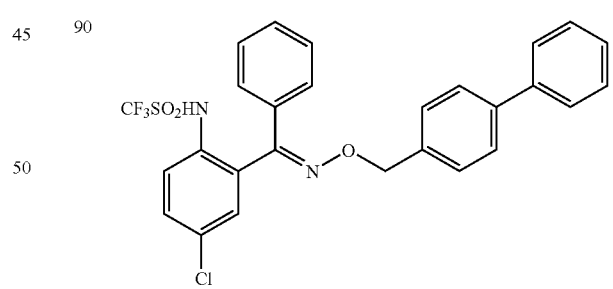 |
| 91 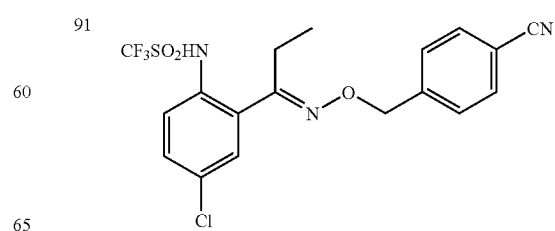 |

| Compound structure | | Compound structure |
|---|---|---|
| 92 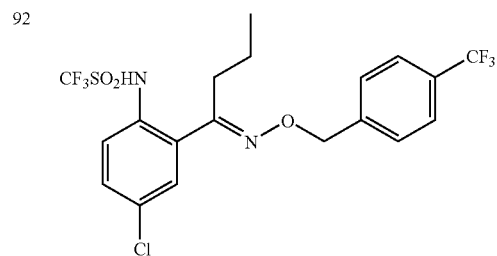 | | 98 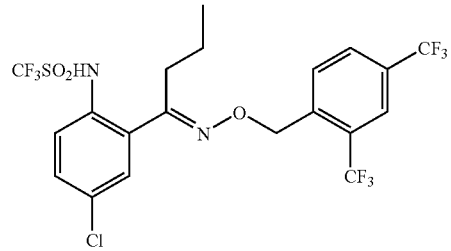 |
| 93 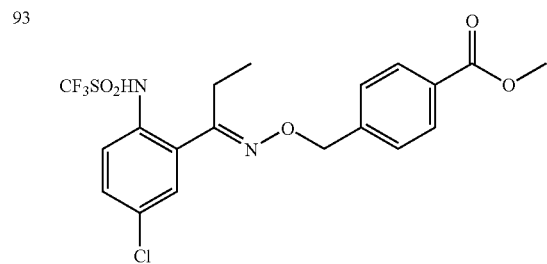 | | 99 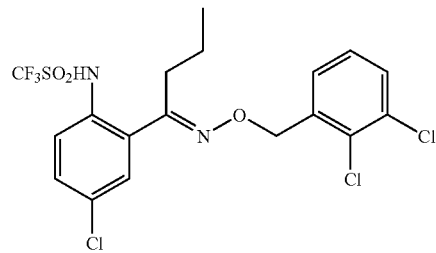 |
| 94 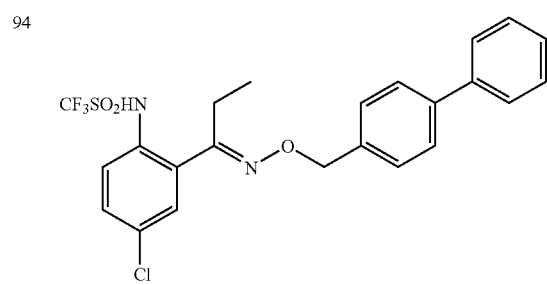 | | 100 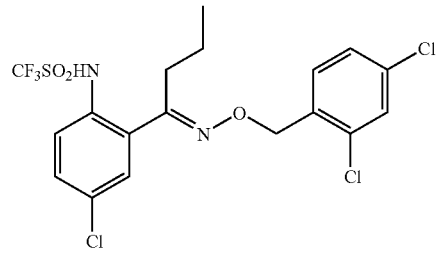 |
| 95 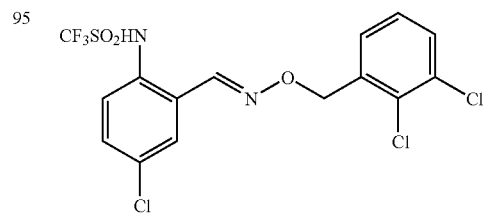 | | 101 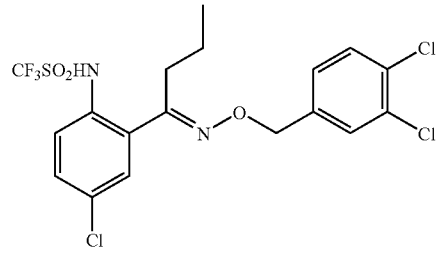 |
| 96 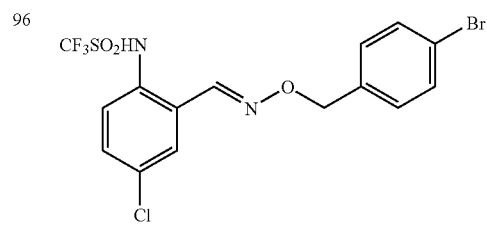 | | 102 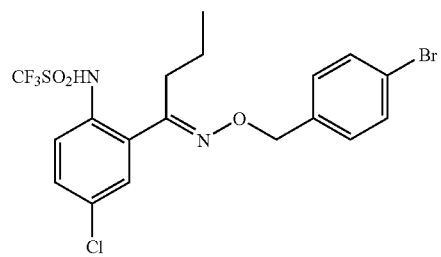 |
| 97 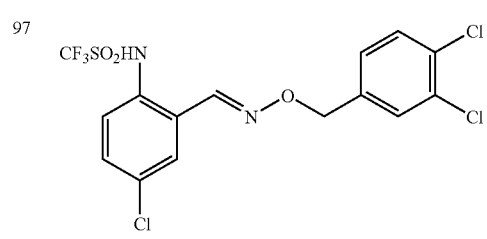 | | 103 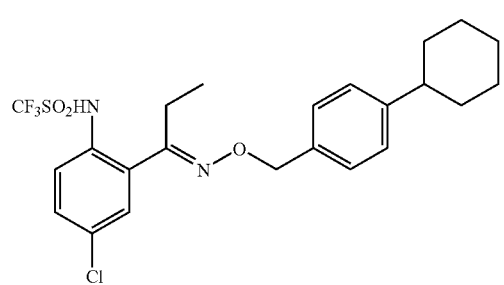 |

-continued
Compound structure
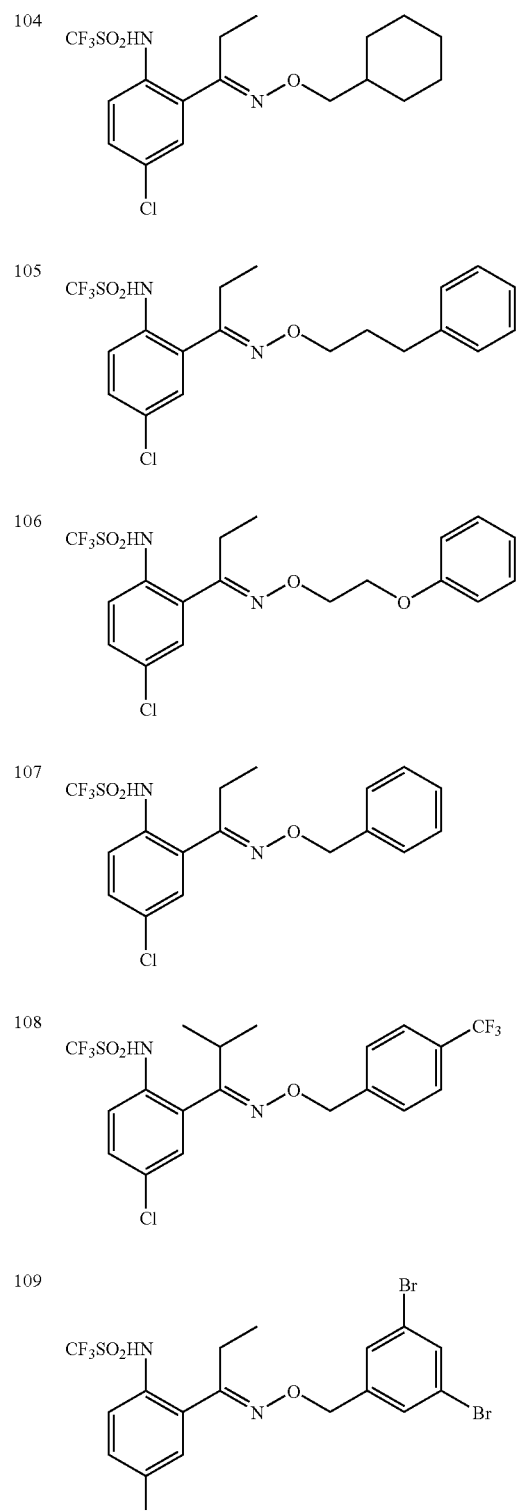
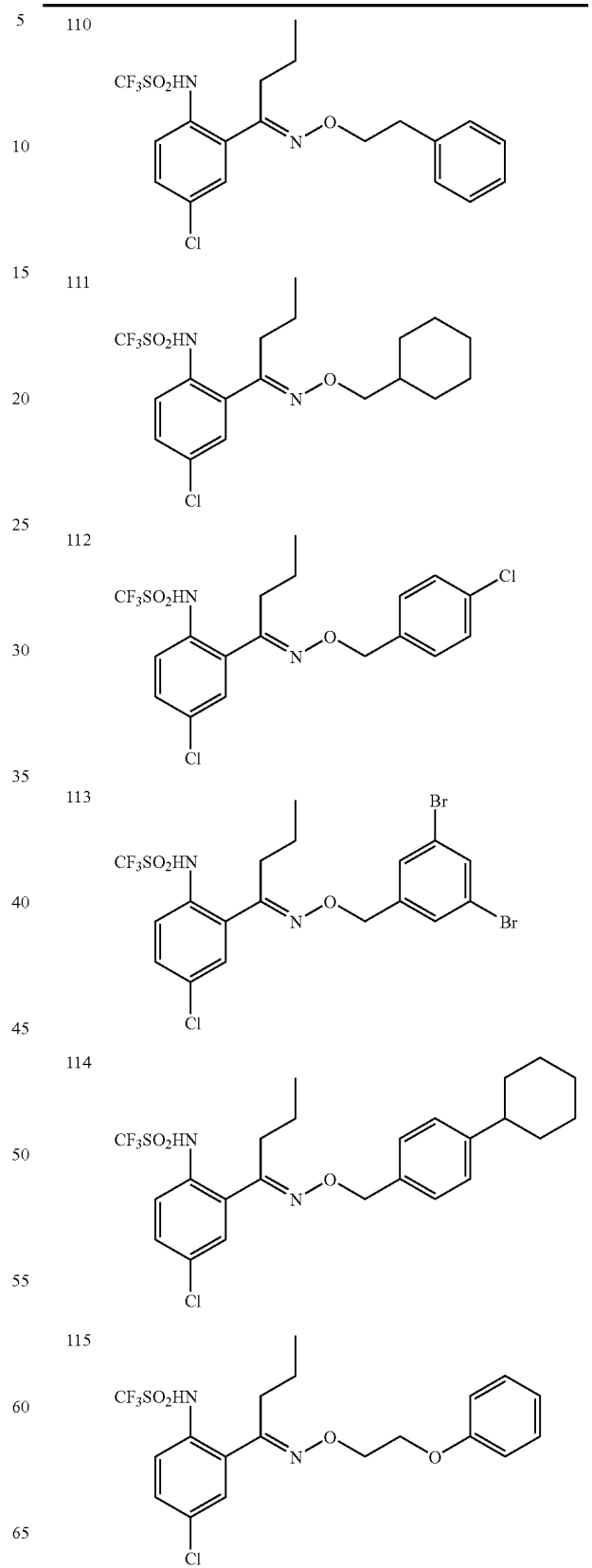

-continued

| | Compound structure |
|---|---|
| 116 | (structure) |
| 117 | (structure) |
| 118 | (structure) |
| 119 | (structure) |
| 120 | (structure) |
| 121 | (structure) |

-continued

| | Compound structure |
|---|---|
| 122 | (structure) |
| 123 | (structure) |
| 124 | (structure) |
| 125 | (structure) |
| 126 | (structure) |
| 127 | (structure) |
| 128 | (structure) |

-continued
| | Compound structure |
|---|---|
| 129 | 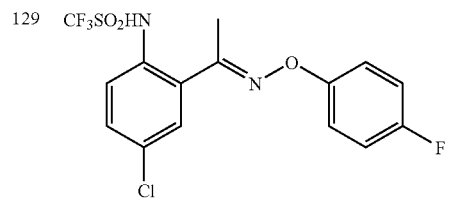 |
| 130 | 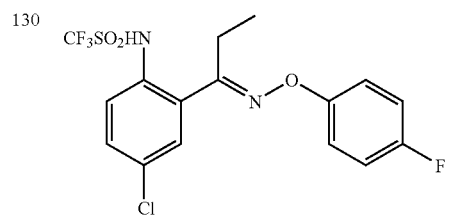 |
| 131 | 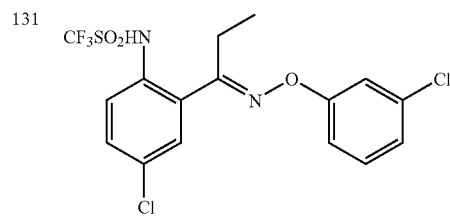 |
| 132 | 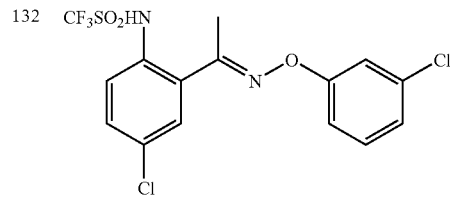 |
| 133 | 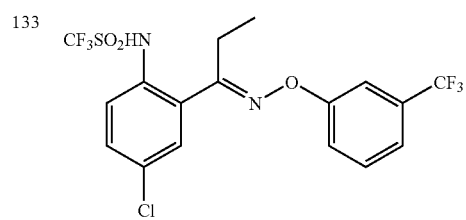 |
| 134 | 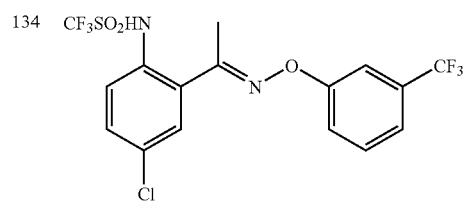 |
| 135 | 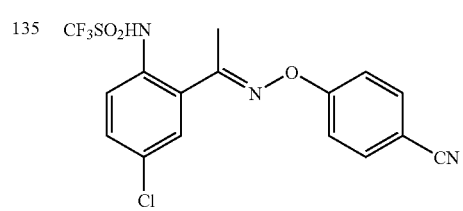 |
-continued
| | Compound structure |
|---|---|
| 136 | 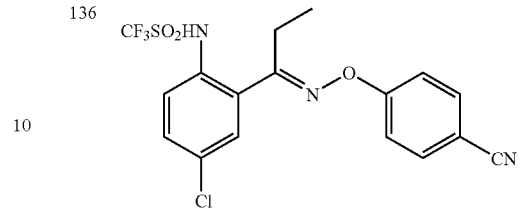 |
| 137 | 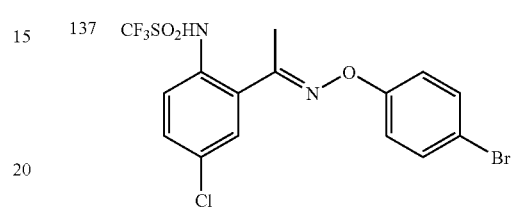 |
| 138 | 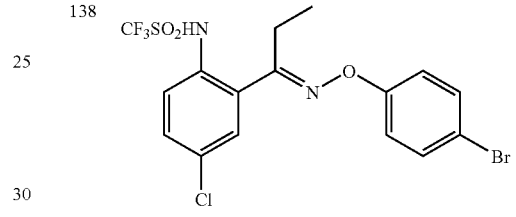 |
| 139 | 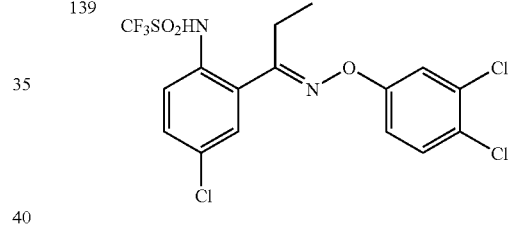 |
| 140 | 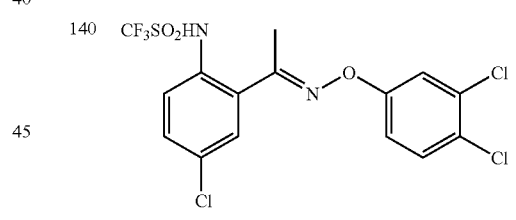 |
| 141 | 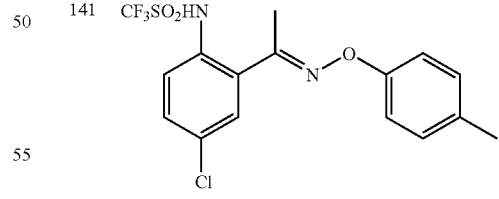 |
| 142 | 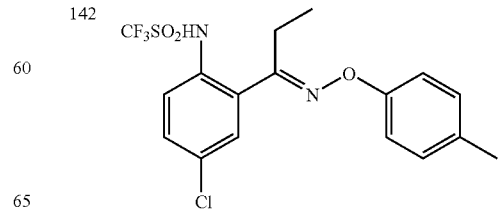 |

-continued
| Compound structure |
|---|
| 143 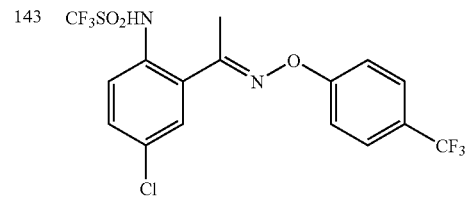 |
| 144 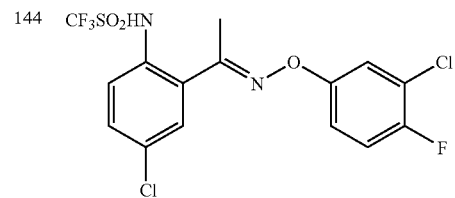 |
| 145 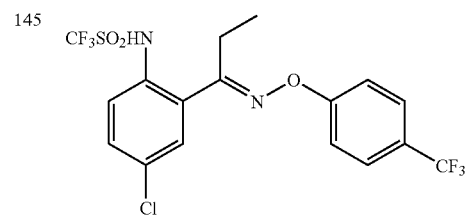 |
| 146 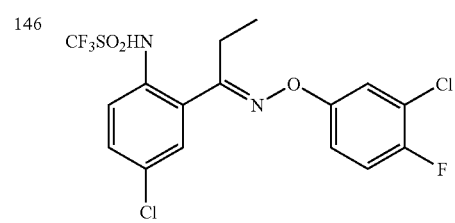 |
| 147 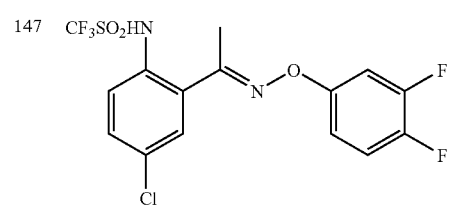 |
| 148 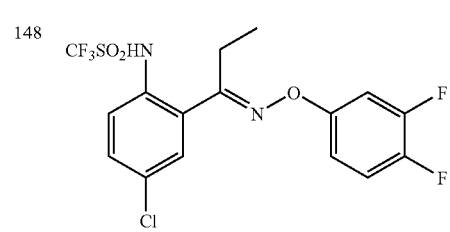 |
| 149 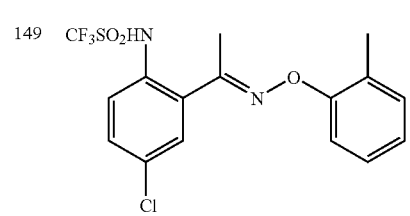 |
-continued
| Compound structure |
|---|
| 150 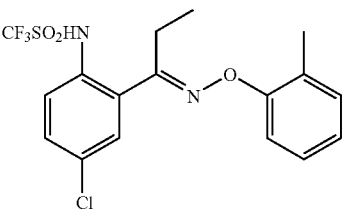 |
| 151 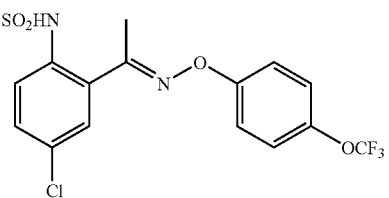 |
| 152 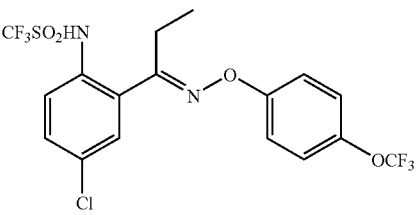 |
| 153 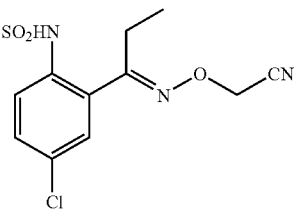 |
| 154 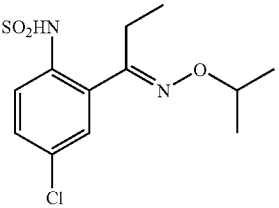 |
| 155 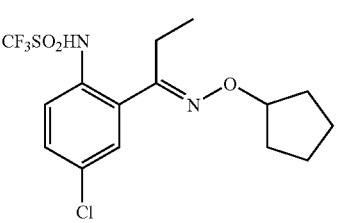 |
| 156 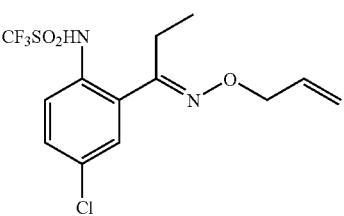 |

-continued
| Compound structure | |
|---|---|
| 157 | 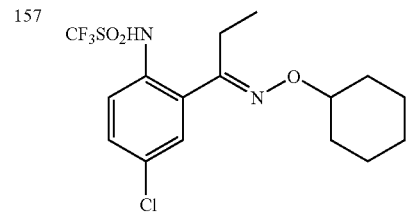 |
| 158 | 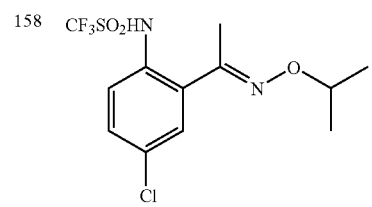 |
| 159 | 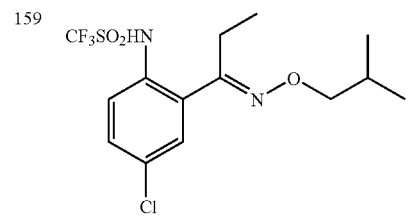 |
| 160 | 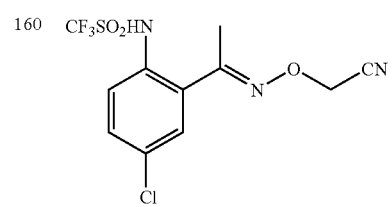 |
| 161 | 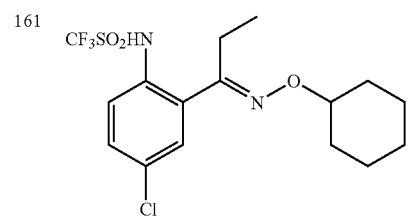 |
| 162 | 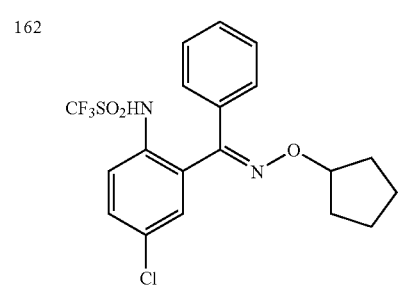 |
| 163 | 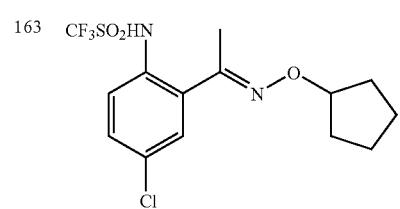 |
-continued
| Compound structure | |
|---|---|
| 164 | 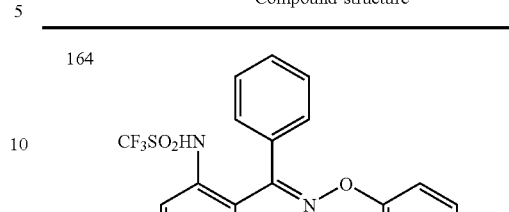 |
| 165 | 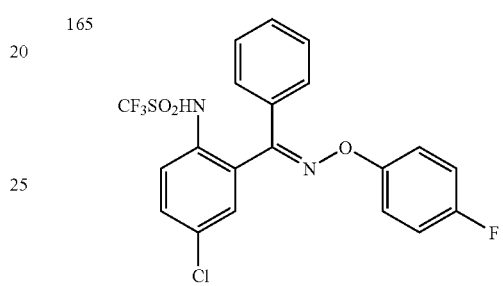 |
| 166 | 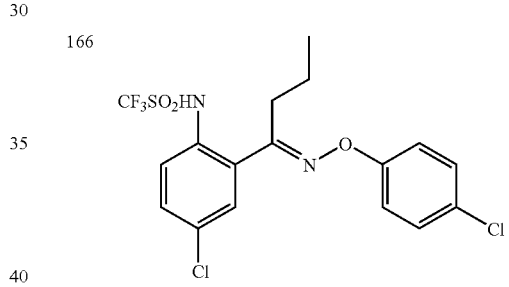 |
| 167 | 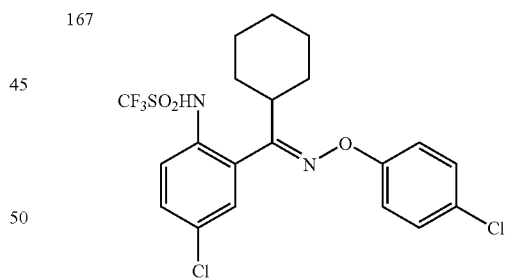 |
| 168 |  |

-continued
| Compound structure | |
|---|---|
| 169 | 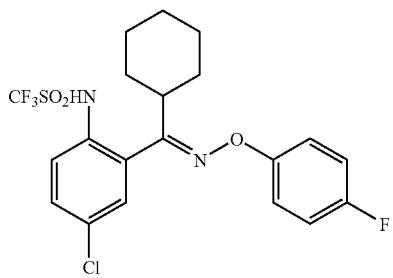 |
| 170 | 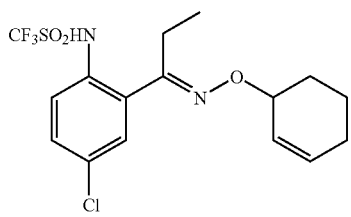 |
| 171 | 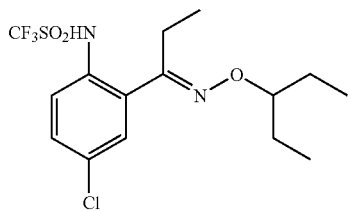 |
| 172 | 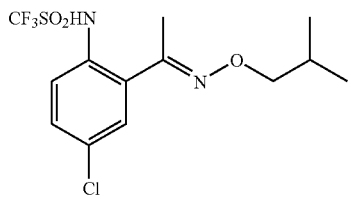 |
| 173 | 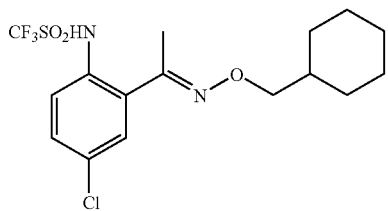 |
| 174 | 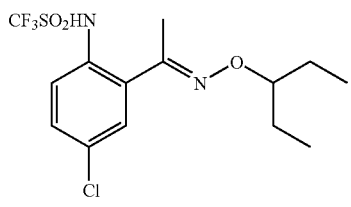 |
| 175 | 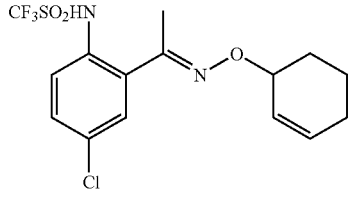 |
-continued
| Compound structure | |
|---|---|
| 176 | 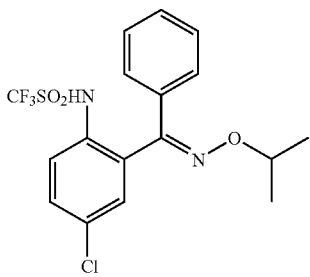 |
| 177* | 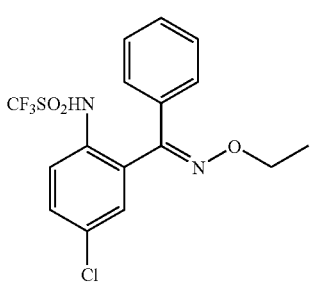 |
| 178** | 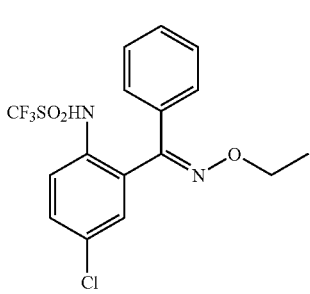 |
| 179 | 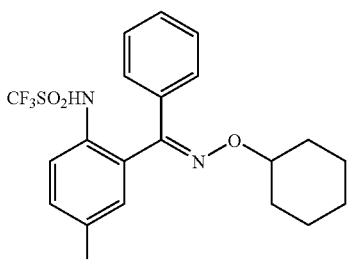 |
| 180 | 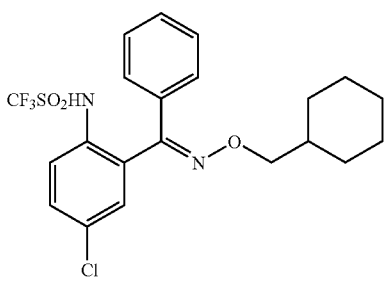 |

| Compound structure | | Compound structure |
|---|---|---|
| 181 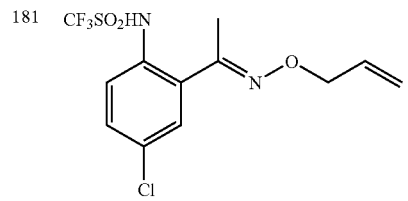 | 188 | 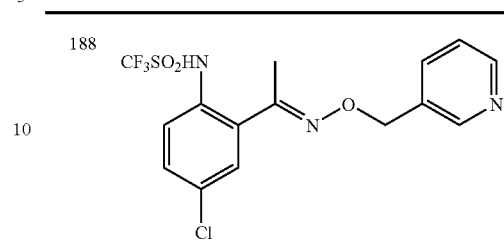 |
| 182 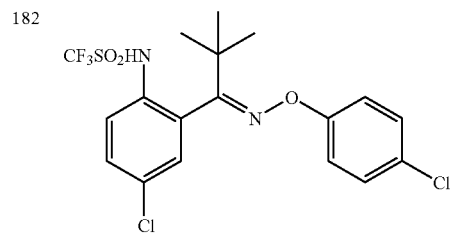 | 189 | 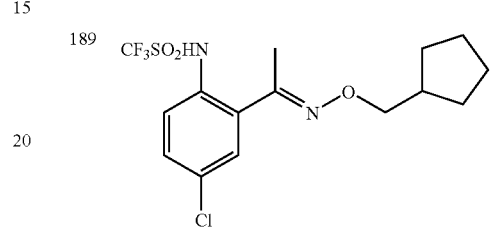 |
| 183 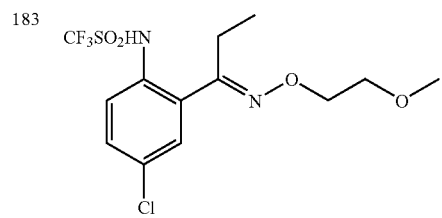 | 190 | 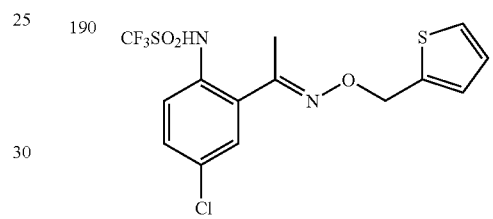 |
| 184 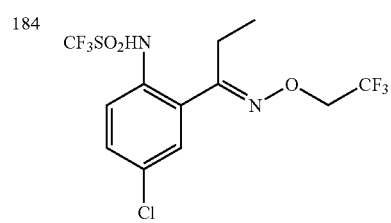 | 191 | 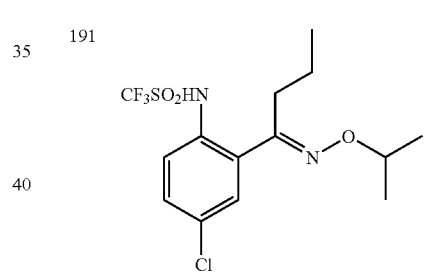 |
| 185 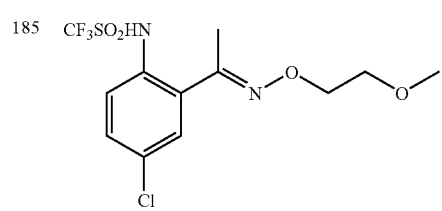 | 192 | 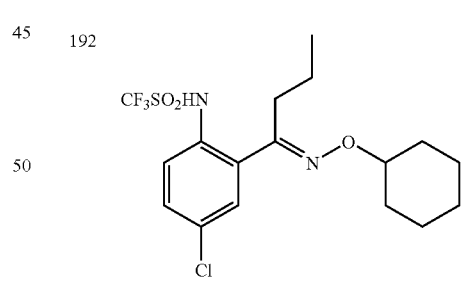 |
| 186 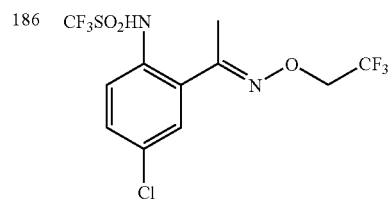 | 193 | 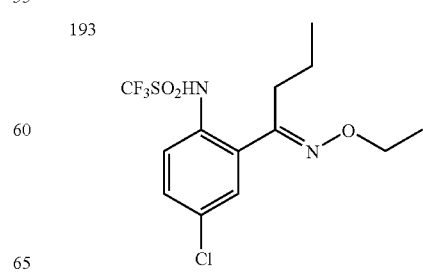 |
| 187 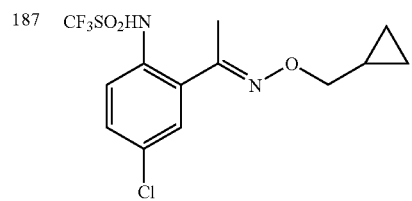 | | |

US 7,312,248 B2
-continued
| | Compound structure |
|---|---|
| 194 | 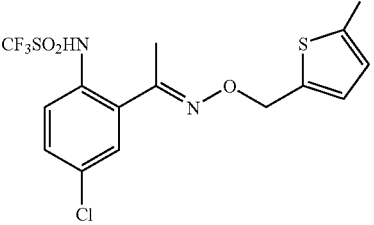 |
| 195 | 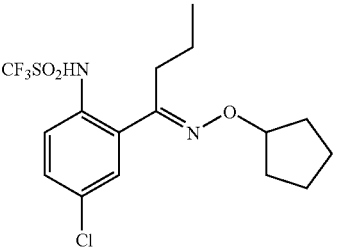 |
| 196 | 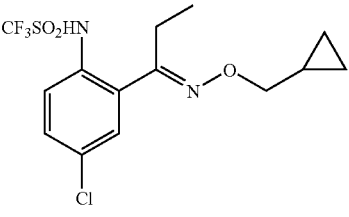 |
| 197 | 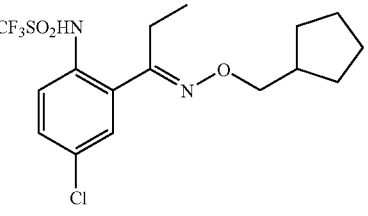 |
| 198 | 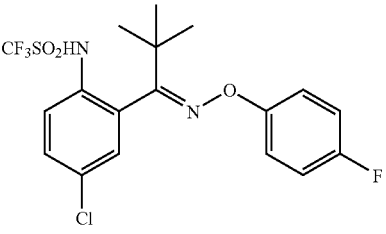 |
| 199 | 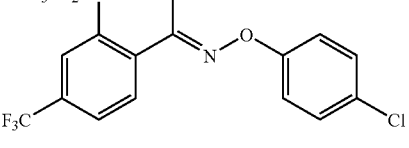 |
| 200 | 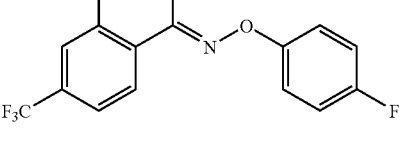 |
-continued
| | Compound structure |
|---|---|
| 201 | 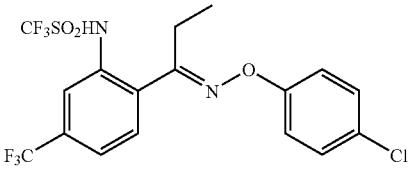 |
| 202 | 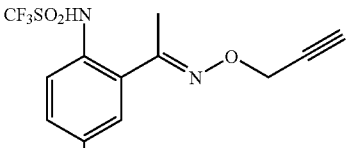 |
| 203 | 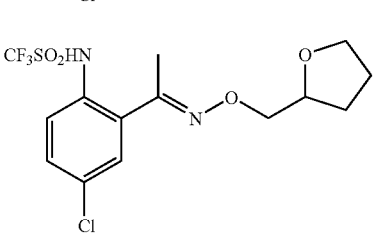 |
| 204 | 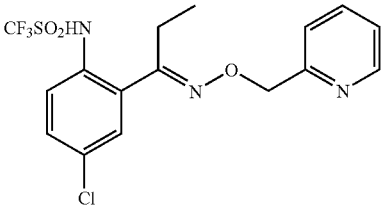 |
| 205 | 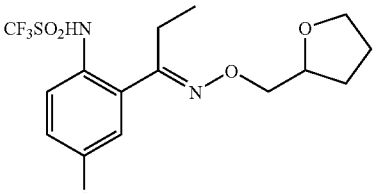 |
| 206 | 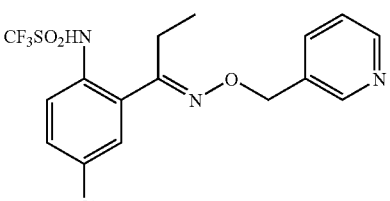 |
| 207 | 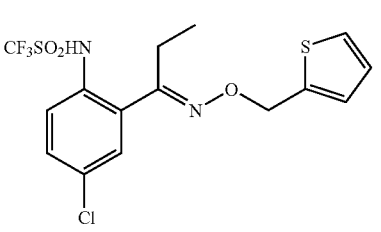 |

-continued
| | Compound structure |
|---|---|
| 208 | 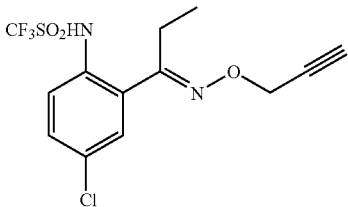 |
| 209 | 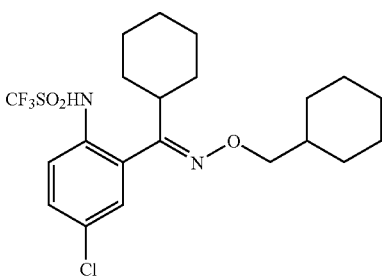 |
| 210 | 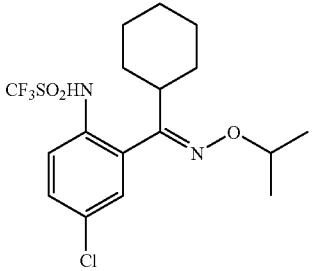 |
| 211 | 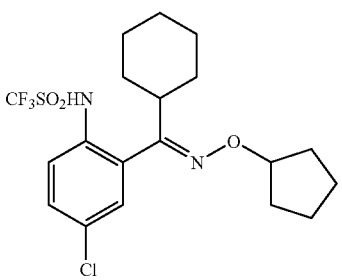 |
| 212 | 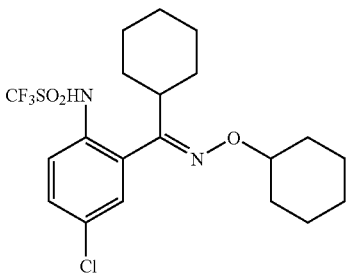 |
-continued
| | Compound structure |
|---|---|
| 213 | 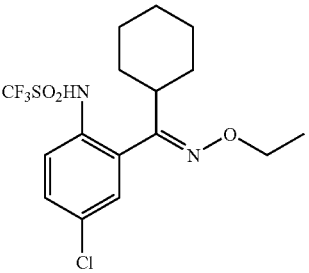 |
| 214 | 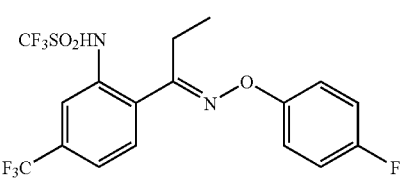 |
| 215 | 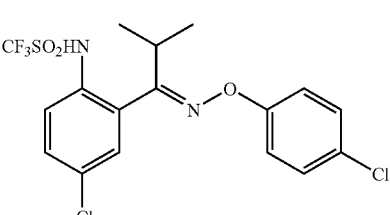 |
| 216 | 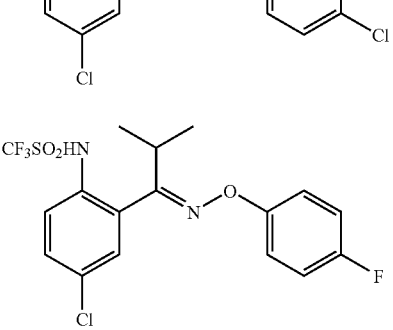 |
| 217 | 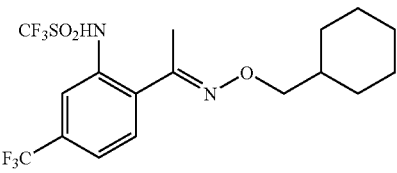 |
| 218 | 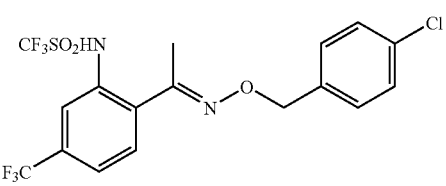 |
| 219 | 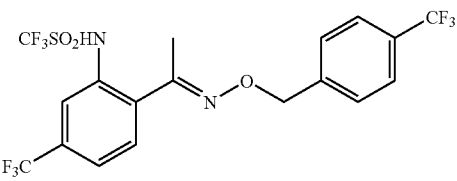 |

| Compound structure |
|---|
| 220 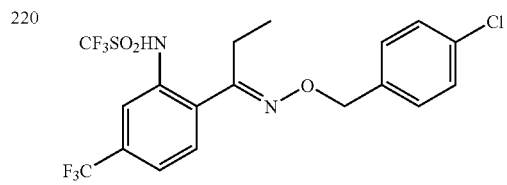 |
| 221 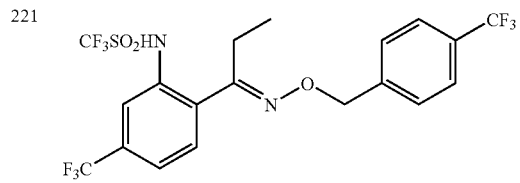 |
| 222 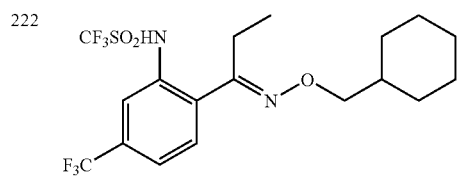 |
| 223 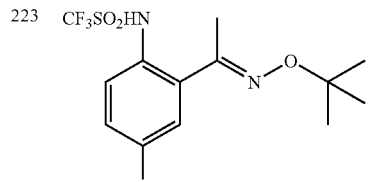 |
| 224 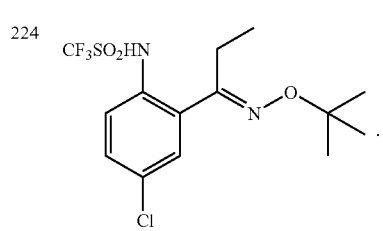 |

*Compound 177 exists as either a single syn(Z) or anti(E) isomer.
**Compound 178 exists as a mixture of syn(Z) and anti(E) isomers.

13. A pharmaceutical composition for treatment of animals infected with parasites that comprises a therapeutically effective dosage amount of the trifluoromethanesulfonanilide oxime ether compound of claim 1, and a pharmaceutically acceptable excipient.

14. The pharmaceutical composition of claim 13 wherein the trifluoromethanesulfonanilide oxime ether compound is selected from the compounds listed in the table below, and combinations thereof:

| Compound structure |
|---|
| 1 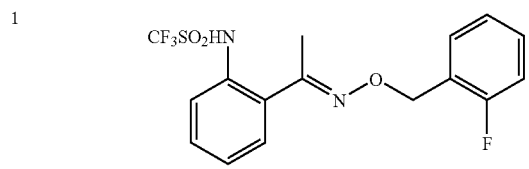 |
| 2 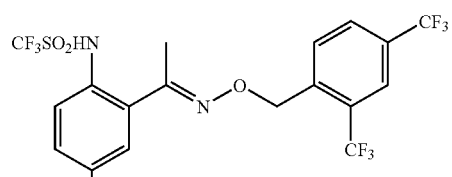 |
| 3 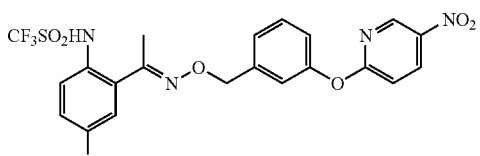 |
| 4 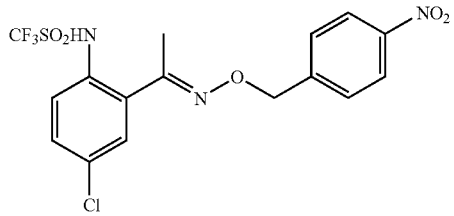 |
| 5 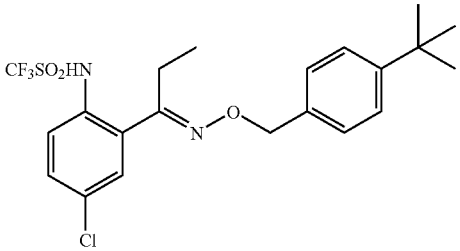 |
| 6 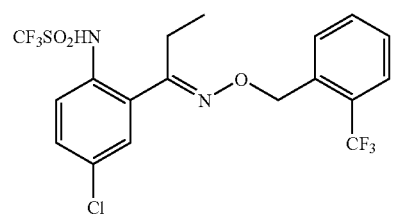 |
| 7 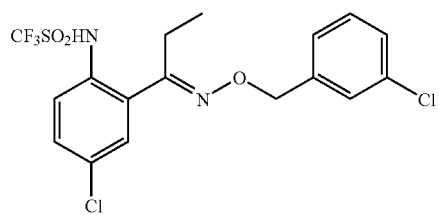 |
| 8 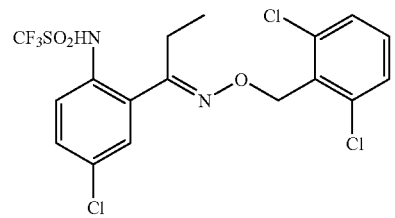 |

-continued

| | Compound structure |
|---|---|
| 9 | (structure) |
| 10 | (structure) |
| 11 | (structure) |
| 12 | (structure) |
| 13 | (structure) |
| 14 | (structure) |
| 15 | (structure) |

-continued

| | Compound structure |
|---|---|
| 16 | (structure) |
| 17 | (structure) |
| 18 | (structure) |
| 19 | (structure) |
| 20 | (structure) |
| 21 | (structure) |
| 22 | (structure) |

US 7,312,248 B2
229                                                         230
-continued                                                  -continued
Compound structure                                          Compound structure
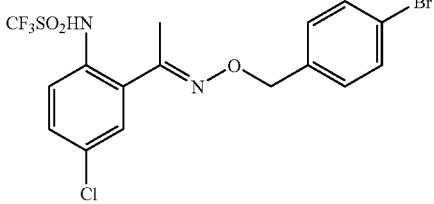
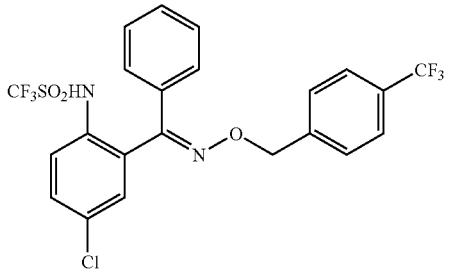
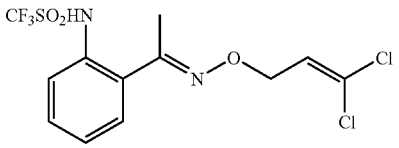
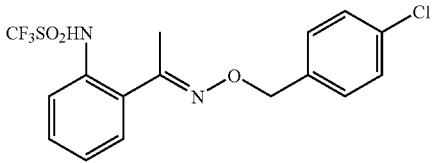
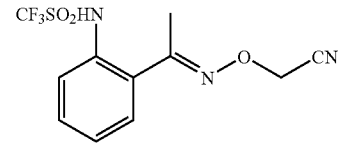
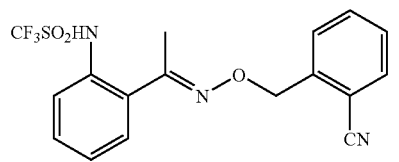
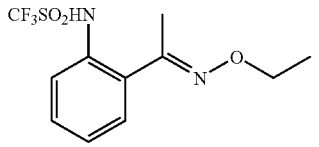
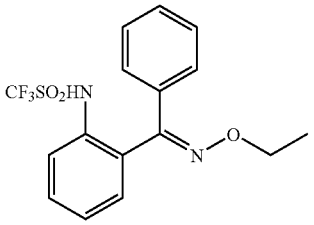
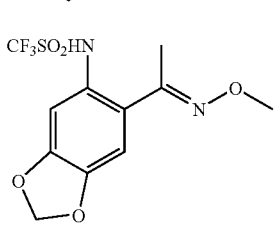
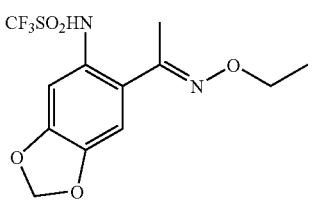
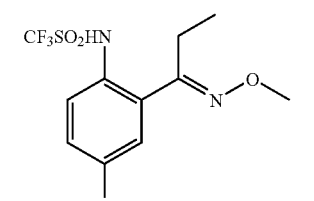
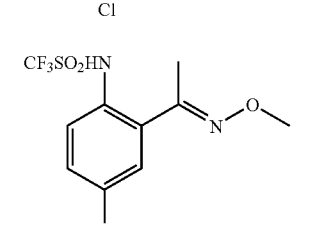
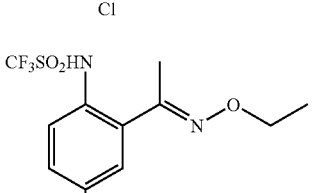
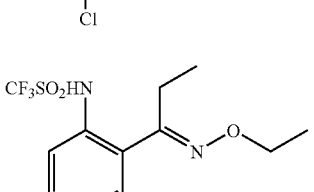
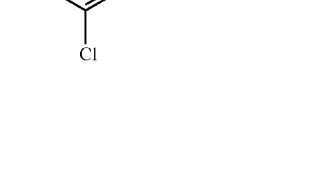

-continued

| | Compound structure |
|---|---|
| 38 | (structure) |
| 39 | (structure) |
| 40 | (structure) |
| 41 | (structure) |
| 42 | (structure) |
| 43 | (structure) |
| 44 | (structure) |
| 45 | (structure) |

-continued

| | Compound structure |
|---|---|
| 46 | (structure) |
| 47 | (structure) |
| 48 | (structure) |
| 49 | (structure) |
| 50 | (structure) |
| 51 | (structure) |
| 52 | (structure) |

-continued

| | Compound structure |
|---|---|
| 53 | |
| 54 | |
| 55 | |
| 56 | |
| 57 | |
| 58 | |
| 59 | |
| 60 | |

-continued

| | Compound structure |
|---|---|
| 61 | |
| 62 | |
| 63 | |
| 64 | |
| 65 | |

-continued

| | Compound structure |
|---|---|
| 66 | (structure: 2-(CF₃SO₂NH)-5-chlorophenyl phenyl ketone O-benzyl oxime) |
| 67 | (structure: 2-(CF₃SO₂NH)-5-chlorobenzaldehyde O-(2,4-dichlorobenzyl) oxime) |
| 68 | (structure: 2-(CF₃SO₂NH)-5-chlorophenyl phenyl ketone O-(3-trifluoromethylbenzyl) oxime) |
| 69 | (structure: 2-(CF₃SO₂NH)-5-chlorophenyl phenyl ketone O-(2-trifluoromethylbenzyl) oxime) |
| 70 | (structure: 2-(CF₃SO₂NH)-5-chlorobenzaldehyde O-(4-trifluoromethylbenzyl) oxime) |
| 71 | (structure: 2-(CF₃SO₂NH)-5-chlorophenyl phenyl ketone O-(3-chlorobenzyl) oxime) |

-continued

| | Compound structure |
|---|---|
| 72 | (structure: 2-(CF₃SO₂NH)-5-chlorophenyl ethyl ketone O-(2,3-dichlorobenzyl) oxime) |
| 73 | (structure: 2-(CF₃SO₂NH)-5-chlorophenyl methyl ketone O-(4-cyanobenzyl) oxime) |
| 74 | (structure: 2-(CF₃SO₂NH)-5-chlorophenyl ethyl ketone O-(2,4-dichlorobenzyl) oxime) |
| 75 | (structure: 2-(CF₃SO₂NH)-5-chlorophenyl ethyl ketone O-(4-bromobenzyl) oxime) |
| 76 | (structure: 2-(CF₃SO₂NH)-5-chlorophenyl ethyl ketone O-(2,4-bis(trifluoromethyl)benzyl) oxime) |
| 77 | (structure: 2-(CF₃SO₂NH)-5-chlorophenyl ethyl ketone O-(pentafluorobenzyl) oxime) |

-continued

| | Compound structure |
|---|---|
| 78 | (structure) |
| 79 | (structure) |
| 80 | (structure) |
| 81 | (structure) |
| 82 | (structure) |
| 83 | (structure) |

-continued

| | Compound structure |
|---|---|
| 84 | (structure) |
| 85 | (structure) |
| 86 | (structure) |
| 87 | (structure) |
| 88 | (structure) |
| 89 | (structure) |

-continued
| Compound structure |
|---|
| 90 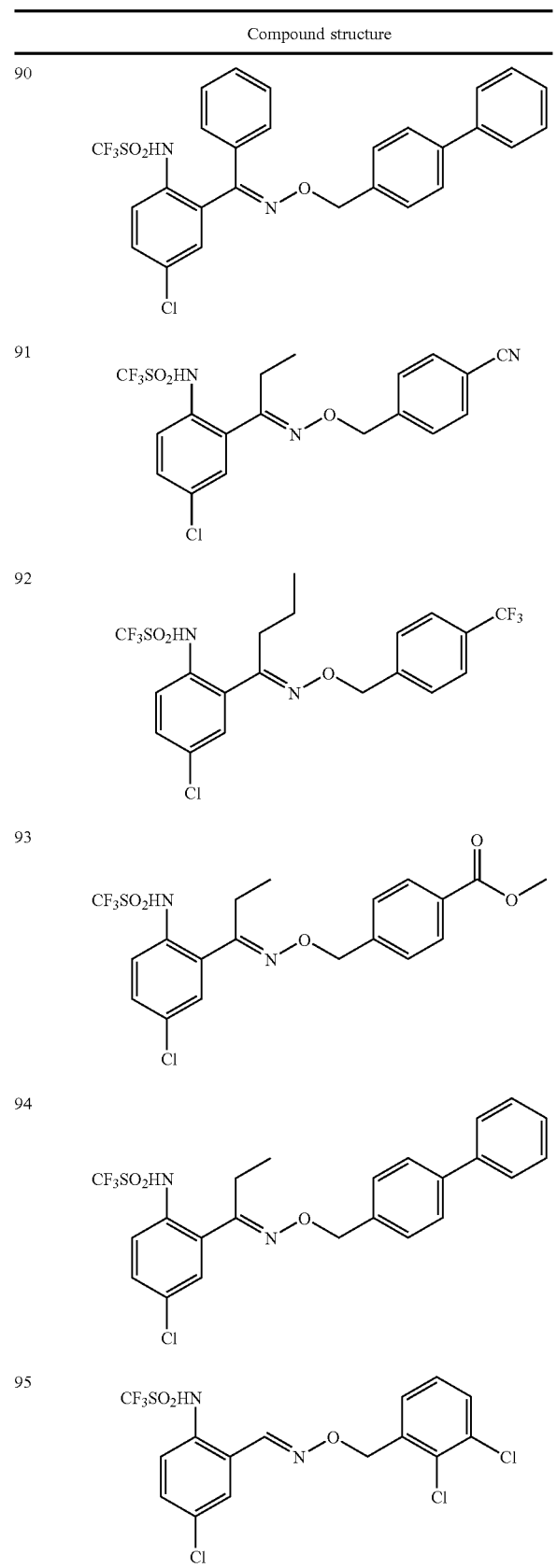 |
| 91 |
| 92 |
| 93 |
| 94 |
| 95 |
-continued
| Compound structure |
|---|
| 96 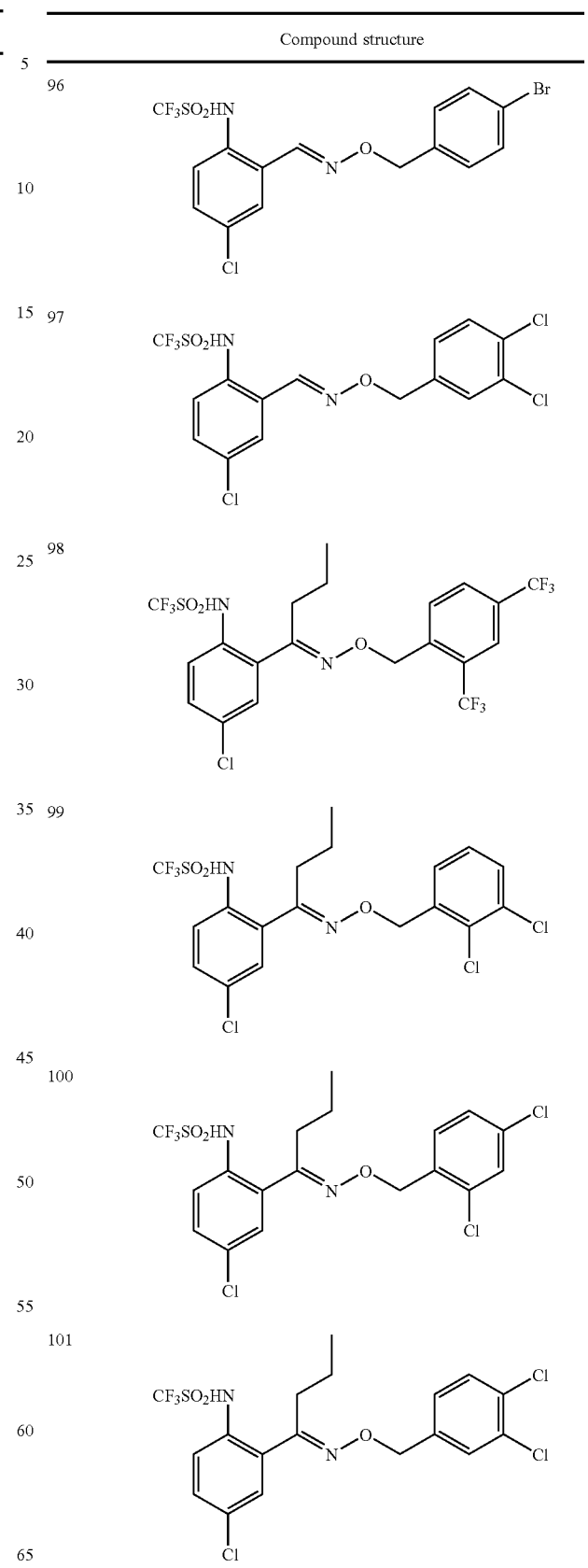 |
| 97 |
| 98 |
| 99 |
| 100 |
| 101 |

| | Compound structure |
|---|---|
| 102 | 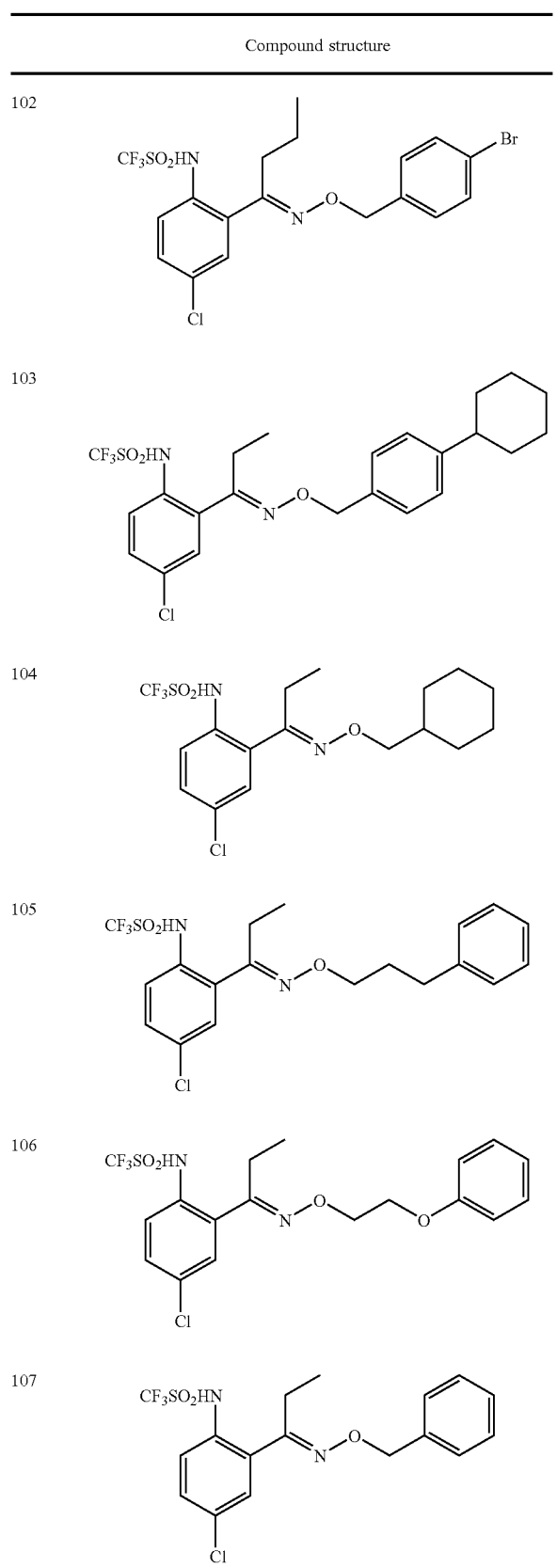 |
| 103 | |
| 104 | |
| 105 | |
| 106 | |
| 107 | |
| | Compound structure |
|---|---|
| 108 | 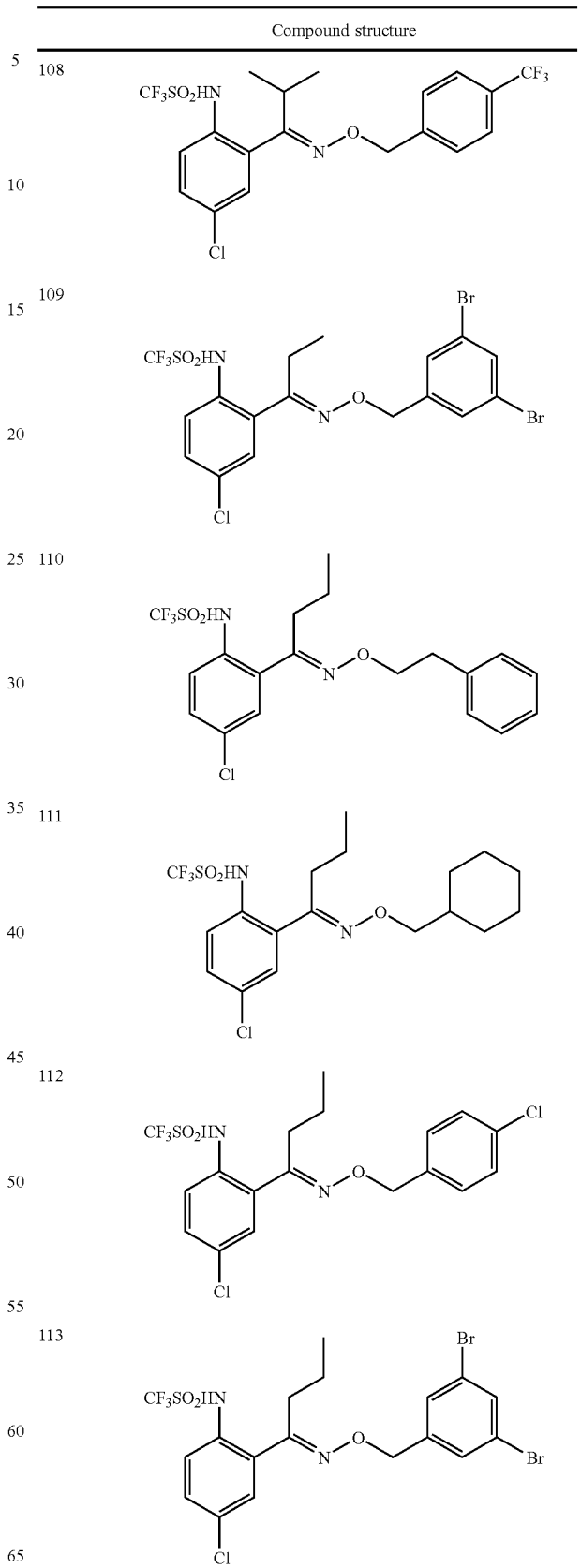 |
| 109 | |
| 110 | |
| 111 | |
| 112 | |
| 113 | |

-continued

| | Compound structure |
|---|---|
| 114 | |
| 115 | |
| 116 | |
| 117 | |
| 118 | |
| 119 | |

-continued

| | Compound structure |
|---|---|
| 120 | |
| 121 | |
| 122 | |
| 123 | |
| 124 | |
| 125 | |
| 126 | |

-continued

| Compound structure | |
|---|---|
| 127 | (CF₃SO₂HN, 4-Cl phenyl, C=N-O-(4-chlorophenyl), methyl) |
| 128 | (CF₃SO₂HN, 4-Cl phenyl, C=N-O-(4-chlorophenyl), ethyl) |
| 129 | (CF₃SO₂HN, 4-Cl phenyl, C=N-O-(4-fluorophenyl), methyl) |
| 130 | (CF₃SO₂HN, 4-Cl phenyl, C=N-O-(4-fluorophenyl), ethyl) |
| 131 | (CF₃SO₂HN, 4-Cl phenyl, C=N-O-(3-chlorophenyl), ethyl) |
| 132 | (CF₃SO₂HN, 4-Cl phenyl, C=N-O-(3-chlorophenyl), methyl) |
| 133 | (CF₃SO₂HN, 4-Cl phenyl, C=N-O-(3-CF₃-phenyl), ethyl) |

-continued

| Compound structure | |
|---|---|
| 134 | (CF₃SO₂HN, 4-Cl phenyl, C=N-O-(3-CF₃-phenyl), methyl) |
| 135 | (CF₃SO₂HN, 4-Cl phenyl, C=N-O-(4-CN-phenyl), methyl) |
| 136 | (CF₃SO₂HN, 4-Cl phenyl, C=N-O-(4-CN-phenyl), ethyl) |
| 137 | (CF₃SO₂HN, 4-Cl phenyl, C=N-O-(4-Br-phenyl), methyl) |
| 138 | (CF₃SO₂HN, 4-Cl phenyl, C=N-O-(4-Br-phenyl), ethyl) |
| 139 | (CF₃SO₂HN, 4-Cl phenyl, C=N-O-(3,4-dichlorophenyl), ethyl) |
| 140 | (CF₃SO₂HN, 4-Cl phenyl, C=N-O-(3,4-dichlorophenyl), methyl) |

-continued

Compound structure

141

142

143

144

145

146

147

-continued

Compound structure

148

149

150

151

152

153

154

-continued

| Compound structure |
|---|
| 155 |
| 156 |
| 157 |
| 158 |
| 159 |
| 160 |
| 161 |

-continued

| Compound structure |
|---|
| 162 |
| 163 |
| 164 |
| 165 |
| 166 |
| 167 |

-continued

| | Compound structure |
|---|---|
| 168 | (structure) |
| 169 | (structure) |
| 170 | (structure) |
| 171 | (structure) |
| 172 | (structure) |
| 173 | (structure) |

-continued

| | Compound structure |
|---|---|
| 174 | (structure) |
| 175 | (structure) |
| 176 | (structure) |
| 177* | (structure) |
| 178** | (structure) |
| 179 | (structure) |

-continued
| Compound structure |
|---|
| 180 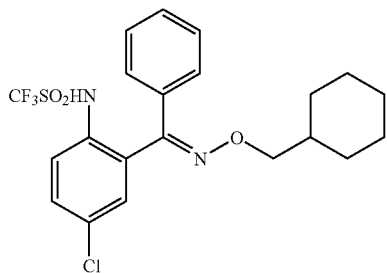 |
| 181 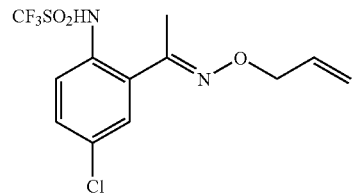 |
| 182 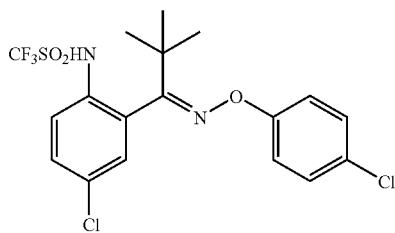 |
| 183 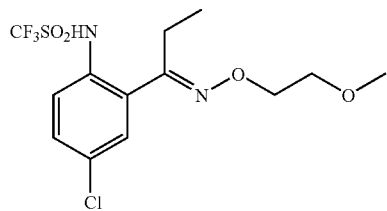 |
| 184 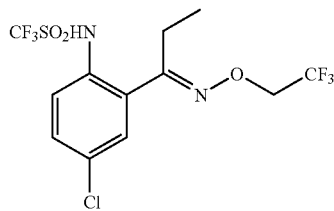 |
| 185 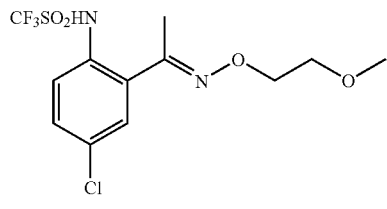 |
| 186 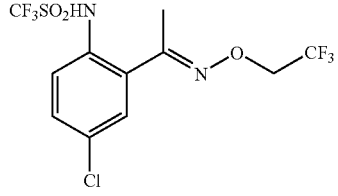 |
-continued
| Compound structure |
|---|
| 187 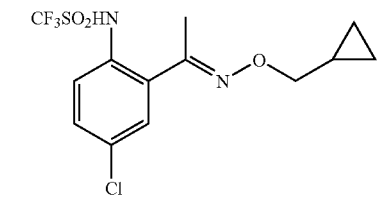 |
| 188 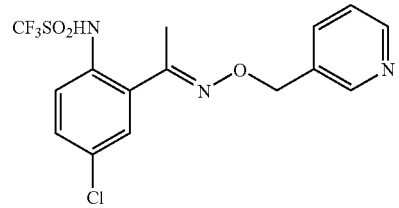 |
| 189 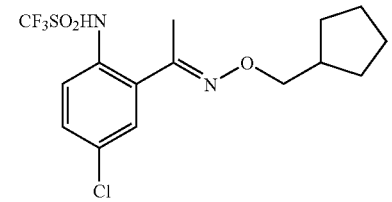 |
| 190 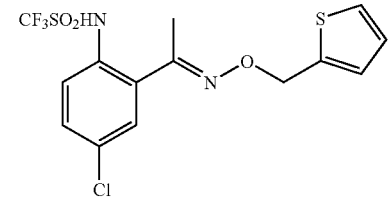 |
| 191 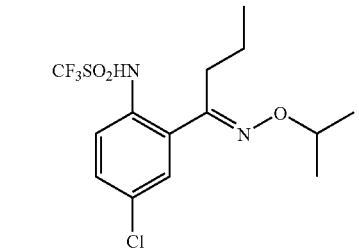 |
| 192 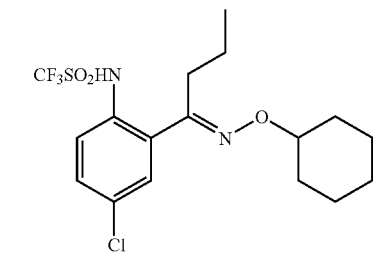 |

-continued

| Compound structure |
|---|
| 193 — CF₃SO₂HN-(5-Cl-phenyl)-C(=N-O-ethyl)-propyl |
| 194 — CF₃SO₂HN-(5-Cl-phenyl)-C(CH₃)=N-O-CH₂-(5-chlorothiophen-2-yl) |
| 195 — CF₃SO₂HN-(5-Cl-phenyl)-C(=N-O-cyclopentyl)-propyl |
| 196 — CF₃SO₂HN-(5-Cl-phenyl)-C(Et)=N-O-CH₂-cyclopropyl |
| 197 — CF₃SO₂HN-(5-Cl-phenyl)-C(Et)=N-O-CH₂-cyclopentyl |
| 198 — CF₃SO₂HN-(5-Cl-phenyl)-C(tBu)=N-O-(4-fluorophenyl) |

-continued

| Compound structure |
|---|
| 199 — CF₃SO₂HN-(4-CF₃-phenyl)-C(CH₃)=N-O-(4-chlorophenyl) |
| 200 — CF₃SO₂HN-(4-CF₃-phenyl)-C(CH₃)=N-O-(4-fluorophenyl) |
| 201 — CF₃SO₂HN-(4-CF₃-phenyl)-C(Et)=N-O-(4-chlorophenyl) |
| 202 — CF₃SO₂HN-(5-Cl-phenyl)-C(CH₃)=N-O-CH₂-C≡CH |
| 203 — CF₃SO₂HN-(5-Cl-phenyl)-C(CH₃)=N-O-CH₂-(tetrahydrofuran-2-yl) |
| 204 — CF₃SO₂HN-(5-Cl-phenyl)-C(Et)=N-O-CH₂-(pyridin-2-yl) |
| 205 — CF₃SO₂HN-(5-Cl-phenyl)-C(Et)=N-O-CH₂-(tetrahydrofuran-2-yl) |

-continued

| | Compound structure |
|---|---|
| 206 | (structure) |
| 207 | (structure) |
| 208 | (structure) |
| 209 | (structure) |
| 210 | (structure) |
| 211 | (structure) |

-continued

| | Compound structure |
|---|---|
| 212 | (structure) |
| 213 | (structure) |
| 214 | (structure) |
| 215 | (structure) |
| 216 | (structure) |
| 217 | (structure) |
| 218 | (structure) |

-continued

| | Compound structure |
|---|---|
| 219 | 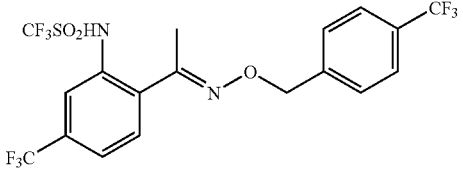 |
| 220 | 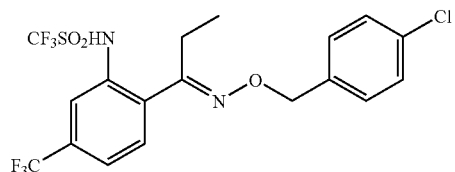 |
| 221 | 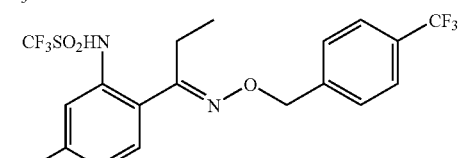 |
| 222 | 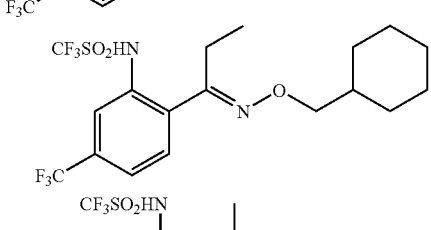 |
| 223 | 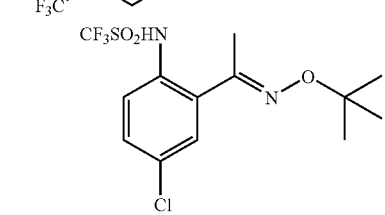 |

-continued

| | Compound structure |
|---|---|
| 224 | 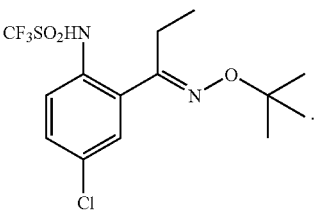 |

*Compound 177 exists as either a single syn(Z) or anti(E) isomer.
**Compound 178 exists as a mixture of syn(Z) and anti(E) isomer.

15. A pharmaceutical composition for treatment of animals infected with parasites that comprises a therapeutically effective dosage amount of the trifluoromethanesulfonanilide oxime ether compound of claim 7 and a pharmaceutically acceptable excipient.

16. A pharmaceutical composition for treatment of animals infected with parasites that comprises a therapeutically effective dosage amount of the trifluoromethanesulfonanilide oxime ether compound of claim 9, and a pharmaceutically acceptable excipient.

17. A pharmaceutical composition for treatment of animals infected with parasites that comprises a therapeutically effective dosage amount of the trifluoromethanesulfonanilide oxime ether compound of claim 11, and a pharmaceutically acceptable excipient.

* * * * *

UNITED STATES PATENT AND TRADEMARK OFFICE
CERTIFICATE OF CORRECTION

PATENT NO. : 7,312,248 B2
APPLICATION NO. : 11/231423
DATED : December 25, 2007
INVENTOR(S) : Adam Gerhard Meyer et al.

It is certified that error appears in the above-identified patent and that said Letters Patent is hereby corrected as shown below:

In Claim 7, Column 189, line 38 replace "$(C_1-C_6)$haloallyl" with --$(C_1-C_6)$haloalkyl--.

Signed and Sealed this

Twenty-sixth Day of August, 2008

JON W. DUDAS
*Director of the United States Patent and Trademark Office*